United States Patent
Nobile et al.

(10) Patent No.: US 11,112,409 B2
(45) Date of Patent: Sep. 7, 2021

(54) SYSTEMS AND COMPOSITIONS FOR DIAGNOSING PATHOGENIC FUNGAL INFECTION AND METHODS OF USING THE SAME

(71) Applicant: THE REGENTS OF THE UNIVERSITY OF CALIFORNIA, Oakland, CA (US)

(72) Inventors: Clarissa Nobile, Oakland, CA (US); Michael Winter, Oakland, CA (US); Charles Craik, Oakland, CA (US); Alexander Johnson, Oakland, CA (US); Anthony O'Donoghue, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 65 days.

(21) Appl. No.: 16/077,690

(22) PCT Filed: Feb. 10, 2017

(86) PCT No.: PCT/US2017/017526
§ 371 (c)(1),
(2) Date: Aug. 13, 2018

(87) PCT Pub. No.: WO2017/139679
PCT Pub. Date: Aug. 17, 2017

(65) Prior Publication Data
US 2019/0056395 A1 Feb. 21, 2019

Related U.S. Application Data

(60) Provisional application No. 62/294,960, filed on Feb. 12, 2016.

(51) Int. Cl.
*G01N 33/52* (2006.01)
*G01N 33/569* (2006.01)
*C12N 9/60* (2006.01)
*C12N 9/48* (2006.01)
*C07K 14/40* (2006.01)

(52) U.S. Cl.
CPC ....... *G01N 33/56961* (2013.01); *C07K 14/40* (2013.01); *C12N 9/48* (2013.01); *C12N 9/60* (2013.01); *C12Y 304/23024* (2013.01); *G01N 2333/40* (2013.01); *G01N 2333/8142* (2013.01); *G01N 2333/96* (2013.01); *G01N 2333/96416* (2013.01)

(58) Field of Classification Search
None
See application file for complete search history.

(56) References Cited

U.S. PATENT DOCUMENTS

| | | | |
|---|---|---|---|
| 6,251,621 B1 | 6/2001 | Lawrence et al. | |
| 2004/0123343 A1* | 6/2004 | La Rosa | C07K 14/415 800/278 |
| 2007/0134743 A1 | 6/2007 | Phillips et al. | |

FOREIGN PATENT DOCUMENTS

| | | |
|---|---|---|
| EP | 17750898.3 | 9/2018 |
| EP | 3414339 A1 | 12/2018 |
| WO | PCT/US2017/017526 | 2/2017 |
| WO | WO-2017/139679 A1 | 8/2017 |

OTHER PUBLICATIONS

Kalkanci et al (Folia Microbiologica (Prague, Czech Republic) (2005),50(5), 409-413. Abstract Only.*
Stover et al Nature 406, 959-964, 2000.*
Dunlop et al. Accession: T47213. Apr. 20, 2000.*
Mikayama et al. (Nov. 1993. Proc.Natl.Acad.Sci. USA, vol. 90 : 10056-10060).*
Rudinger et al. (Jun. 1976. Peptide Hormones. Biol.Council, pp. 5-7).*
Kojic et al "Candida Infections of Medical Devices", Clin Microbiol Rev. (2004) 17(2): 255-267.
Kumar et al: "Novel Aggregation Properties of Candida albicans Secreted Aspartyl Proteinase Sap6 Mediate Virulence in Oral Candidiasis", Infect Immun. (2015), 83(7): 2614-2626.
Ramage et al: "In vitro Candida albicans biofilm induced proteinase activity and SAP8 expression correlates with in vivo denture stomatitis severity", Mycopathologia. (2012), 174(1):11-19.
Staib et al: "Differential activation of a Candida albicans virulence gene family during infection", PNAS, vol. 97, No. 11, (2000), pp. 6102-6107.
Winter et al: "Global Identification of Biofilm-Specific Proteolysis in Candida albicans", mBio. (2016) 7(5): e01514-16.
International Search Report and Written Opinion dated Apr. 28, 2017 by the International Searching Authority for International Application No. PCT/US2017/017526, filed on Feb. 10, 2017 and published as WO 2017/139679 on Aug. 17, 2017 (Applicant—The Regents of the University of California) (12 Pages).
International Preliminary Report on Patentability dated Aug. 14, 2018 by the International Searching Authority for International Application No. PCT/US2017/017526, filed on Feb. 10, 2017 and published as WO 2017/139679 on Aug. 17, 2017 (Applicant—The Regents of the University of California) (9 Pages).
European Search Report and Written Opinion dated Jul. 25, 2019 by the European Patent Office for EP Application No. 17750898.3, filed on Sep. 11, 2018 and published as EP 3414339 on Dec. 19, 2018 (Applicant—The Regents of the University of California) (9 Pages).
U.S. Appl. No. 62/294,960, filed Feb. 12, 2016, Clarissa Nobile.

(Continued)

*Primary Examiner* — Jennifer E Graser
(74) *Attorney, Agent, or Firm* — Ballard Spahr LLP

(57) ABSTRACT

The present disclosure relates generally to detection of contamination of a sample or diagnosis of subject based upon detection or quantification of amino acid sequences in a sample, specifically to the identification and use of molecular biomarkers for *Candida albicans* biofilm infections.

Figure 1A:
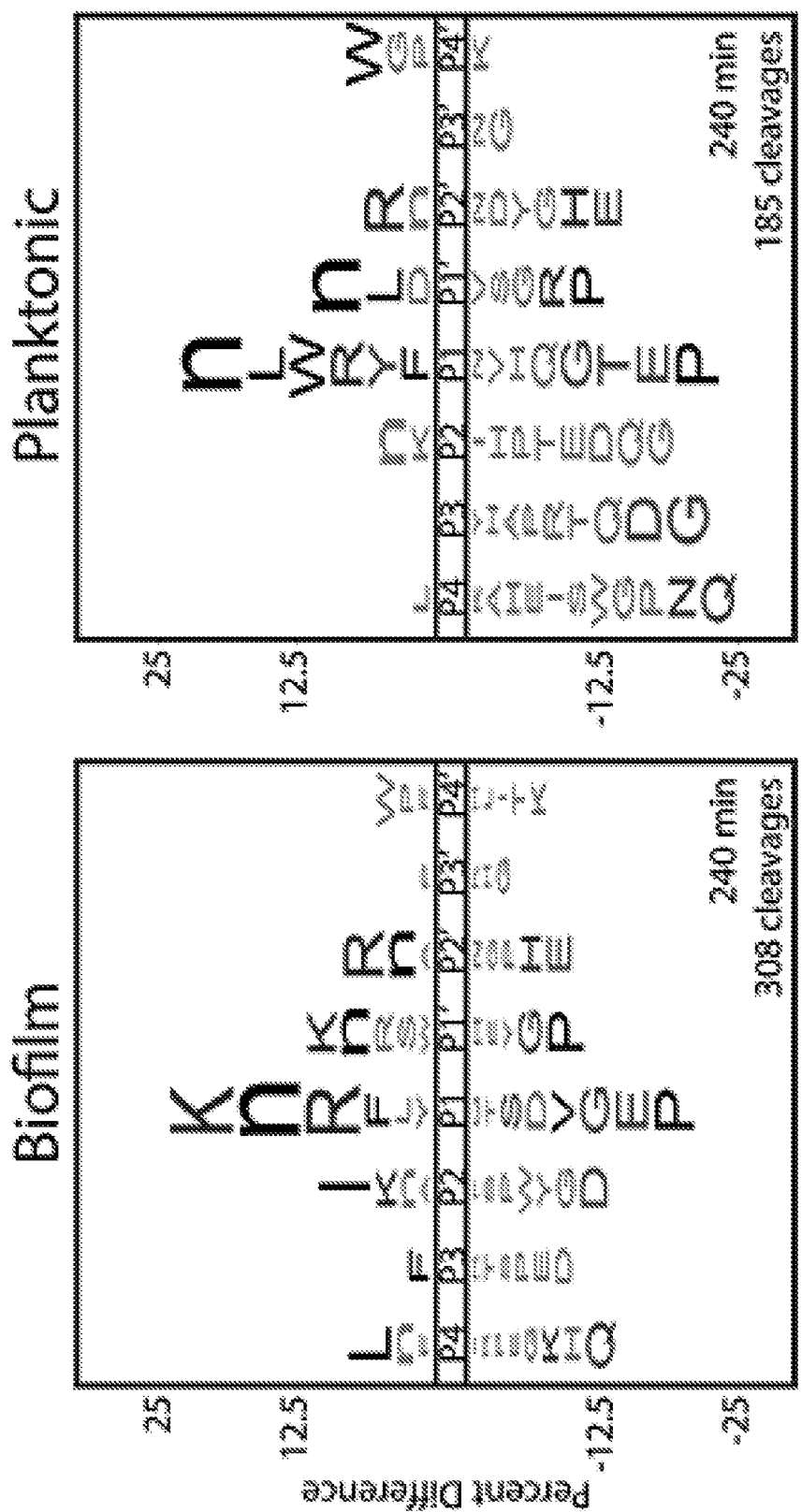

21 Claims, 32 Drawing Sheets
Specification includes a Sequence Listing.

(56) References Cited

OTHER PUBLICATIONS

Parra-Ortega, B., et al., "Phylogeny and Evolution of the Aspartyl Protease Family from Clinically Relevant *Candida* Species," Memórias do Instituto Oswaldo Cruz, Rio de Janeiro, 2009, vol. 104(3), pp. 505-512.

Examination Report Issued by the European Patent Office for EP Application No. 17750898.3 dated Nov. 24, 2020 (8 Pages).

* cited by examiner

WT SN250

1000X sap5/6 ΔΔ/ΔΔ

1000X

| Planktonic-Selective | Broad Spectrum | Biofilm-Selective |
|---|---|---|
| Hn^IALYWGRDTnFl | PYWDTKn^HAENIAQ | WTInGPDAFNLY^AL |
| W^NPIKILnFYWHEF | VFI^DLRWnAYEEPW | nLDKLnNWPQR^RGn |
| AYNnWSLYRnIRQ^E | EAWnTFIVPPR^SAG | LVAT^VYEFGHIDHn |

FIG. 20

SYSTEMS AND COMPOSITIONS FOR DIAGNOSING PATHOGENIC FUNGAL INFECTION AND METHODS OF USING THE SAME

CROSS-REFERENCE TO RELATED APPLICATIONS

The present application is a United States non-provisional application filed under 35 U.S.C. § 120, which is a United States National Stage filing under 35 U.S.C. § 371 claiming priority to International PCT Application Serial No. PCT/US2017/017,526, filed Feb. 10, 2017, which claims priority to U.S. Provisional Patent Application No. 62/294,960, filed Feb. 12, 2016, the contents of each of which are hereby incorporated by reference in its entirety.

STATEMENT REGARDING FEDERALLY SPONSORED RESEARCH

This invention was made with government support under grant numbers R00 AI100896 and R01 AI083311 awarded by the National Institutes of Health. The government has certain rights in this invention.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 37944_0004U2_SL. The size of the text file is 99 KB and the text file was created on Apr. 19, 2021.

TECHNOLOGY FIELD

The present disclosure relates generally to detection of contamination of a sample or diagnosis of subject based upon detection or quantification of amino acid sequences in a sample, specifically to identify and use of molecular biomarkers for fungal biofilm infection including *Candida albicans* biofilm infections.

BACKGROUND

*Candida albicans* is a commensal fungus that comprises part of the normal microbiota in humans. However, *Candida albicans* is also an opportunistic pathogen, capable of causing both mucosal and systemic infections. In addition to existing in a free yeast (planktonic) form, *Candida albicans* cells can form biofilms, organized microbial communities, which colonize many niches of the human body and can persist on implanted medical devices, causing biofilms to be a major source of new infections. Here, we use a global mass spectrometry-based peptide library assay to characterize biofilm-specific proteolysis of *Candida albicans* with the goal of identifying functional biomarkers for diagnosis and potential therapeutic intervention.

SUMMARY

The present disclosure relates to a method of diagnosing a subject with a pathogenic fungal infection comprising: detecting the presence, absence and/or quantity of at least one secreted aspartyl protease (Sap) or functional fragment thereof in a sample. In some embodiments, the subject is a human diagnosed with or suspected as having inflammation, a pathogenic fungal infection, or an idiopathic disorder.

The present disclosure also relates to a method of diagnosing a subject with a pathogenic fungal infection (either in planktonic or biofilm form) comprising: detecting the presence, absence, and/or quantity of at least one subtilisin-family protease, aminopeptidase or functional fragment thereof in a sample. The present disclosure also relates to a method of diagnosing a subject with a pathogenic fungal infection (either in planktonic or biofilm form) comprising: detecting the presence, absence, and/or quantity of at least one aminopeptidase or functional fragment thereof in a sample. In some embodiments, the methods herein comprise exposing a sample to at least one substrate of the proteases from Table 1 or at least one molecule capable of binding at least one protease from Table 1, or functional fragments thereof, wherein, when the protease is exposed to the substrate, the substrate is broken down into reaction products which can be quantified by a probe or other quantitative protein assay.

In some embodiments, the methods herein further comprise exposing a sample from a subject to at least one substrate of a Sap or at least one molecule capable of binding at least one Sap. In some embodiments, the at least one Sap is Sap5 and/or Sap6 or a functional fragment thereof. In some embodiments, wherein the step of detecting the presence, absence and/or quantity of at least one secreted aspartyl protease (Sap) or functional fragment thereof in a sample comprises measuring the quantity of at least one Sap or functional fragment thereof in a sample and normalizing the quantity in the sample with a measurement taken from a control sample.

In some embodiments, the method further comprises correlating the amount of at least one Sap or fragment thereof in the sample to the probability or likelihood the subject has a fungal infection relative to the measurement of the amount of Sap or functional fragment thereof of a control sample. In some embodiments, the pathogenic fungal infection is from the genus *Candida*. In some embodiments, the pathogenic infection comprises a biofilm of *Candida albicans*.

In some embodiments, the sample is taken from a culture of cells grown in vitro. In some embodiments, the sample is taken from a culture of cells seeded or inoculated by at least one cell from a subject. In some embodiments, the sample is taken from fluid or swatch or wipe from a solid surface, such as a catheter or piece of surgical equipment or other surface expected to be free of fungal cells.

The disclosure also relates to any of the methods disclosed herein further comprising a step of culturing at least one sample or cell from a biopsy taken from a subject with a culture medium under conditions and for a time period sufficient to grow at least one fungal cell. In some embodiments, the method further comprises culturing at least one biopsy from a subject with a culture medium under conditions and for a time period sufficient to grow at least one fungal cell from the genus *Candida*. In some embodiments, the step of measuring the quantity of at least one Sap or functional fragment thereof in a sample comprises one or a combination of: digitally imaging a sample, exposing a sample to a known amount of labeled antibody specific for an epitope of Sap5 and/or Sap6 or a functional fragment thereof, exposing a sample to a library of substrates for Sap5 and/or Sap6 or a functional fragment thereof, exposing a sample to at least one labeled antibody specific for an epitope of Sap5 and/or Sap6 or a functional fragment thereof, exposing a sample to chromatography, and/or exposing the sample to mass spectrometry. In some embodiments, the step of measuring the quantity of at least one aminopeptidase or functional fragment thereof in a sample comprises one or a combination of: digitally imaging a sample, exposing a sample to a known amount of labeled antibody specific for an epitope of aminopeptidase or functional fragment thereof, exposing a sample to a library of substrates for aminopeptidase or functional fragment thereof, exposing a sample to at least one labeled antibody specific for an epitope of aminopeptidase or functional fragment thereof, exposing a sample to chromatography, and/or exposing the sample to mass spectrometry.

In some embodiments, the step of measuring the quantity of at least one subtilisin or functional fragment thereof in a sample comprises one or a combination of: digitally imaging a sample, exposing a sample to a known amount of labeled antibody specific for an epitope of subtilisin or functional fragment thereof, exposing a sample to a library of substrates for subtilisin or functional fragment thereof, exposing a sample to at least one labeled antibody specific for an epitope of aminopeptidase or functional fragment thereof, exposing a sample to chromatography, and/or exposing the sample to mass spectrometry.

In some embodiments, wherein the sample is a human tissue sample comprising a tissue from a brushing, biopsy, or surgical resection of a subject. In some embodiments, the sample comprises a cell that is freshly obtained, formalin fixed, alcohol-fixed and/or paraffin embedded. In some embodiments, the step of measuring the quantity of at least one Sap or functional fragment thereof in a sample comprises using a bright field microscope and/or fluorescence microscopy after staining or labeling the Sap protein with one or a plurality of Sap specific molecules (such as a stain or fluorescent molecule) which is capable of detection by bright field microscopy or fluorescent microscopy.

The present disclosure also relates to a method of diagnosing a pathogenic infection of *Candida* (such as *C. albicans*) in a subject comprising: (a) contacting a plurality of probes specific for Sap5 and/or Sap6, or a functional fragment thereof with a sample; (b) quantifying the amount of Sap5 and/or Sap6, or a functional fragment thereof in the sample; (c) calculating one or more scores based upon the presence, absence, or quantity of Sap5 and/or Sap6, or a functional fragment thereof; and (d) correlating the one or more scores to the presence, absence, or quantity of Sap5 and/or Sap6, or a functional fragment thereof, such that if the amount of Sap5 and/or Sap6, or functional fragment thereof, is greater than the quantity of Sap5 and/or Sap6, or a functional fragment thereof in a control sample, the correlating step comprises diagnosing a subject with a pathogenic infection of *Candida*.

The present disclosure also relates to a method of diagnosing systemic infection of *Candida* (such as *C. albicans*) in a subject comprising: (a) contacting a plurality of probes specific for Sap5 and/or Sap6, or a functional fragment thereof with a sample; (b) quantifying the amount of Sap5 and/or Sap6, or a functional fragment thereof in the sample; (c) calculating one or more scores based upon the presence, absence, or quantity of Sap5 and/or Sap6, or a functional fragment thereof; and (d) correlating the one or more scores to the presence, absence, or quantity of Sap5 and/or Sap6, or a functional fragment thereof, such that if the amount of Sap5 and/or Sap6, or functional fragment thereof, is greater than the quantity of Sap5 and/or Sap6, or a functional fragment thereof in a control sample, the correlating step comprises diagnosing a subject with a pathogenic infection of *Candida*.

In some embodiments, the step of quantifying the amount of at least one Sap or functional fragment thereof in a sample comprises one or a combination of: digitally imaging a sample, exposing a sample to a known amount of labeled antibody specific for an epitope of Sap5 and/or Sap6 or a functional fragment thereof, exposing a sample to a library of substrates for Sap5 and/or Sap6 or a functional fragment thereof, exposing a sample to at least one labeled antibody specific for an epitope of Sap5 and/or Sap6 or a functional fragment thereof, exposing a sample to chromatography, and exposing the sample to mass spectrometry.

In some embodiments, the sample is a human tissue sample comprising a tissue from a brushing, biopsy, or surgical resection of a subject. In some embodiments, the sample comprises a cell that is freshly obtained, formalin fixed, alcohol-fixed and/or paraffin embedded. In some embodiments, the step of quantifying at least one Sap or functional fragment thereof in a sample comprises using a bright field microscope and/or fluorescence microscopy.

The present disclosure also relates to a method of treating or preventing a subject in need thereof diagnosed with or suspected a having a pathogenic fungal infection, comprising: (a) contacting a plurality of probes specific for one subtilisin-family protease, aminopeptidase or functional fragment thereof with a sample; (b) quantifying the amount of one subtilisin-family protease, aminopeptidase or functional fragment thereof in the sample; (c) calculating one or more scores based upon the presence, absence, or quantity of one subtilisin-family protease, aminopeptidase or functional fragment thereof; (d) correlating the one or more scores to the presence, absence, or quantity of one subtilisin-family protease, aminopeptidase or functional fragment thereof, such that, if the amount of one subtilisin-family protease, aminopeptidase or functional fragment thereof, is greater than the quantity of one subtilisin-family protease, aminopeptidase or functional fragment thereof, in a control sample, the correlating step comprises diagnosing a subject with a pathogenic infection of a fungus; and (e) administering to the subject a therapeutically effective amount of treatment for the pathogenic fungal infection. In some embodiments the step of calculating one or more scores based upon the presence, absence, or quantity of one subtilisin-family protease, aminopeptidase or functional fragment thereof, comprises normalizing the values corresponding to the amount of one subtilisin-family protease, aminopeptidase or functional fragment thereof in the sample against the values corresponding to the amount of one subtilisin-family protease, aminopeptidase or functional fragment thereof in a control sample. In some embodiments, the control sample is taken from a planktonic sample of fungal cells whereas, if the values corresponding to the amount of one subtilisin-family protease, aminopeptidase or functional fragment thereof are significantly higher than the levels in the control, the fungal cells in the sample are considered part of pathogenic fungal infection, or part of a biofilm, and not from commensal *Candida*.

The present disclosure also relates to a system comprising: one or a plurality of probes and/or stains that bind to at least one Sap, subtilisin-family protease, aminopeptidase or functional fragment thereof; and (c) one or more devices capable of quantifying the presence, absence and/or intensity of at least one probe or stain that binds Sap, subtilisin-family protease, aminopeptidase or functional fragment thereof in the sample. In some embodiments, the sample is taken from a subject identified as having or suspected of having a fungal infection.

The present disclosure also relates to a method for characterizing the stage of development or pathology of a fungal infection, comprising: (a) contacting a plurality of probes specific for Sap, subtilisin-family protease, aminopeptidase or functional fragment thereof with a sample; (b) quantifying the amount of Sap, subtilisin-family protease, aminopeptidase or functional fragment thereof in the sample; (c) calculating one or more normalized scores based upon the presence, absence, or quantity of Sap, subtilisin-family protease, aminopeptidase or functional fragment thereof; and (d) correlating the one or more scores to the presence, absence, or quantity of Sap, subtilisin-family protease, aminopeptidase or functional fragment thereof, such that, if the amount Sap, subtilisin-family protease, aminopeptidase or functional fragment thereof is greater than the quantity of Sap, subtilisin-family protease, aminopeptidase or functional fragment thereof in a control sample, the correlating step comprises characterizing the sample as comprising a fungal infection as pathogenic. The present disclosure also relates to a method for characterizing the stage of development or pathology of a fungal infection, comprising: (a) contacting a plurality of probes specific for Sap, subtilisin-family protease, aminopeptidase or functional fragment thereof with a sample; (b) quantifying the amount of Sap, subtilisin-family protease, aminopeptidase or functional fragment thereof in the sample; (c) calculating one or more normalized scores based upon the presence, absence, or quantity of Sap, subtilisin-family protease, aminopeptidase or functional fragment thereof; and (d) correlating the one or more scores to the presence, absence, or quantity of Sap, subtilisin-family protease, aminopeptidase or functional fragment thereof, such that, if the amount Sap, subtilisin-family protease, aminopeptidase or functional fragment thereof is less than the quantity of Sap, subtilisin-family protease, aminopeptidase or functional fragment thereof, in a control sample, the correlating step comprises characterizing the sample as comprising a fungal infection as a planktonic infection, wherein the control sample is a sample taken from or known to be from a subject with a biofilm infection.

The present disclosure also relates to a method for characterizing the stage of development or pathology of a fungal infection, comprising: (a) contacting a plurality of probes specific for at least one Sap, subtilisin-family protease, aminopeptidase or functional fragment thereof with a sample; (b) quantifying the amount of at least one Sap, subtilisin-family protease, aminopeptidase or functional fragment thereof in the sample; (c) calculating one or more normalized scores based upon the presence, absence, or quantity of at least one Sap, subtilisin-family protease, aminopeptidase or functional fragment thereof; and (d) correlating the one or more scores to the presence, absence, or quantity of at least one Sap, subtilisin-family protease, aminopeptidase or functional fragment thereof, such that, if the amount at least one Sap, subtilisin-family protease, aminopeptidase or functional fragment thereof is less than the quantity of at least one Sap, subtilisin-family protease, aminopeptidase or functional fragment thereof, in a control sample, the correlating step comprises characterizing the sample as comprising a fungal infection as a planktonic infection, wherein the control sample is a sample taken from or known to be from a subject with a biofilm infection.

The present disclosure also relates to a method of treating or preventing a subject in need thereof diagnosed with or suspected a having a pathogenic fungal infection, comprising: (a) contacting a plurality of probes specific for Sap5 and/or Sap6, or a functional fragment thereof with a sample; (b) quantifying the amount of Sap5 and/or Sap6, or a functional fragment thereof in the sample; (c) calculating one or more scores based upon the presence, absence, or quantity of Sap5, Sap6, and/or a functional fragment thereof; (d) correlating the one or more scores to the presence, absence, or quantity of Sap5 and/or Sap6, or a functional fragment thereof, such that, if the amount of Sap5 and/or Sap6, or functional fragment thereof, is greater than the quantity of Sap5 and/or Sap6, or a functional fragment thereof, in a control sample, the correlating step comprises diagnosing a subject with a pathogenic infection of a fungus; and (e) administering to the subject a therapeutically effective amount of treatment for the pathogenic fungal infection. In some embodiments the step of calculating one or more scores based upon the presence, absence, or quantity of Sap5, Sap6, and/or a functional fragment thereof, comprises normalizing the values corresponding to the amount of Sap5, Sap6, and/or a functional fragment thereof in the sample against the values corresponding to the amount of Sap5, Sap6, and/or functional fragment thereof in a control sample. In some embodiments, the control sample is taken from a planktonic sample of fungal cells whereas, if the values corresponding to the amount of Sap5, Sap6 or functional fragment thereof are significantly higher than the levels in the control, the fungal cells in the sample are considered part of pathogenic fungal infection, or part of a biofilm, and not from commensal *Candida*.

The present disclosure also relates to a system comprising: (a) a sample; (b) one or a plurality of probes and/or stains that bind to at least one Sap5 and/or Sap6, or functional fragment thereof; and (c) one or more devices capable of quantifying the presence, absence and/or intensity of at least one probe or stain that binds Sap5 and/or Sap6, or functional fragments thereof in the sample. In some embodiments, the sample is taken from a subject identified as having or suspected of having a fungal infection.

The present disclosure also relates to a method for characterizing the stage of development or pathology of a fungal infection, comprising: (a) contacting a plurality of probes specific for Sap5 and/or Sap6, or a functional fragment thereof with a sample; (b) quantifying the amount of Sap5 and/or Sap6, or a functional fragment thereof in the sample; (c) calculating one or more normalized scores based upon the presence, absence, or quantity of Sap5 and/or Sap6 or a functional fragment thereof; and (d) correlating the one or more scores to the presence, absence, or quantity of Sap5 and/or Sap6, or a functional fragment thereof, such that, if the amount Sap5 and/or Sap6, or functional fragment thereof is greater than the quantity of Sap5 and/or Sap6, or a functional fragment thereof in a control sample, the correlating step comprises characterizing the sample as comprising a fungal infection as pathogenic. The present disclosure also relates to a method for characterizing the stage of development or pathology of a fungal infection, comprising: (a) contacting a plurality of probes specific for Sap5 and/or Sap6, or a functional fragment thereof with a sample; (b) quantifying the amount of Sap5 and/or Sap6, or a functional fragment thereof in the sample; (c) calculating one or more normalized scores based upon the presence, absence, or quantity of Sap5 and/or Sap6 or a functional fragment thereof; and (d) correlating the one or more scores to the presence, absence, or quantity of Sap5 and/or Sap6, or a functional fragment thereof, such that, if the amount Sap5 and/or Sap6, or functional fragment thereof is less than the quantity of Sap5 and/or Sap6, or a functional fragment thereof, in a control sample, the correlating step comprises characterizing the sample as comprising a fungal infection as a planktonic infection, wherein the control sample is a sample taken from or known to be from a subject with a biofilm infection. The present disclosure also relates to a method for characterizing the stage of development or pathology of a fungal infection, comprising: (a) contacting a plurality of probes specific for at least one secreted aspartyl protease, or a functional fragment thereof with a sample; (b) quantifying the amount of at least one secreted aspartyl protease, or a functional fragment thereof in the sample; (c) calculating one or more normalized scores based upon the presence, absence, or quantity of at least one secreted aspartyl protease or a functional fragment thereof; and (d) correlating the one or more scores to the presence, absence, or quantity of at least one secreted aspartyl protease, or a functional fragment thereof, such that, if the amount at least one secreted aspartyl protease, or functional fragment thereof is less than the quantity of at least one secreted aspartyl protease, or a functional fragment thereof, in a control sample, the correlating step comprises characterizing the sample as comprising a fungal infection as a planktonic infection, wherein the control sample is a sample taken from or known to be from a subject with a biofilm infection.

The present disclosure also relates to a method for characterizing the stage of development or pathology of a fungal infection, comprising: (a) contacting a plurality of probes specific for a protease at least 70% homologous to any one of SEQ ID NO:1, 2, 3, 4, 5, 6, 7, 8, 9, 10, 11, or 12 or a functional fragment thereof with a sample; (b) quantifying the amount of the protease, or a functional fragment thereof in the sample; (c) calculating one or more normalized scores based upon the presence, absence, or quantity of the protease or a functional fragment thereof; and (d) correlating the one or more scores to the presence, absence, or quantity of the protease, or a functional fragment thereof, such that, if the amount the protease, or functional fragment thereof is less than the quantity of at least one protease, or a functional fragment thereof, in a control sample, the correlating step comprises characterizing the sample as comprising a fungal infection as a planktonic infection, wherein the control sample is a sample taken from or known to be from a subject with a biofilm infection.

The present disclosure also relates to a method for characterizing the stage of development or pathology of a fungal infection, comprising: (a) contacting a plurality of probes specific for at least one aminopeptidase, or a functional fragment thereof with a sample; (b) quantifying the amount of aminopeptidase, or a functional fragment thereof in the sample; (c) calculating one or more normalized scores based upon the presence, absence, or quantity of at least one aminopeptidase or a functional fragment thereof; and (d) correlating the one or more scores to the presence, absence, or quantity of at least one aminopeptidase, or a functional fragment thereof, such that, if the amount at least one aminopeptidase, or functional fragment thereof is less than the quantity of at least one aminopeptidase, or a functional fragment thereof, in a control sample, the correlating step comprises characterizing the sample as comprising a fungal infection as a planktonic infection, wherein the control sample is a sample taken from or known to be from a subject free of a systemic fungal infection or fungal biofilm infection.

The present disclosure also relates to a method of determining whether a fungal colony is capable of forming a biofilm comprising: (a) detecting the presence, absence or quantity of Sap5 and/or Sap6, or functional fragment thereof in a sample in contact with or contacted with a culture of fungal cells.

The present disclosure further relates to a method of detecting the presence of a pathogenic fungus in a sample comprising: (a) contacting a plurality of probes specific for Sap5 and/or Sap6, or a functional fragment thereof with a sample; (b) quantifying the amount of Sap5 and/or Sap6, or a functional fragment thereof in the sample; (c) calculating one or more normalized scores based upon the presence, absence, or quantity of Sap5 and/or Sap6 or a functional fragment thereof; and (d) correlating the one or more scores to the presence, absence, or quantity of Sap5 and/or Sap6, or a functional fragment thereof, such that if the amount Sap5 and/or Sap6, or functional fragment thereof is greater than the quantity of Sap5 and/or Sap6, or a functional fragment thereof in a control sample, the correlating step comprises characterizing the sample as comprising a fungal infection as pathogenic.

The present disclosure further relates to a method of detecting the presence of a planktonic fungus in a sample comprising: (a) contacting a plurality of probes specific for Sap5 and/or Sap6, or a functional fragment thereof with a sample; (b) quantifying the amount of Sap5 and/or Sap6, or a functional fragment thereof in the sample; (c) calculating one or more normalized scores based upon the presence, absence, or quantity of Sap5 and/or Sap6 or a functional fragment thereof; and (d) correlating the one or more scores to the presence, absence, or quantity of Sap5 and/or Sap6, or a functional fragment thereof, such that if the amount Sap5 and/or Sap6, or functional fragment thereof is less than the quantity of Sap5 and/or Sap6, or a functional fragment thereof in a control sample, the correlating step comprises characterizing the sample as comprising a fungal infection as planktonic, wherein the control sample is taken from a subject known to have a biofilm infection.

The present disclosure also relates to a method of detecting the presence of a planktonic fungus in a sample or subject comprising: (a) contacting a plurality of probes specific for Sap, or a functional fragment thereof with a sample; (b) quantifying the amount of Sap, or a functional fragment thereof in the sample; (c) calculating one or more normalized scores based upon the presence, absence, or quantity of Sap or a functional fragment thereof; and (d) correlating the one or more scores to the presence, absence, or quantity of Sap, or a functional fragment thereof, such that if the amount Sap, or functional fragment thereof is less than the quantity of Sap, or a functional fragment thereof in a control sample, the correlating step comprises characterizing the sample as comprising a fungal infection as planktonic, wherein the control sample is taken from a subject known to have a biofilm infection. The present disclosure also relates to a method of detecting the presence of a planktonic fungus in a sample or subject comprising: (a) contacting a plurality of probes specific for a protein at least 70% homologous to SEQ ID NO: 1, 2, 3, 4, 5, 6, 7, 8, 9, or 10, or a functional fragment thereof with a sample; (b) quantifying the amount of the protein, or a functional fragment thereof in the sample; (c) calculating one or more normalized scores based upon the presence, absence, or quantity of the protein or a functional fragment thereof; and (d) correlating the one or more scores to the presence, absence, or quantity of the protein, or a functional fragment thereof, such that if the amount of protein, or functional fragment thereof is less than the quantity of protein, or a functional fragment thereof in a control sample, the correlating step comprises characterizing the sample as comprising a fungal infection as planktonic, wherein the control sample is taken from a subject known to have a biofilm infection.

The present disclosure also relates to a method of detecting the presence of a planktonic fungus in a sample or subject comprising: (a) contacting a plurality of probes specific for a substrate cleaved in the presence of a peptide at least 70% homologous to SEQ ID NO: 1, 2, 3, 4, 5, 6, 7, 8, 9, or 10, or a functional fragment thereof with a sample (i.e. a reaction product); (b) quantifying the amount of the cleaved substrate or reaction product in the sample; (c) calculating one or more normalized scores based upon the presence, absence, or quantity of the cleaved substrate or a reaction product; and (d) correlating the one or more scores to the presence, absence, or quantity of the reaction product, or a functional fragment thereof, such that if the amount of reaction product is less than the quantity of a reaction product in a control sample, the correlating step comprises characterizing the sample as comprising a planktonic fungal infection, wherein the control sample is taken from a subject known to have a biofilm infection.

The present disclosure also relates to a method of detecting the presence of a fungal biofilm in subject or a sample taken from a subject comprising: (a) contacting a plurality of probes specific for a substrate cleaved in the presence of a peptide at least 70% homologous to SEQ ID NO: 1, 2, 3, 4, 5, 6, 7, 8, 9, or 10, or a functional fragment thereof with a sample (i.e. a reaction product); (b) quantifying the amount of the cleaved substrate or reaction product in the sample; (c) calculating one or more normalized scores based upon the presence, absence, or quantity of the cleaved substrate or the reaction product; and (d) correlating the one or more scores to the presence, absence, or quantity of the reaction product, or a functional fragment thereof, such that if the amount of reaction product is more than the quantity of the reaction product in a control sample, the correlating step comprises characterizing the sample as comprising a or subject as having a fungal biofilm infection, wherein the control sample is taken from a subject known to have a planktonic fungal infection or an absence of a fungal infection.

The present disclosure also relates to a method of detecting the presence of a fungal biofilm in subject or a sample taken from a subject comprising: (a) contacting a plurality of probes specific for a substrate cleaved in the presence of a Sap, or a functional fragment thereof with a sample (i.e. a reaction product); (b) quantifying the amount of the cleaved substrate or reaction product in the sample; (c) calculating one or more normalized scores based upon the presence, absence, or quantity of the cleaved substrate or the reaction product; and (d) correlating the one or more scores to the presence, absence, or quantity of the reaction product, or a functional fragment thereof, such that if the amount of reaction product is more than the quantity of the reaction product in a control sample, the correlating step comprises characterizing the sample as comprising a or subject as having a fungal biofilm infection, wherein the control sample is taken from a subject known to have a planktonic fungal infection or an absence of a fungal infection.

The present disclosure also relates to a method of detecting the presence of a fungal biofilm in subject or a sample taken from a subject comprising: (a) contacting a plurality of probes specific for a substrate cleaved in the presence of any of the enzymes in Tables 1 and/or 2, or a functional fragment thereof with a sample (i.e. a reaction product); (b) quantifying the amount of the cleaved substrate or reaction product in the sample; (c) calculating one or more normalized scores based upon the presence, absence, or quantity of the cleaved substrate or the reaction product; and (d) correlating the one or more scores to the presence, absence, or quantity of the reaction product, or a functional fragment thereof, such that if the amount of reaction product is more than the quantity of the reaction product in a control sample, the correlating step comprises characterizing the sample as comprising a or subject as having a fungal biofilm infection, wherein the control sample is taken from a subject known to have a planktonic fungal infection or an absence of a fungal infection.

In one embodiment, the present invention is directed to a diagnostic test kit for detecting a Sap protein, a aminopeptidase, and/or a subtilisin-like protease within a test sample or within a subject. The diagnostic test kit may include, for instance, an assay device comprising a fluidic medium. The fluidic medium in turn defines a detection zone within which is immobilized to a receptive material. In addition, the detection zone is capable of generating a detection signal that represents the presence or absence of a Sap protein, a aminopeptidase, and/or a subtilisin-like protease. In some embodiments, the diagnostic kit also includes a probe. In some embodiments, the receptive material comprises an antibody that specifically binds to the Sap protein, aminopeptidase, and/or subtilisin-like protease.

In another embodiment, the invention is directed to a method for detecting the presence of a Sap protein, a aminopeptidase, and/or a subtilisin-like protease within a test sample or within a subject. For example, the method may include contacting an assay device with the test sample and generating a detectable signal at the detection zone that corresponds to the presence or absence of the Sap protein, the aminopeptidase, and/or the subtilisin-like protease.

BRIEF DESCRIPTIONS OF THE DRAWINGS

Figure 1B:
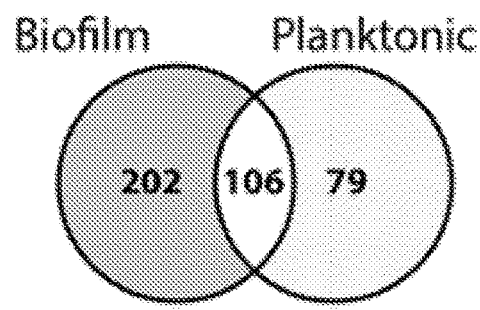
Figure 1C:
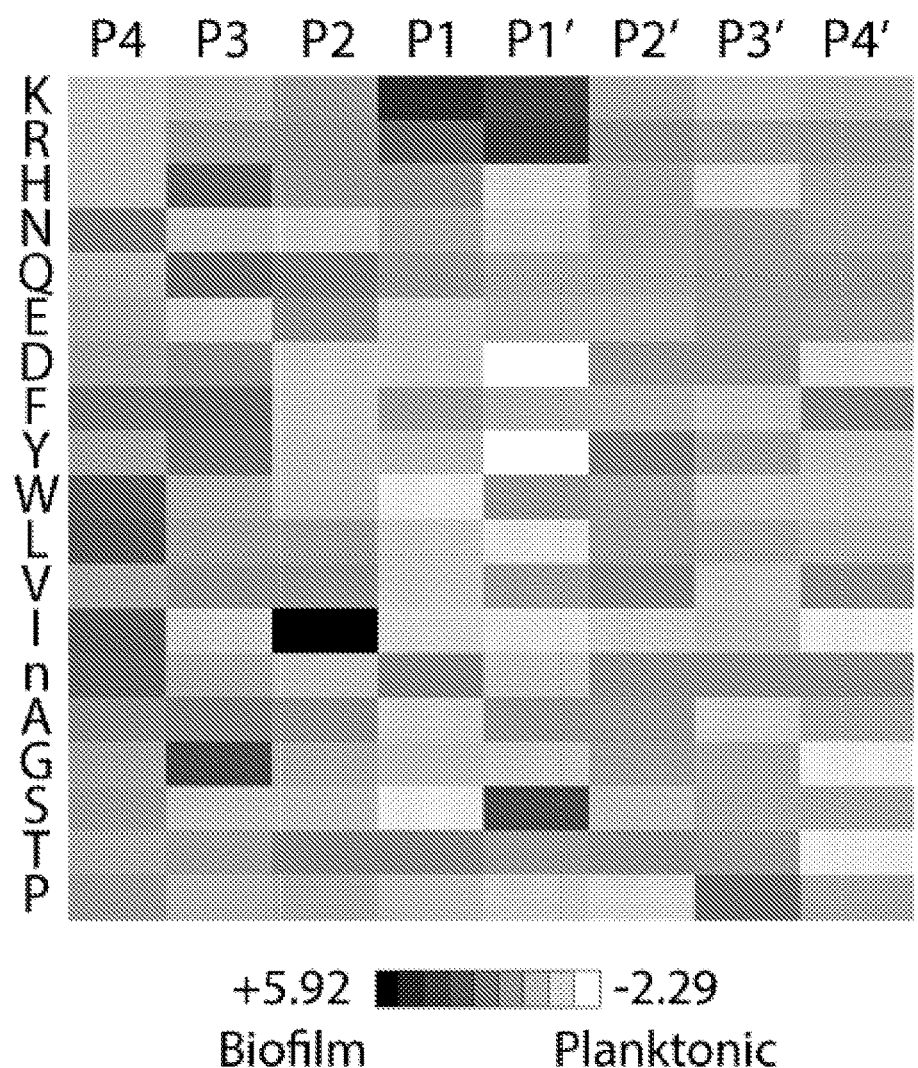
Figure 6:
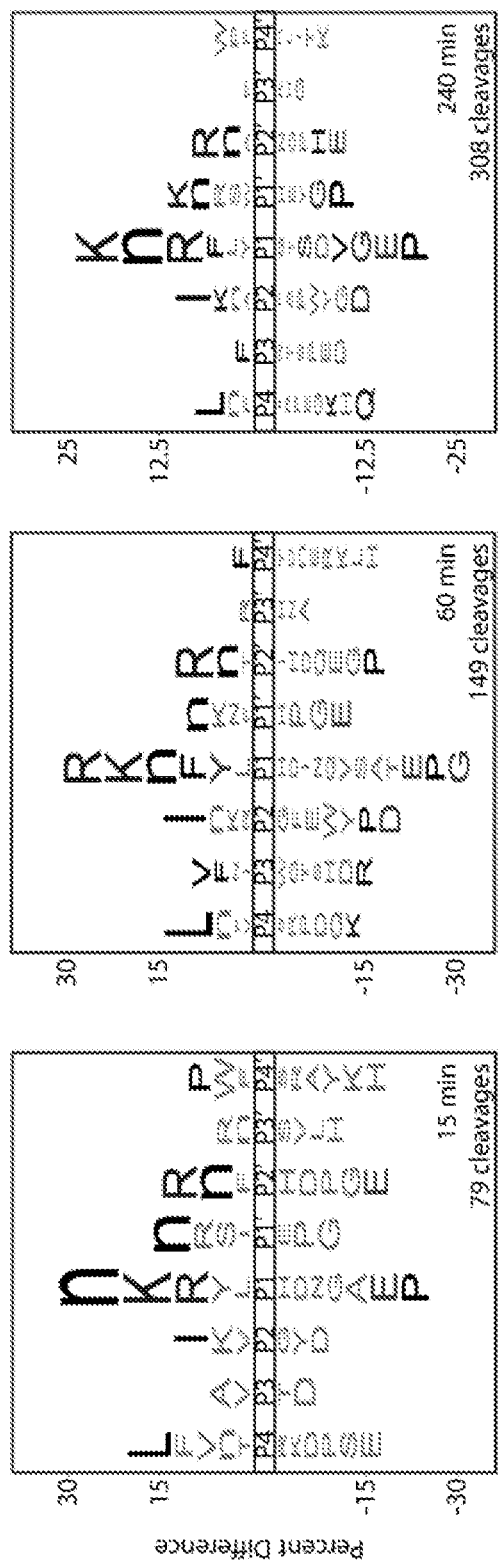
Figure 6:
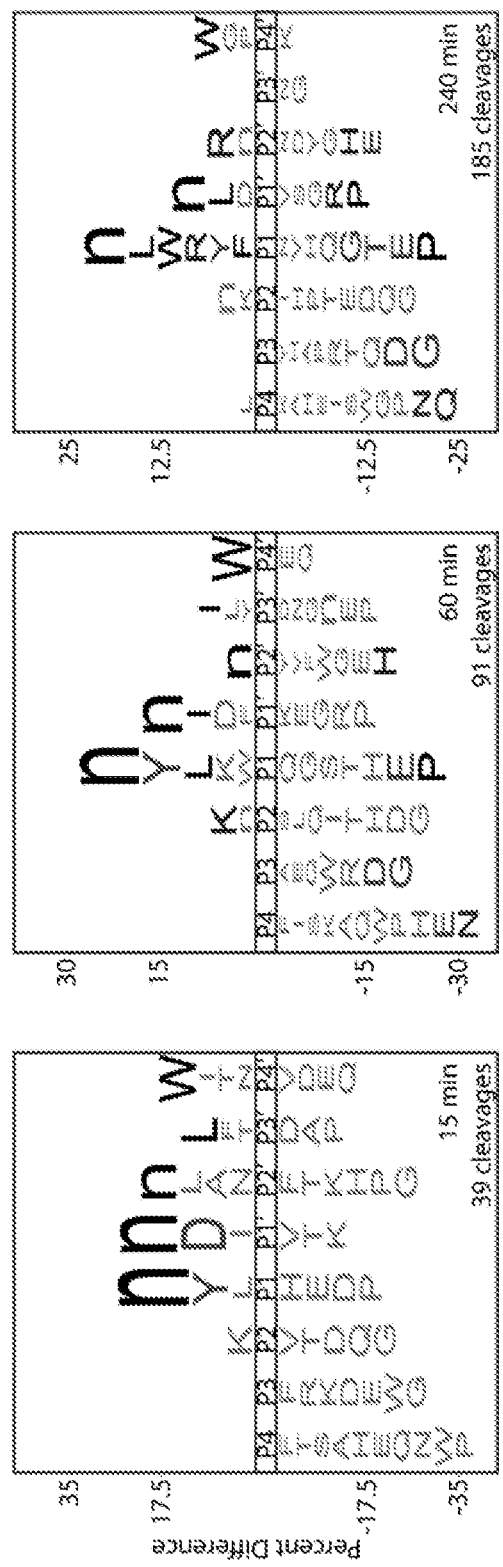

FIGS. 1A-1C depict global substrate specificity profiles of protease activity in conditioned media from wild-type *C. albicans* (SN425) under biofilm and planktonic conditions. FIG. 1A depicts iceLogo substrate specificity representations for 20 μg/mL of 24-hour conditioned media following 240 min incubation with the MSP-MS peptide library (P=0.05 for non-grayed residues and "n" is norleucine). Specificity profiles for the 15 min and 60 min assay time points are provided (FIG. 6). FIG. 1B depicts quantification of the total shared and unique cleavages for the biofilm and planktonic conditions at the 240 min assay time point.

FIG. 1C depicts a heat map representation of biofilm and planktonic specificity differences at the 240 min time point calculated using Z-score differences at the P4-P4' positions. Biofilm-favored residues are colored black and planktonic-favored residues are colored white.

Figure 2A:
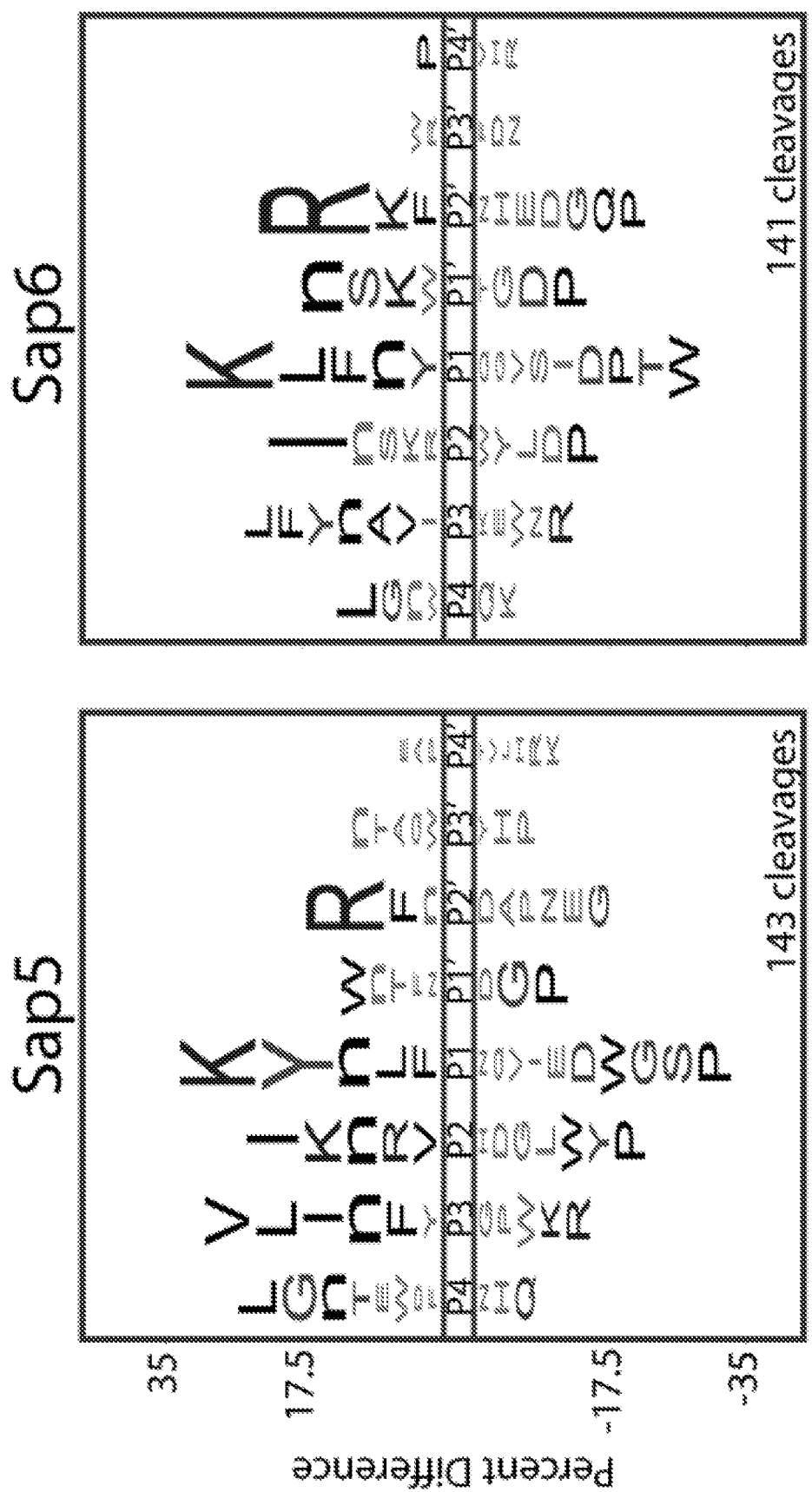

FIGS. 2A-2E depict global substrate specificity profiling of recombinantly-produced Sap5 and Sap6 and comparison to the substrate specificity profiles from biofilm and planktonic conditioned media. FIG. 2A depicts iceLogo representations for Sap5 and Sap6 following 240 min incubation with the MSP-MS peptide library (P=0.05 for non-grayed residues). Sap6 was assayed at 10-fold lower concentration due to higher specific activity against the peptide library based on total cleavage number.

Figure 2B:
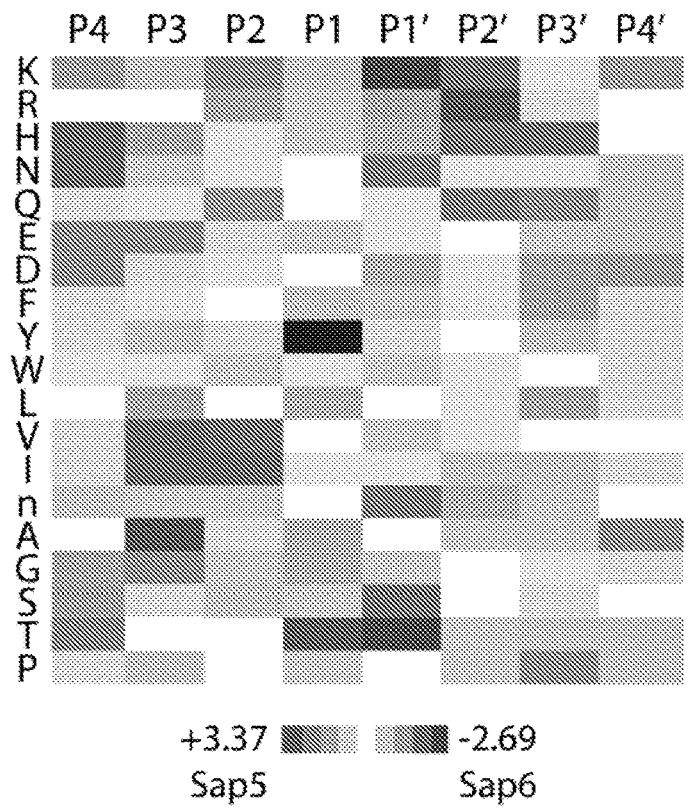

FIG. 2B depicts a heat map representation of Sap5 and Sap6 specificity differences calculated using Z-score differences at the P4-P4' positions. Sap5-favored residues are colored black and Sap6-favored residues are colored white.

Figure 2C:
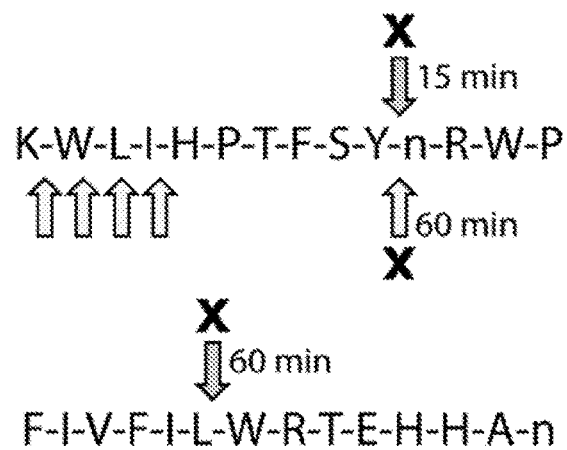
Figure 2C:
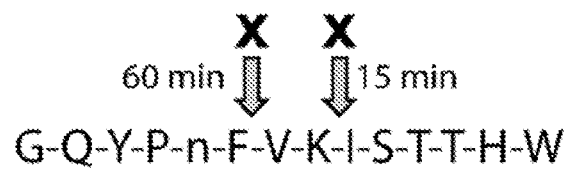

FIG. 2C. Example peptide cleavages from the biofilm (upper arrow) and planktonic (lower arrow) MSP-MS assays with pepstatin-sensitive cleavages indicated using an "X" and the time point of first appearance indicated. Select cleavages were omitted for clarity.

Figure 2D:
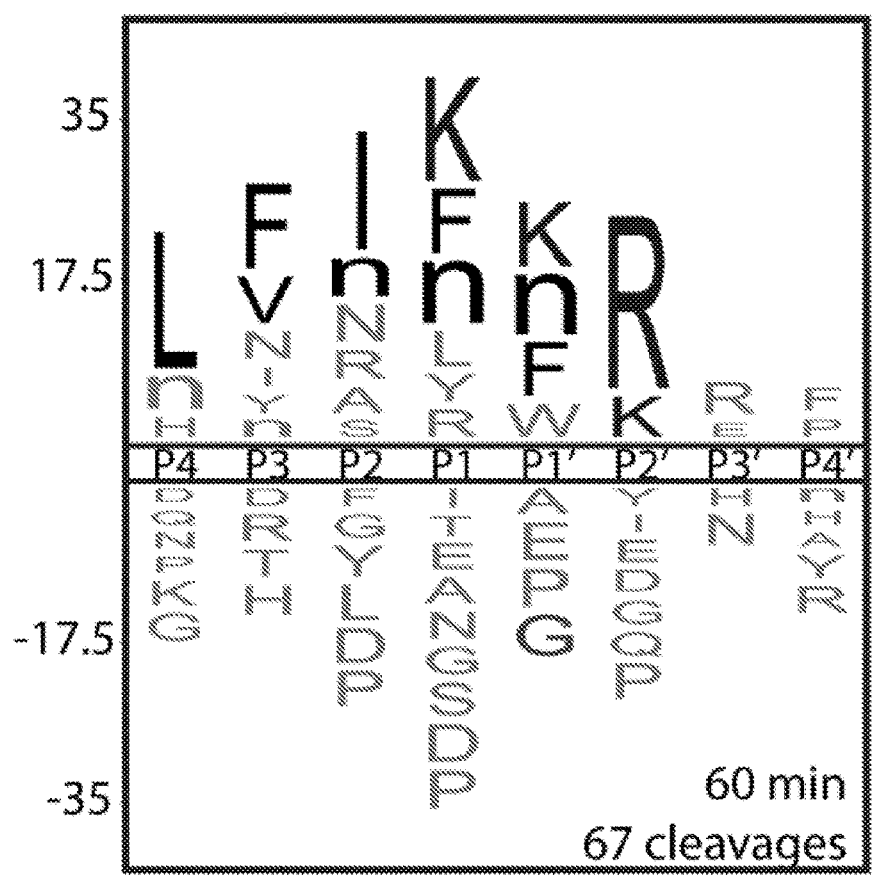
Figure 2E:
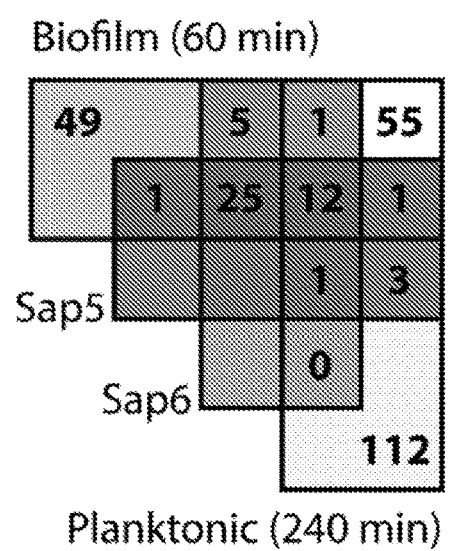
Figure 9:
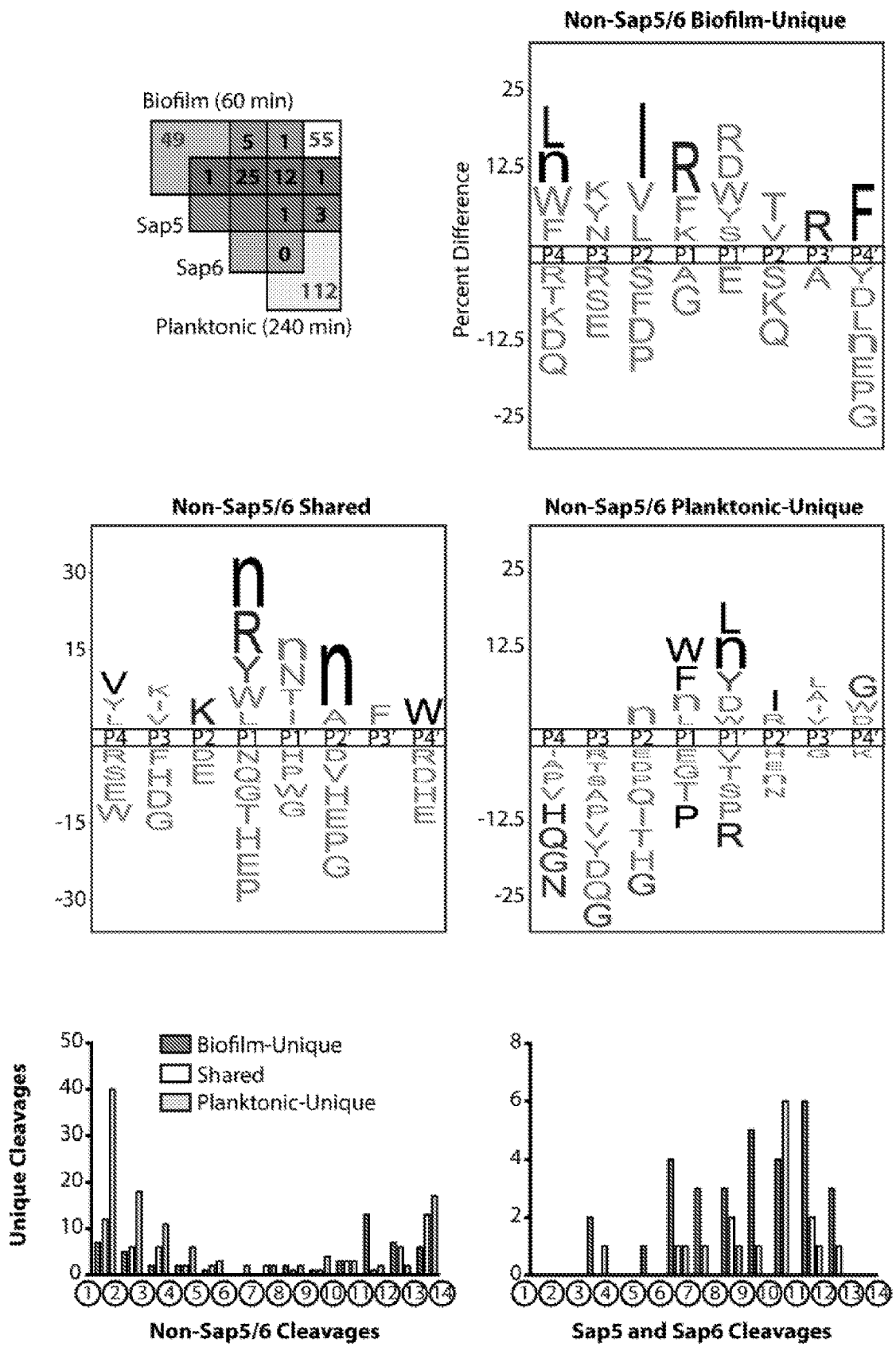

FIG. 2D depicts an iceLogo representation of pepstatin-sensitive cleavages in the biofilm conditioned media assay. FIG. 2E depicts an assignment of pepstatin-sensitive cleavages in the conditioned media profiles using recombinantly produced Sap5 and Sap6. Biofilm (60 min) and planktonic (240 min) time points were chosen to normalize for total cleavage number, demonstrating an enrichment of both Sap5 and Sap6 activity in the biofilm condition. iceLogo representations for unassigned cleavages are distinct from the Sap5 and Sap6 specificity profiles (FIG. 9).

Figures 3A, 3B:
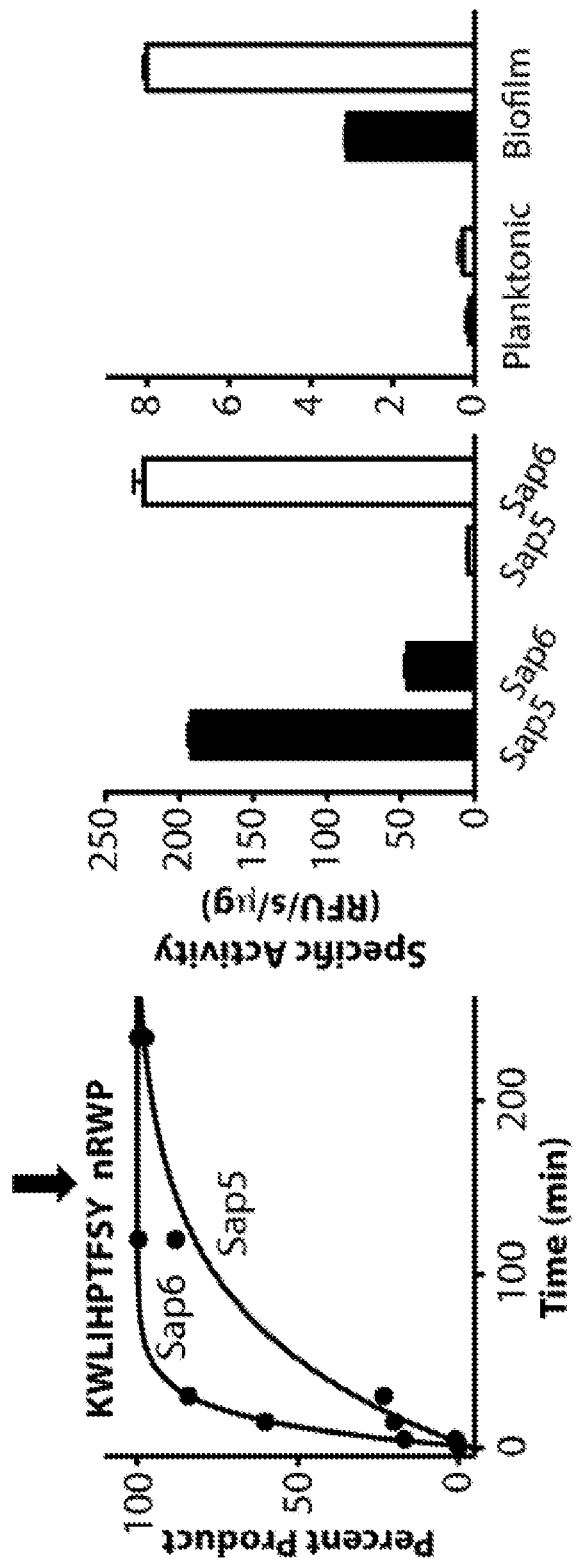

FIGS. 3A-3B depict the development of internally quenched fluorogenic substrates to distinguish Sap5 and Sap6 activity using their differential cleavage site preferences. FIG. 3A depicts an example mass spectrometry-based time course showing Sap6-favored cleavage of KWLIHPTFSYnRWP (SEQ ID NO: 26) within a 25-member MSP-MS peptide sub-library. Complete hydrolysis of the parent substrate and cleavage at a single site allowed for the calculation of $k_{cat}/K_M$ values of $4.4\times10^4$ M$^{-1}$s$^{-1}$ (Sap5) and $2.0\times10^5$ M$^{-1}$s$^{-1}$ (Sap6). Cleavage time courses for remaining peptides used in sequence selection are provided (FIG. 10). FIG. 3B depicts an evaluation of Sap5 and Sap6 internally quenched fluorescent substrates, VFILWRTE (black; SEQ ID NO: 22) and TFSYnRWP (white; SEQ ID NO: 23), using recombinantly produced proteases and conditioned media from biofilm and planktonic cultures.

Figures 4A, 4B:
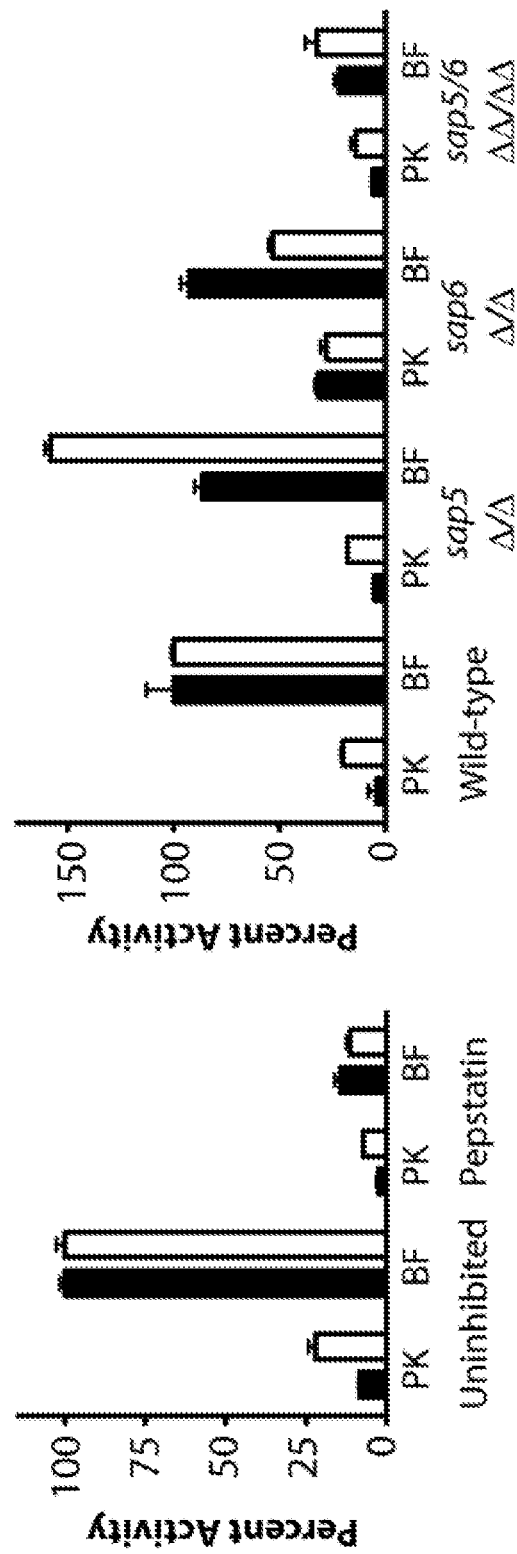
Figure 12:
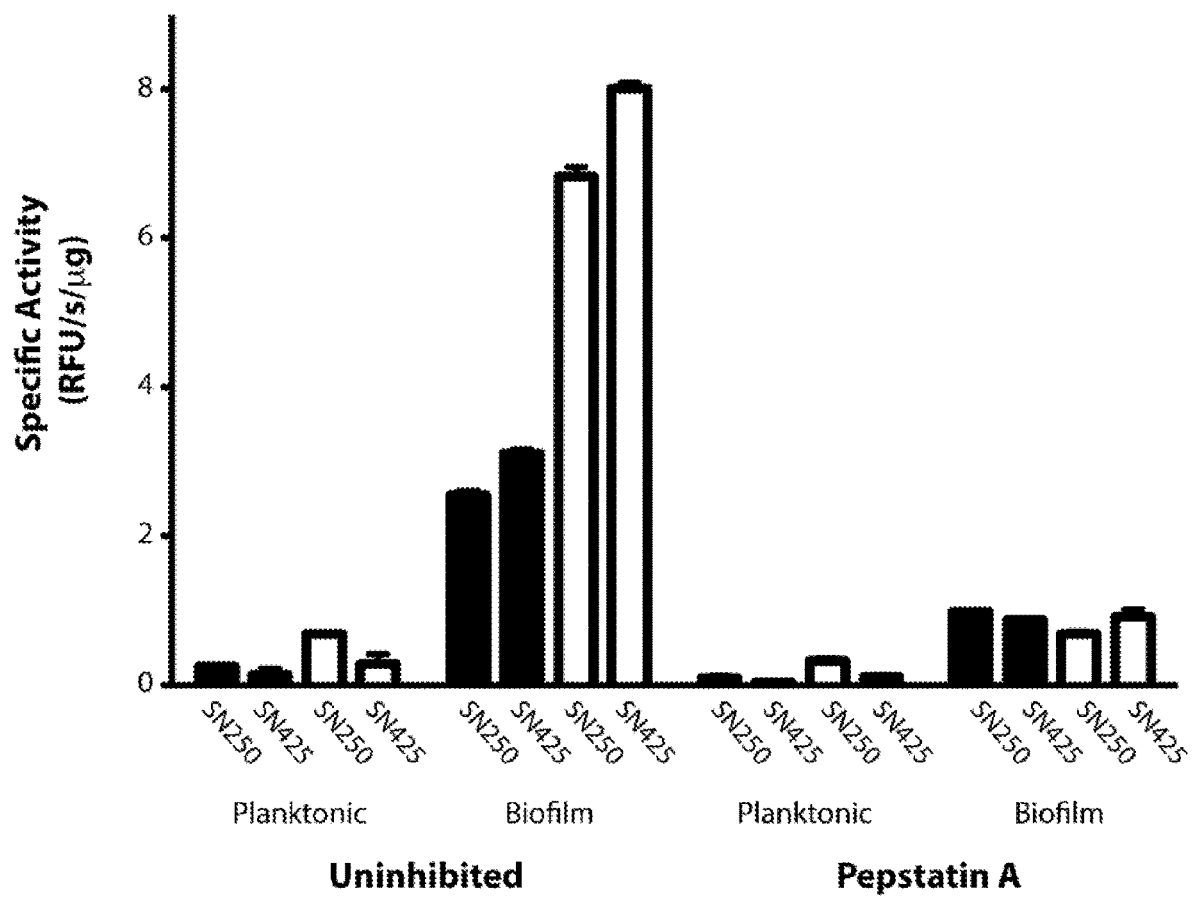

FIGS. 4A-4B depict probe activity in biofilm and planktonic conditioned media following pepstatin A pretreatment and in conditioned media from sap5Δ/Δ, sap6Δ/Δ, and sap5/6ΔΔ/ΔΔ deletion strains. FIG. 4A depicts activity of VFILWRTE (black; SEQ ID NO: 22) and TFSYnRWP (white; SEQ ID NO: 23) in conditioned media from the wild-type (SN250) reference strain following pre-treatment with 10 μM pepstatin. Matched comparison to wild-type (SN425) conditioned media is provided (FIG. 12). FIG. 4B depicts activity of VFILWRTE (black; SEQ ID NO: 22) and TFSYnRWP (white; SEQ ID NO: 23) in the conditioned media from the deletion strains normalized to the wild-type biofilm activity for each substrate.

Figure 5A:
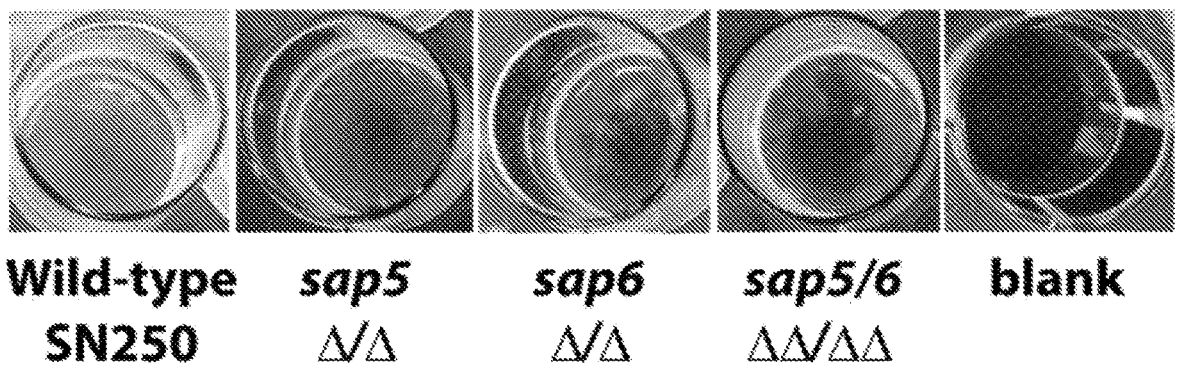
Figure 5B:
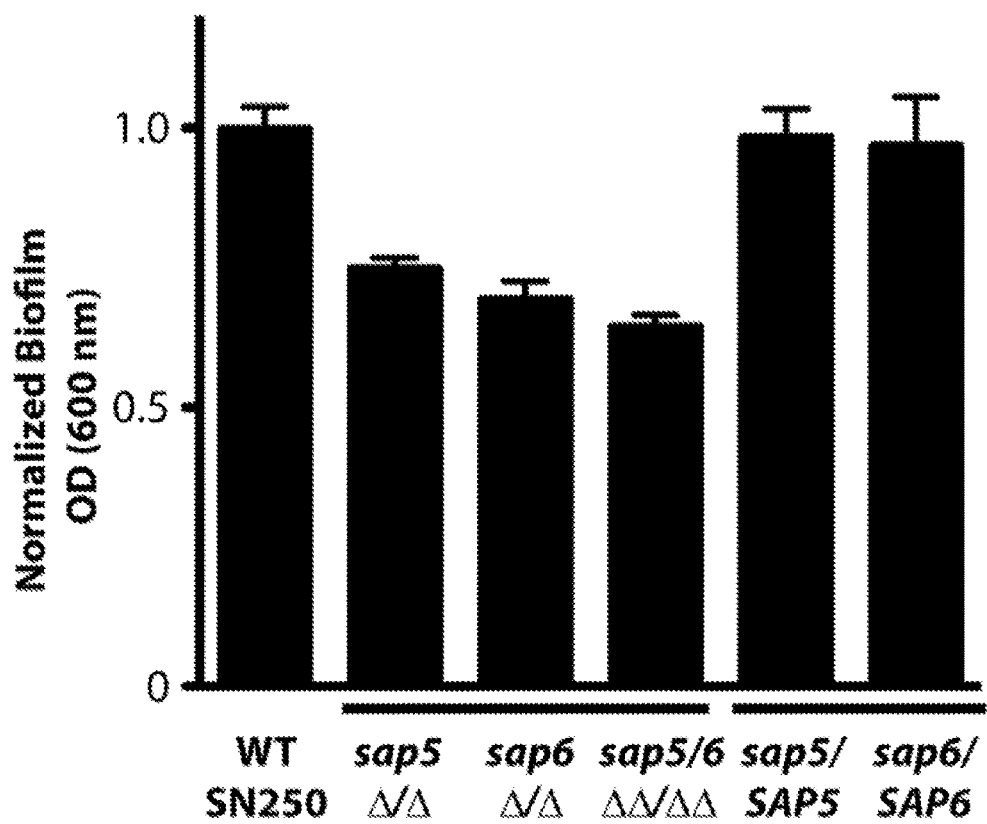
Figure 5C:
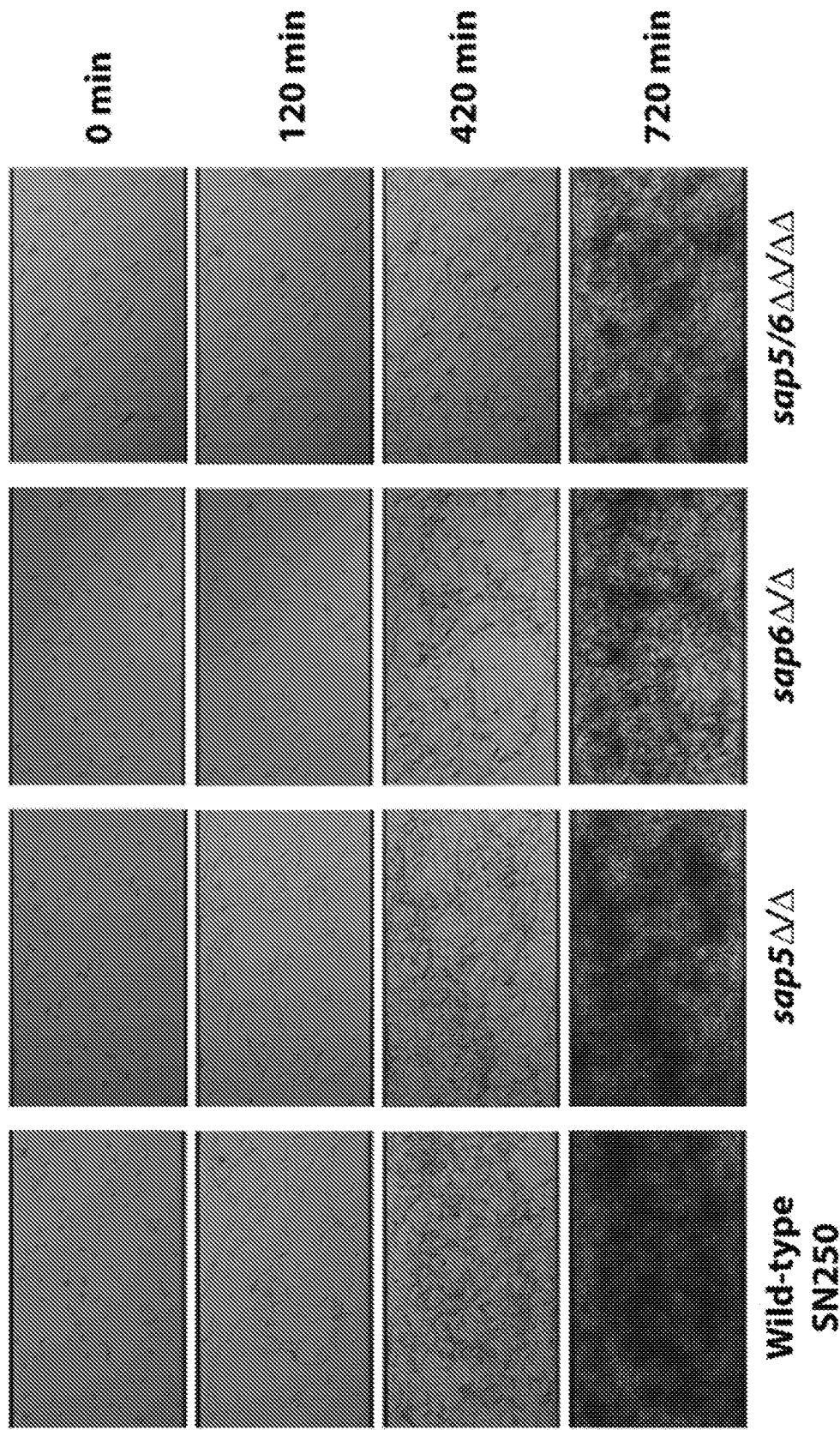

FIGS. 5A-5C depict biofilm phenotype characterization for the wild-type reference (SN250) and sap5Δ/Δ, sap6Δ/Δ, and sap5/6ΔΔ/ΔΔ deletion strains. FIG. 5A depicts biofilm formation in Spider medium after 24 hours of growth with representative biofilm defects shown. FIG. 5B depicts $OD_{600}$ readings measured for adhered biofilms after removal of the medium. OD was normalized to 1.0 for the wild-type strain. Statistical significance (P values) was calculated with a two-tailed paired t-test with $OD_{600}$ measurement significantly deviating from the reference strain for the sap5Δ/Δ (P=4.5×10$^4$), sap6Δ/Δ (P=3.5×10$^{-3}$), and sap5/6ΔΔ/ΔΔ (P=4.8×10$^4$) deletion strains. Complementation of SAP5 and SAP6 into the sap5Δ/Δ and sap6Δ/Δ deletion mutant strains, respectively, restored biofilm formation to wild-type reference levels with P=0.70 for sap5/SAP5 and P=0.66 for sap6/SAP6 (P-values calculated by comparison to the reference strain). FIG. 5C depicts time-dependent visualization of biofilm formation under dynamic flow (0.5 dyne/cm2) in Spider media over a 720 min period post-adherence using a BioFlux 1000z instrument.

FIG. 6 depicts global substrate specificity profiles of protease activity in conditioned media from wild-type *C. albicans* (SN425) under biofilm and planktonic conditions. iceLogo representations for 20 μg/mL of 24-hour conditioned media following 15, 60 and 240 min incubation with the MSP-MS peptide library (P=0.05 for non-grayed residues and "n" is norleucine).

Figure 7:
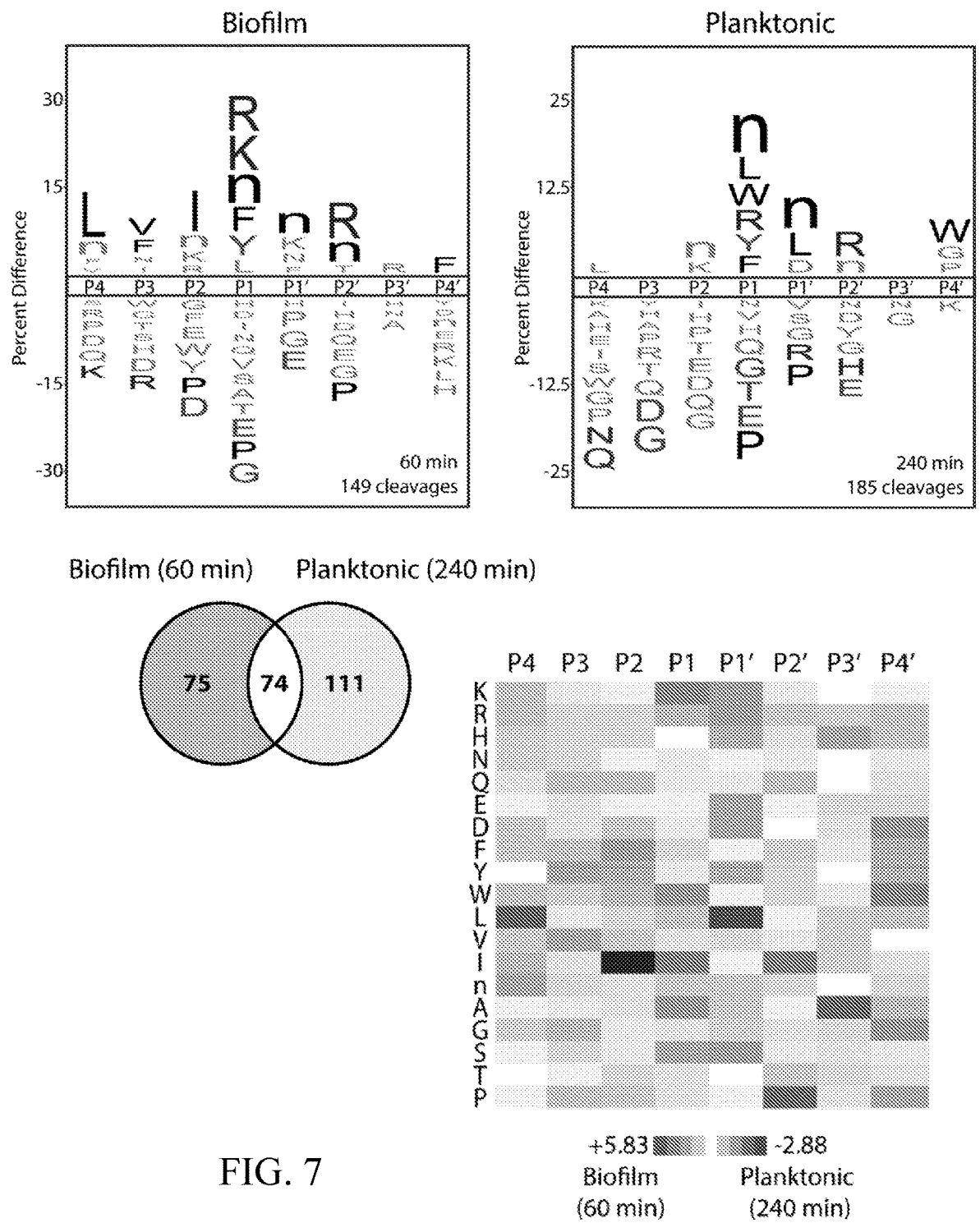

FIG. 7 depicts activity-normalized comparison of cleavage specificity for wild-type *C. albicans* (SN425) under biofilm and planktonic conditions using MSP-MS time points with approximately the same number of cleavages (60 min and 240 min, respectively). Data were adapted from FIG. 6. (top) iceLogo substrate specificity representations for 24-hour biofilm and planktonic conditioned media (P=0.05 for non-grayed residues). (bottom left) Quantification of the total shared and unique cleavages for the biofilm and planktonic conditions. Among the 74 shared cleavage sites indicated here, five were re-categorized for FIGS. 2A-2E and 9 because they were differentially sensitive to pepstatin in the biofilm and planktonic assays (and therefore, could not be assigned to the Saps in both conditions). Three of these shared sequences (P4-P4') were recategorized as "unassigned planktonic" (WPSnNKVG, XSAnnKIG, and TVNKQLRX), and two of these shared sequences (EVNDDVKX and GHVKLFRF) were re-categorized as "unassigned biofilm." (Bottom right) Heat map representation of biofilm and planktonic specificity differences using Z-scores at the P4-P4' positions. Biofilm-favored residues are colored black and planktonic-favored residues are colored white.

Figure 8:
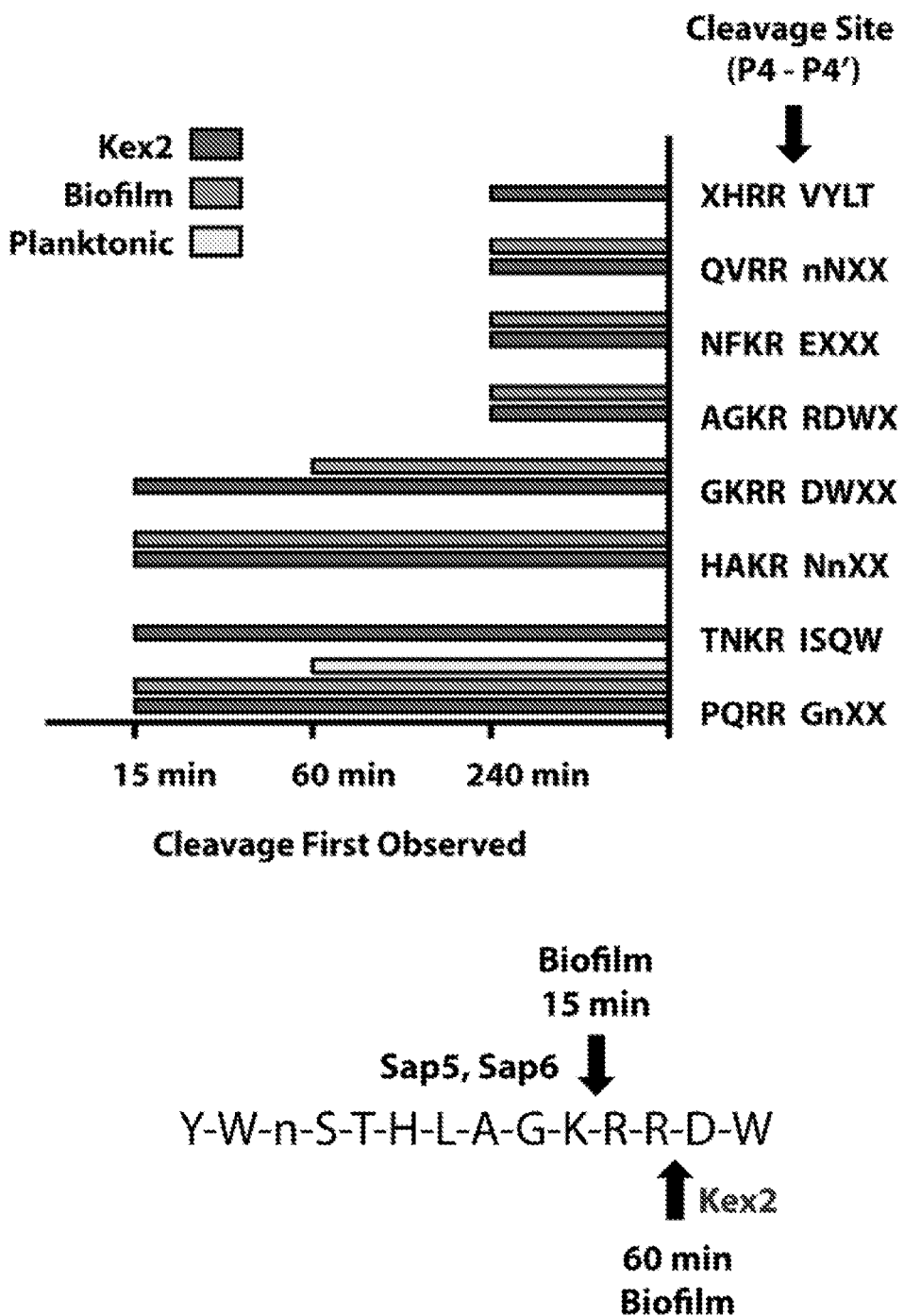

FIG. 8 depicts global substrate specificity profiling of recombinant Kex2 from *Saccharomyces cerevisiae*. (top) Time-dependent generation of cleavages following dibasic (P2-P1) K/R-R residues in the MSP-MS library for recombinant Kex2 and *C. albicans* wild-type (SN425) conditioned media from 24-hour biofilm and planktonic cultures. Cleavage sites assigned to Kex2 in the conditioned media profiles were sensitive to EDTA and insensitive to pepstatin treatments. (bottom) Recombinant Kex2 displays distinct MSP-MS cleavage sites from recombinant Sap5 and Sap6. This is illustrated in the differential cleavage pattern of an example MSP-MS peptide.

FIG. 9 depicts global biofilm and planktonic substrate specificity profiles for cleavages not assignable to Sap5 or Sap6. (top) iceLogo representations of biofilm-unique (N=49), planktonic-unique (N=112), and shared (N=55) cleavages using activity-matched MSP-MS time points (P=0.05 for non-grayed residues). Data were adapted from FIGS. 2A-2E. (bottom) Distribution of cleavage sites along the 14-mer peptide substrates. Planktonic-unique cleavages not assignable to Sap5 or Sap6 have an enrichment of aminopeptidase-like activity compared to unassigned shared and biofilm-unique cleavages. Sap5 and Sap6 activity reflects endopeptidase-like specificity.

Figure 10A:
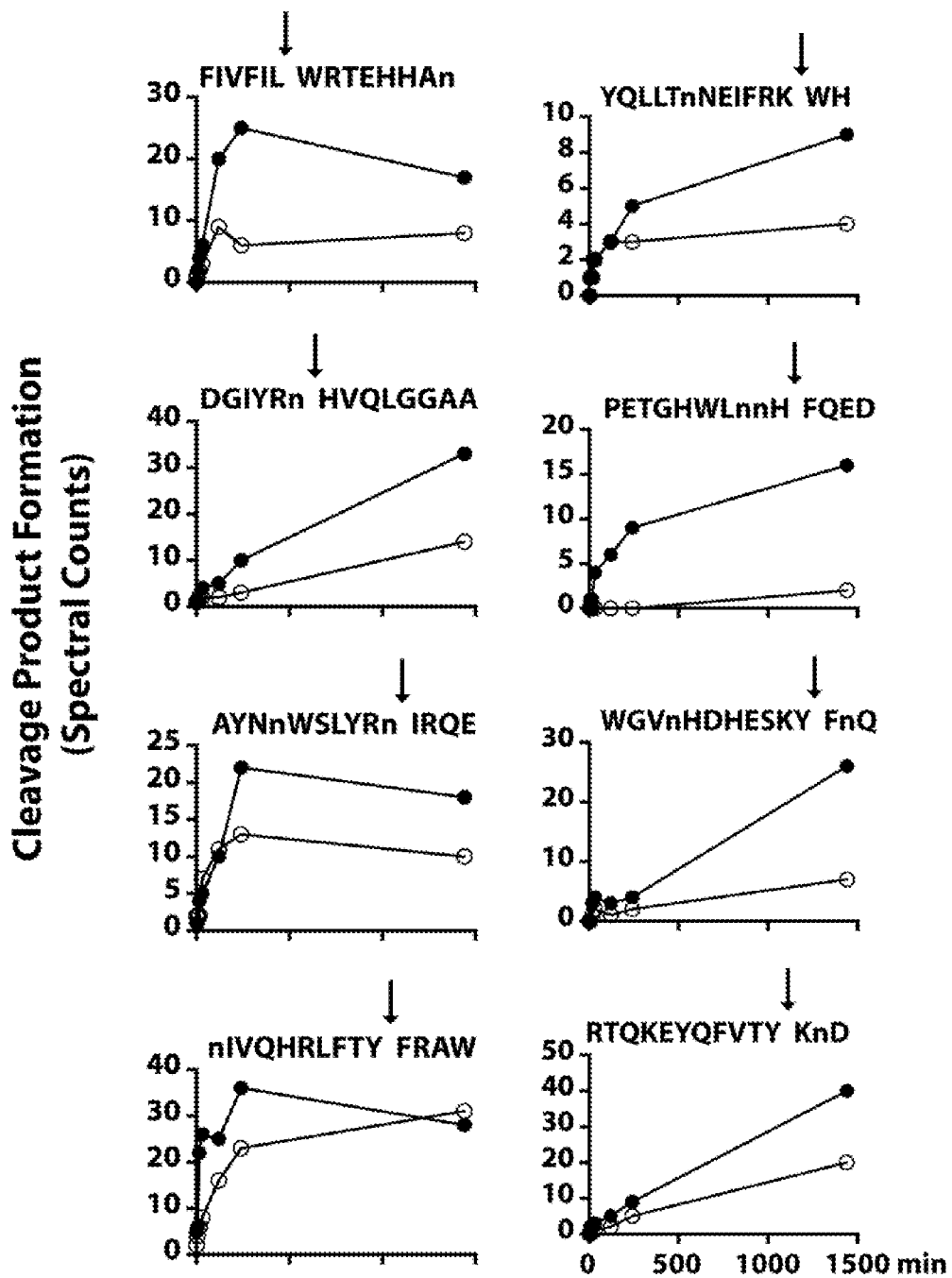
Figure 10B:
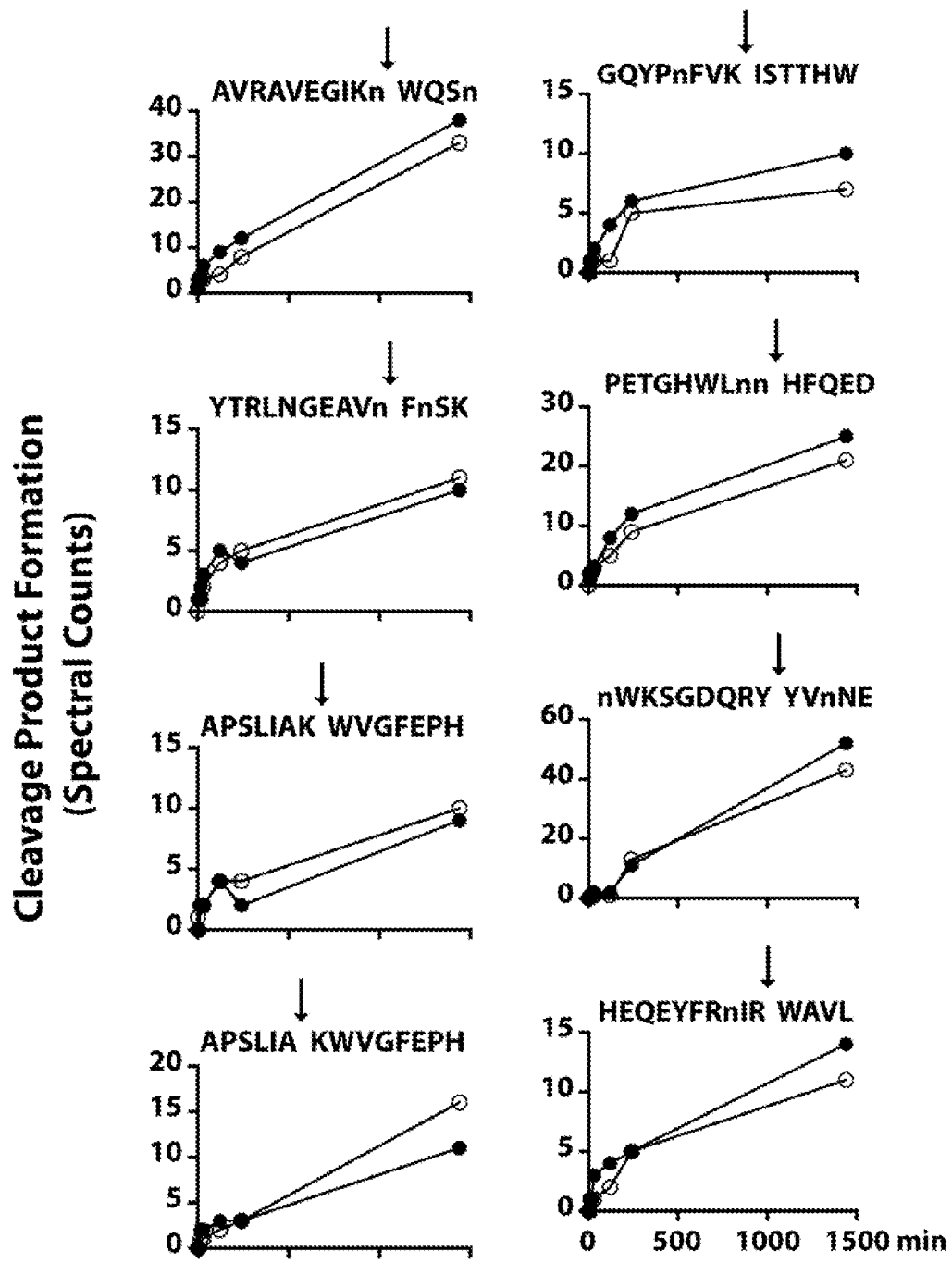
Figure 10C:
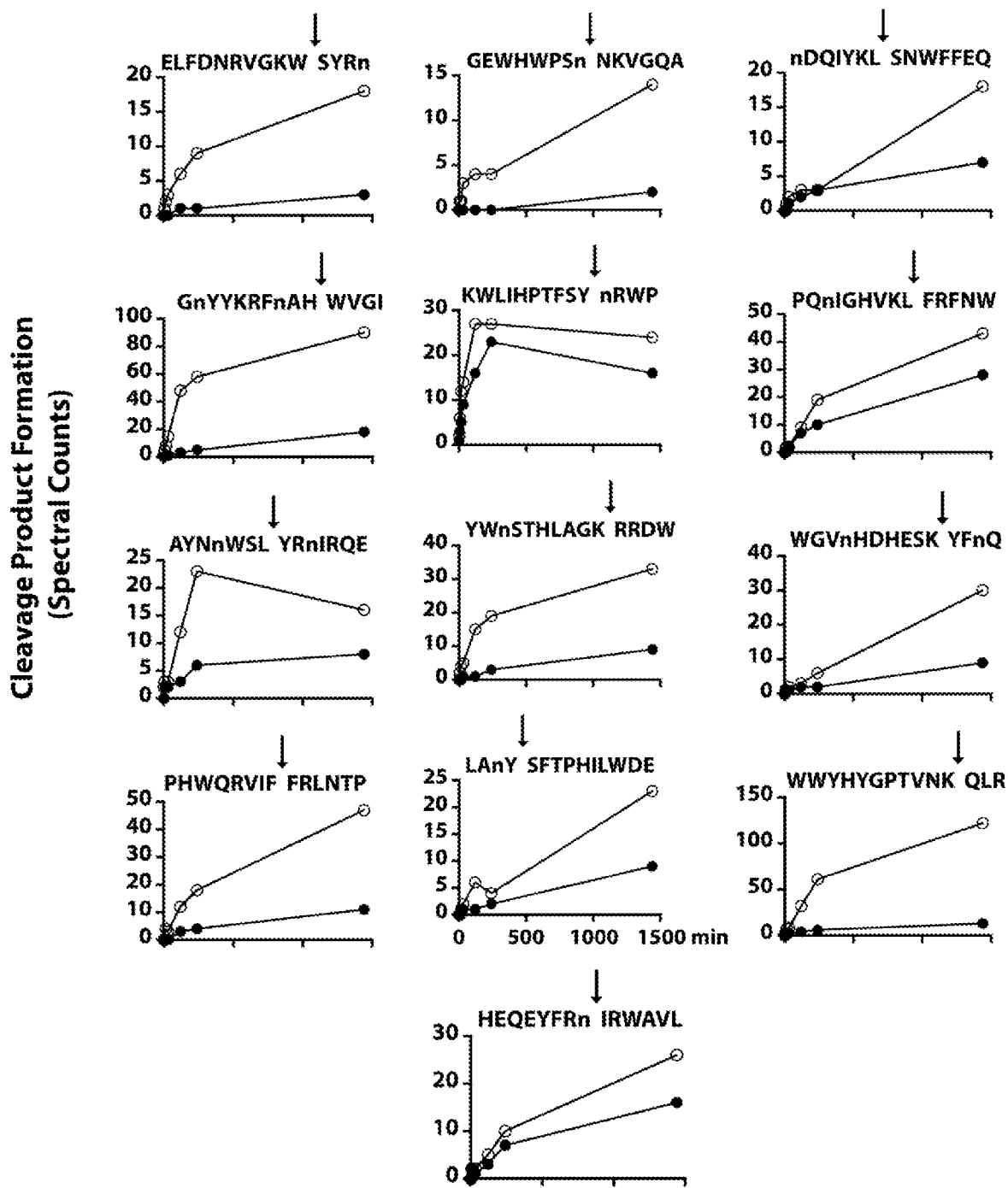

FIGS. 10A, 10B, and 10C depict cleavage time courses for recombinant Sap5 (black) and Sap6 (white) against a 25-member sub-library of MSP-MS peptide substrates. Spectral counts are plotted at 1, 5, 15, 30, 120, 240, and 1440 min. Cleavage products are separated by preference: FIG. 10A depicts Sap5; FIG. 10B depicts both Sap5 and Sap6; FIG. 10C depicts Sap6. Duplicated peptides are cleaved at distinct sites. Although included in the sub-library, the peptide HIGLQVHnRYINVn was omitted due to inconsistent time-dependent spectral count data.

Figure 11:
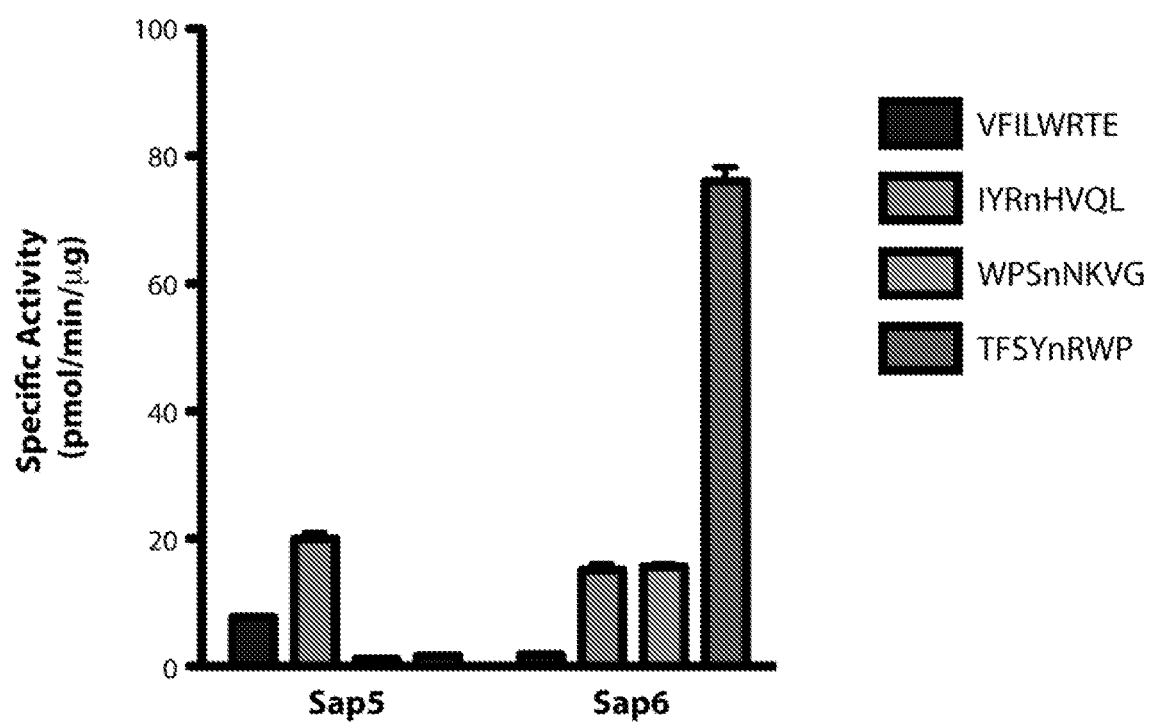

FIG. 11 depicts selectivity of internally quenched fluorogenic substrates for recombinant Sap5 and Sap6. Specific activity was determined with 2 μg/mL recombinant Saps and the substrates VFILWRTE (10 μM, SEQ ID NO: 22), IYRnHVQL (25 μM; SEQ ID NO: 24), WPSnNKVG (25 μM; SEQ ID NO: 25), and TFSYnRWP (10 μM; SEQ ID NO: 23). RFU was converted to moles of product formation using a correction factor experimentally determined for each substrate.

FIG. 12 depicts a comparison of probe activity in 24-hour conditioned from wild-type (SN425 and SN250) strains under biofilm and planktonic conditions. Specific activity of 10 µM VFILWRTE (black bars; SEQ ID NO: 22) and TFSYnRWP (white bars; SEQ ID NO: 23) was determined using 20 µg/mL and 10 µg/mL conditioned media, respectively. Aspartyl protease activity was confirmed through pretreatment with 10 µM pepstatin A.

Figure 13:
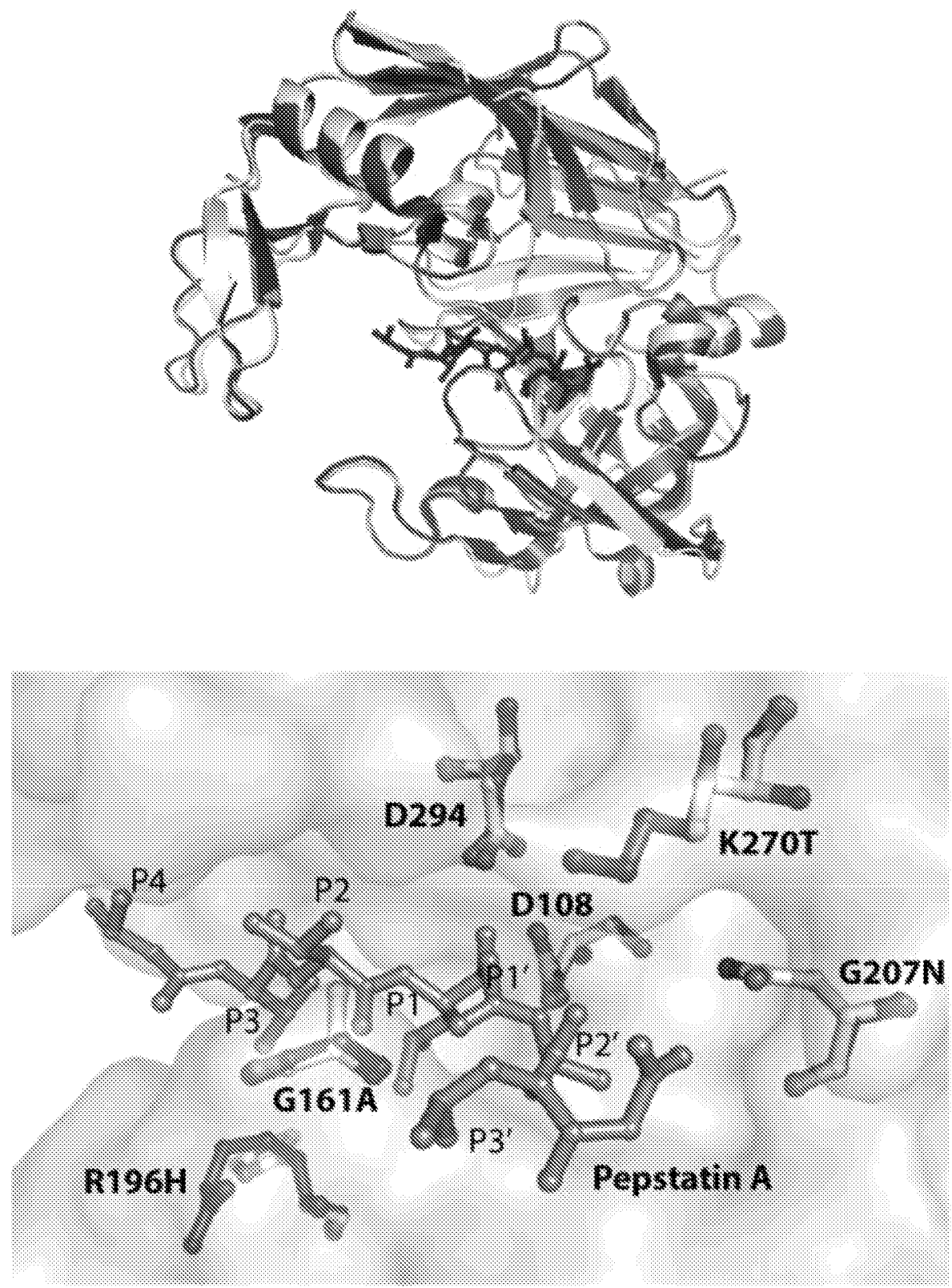

FIG. 13 depicts the structural alignment of Sap5 and Sap6. (top) depicts the overall structural alignment using the crystallographic structure of pepstatin-bound Sap5 (molecule A, PDB 2QZX) shown in dark gray and a comparative model of Sap6 (light gray) prepared from the Sap5 structure. (bottom) depicts Sap5 and Sap6 residue differences near the pepstatin binding site. Residues are numbered according to the Sap5 sequence.

Figure 14A:
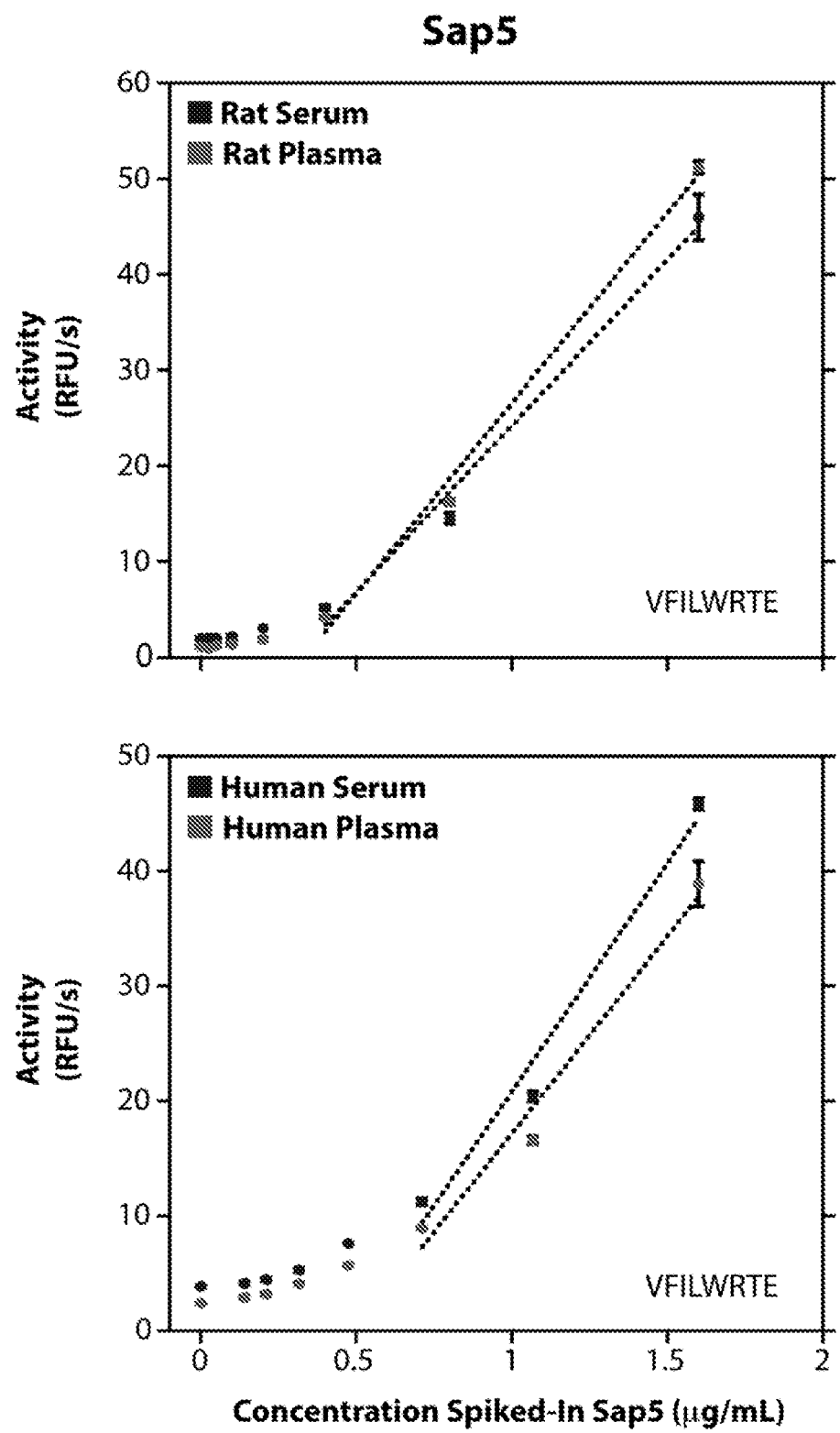
Figure 14B:
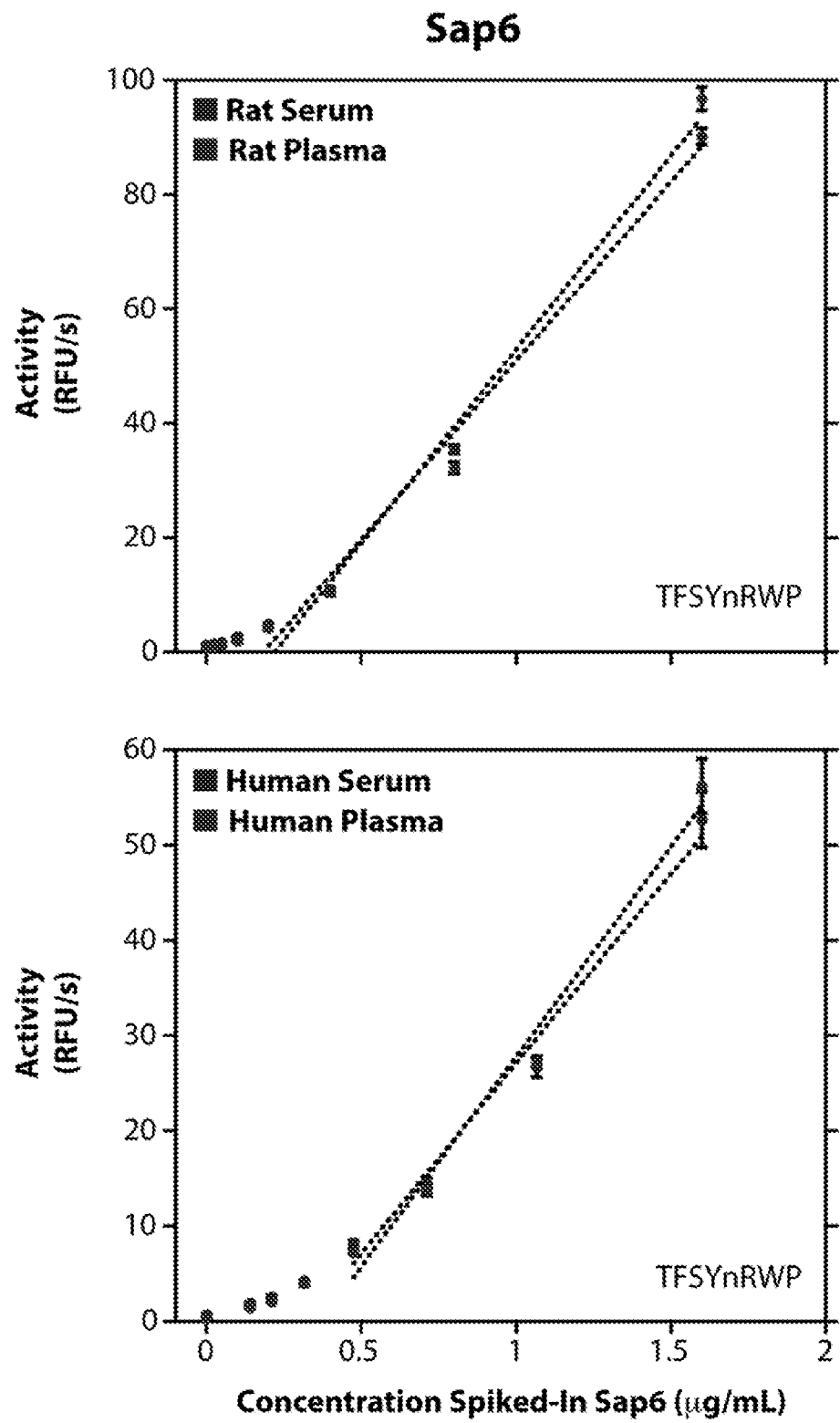

FIGS. 14A and 14B depict the detection of Sap5 and Sap6 spiked into rat and human blood samples. Activity of purified, recombinantly produced Sap5 (FIG. 14A) and Sap6 (FIG. 14B) spiked into commercially available human and rat serum and plasma. Activity was assayed using 10 µM VFILWRTE (Sap5, SEQ ID NO: 22) or TFSYnRWP (Sap6, SEQ ID NO: 23) fluorogenic probes. Serum and plasma samples were diluted 25-fold into pH 5.5 buffer. Saps were assayed from 0.025 to 1.6 µg/mL for rat blood samples and from 0.14 to 1.6 µg/mL for human blood samples. A linear fit of activity is shown where applicable.

Figure 15A:
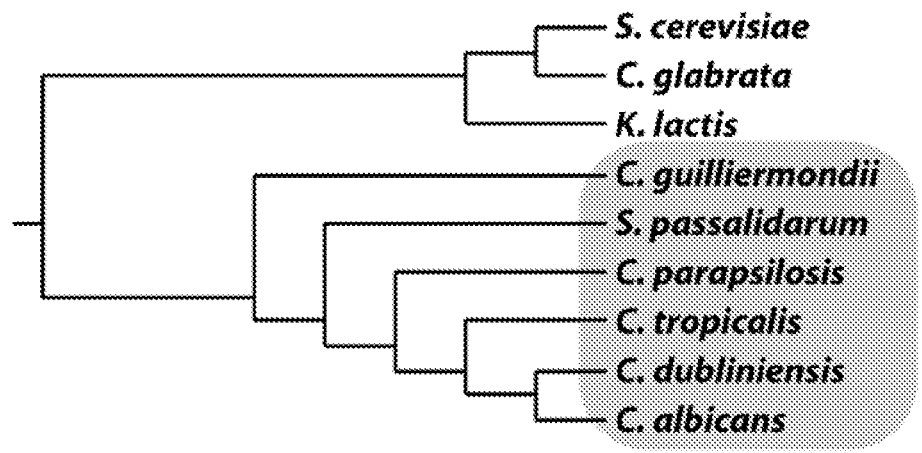
Figure 15B:
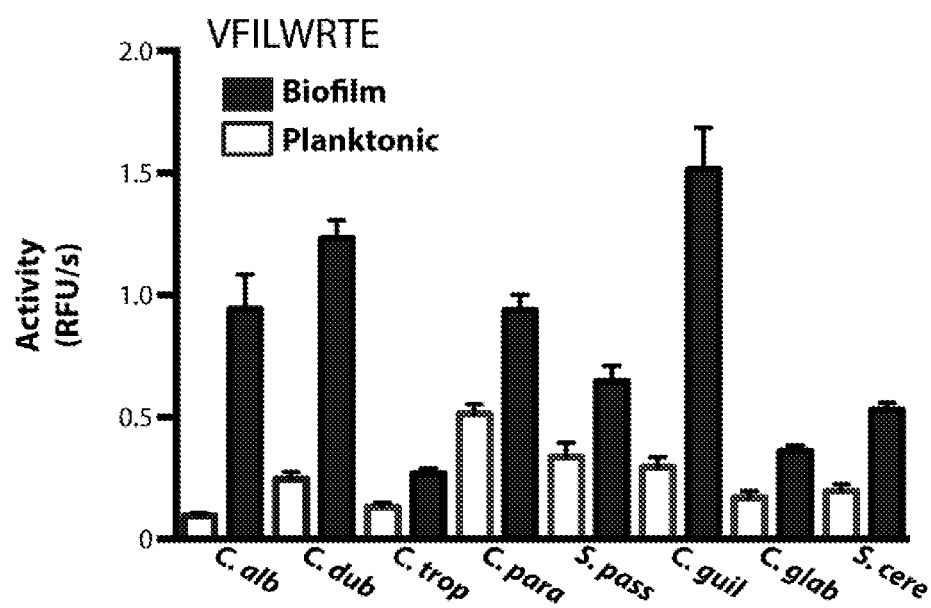
Figure 15C:
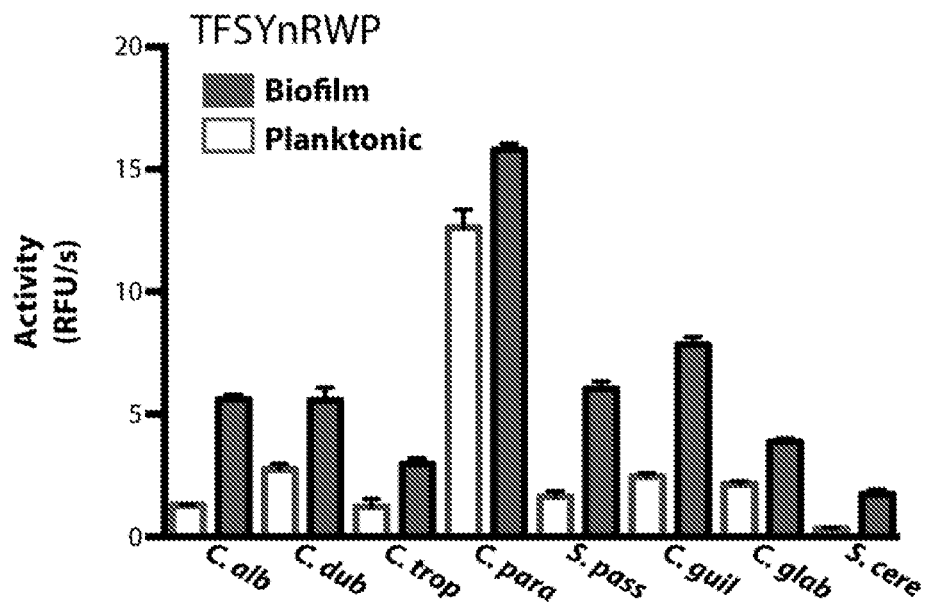
Figure 15D:
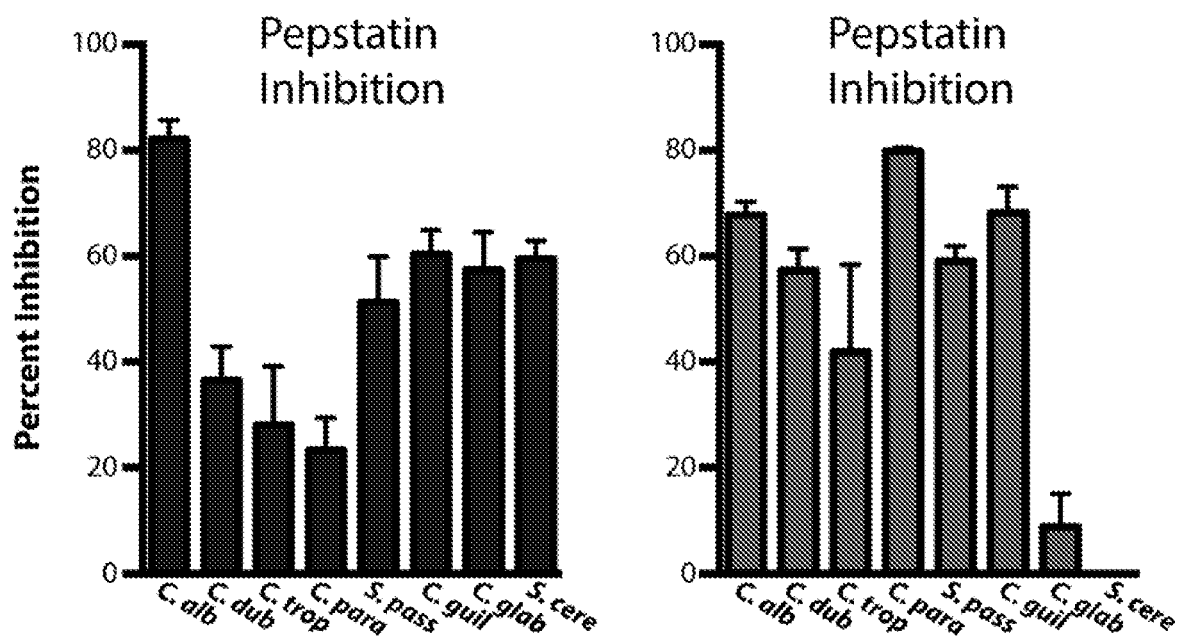

FIGS. 15A-15D depict the detection of biofilm and planktonic protease activity in established and emerging pathogenic Candida species. FIG. 15A depicts a phylogenetic tree for Candida clade (gray) and more distantly related fungal species. FIGS. 15B and 15C depict the detection of protease activity in biofilm and planktonic conditioned media from select fungal species in FIG. 15A. Conditioned media preparations were generated as described for C. albicans. Activity was assayed using 10 µM VFILWRTE (FIG. 15B, SEQ ID NO: 22) or TFSYnRWP (FIG. 15C, SEQ ID NO: 23) fluorogenic probes in pH 5.5 buffer. In FIG. 15D, inhibitor pre-incubations were performed on biofilm conditioned media with 10 µM pepstatin A to confirm aspartyl protease activity.

Figure 16:
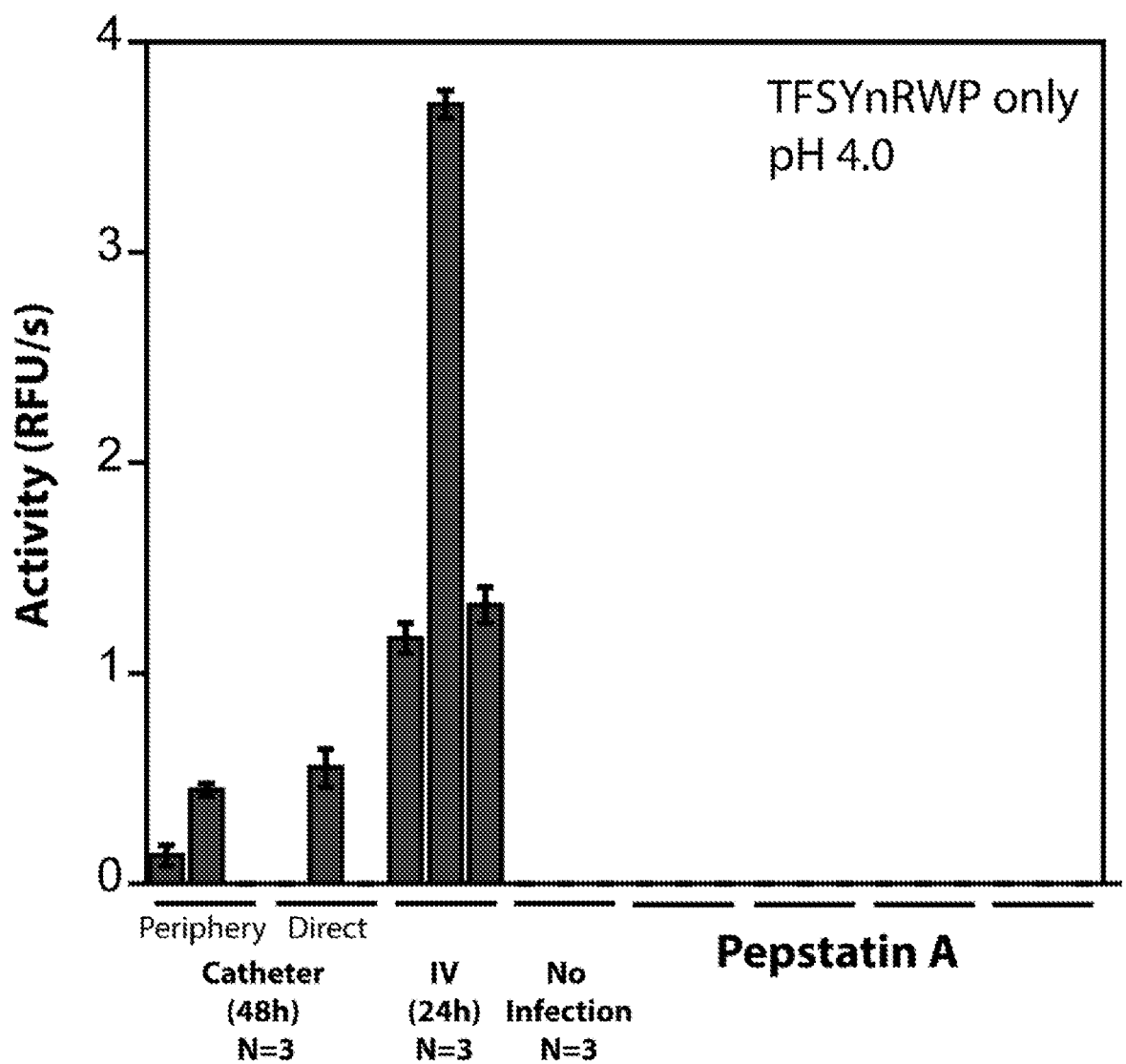

FIG. 16 depicts the detection of pepstatin-sensitive activity in serum from C. albicans biofilm rat catheter and disseminated infection models. Detection of pepstatin-sensitive protease activity with the TFSYnRWP (SEQ ID NO: 23) fluorogenic probe in rat serum samples. Blood was collected both directly from C. albicans biofilm-infected catheters and peripherally 48 hours post biofilm infection (N=3 rats). Blood was also sampled peripherally 24 hours post IV infection with C. albicans ($10^6$ CFUs) (N=3 rats). Uninfected rats were used as a healthy control (N=3 rats). Activity assays were carried out using serum samples that had been diluted 25-fold into pH 4.0 buffer.

Figure 17:
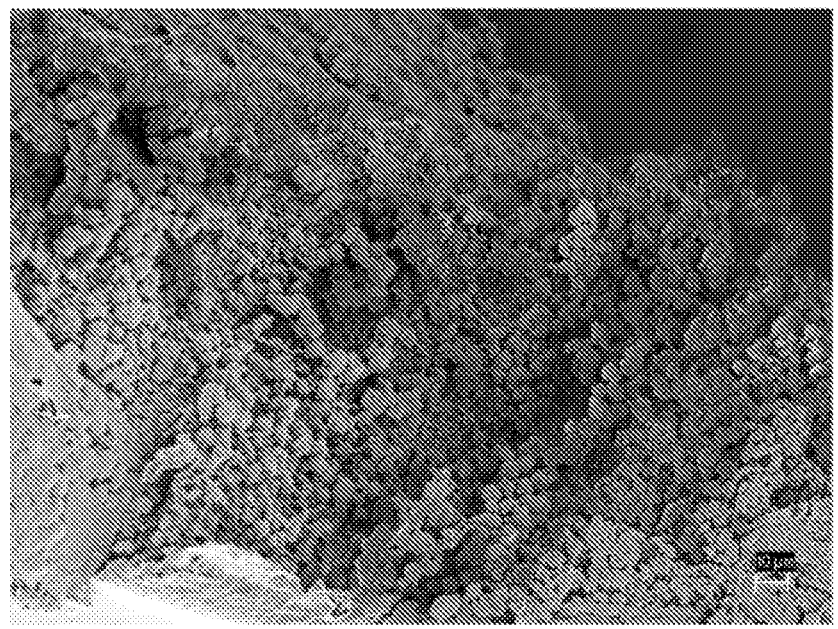
Figure 17:
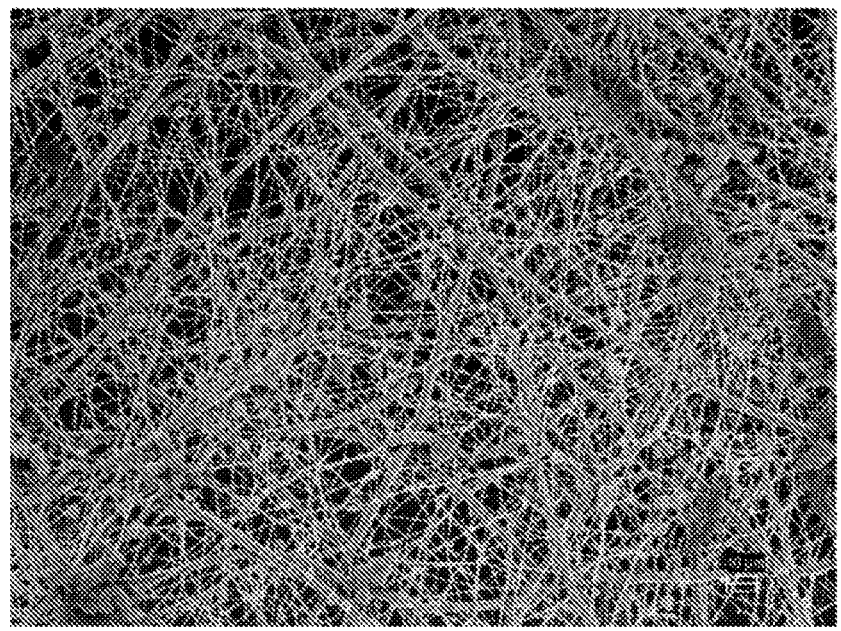

FIG. 17 depicts scanning electron microscopy (SEM) images showing that the C. albicans SAP5/6 deletion mutant strain displays a significant reduction in biofilm formation in a rat catheter biofilm infection model compared to the wild-type reference strain (SN250). SEM images (presented at 1000× magnification) were recorded on rat catheters removed 24 hours post biofilm infection.

Figure 18:
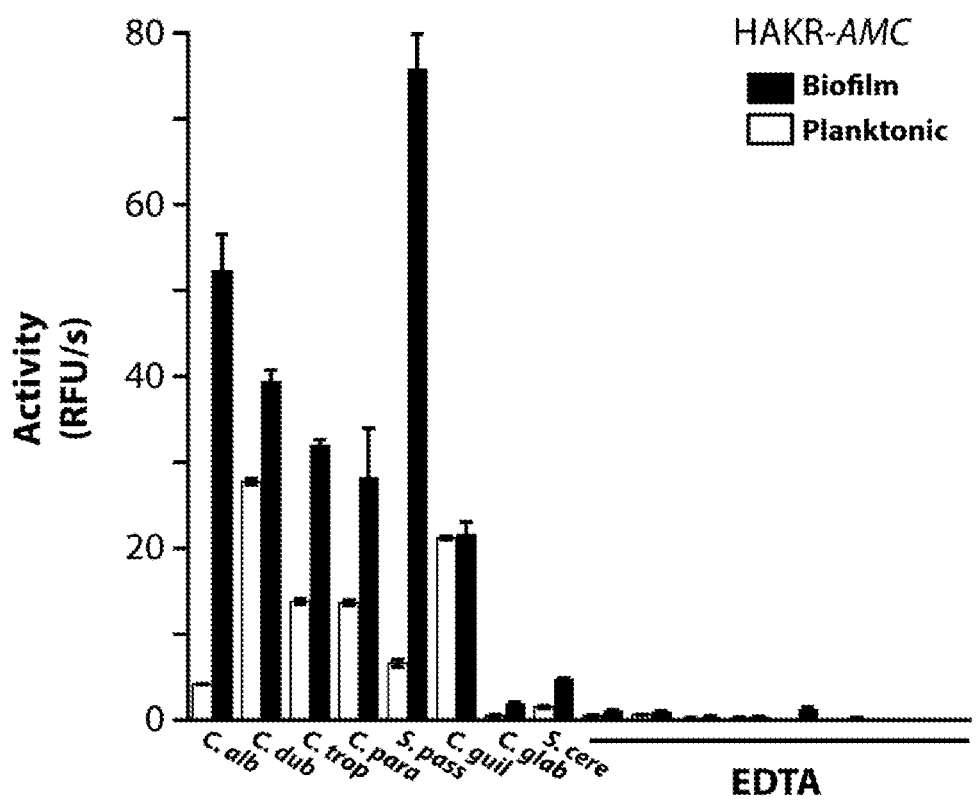

FIG. 18 depicts the detection of in vitro biofilm and planktonic Kex2 activity in established and emerging pathogenic Candida species (see FIG. 15A). Conditioned media preparations were generated as described for C. albicans. Activity was assayed using HAKR-AMC in D-PBS (pH 7.4). Inhibitor pre-incubation was performed with 1 mM EDTA. The HAKR-AMC substrate was developed based on a Kex2-cleavable sequence from the MSP-MS peptide library (FIG. 8, top). HAKR-AMC was custom-synthesized by GenScript bearing an N-terminal acetyl group and C-terminal 7-amino-4-methylcoumarin (AMC) fluorophore as the sequence acetyl-His-Ala-Lys-Arg-AMC.

Figure 19A:
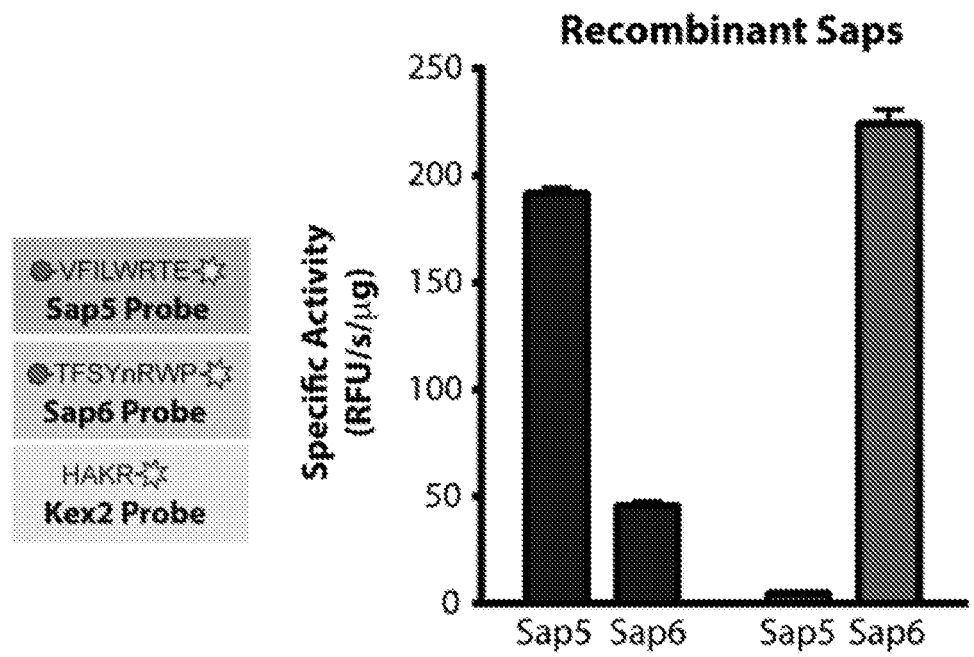
Figure 19B:
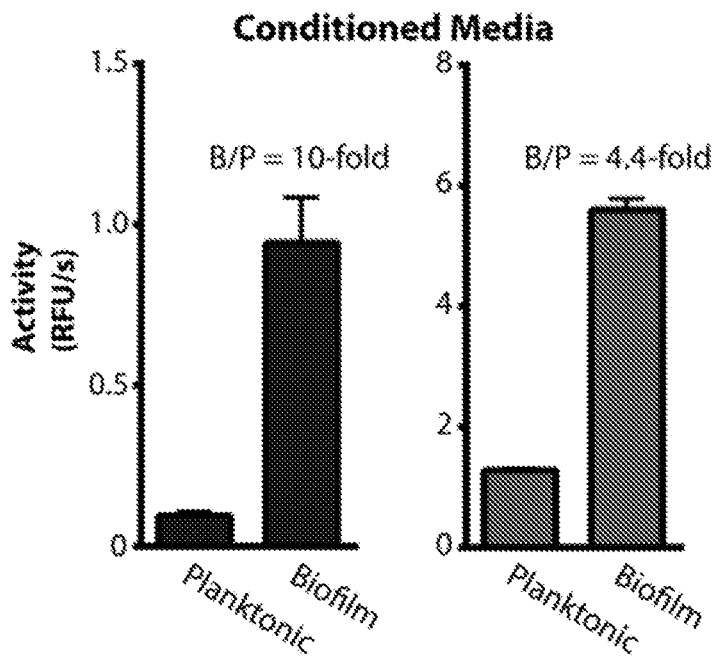
Figure 19C:
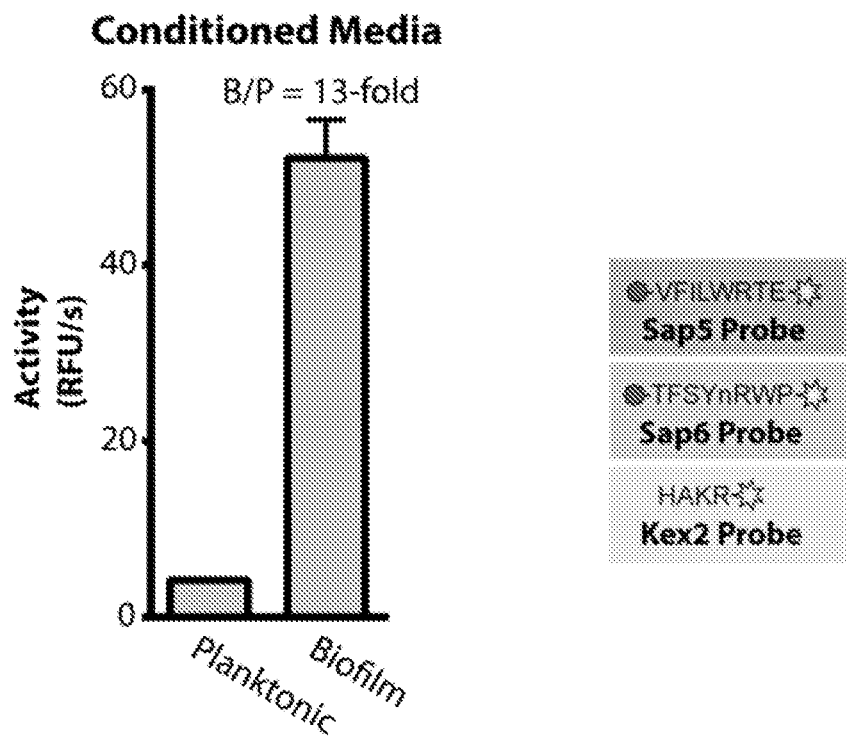
Figure 19D:
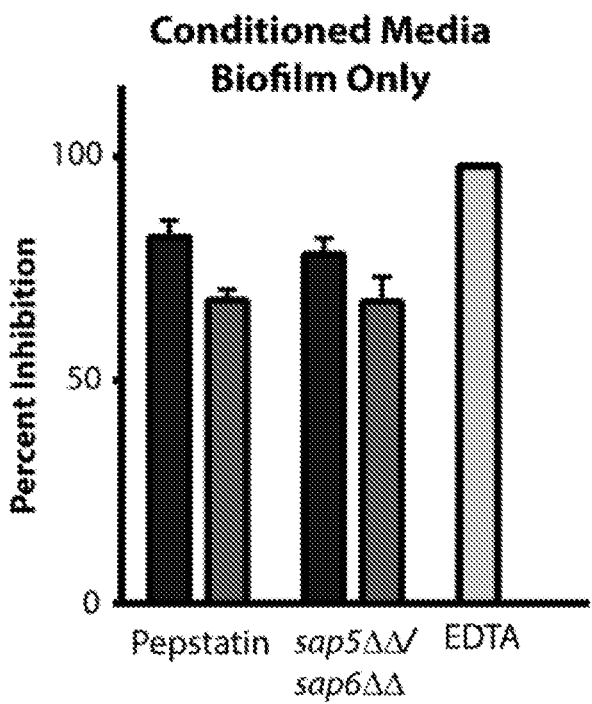

FIGS. 19A-19D depict the development and evaluation of a first-generation Sap5-, Sap6-, and Kex2-cleavable fluorogenic substrates. FIG. 19A depicts Sap5 and Sap6 probe selectivity assessed using recombinantly produced proteases. FIG. 19B depicts activity of the Sap5 and Sap6 probes in C. albicans conditioned media under biofilm and planktonic conditions. FIG. 19C depicts activity of the Kex2 probe in C. albicans conditioned media under biofilm and planktonic conditions. FIG. 19D depicts reduction in probe cleavage following inhibitor treatment of genetic deletions of SAP5 and SAP6.

FIG. 20 depicts non-Sap5, non-Sap6, and non-Kex2 cleavages that are planktonic-specific, biofilm-specific, and broad-spectrum.

Figure 21A:
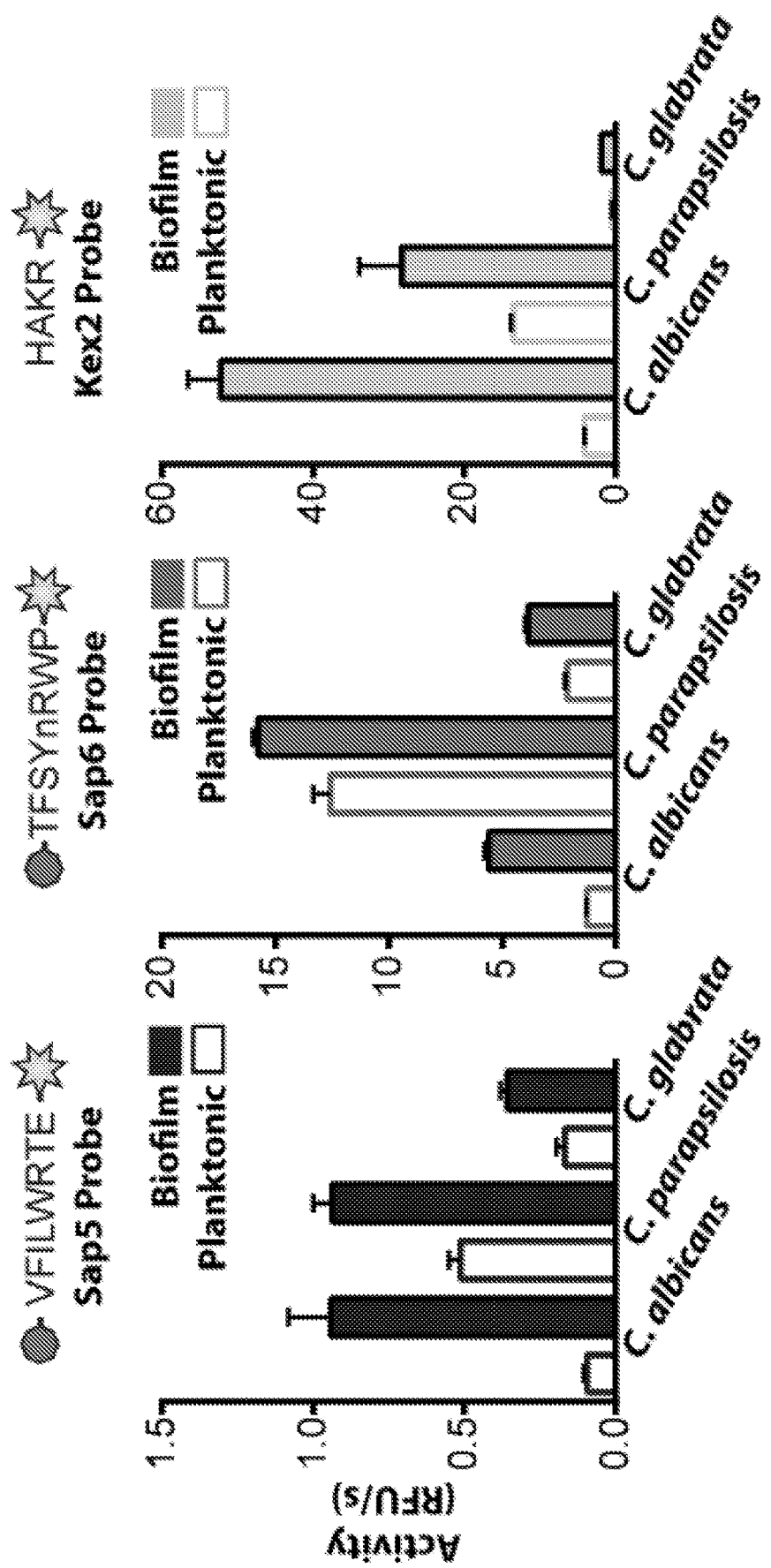
Figure 21B:
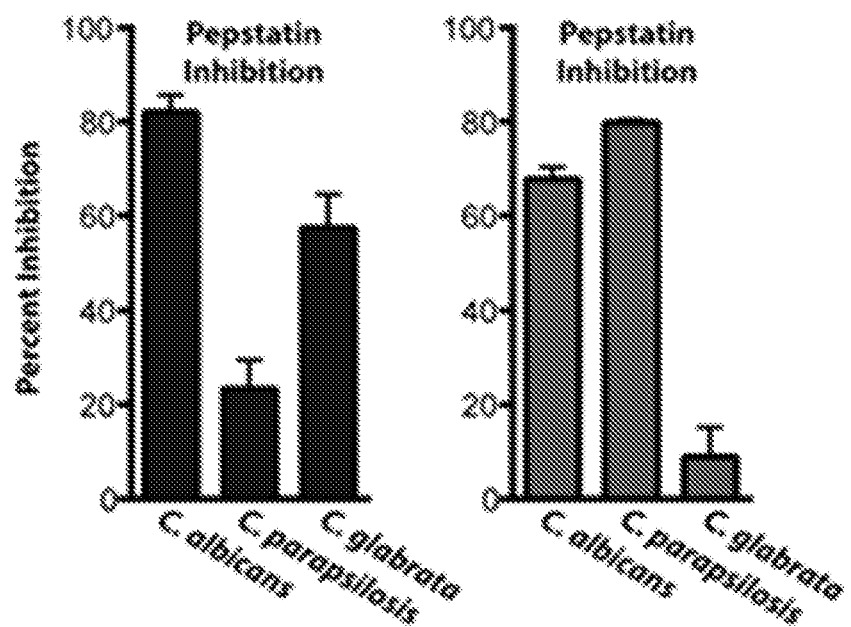
Figure 21C:
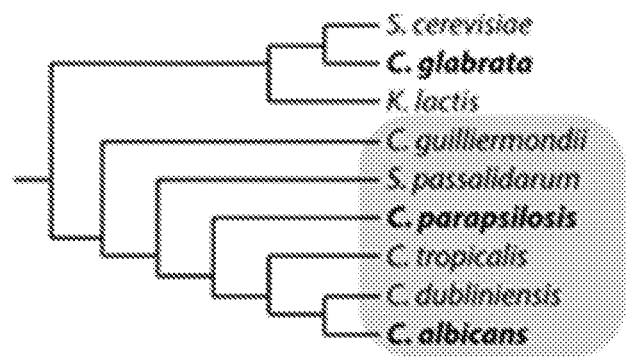

FIGS. 21A-21C depicts protease activity from additional pathogenic Candida species grown under biofilm and planktonic conditions. FIG. 21A depicts application of the fluorogenic substrates designed against Sap5, Sap6, and Kex2. FIG. 21B depicts differential inhibition of Sap5 and Sap6 substrate cleavage by aspartyl protease activity under biofilm conditions. FIG. 21C depicts a phylogenetic tree with the strict Candida clade species highlighted.

Figure 22:
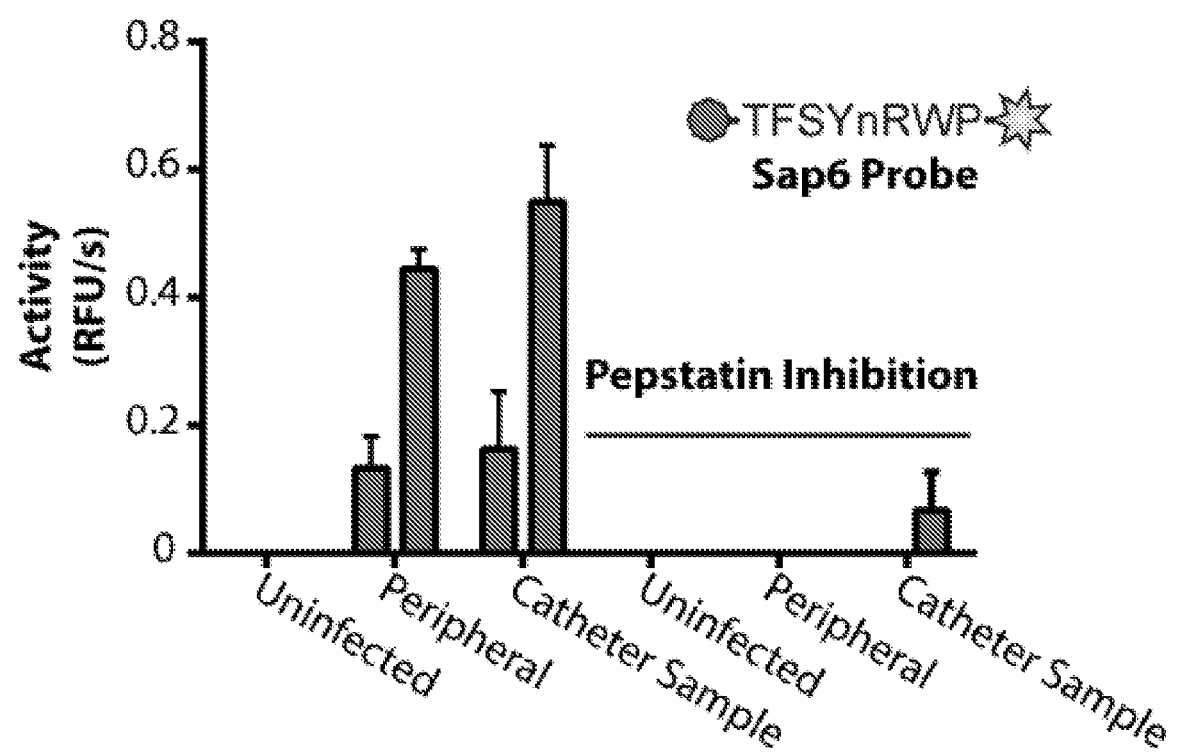

FIG. 22 depicts detection of infection-specific aspartyl protease activity in serum from a rat catheter biofilm model using the Sap6-cleavable probe. Serum was collected both directly from the biofilm-infected catheter, peripherally from the rat jugular vein, and from the jugular vein of an uninfected control rat (n=2).

DETAILED DESCRIPTION OF ILLUSTRATIVE EMBODIMENTS

Before the present compositions and methods are described, it is to be understood that this disclosure is not limited to the particular molecules, compositions, methodologies or protocols described, as these may vary. It is also to be understood that the terminology used in the description is for the purpose of describing the particular versions or embodiments only, and is not intended to limit the scope of the present disclosure which will be limited only by the appended claims. It is understood that these embodiments are not limited to the particular methodology, protocols, cell lines, vectors, and reagents described, as these may vary. It also is to be understood that the terminology used herein is for the purpose of describing particular embodiments only, and is not intended to limit the scope of the present embodiments or claims.

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference. Nothing herein is to be construed as an admission that the disclosure is not entitled to antedate such disclosure by virtue of prior disclosure.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

As used herein, the phrase "integer from X to Y" means any integer that includes the endpoints. That is, where a range is disclosed, each integer in the range including the endpoints is disclosed. For example, the phrase "integer from X to Y" discloses 1, 2, 3, 4, or 5 as well as the range 1 to 5.

As used herein, the term "subject," "individual" or "patient," used interchangeably, means any animal, including mammals, such as mice, rats, other rodents, rabbits, dogs, cats, swine, cattle, sheep, horses, or primates, such as humans.

As used herein, the term "kit" refers to a set of components provided in the context of a system for delivering materials or diagnosing a subject with having a planktonic or biofilm infection of fungal cells. Such delivery systems may include, for example, systems that allow for storage, transport, or delivery of various diagnostic or therapeutic reagents (e.g., oligonucleotides, enzymes, extracellular matrix components etc. in appropriate containers) and/or supporting materials (e.g., buffers, media, cells, written instructions for performing the assay etc.) from one location to another. For example, in some embodiments, kits include one or more enclosures (e.g., boxes) containing relevant reaction reagents and/or supporting materials. As used herein, the term "fragmented kit" refers to a diagnostic assay comprising two or more separate containers that each contain a subportion of total kit components. Containers may be delivered to an intended recipient together or separately. For example, a first container may contain a petri dish or polysterene plate for use in a cell culture assay, while a second container may contain cells, such as control cells. As another example, the kit may comprise a first container comprising a solid support such as a chip or slide with one or a plurality of ligands with affinities to one or a plurality of biomarkers disclosed herein and a second container comprising any one or plurality of reagents necessary for the detection and/or quantification of the amount of biomarkers in a sample. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contain a sub-portion of total kit components are included in the term "fragmented kit." In contrast, a "combined kit" refers to a delivery system containing all components in a single container (e.g., in a single box housing each of the desired components). The term "kit" includes both fragmented and combined kits.

As used herein, the term "animal" includes, but is not limited to, humans and non-human vertebrates such as wild animals, rodents, such as rats, ferrets, and domesticated animals, and farm animals, such as dogs, cats, horses, pigs, cows, sheep, and goats. In some embodiments, the animal is a mammal. In some embodiments, the animal is a human. In some embodiments, the animal is a non-human mammal.

As used herein, the term "mammal" means any animal in the class Mammalia such as rodent (i.e., a mouse, a rat, or a guinea pig), a monkey, a cat, a dog, a cow, a horse, a pig, or a human. In some embodiments, the mammal is a human. In some embodiments, the mammal refers to any non-human mammal. The present disclosure relates to any of the methods or compositions of matter disclosed herein wherein the sample is taken from a mammal or non-human mammal. The present disclosure relates to any of the methods or compositions of matter disclosed herein wherein the sample is taken from a human.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof. In some embodiments, the animal or mammal is in an environment or will be traveling to an environment in which a particular disorder or condition is prevalent or more likely to occur.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the phrase "therapeutically effective amount" means the amount of active compound or pharmaceutical agent or agent within a pharmaceutical composition that elicits the biological or medicinal response that is being sought in a tissue, system, animal, individual or human by a researcher, veterinarian, human physician or other clinician, such as a pathologist. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; transition of a predominantly biofilm population of fungal cells to a predominantly planktonic population of fungal cells; transition of a predominantly pathogenic population of fungal cells to a predominantly non-pathogenic population of fungal cells; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment.

As used herein, the term "pathogen" or "pathogenic" is anything that can produce infection or disease. Typically a pathogen is an infectious agent, such as a virus, bacterium, prion, fungus, viroid, or parasite that is capable of causing or has caused disease or infection in its host. In some embodiments, the host may be an animal, plant, fungus, or other microorganisms. In some embodiments, the host may be human. In some embodiments, fungi of the genus *Candida* are pathogens.

Any probes may be used in concert with any of the devices, kits, or methods disclosed herein. As used herein, the term "probe" refers to any molecule that may bind or associate, indirectly or directly, covalently or non-covalently, to any of the substrates and/or reaction products and/or proteases disclosed herein and whose association or binding is detectable using the methods disclosed herein. In some embodiments, the probe is a fluorogenic probe, antibody or absorbance-based probes. If an absorbance-based probe, the chromophore pNA (para-nitroanaline) may be used as a probe for detection and/or quantification of a protease disclosed herein.

As used herein, the terms "fluorogenic probe" refers to any molecule (dye, peptide, or fluorescent marker) that emits a known and/or detectable wavelength of light upon exposure to a known wavelength of light. In some embodiments, the substrates or peptides with known cleavage sites recognizable by any of the enzymes expressed by the one or plurality of planktonic and/or biofilm forms of fungal cells are covalently or non-covalently attached to a fluorogenic probe. In some embodiments, the attachment of the fluorogenic probe to the substrate creates a chimeric molecule capable of a fluorescent emission or emissions upon exposure of the substrate to the enzyme and the known wavelength of light, such that exposure to the enzyme creates a reaction product which is quantifiable in the presence of a fluorimeter. In some embodiments, the fluorogenic probe is fully quenched upon exposure to the known wavelength of light before enzymatic cleavage of the substrate and the fluorogenic probe emits a known wavelength of light the intensity of which is quantifiable by absorbance readings or intensity levels in the presence of a fluorimeter and after enzymatic cleavage of the substrate. In some embodiments, the fluorogenic probe is a coumarin-based dye or rhodamine-based dye with fluorescent emission spectra measureable or quantifiable in the presence of or exposure to a predetermined wavelength of light. In some embodiments, the fluorogenic probe comprises rhodamine. In some embodiments, the fluorogenic probe comprises rhodamine-100. Coumarin-based fluorogenic probes are known in the art, for example in a U.S. Pat. Nos. 7,625,758 and 7,863,048, which are herein incorporated by reference in their entireties. In some embodiments, the fluorogenic probes are a component to, covalently bound to, non-covalently bound to, intercalated with one or a plurality of substrates to any of the enzymes disclosed herein. In some embodiments, the fluorogenic probes are chosen from ACC or AMC. In some embodiments, the fluorogenic probe is a fluorescein molecule. In some embodiments, the fluorogenic probe is capable of emitting a resonance wave detectable and/or quantifiable by a fluorimeter after exposure to one or a plurality of enzymes disclosed herein.

As used herein, the terms "fungal infection" or "mycosis" refers to an infection of animals, including humans, by pathogenic fungus or fungi. Mycoses are common and a variety of environmental and physiological conditions can contribute to the development of fungal diseases. In some embodiments, inhalation of fungal spores, localized colonization of the skin or other surfaces, or pathogenic growth of fungi native to a subject microbiota can cause fungal infections. In some embodiments, subjects with weakened immune systems, under steroid treatment, under antibiotic treatment, under chemotherapy treatment, under increased levels of stress, are at higher risk for mycosis. In some embodiments, fungi of the genus *Candida* are capable of causing a fungal infection. In some embodiments, the terms "fungal infection" refer to a planktonic fungal infection and/or a fungal biofilm infection. In some embodiments, the terms "fungal infection" refer to a pathogenic planktonic fungal infection and/or a fungal biofilm infection.

As used herein, the terms "inflammatory response" or "inflammation" refers to the local accumulation of fluid, plasma proteins, and white blood cells initiated by physical injury, infection, or a local immune response. Inflammation is an aspect of many diseases and disorders, including but not limited to diseases related to immune disorders, viral infection, arthritis, autoimmune diseases, collagen diseases, allergy, asthma, pollinosis, and atopy. Inflammation is characterized by rubor (redness), dolor (pain), calor (heat) and tumor (swelling), reflecting changes in local blood vessels leading to increased local blood flow which causes heat and redness, migration of leukocytes into surrounding tissues (extravasation), and the exit of fluid and proteins from the blood and their local accumulation in the inflamed tissue, which results in swelling and pain, as well as the accumulation of plasma proteins that aid in host defense. These changes are initiated by cytokines produced by activated macrophages. Inflammation is often accompanied by loss of function due to replacement of parenchymal tissue with damaged tissue (e.g., in damaged myocardium), reflexive disuse due to pain, and mechanical constraints on function, e.g., when a joint swells during acute inflammation, or when scar tissue bridging an inflamed joint contracts as it matures into a chronic inflammatory lesion. In some embodiments, inflammation can be a response to a pathogen or pathogenic infection. In some embodiments, inflammation can be a response to mycosis from fungi of the genus *Candida*.

As used herein, the terms "subject suspected of having a fungal infection" refers to a subject that is non-responsive to antibiotics typically used for treatment of a bacterial infection or a subject that presents with one or a plurality of symptoms consistent with a fungal infection.

As used herein, the term "sample" refers generally to a limited quantity of something which is intended to be similar to and represent a larger amount of that thing. In the present disclosure, a sample is a collection, swab, brushing, scraping, biopsy, removed tissue, or surgical resection that is to be testing for a fungal infection. In some embodiments, samples are taken from a patient or subject that is believed to have a fungal infection. In some embodiments, a sample may contain fungi of the genus *Candida*. In some embodiments, a sample believed to contain a fungal infection (in the planktonic or biofilm form) is compared to a "control sample" that is known not to contain one or plurality of pathogenic fungal cells in either the planktonic or biofilm forms. In some embodiments, a sample believed to contain a fungal biofilm infection is compared to a control sample that is known to not contain a fungal biofilm infection. In some embodiments, a sample believed to contain a fungal biofilm infection is compared to a control sample that contains the same fungus, but not in biofilm form. In some embodiments, a sample believed to contain a fungal biofilm infection from the genus *Candida* is compared to a control sample known not to contain a fungal biofilm infection from the genus *Candida*. In some embodiments, a sample believed to contain a fungal biofilm infection from the genus *Candida* is compared to a control sample of fungus of the genus *Candida* that is not in a biofilm form. In some embodiments, the sample is a brushing of an environmental are or location, such as a lab bench or medical device. This disclosure contemplates using any one or a plurality of disclosed methods herein to identify, detect, and/or quantify the amount of potentially harmful or pathogenic fungal cells on a particular item or location. These methods include methods of detecting harmful fungal cells on medical devices such as scalpels, knives, or other surgical equipment that may be used to treat a subject in need of surgery. These methods include methods of detecting harmful fungal cells on medical devices such as scalpels, knives, or other surgical equipment that may be used to treat a subject. Some embodiments relate to methods comprising the step of obtaining a sample from a location having or suspected as having been contaminated with one or a plurality of pathogens comprising a fungal cell such as a cell from or derived from the genus *Candida*. In some embodiments, the methods relate to the step of exposing a swab, brushing or other sample from an environment to one or a plurality of solid supports disclosed herein. In some embodiments the swab is taken from medical equipment used in invasive medical procedures, such as surgery, to assure that medical equipment is not contaminated with one or a plurality of pathogenic fungal cells. In some embodiments, the piece of medical equipment is or comprises an implant positioned in, adjacent to or on a subject. In some embodiments, the piece of medical equipment is or comprises or a catheter or IV. In some embodiments, the piece of medical equipment is or comprises a heart valve and/or pacemaker.

The disclosure relates to a system, composition, and series of methods of using the systems and compositions for the analysis of a sample from a subject to accurately diagnose, prognose, or classify the subject with a planktonic and/or biofilm fungal infection. The disclosure also relates to a system, composition, and series of methods of using the systems and compositions for the analysis of a sample from a subject to accurately diagnose, prognose, or classify the subject with a planktonic and/or biofilm fungal infection caused by one or a combination of fungal species in Tables 2 and/or 3. The disclosure relates to a system, composition, and series of methods of using the systems and compositions for the analysis of a sample from a subject to accurately diagnose, prognose, or classify the subject with certain fungal infection of the genus *Candida*. In some embodiments, the system of the present invention comprises a means of detecting and/or quantifying morphological features, the expression of protein, or the expression of nucleic acids in a plurality of cells and correlating that data with a subject's medical history to predict clinical outcome, treatment plans, preventive medicine plans, or effective therapies.

The disclosure also relates to a method of detecting the presence, absence, or quantity of pathogenic fungal cells, optionally in a biofilm producing species, of *Candida* based upon measurements of the levels of protease in a sample. The disclosure also relates to a method of detecting the presence, absence, or quantity of pathogenic planktonic fungal cells, optionally in any of the species disclosed in Tables 2 and/or 3 based upon measurements of the levels of aminopeptidase in a sample. In some embodiments, one can take measurements of the presence, absence, or quantity of Sap proteins, such as Sap5 and/or Sap6 and/or functional fragments thereof, in any of the methods disclosed herein. The method may comprise a step of quantifying the amount of Sap5, Sap6 or functional fragment in a sample by exposing a sample known to comprise or suspected of comprising the enzyme(s) or functional fragments to one or a plurality of substrates known to degrade or cleave into peptide domains or components after exposure to a Sap or functional fragment in a sample for a period sufficient to degrade or cleave the protein or peptide substrate. The pieces or domains or fragments of the substrate proteins or peptides can form a predetermined or expected number of fragments of a particular size depending upon the concentration of the Sap or Saps in a sample, the concentration of substrates in a sample, and/or the length of exposure time. In some embodiments, the amount of Sap in a sample is determined by the number and concentration of peptide fragments from a Sap substrate detected in a sample after exposure of that sample to a Sap substrate library or plurality of libraries. The data collected on the number and concentration of substrate fragments can be compiled in a cleavage signature that, when compared to cleavage signature of known planktonic or known biofilm sample, can be used as evidence to correlate the signature to a diagnosis or detection of the presence of pathogenic or biofilm fungal cells.

As used herein, the term "microbiota" refers to bacterial, fungal, and other microbial life that resides primarily inside or on a host species, for example, a human. In some embodiments, *Candida albicans* is a normal resident of the human microbiota and can be commensal in nature. Under such conditions, in some embodiments, *C. albicans* can colonize many areas of the body, for example, the gastrointestinal tract, genitourinary tract, oral cavity, and skin of humans without causing a fungal infection. In some embodiments, *C. albicans* is a pathogenic in one or more mammals. In some embodiments, *C. albicans* infections can be especially serious in immunocompromised individuals, such as patients undergoing chemotherapy, transplantation patients receiving immunosuppression therapy, and healthy individuals with implanted medical devices. In such embodiments, the disclosed methods may be useful in identifying pathogenic infections or potential for development of pathogenic infections in a subject undergoing chemotherapy, a subject receiving immunosuppression therapy, or a subject with at least one implanted medical devices. In some embodiments, a sample is a fluid sample comprising one or more cells. In some embodiments, the sample can be a blood sample taken at or near a location of the body suspected of having an infection. In some embodiments, the sample is a bodily fluid sample taken from a site of the body that is in contact with a microenvironment within a subject suspected of having an infection. In some embodiments, the sample is a punch biopsy or composition of cells optional suspended in fluid from a site in a subject suspected of having an infection.

As used herein, the term "biofilm" refers to any group of microorganisms in which cells adhere to each other to form at least one three dimensional layer or coating. In some embodiments, cells of a biofilm are embedded within a self-produced matrix of extracellular polymeric substance (EPS). The methods disclosed herein may be useful to distinguish those fungal cells in suspension from those fungal cells that are part of a biofilm or are potentiated to form a biofilm. Biofilm EPS, also referred to as slime, is a polymeric conglomeration generally composed of extracellular DNA, proteins, and polysaccharides. In some embodiments, biofilms may form on or in living or non-living surfaces and can be prevalent in natural, industrial and hospital settings. In some embodiments, cells growing in a biofilm are physiologically distinct from planktonic cell of the same organism, which, by contrast, are single-cells that may float or swim in a liquid medium. Microorganisms form biofilm in response to many factors, which may include cellular recognition of specific or non-specific attachment sites on a surface, nutritional cues, and/or by exposure of planktonic cells to sub-inhibitory concentrations of antibiotics. In some embodiments, when a cell switches to the biofilm form of growth, it undergoes a phenotypic shift in behavior in which large suites of genes are differentially regulated. In some embodiments, one or more genes may be up-regulated during biofilm formation. In some embodiments, one or more genes may be down-regulated during biofilm formation. The methods of this disclosure generally relate to the detection or identification of fungal cells that are capable of forming a biofilm or a component of biofilm.

As used herein the term "contaminated" means that the sample or surface contains a plurality of any one or more pathogenic fungal cells in an amount sufficient to cause disease in a subject if the subject is exposed to the surface or the sample.

As used herein the term "systemic" means the presence of any one or plurality of fungal cells disseminated throughout a subject. In some embodiments, the terms systemic refers to colonization or presence of any one or plurality of fungal cells disseminated throughout the bloodstream of a subject. In some embodiments, the terms systemic refers to a colonization or presence of any one or plurality of fungal cells in more than a single microenvironment of a subject. In some embodiments, the term systemic refers to the presence of any one or a plurality of fungal cells that are derived from commensal species of organisms. In some embodiments, the term systemic refers to the presence of any one or a plurality of fungal cells that are derived from commensal species of *Candida*. In some embodiments, the term systemic refers to the presence of any one or plurality of fungal cells that are derived from commensal species of Table 1 and 2.

In some embodiments, *C. albicans* or any of those species listed herein can form biofilms. In some embodiments, *C. albicans* or any of those species listed herein, biofilms can be formed on all implanted medical devices, such as but not necessarily limited to catheters, pacemakers, dentures, contact lenses, and prosthetic joints, which provide efficient substrates for biofilm growth. In such cases, samples may be taken from any one or plurality of substrates that comprise a sufficient material which, under sufficient conditions, encourages or enables growth of pathogenic fungal cells. In such cases, samples may be taken from any one or plurality of substrates that comprise a sufficient material which, under sufficient conditions, encourages or enables growth of a biofilm. Biofilms can also colonize biotic surfaces, such as mucosal and epithelial cells, with life-threatening colonization and invasion of parenchymal organs occurring during disseminated infections. In some embodiments, the sample is a biopsy or swab of cells taken from one or a plurality of parenchymal organs. Because *C. albicans* biofilms are resistant to existing antifungal drugs and can be a constant reservoir for systemic infections, early detection of biofilm infections is critical to improving patient outcome. In individuals with implanted medical devices, the only current treatment for device associated biofilm infections is removal of the implanted device, often times through surgical intervention. The present disclosure therefore relates to a method of reducing the incidence or probability for replacement of a medical device or a catheter in operation within or near a subject said method comprising quantifying the amount of Sap, Sap6, and/or functional fragments thereof at or near a surface or tissue in contact with a surface of the biomedical device.

As used herein, the terms "peptide," "polypeptide" and "protein" are used interchangeably and refer to two or more amino acids covalently linked by an amide bond or non-amide equivalent. The peptides of the disclosure can be of any length. For example, the peptides can have from about two to about 100 or more residues, such as, 5 to 12, 12 to 15, 15 to 18, 18 to 25, 25 to 50, 50 to 75, 75 to 100, or more in length. Preferably, peptides are from about 2 to about 18 residues in length. The peptides of the disclosure also include 1- and d-isomers, and combinations of 1- and d-isomers. The peptides can include modifications typically associated with posttranslational processing of proteins, for example, cyclization (e.g., disulfide or amide bond), phosphorylation, glycosylation, carboxylation, ubiquitination, myristylation, or lipidation. In some embodiments, the systems or methods of the disclosure relate to analogs of any Sap sequence set forth in Table 1 that share no less than about 70%, about 75%, about 79%, about 80%, about 85%, about 86%, about 87%, about 90%, about 93%, about 94% about 95%, about 96%, about 97%, about 98%, about 99% homology with any one or combination of Sap sequences set forth in Table 1. In some embodiments, Sap may refer to an amino acid sequence selected from SEQ ID NOs: 1, 2, 3, 4, 5, 6, 7, 8, 9 and/or 10, or a functional fragment thereof that is at least about 70%, 75%, 80%, 85%, 90%, 91%, 92%, 93%, 94%, 95%, 96%, 97%, 98%, or 99% homologous to any such amino acid sequence. In some embodiments, the systems, devices and methods disclosed herein utilize or comprise an aminopeptidase comprising any one or combination of SEQ ID NOs: 13, 14, 15, 16, 17, 18, 19, 20 and/or 21, or a functional fragment thereof that are at least about 70%, 75%, 80%, 85%, 90%, 91%, 92%, 93%, 94%, 95%, 96%, 97%, 98%, or 99% homologous to any such amino acid sequence. In some embodiments, the systems, devices and methods disclosed herein utilize or comprise a subtilisin family of protease comprising any one or combination of SEQ ID NOs: 11 and/or 12, or a functional fragment thereof that are at least about 70%, 75%, 80%, 85%, 90%, 91%, 92%, 93%, 94%, 95%, 96%, 97%, 98%, or 99% homologous to any such amino acid sequence.

As used herein, the terms "substrate cleaved in the presence of" is a molecule comprising an amino acid sequence recognized by any of a Sap, aminopeptidase or subtilisin family of proteases disclosed herein and cleaved at that amino acid sequence. Examples of such sequences are those amino acid sequences cleaved in the Examples section of the application.

TABLE 1

Sap proteins 1-10

| Name | Protein Sequence |
|------|------------------|
| Sap1<br>SEQ ID NO: 1 | MFLKNIFIAL AIALLVDASP AKRSPGFVTL DFDVIKTPVN ATGQEGKVKR<br>QAIPVTLNNE LVSYAADITI GSNKQKFNVI VDTGSSDLWV PDASVTCDKP<br>RPGQSADFCK GKGIYTPKSS TTSQNLGSPF YIGYGDGSSS QGTLYKDTVG<br>FGGASITKQV FADITKTSIP QGILGIGYKT NEAAGDYDNV PVTLKNQGVI<br>AKNAYSLYLN SPNAATGQII FGGVDKAKYS GSLIAVPVTS DRELRITLNS<br>LKAVGKNING NIDVLLDSGT TITYLQQDVA QDIIDAFQAE LKSDGQGHTF<br>YVTDCQTSGT VDFNFDNNAK ISVPASEFTA PLSYANGQPY PKCQLLLGIS<br>DANILGDNFL RSAYLVYDLD DDKISLAQVK YTSASNIAAL T |
| Sap2<br>SEQ ID NO: 2 | MFLKNIFIGL AIALLVDATP TTTKRSAGFV ALDFSVVKTP KAFPVTNGQE<br>GKTSKRQAVP VTLHNEQVTY AADITVGSNN QKLNVIVDTG SSDLWVPDVN<br>VDCQVTYSDQ TADFCKQKGT YDPSGSSASQ DLNTPFKIGY GDGSSSQGTL<br>YKDTVGFGGV SIKNQVLADV DSTSIDQGIL GVGYKTNEAG GSYDNVPVTL<br>KKQGVIAKNA YSLYLNSPDA ATGQIIFGGV DNAKYSGSLI ALPVTSDREL<br>RISLGSVEVS GKTINTDNVD VLLDSGTTIT YLQQDLADQI IKAFNGKLTQ<br>DSNGNSFYEV DCNLSGDVVF NFSKNAKISV PASEFAASLQ GDDGQPYDKC<br>QLLFDVNDAN ILGDNFLRSA YIVVYDLDNNE ISLAQVKYTS ASSISALT |
| Sap3<br>SEQ ID NO: 3 | MFLKNIFIAL AIALLADATP TTFNNSPGFV ALNFDVIKTH KNVTGPQGEI<br>NTNVNVKRQT VPVKLINEQV SYASDITVGS NKQKLTVVID TGSSDLWVPD<br>SQVSCQAGQG QDPNFCKNEG TYSPSSSSSS QNLNSPFSIE YGDGTTSQGT<br>WYKDTIGFGG ISITKQQFAD VTSTSVDQGI LGIGYKTHEA EGNYDNVPVT<br>LKNQGIISKN AYSLYLNSRQ ATSGQIIFGG VDNAKYSGTL IALPVTSDNE<br>LRIHLNTVKV AGQSINADVD VLLDSGTTIT YLQQGVADQV ISAFNGQETY<br>DANGNLFYLV DCNLSGSVDF AFDKNAKISV PASEFTAPLY TEDGQVYDQC<br>QLLFGTSDYN ILGDNFLRSA YIVVYDLDDNE ISLAQVKYTT ASNIAALT |
| Sap4<br>SEQ ID NO: 4 | MFLQNILSVL AFALLIDAAP VKRSTGFVTL DFNVKRSLVD PKDPTVEVKR<br>SPLFLDIEPT EIPVDDTGRN DVGKRGPVAV KLDNEIITYS ADITIGSNNQ<br>KLSVIVDTGS SDLWVPDSNA VCIPKWPGDR GDFCKNNGSY SPAASSTSKN<br>LNTPFEIKYA DGSVAQGNLY QDTVGIGGVS VRDQLFANVR STSAHKGILG<br>IGFQSNEATR TPYDNLPITL KKQGIISKNA YSLFLNSPEA SSGQIIFGGI<br>DKAKYSGSLV DLPITSDRTL SVGLRSVNVM GQNVNVNAGV LLDSGTTISY<br>FTPNIARSII YALGGQVHYD SSGNEAYVAD CKTSGTVDFQ FDRNLKISVP<br>ASEFLYQLYY TNGEPYPKCE IRVRESEDNI LGDNFMRSAY IVYDLDDRKI<br>SMAQVKYTSQ SNIVGIN |
| Sap5<br>SEQ ID NO: 5 | MFLKNILSVL AFALLIDAAP VKRSPGFVTL DFNVKRSLVD PDDPTVEAKR<br>SPLFLEFTPS EFPVDETGRD GDVDKRGPVA VTLHNEAITY TADITVGSDN<br>QKLNVIVDTG SSDLWIPDSN VICIPKWRGD KGDFCKSAGS YSPASSRTSQ<br>NLNTRFDIKY GDGSYAKGKL YKDTVGIGGV SVRDQLFANV WSTSARKGIL<br>GIGFQSGEAT EFDYDNLPIS LRNQGIIGKA AYSLYLNSAE ASTGQIIFGG<br>IDKAKYSGSL VDLPITSEKK LTVGLRSVNV RGRNVDANTN VLLDSGTTIS<br>YFTRSIVRNI LYAIGAQMKF DSAGNKVYVA DCKTSGTIDF QFGNNLKISV<br>PVSEFLFQTY YTSGKPFPKC EVRIRESEDN ILGDNFLRSA YVVYNLDDKK<br>ISMAPVKYTS ESDIVAIN |
| Sap6<br>SEQ ID NO: 6 | MFLKNILSVL RFALLIDAAP VKRSPGFVTL DFNVKRSLVV PDDPTAESKR<br>SPLFLDLDPT QIPVDDTGRN VGVDKRGPVA VKLDNEIITY SADITVGSNN<br>QKLSVIVDTG SSDLWIPDSK AICIPKWRGD CGDFCKNNGS YSPAASSTSK<br>NLNTRFEIKY ADGSYAKGNL YQDTVGIGGA SVKNQLFANV WSTSAHKGIL<br>GIGFQTNEAT RTPYDNLPIS LKKQGIIAKN AYSLFLNSPE ASSGQIIFGG<br>IDKAKYSGSL VELPITSDRT LSVGLRSVNV MGRNVNVNAG VLLDSGTTIS<br>YFTPSIARSI IYALGGQVHF DSAGNKAYVA DCKTSGTVDF QFDKNLKISV<br>PASEFLYQLY YTNGKPYPKC EIRVRESEDN ILGDNFMRSA YIVYDLDDKK<br>ISMAQVKYTS ESNIVAIN |
| Sap7<br>SEQ ID NO: 7 | MQRVLELLLL SSTALAVIGD GFIALPVHKL QAGEGSAHFP NRLPIFDVVN<br>GVAKSVEDDV NQIIQPIFGN GIFSGGSIQG THSGNGHSVK YEVSLPSSSA<br>QKGSNGPSST DNKDTDPSKT GFSLDDLMNS ISTDFWNLIG LNKAPTSSDN<br>GSKDADFTPS AVSQVEQPTS KSVESTAPGP ASSASSSSSS EAASSSQPSE<br>DSQPSSSANK KTGAFFLSLD NTQTLYTATL KVGSPAQEVQ VMIDTGSSDL<br>WFISSGNSQC KVNGGSIDCD KYGVFDKSKS STWHDNKTDY SISYYDGDKA<br>SGTMGQDNIT FADGFSIENA NFAVIDNTTS SIGVFGGVYP ELEAVKSKYT<br>NLPFAMKEQN LIAKVAYSLY LDSRDAVQGY ILFGGIDHAK YTGDLKAFDI<br>VQSNDKYVYS QIPLTSVASS LNNYTNAYGL PAGSNHPKVG AVIYNGTDSF |

TABLE 1-continued

Sap proteins 1-10

| Name | Protein Sequence |
|---|---|
| | NGGVDLKDTP TLLDTGTTYS YLSKDQVESI VGLYGNVTYN DAGKAYEVPC<br>WVGNPGNYLE FNFKNEQYIK VPTSEFVISV GTYASGAELC VFGILPGTHS<br>ILGDNFMRSV YAVFDLEDHV ISIAQAAYND NHAVVPIE |
| Sap8<br>SEQ ID NO: 8 | MVSIITFTKN VLVTLAFALL AQGLAIPEDI DKRAEKVVSL DFTVTRKPFN<br>ATAHGQHHQS QQQQQQQQQQ PAQKRGTVQT SLINEGPSYA ATITVGSNKQ<br>QQTVIVDTGS SDLWVVDSAA VCQVTYPGQS PTFCKQDGTY KPSSSTTSQN<br>LGKAFSIRYE DGSSSQGTVY KDTVGLGGAS ITNQQFADVT TTSVDQGILG<br>IGFTGDESSP TYDNVPVTLK KQGIIINKNAY SLYLNSASAS SGTIIFGGVD<br>NAKYTGSLTA LPITSSNELR VQLSTINIAG TTVSASTTPV LDSGTTLTYF<br>SQTIADKLAA AVGAKWNSYY QLYTSSCNLA GNIVFNFAKG VTISVPLSEF<br>VLQDGNSCYF GVSRDSATIL GDNFLRRAYA VYDLDGNTIS LAQVKYTTSS<br>SISTL |
| Sap9<br>SEQ ID NO: 9 | MRLNSVALLS LVATALAAKA PFKIDFEVRR GESKDDLSPE DDSNPRFVKR<br>DGSLDMTLTN KQTFYMATLK IGSNEDENRV LEDTGSSDLW VMSHDLKCVS<br>APISKRNERS FGHGTGVKLN ERELMQKRKN LYQPSRTIET DEEKEASEKI<br>HNKLFGFGSI YSTVYITEGP GAYSTFSPLV GTEGGSGGSG GSNTCRSYGS<br>FNTENSDTFK KNNTNDFEIQ YADDTSAIGI WGYDDVTISN VTVKDLSFAI<br>ANETSSDVGV LGIGLPGLEV TTQLRYTYQN LPLKLKADGI IAKSLYSLYL<br>NTADAKAGSI LFGAIDHAKY QGDLVTVKMM RTYSQISYPV RIQVPVLKID<br>VESSSGSTTN ILSGTTGVVL DTGSTLSYVF SDTLQSLGKA LNGQYSNSVG<br>AYVVNCNLAD SSRTVDIEFG GNKTIKVPIS DLVLQASKST CILGVMQQSS<br>SSSYMLFGDN ILRSAYIVYD LDDYEVSLAQ VSYTNKESIE VIGASGITNS<br>SGSGTTSSSG TSTSTSTRHS AGSIISNPVY GLLLSLLISY YVLV |
| Sap10<br>SEQ ID NO: 10 | MDLVIMNFVF LLYLTSVVKC SIKLDFNKVS TPSKYTKRDA LPMPLINDKI<br>LYTTELEIGS NKDKVSVSID TGSYDLWVMS NDAVCYKVSE FQTEGAPQLP<br>DIFNDIDQDY SCTFNGTYNS KSSKTFKNTS EDFSIGYVDG SAAQGVWGYD<br>SVQFGQYGVT GLKIGIANRS SVSDGILGIG IANGYDNFPV LLQKQGLINK<br>IAYSVYLNSS NSTTGTILFG AIDHAKYKGA LSTVPVDSKS QLSVNVTNLK<br>TKNGNVASGG HSILLDTGST FSIFPDEWID ALGHSLNATY DEDESVYEIE<br>CDGYDEHFFG FSIGDSDFSV PIQDLKTEKD GQCYLAIMSN SVIGGGGILF<br>GDDILRQIYL VYDLQDMTIS VAPVVYTEDE DIEEILNPNE DQNEVPTSTS<br>FTQSASSSGS QPSSTISGEN MDKNTTSSSS GNCQTRSWIA ILSALFLVYI<br>HII |

Table 1 (continued) Examples of aminopeptidases are the following, which are taken from the *Candida* Genomic database at http://www.candidagenome.org/ and referenced by the Associated Gene identifier on that website (such gene identifier and website associated therewith is incorporated by reference in its entirety):

| Description(s) | Associated Gene(s) |
|---|---|
| Ortholog(s) have aminopeptidase activity, role in protein processing, protein stabilization and extrinsic to mitochondrial inner membrane, nucleus localization<br>  1 MKSRIALTLR RFISTRPRLF TTYTTGQPTY ETRPHIITQP GDLTPGISAM<br> 51 EYYQRRLKLS THLPSKSLAI IIGNTTQFSS GSVFYDFQQD NDLYYLTGWL<br>101 EPDSIVAIEK KGDNGEDDVV LHMLVPPKDP KKELWEGPKS GLEGAYNIFN<br>151 ADLVEDISQA PSYLKQLIKQ NDYIYWDKKF NSKQNEGLRQ FFNFSTNHRH<br>201 HQGINEIIEN SKKSVQKLSP IVAKLRVIKS DAEVSVMKRA CEISSVAINR<br>251 AMATVGSDDP INSENTLARY LEYQFVKGGC EKNAYIPVVA SGSNALCLHY<br>301 TRNDDLIKKN ELIFIDAGGK LGGYCADISR AWPNSTDGFT DAQRDIYEVV<br>351 LATNKKCITL CSESLGYSFH DIHEVSVNTL KHELKNLPGF GDVTFSDISR<br>401 IYYPHYVGHN VGLDLHDIPS VSNRLPLKQN QVITIEPGLY IPHDGPKHYR<br>451 GIGLRIEDNV VVGKTHRDII NLTSGCKKEV SDIEALVRGG *<br>SEQ ID NO: 13 | C3_03560W_A |
| Protein similar to aminopeptidase I; mutation confers hypersensitivity to amphotericin B; transcript regulated in macrophage response; flow model biofilm induced<br>  1 MNPAYNPNPK ETFVSITRDS DDSLISTTPD ISETEFEDGE NLSTPDISII<br> 51 DDEYTDNEPI DEFENENQIP ADSMFQFQLP DMSTTIPRLP SNQDVPSAKD<br>101 DTFDNYYESY SEKYIEFMNN NPTTYHTISH FKSLLENNGF IFLPDNKPIS<br>151 DLSPGFYFTS KDDQCLVAFI IGGNWKPEKG SCFVGSHCDA LSVKINPRGS<br>201 LRDNVNGYEL LGVAPYSGSL NKLWLSRDLG LAGSVLVKDN DTGKISRKLI<br>251 KSHPDPIAFI PQLPEVFPES PKEYNTQTQM VPICGYTTET LVPTDEEKRS<br>301 KFYKRHSLSL LRYVSKLAEV PLASIVDLDL DLVDIQTSCR GGLDNEFIYS<br>351 GSLDDRLCAF DSVYGLIEYS QRFYLDKDIK TFDGLNGIYL ANHEEIGSGS<br>401 RTGAKGGFLI DVLKSIVSDK YKTHTPEAVA NLTTNTIFLS SDVTHALNPN<br>451 FKNVYLENNF PVPNTGPSIK FDSNFHVLSD SKGNEFLTRI IDDLPGIKLQ | LAP4 |

| Description(s) | Associated Gene(s) |
|---|---|
| 501 HFHIRNDSRS GGTIGPIMSD SRRGINGAKL IIDVGLPILS MHSIRSIAGY<br>551 KDVGIGIRFF KEVFSKWQST INTIENGK*<br>SEQ ID NO: 14 | |
| Putative X-Pro aminopeptidase; Spider biofilm repressed<br>  1 MTTPSKYPAR SHARKVYSHI KAPFFISGED LVLYKYCDQT KPFRQNRYFF<br> 51 YLTGCNIPGS HVLYTHDKLV LYLPDVDHED IMWSGLPLSP EQALAKYDVD<br>101 EVKFAADIES DLKNLGTVYT TDTSHPHLKP YLTESDPAFF FALDESRLIK<br>151 DDYEIELMRH AAKITDNCHL AVMSALPIET KETHIHAEFM YHALRQGAKN<br>201 QSYDPICCSG ETCSTLHWVK NDGDITPEKR SVLIDAGAEW ECYASDVTRC<br>251 FPVNGDWAKE HLEIYNLVLK MQSAAYEMMK PGVEWEDIHL QAHKVLIQGF<br>301 LELGIFNSKY SAEELFAAKA SARFFPHGLG HVLGMDTHDV GGRANYSDPD<br>351 PLLCYLRIRR KLEPNMVVTN EPGCYFSPFL LEEVLNNPDQ AKFINRDVLD<br>401 KYWYVGGVRI EDDVLITPTG YEIFTKITKD PAEISKIVKA GLAKKFHNIV<br>451 *<br>SEQ ID NO: 15 | C1 14450C A |
| Putative aminopeptidase yscl precursor; mutant is viable; protein present in exponential and stationary growth phase yeast cultures; Spider biofilm repressed<br>  1 MSNIDDILLS ISESLKQLQK ASQEKPIEQT QPVQIQNLEV NSTKKFTDDY<br> 51 YSKIADDYIE FTYKNPTIYH VVNFFKSQLE SKGFTYLPES KSWADLKAGK<br>101 YFTTRNGSSL AAFVVGKDWQ ASKGVGAIGS HIDSLTTVLK PNSTKAKVDG<br>151 YELLGVAPYA GTLGSVWWDR DLGIGGRLLV KDGKGKVSQH LVDSTPHPIA<br>201 HIPTLAPHFG APANGPFNTE TQAVPVVGFS GENDKEEEQP TEEEKNAPLY<br>251 GKHPLKLLRY IAKLANVSVG DILQWDLQLY DVQKGTKGGL NKEFVFAPRV<br>301 DDRVCSFAAL NALIDSTVDN NLAEDSFSIV GLFDNEEIGS LTRQGARGGL<br>351 IELVVDRVLS SNFYNPEVLD IQESLRLTYA NSIVLSADVN HLFNPNFPGV<br>401 YLEHHKPLPN IGVTLSLDPN GHMATDSIGL ALAEELAKKN GDKVQYFQIR<br>451 NDSRSGGTIG PAISTSTGAR TIDLGIPQLS MHSIRATLGS KDIGLGIKFF<br>501 YGFFKNWRDV YDNFVDL*<br>SEQ ID NO: 16 | LAP41 |
| Putative aminopeptidase; positively regulated by Sfu1; clade-associated gene expression; virulence-group-correlated expression; induced by alpha pheromone in SpiderM medium; Hap43-induced; Spider and flow model biofilm induced<br>  1 MGSNTSKTIM PASTKSPLPE TEEEIFNEKP YSSTSTFDNF REQFEGLELE<br> 51 NAENEINPIS ENILSKWEDD FKSQTKNLLA QNALAKNAIV DVIAKNSVGK<br>101 QSLKDRYLFN ITVDTIGSPA HLNNQKSSGR CWIFASSNVL RTHVIKNYNL<br>151 KEDDFQLSQS YLYFYDKLEK ANFFLENIED TSSEDLDSRL ISYLFSNPVN<br>201 DGGQWDMIVN LVNKYGVVPN EVFPDNAQST NSSKLNYVVT EKLREYGLKL<br>251 RSLIAKDAPK NVISSFKASA IKSIYKTIAL ALGTPPKPTD EFLWEFIDKD<br>301 GKYKSFKTNP LDFYKTHVRF DASEHFSLIH DPRNEYNKLY TVERLNNIFG<br>351 GKPIEYINLE IDEIKQVAIK MLKDNEPVFF GSDVGKFSDS KSGILDTTAY<br>401 DYSTAFDFSL DITKSQRLKV GSSQMTHAMV ITGVHIDPQT NKPVRWKIEN<br>451 SWGEDSGQKG WFMMTDEWFD EYVFQIVTNK KYSGKKAYDI WKSKEFNTLP<br>501 YYDPMGALA*<br>SEQ ID NO: 17 | LAP3 |
| Putative aspartyl aminopeptidase; stationary phase enriched protein; mutation confers hypersensitivity to 5-fluorouracil (5-FU); Hog1-induced; planktonic growth-induced; rat catheter and Spider biofilm repressed<br>  1 MASASTSKEL KYAQEFVDFV NASPTPYHAV NSVKSLLSEA GFEEIHERTN<br> 51 WFKSHTLQKG GKYFVTRNGS SIIAFTIGEQ FKNGNGIAIV GAHTDSPCLR<br>101 IKPISKKTSE GFIQIGVEQY GGLIAHSWFD RDLSIAGRVY VNENGQFVPK<br>151 LLKIDKPLLR IPTLAIHLDR EVNTKFEFNK ETKLVPIAGQ TSIDKNEKES<br>201 SASASKSCAD DPNLQLTPDQ FESVQNVISR HNKSLVELIA KELNVEPTQI<br>251 EDFELILFDH QKSTIGGLND EFIFSPRLDN LTSCFTAAKG LVESIKNLPK<br>301 EEGISLISLF DHEEIGSVSA QGADSTFLPD IIQRLTKFDF DNTNSSDNVD<br>351 YFHETMSKSF LLSSDMAHGV HPNYADKYEG QNRPQLNLGP VIKINANQRY<br>401 ATNSPGIVLL KKVADKVQVP LQLFVVRNDS PCGSTIGPIL AAKLGIRTLD<br>451 LGNPQLSMHS IRETGGTFDI LKLTDLFKSF FENYIELDRK ILVDHL*<br>SEQ ID NO: 18 | C1 10820C A |
| Putative dipeptidyl aminopeptidase; transcriptionally regulated during macrophage response<br>  1 MTSIRYDYFK ESGGSDGGSP TRTIISYKRF IYVGTLLAIL IYGSSFLITT<br> 51 IENFTLKFES QSISSIDSFK GERPDYASPS SKSTDFKGKI PFSKEVYDKH<br>101 ILSPKLHSIQ WIRAPESIHD DRGTYVIKED KDDKGFRVVV KSIADEEYEK<br>151 ELIGNSIFKY KGEEHEIVDY FASPDLQKVI LKTDVTSLWR YSSIAYYWVL<br>201 DINNGDIKPV FNDVDKISTA SWSPDSSKIA FIYENNLYYK SLQHDEIVQI<br>251 TFDGSTEIFN GKPDWVYEEE VYGSDHVFWW SPESDKVAFL RSNNTQVPEF<br>301 IIPFYAQSDH QDYPEIVKIK YPKAGYPNPI VDVLTYDLNT KNLHNHHLKS<br>351 EKINLENRLI TEVVWIGDSL KVKTSNRHSD LLEIFLVDKH EKVNLIRTLT | DAP2 |

| Description(s) | Associated Gene(s) |
|---|---|
| ```
401 ASDSWFEATS STLYIPANKT LGRKYDGYLD IVVENGYNHL AYFSPPDNSE
451 YELLTKGNWE VTGGVTFDFT SNTVYFTSTA KSPIERHIHS INLLDRSDNG
501 LPYIKDITTK EGWYQSSFSS GARFLFLSEL GPGVPTQRVN DLKMHKNVKT
551 IEDNSELVET LRNYVVPEVK YSQVELDDKE TGQPFLVTAM ETLPLNFDKT
601 KKYPVLFYIY GGPGSQTVTK KWALSFSSLI AAELDAVVVT IDGRGTGFNN
651 LNYKLGSKFK FIVRDRLGQY EPIDVISAAN KWAEKSYVDP ERIAVWGWSY
701 GGFLTLKTLE TDIDNPIFNY AVAIAPVTRW RLYDSIYTER YLNTPQENPK
751 GYETGSIHNV TNFKHVKKFF IGHGSGDDNV HVQNSLQLLD EFNLAEVENF
801 EFMIFPDSNH GMNYHNGFNV VYDRILDFFK RAFDWEFV*
SEQ ID NO: 19
``` | |
| Putative pheromone-processing dipeptidyl aminopeptidase; possible Kex2 substrate; transposon mutation affects filamentous growth; induced by low nitrogen, germ tube formation; flow model biofilm repressed | STE13 |
| ```
  1 MFTHKRVPQH EEYELVNQVP PTQSPTDSPT RSESDFRNST DSQLSDIFED
 51 LENYSGSSGQ KIEDFNDSPL FQSVLMRYKN EGISGRTCGI FSLVAIFLWI
101 GSVIIYSRVN HSTIGNDLTW KTNIIQLNGE NITLNEYNPN FKNITMNDWR
151 KGKYHTFEKQ IRWLTSKQSP KSKHGGGFYV LDEHDKIVVN QIGQVDKSDT
201 FLSNKQFEYG NNFFKIQDFI LNPSQSIEDS EVVHIIITDT VHQWRHSSFA
251 LYWLFKPLVG TYTPIQPPRN NNKGNGLEVD ALDKLHYADF SSDGKYIVFG
301 FEHNLFIQDL ATGEIQQITD DGSPNIINGK SDWIYEEEVI ASNKMIWWSP
351 SGNHFIFAKI NETKVQEVDM DYYTKQNTNI GMQYQQVGES KYEGVNQYPI
401 NTQLKYPKPG TSNPILSLYI YDIANKKTEE IIDGDDNLGT EYILYYAKWI
451 DANSFLMKQS DRTSSVLTKK LYDLDKNHVS IVSSSNVTKE YKGWVERMNP
501 ITLLDDGKYI DNVVIDNRNT LALFDSPHSV SPSKVLVDNK DWDITGEAIY
551 DAQEKFVYFL STVRSSMDAH LVGIDLADNY KLYNITDTKK DGIFETKFSE
601 NGQYLSLVYQ GPNQPWQRLI NMANVHDFIK SEEYGKSTIE EAVILNQPIV
651 NSLANLKEIN LPTVRYKEVT IGKKEDQVTL NIMEILPPNF KAKNQKYPLF
701 VYTYGGPGSQ TVMKKFDIGF LQIVSARLNS IILVIDPRGT GGKGWKFESF
751 AKNNIGYWES RDLKTITSEY IKKNKKLIDK ERVALWGWSY GGFVTLKTLE
801 YDKGEVFKYG MAVAPVTNWL FYDSIYTERY MGLPDTDPNY ETSARINDFD
851 NFKSVKRFLL VHGTGDDNVH VQNLMWLLDQ LNIHNVENYD MHLFPDSDHS
901 ISYDNAGVIV YDKLYYWLQN AFRGNFDELN *
SEQ ID NO: 20
``` | |
| Putative vacuolar aminopeptidase Y; regulated by Gcn2 and Gcn4; rat catheter and Spider biofilm repressed | APE3 |
| ```
  1 MKFLTLTTSL SIIVSINALP TSFGFWKNWF NLGEKLTQEI IMDDISDQFI
 51 NNDENENNNN DNNLIIDGVI DETVYNSLPE IDTESLQSLI NEKGLRSRAE
101 DLFEIAQRSI GKYDHPTRVI GSPGHWGTIG YIISEIKKLK GYYNVKTQSF
151 KALDGKVKSF SLLIDGVEPK SLSPFSLTPP TVDGKPAHGN LVLVDDFGCK
201 PDNFPEFTKG NIVLIKRGEC AFGDKSRNAG IAGALGAIIY DDEPVRGTLG
251 NPTGKEVATV SVAKKDVEKY IEKLSKDPKY AFETTLYVDS YVKYIKTLNV
301 IADSVFGDHD NIVSLGAHSD SVAEGPGIND DGSGTISLLE VAKHLTQFKL
351 NNAVRFAWWA AEEEGLLGST YYAEHLTAEE NSKLRLFMDY DMMASPNYEY
401 QVYDANNKDH PNGSGNLKDL YIDWYTSHGL NYILTPFDGR SDYVGFIENG
451 IPGGGIATGA EGVKDAKGQE KFGGKVGEWF DPCYHQLCDN LDNPDYEAWV
501 INTKLIAHSV AVYAKSFEGF PKREPKKEVA SASNSEKPNE FIYRGSKLIM
551 *
SEQ ID NO: 21
``` | |

Table 1 (continued) Examples of subtilisin-family proteases are the following, which are taken from the *Candida* Genomic database at http://www.candidagenome.org/ and referenced by the Associated Gene identifier on that website (such gene identifier and website associated therewith is incorporated by reference in its entirety):

| Description(s) | Associated Gene(s) |
|---|---|
| Putative subtilisin-family protease; mutation confers hypersensitivity to toxic ergosterol analog | CR_00650W_A |
| ```
  1 MVKLLLSIWI SIYFMAGSSF ASSSYLVSLH SQETIDTFMA YDATYPQDLQ
 51 VGELINSKFK IGNFSGFSGS FSKDIIKRLE RCPLVDEIVP DITVKAYDAV
101 FQDSAPRHLA RISRRKRMKP IKKYSYIYES DFIGKKVSAY VIDSGIAIGH
151 PEFQGRARTG KDFTDEGPGD NNGHGTHVAG LIGSHTYGVA KGVQIIDVKA
201 LNSKGTGSLS TILVAIEFAV NHRLRSGRMG VANLSLGAYK NKLLNKAIDQ
251 ATQTGLVFVV AAGNNNINAC LTSPSSSPYA ITVGAIDDYN DSIASFSNWG
301 ECVDLFASGA YVKSVNIRSD FRPSVLSGTS MAAPIVTGLV ANLLNEGVDP
351 ELIKGQLIEM STKHRISKSS LFLKKRTPN
SEQ ID NO: 11
``` | |

| Description(s) | Associated Gene(s) |
|---|---|
| subtilisin-like protease (proprotein convertase); processes aspartyl proteinase Sap2; required for hyphal growth and wild-type virulence in mice; functional homolog of *S. cerevisiae* Kex2, which processes alpha-factor; Tup1-repressed | KEX2 |

```
  1 MLPIKLLIFI LGYLLSPTLQ QYQQIPPRDY ENKNYFLVEL NTTNSQKPLI
 51 DFISHYRGHY NFEHQLSSLD NHYVFSIDKS HPHNSFLGNH NSNEYNLMKR
101 QLGHEQDYDE LISYVESIHL LPMKKLSKRI PVPIEMEDVV FENRDDTGSD
151 NHEATDEAHQ KLIEIAKKLD IHDPEFTTQW HLINLKYPGH DVNVTGLWLE
201 DILGQGIVTA LVDDGVDAES DDIKQNFNSE GSWDFNNKGK SPLPRLFDDY
251 HGTRCAGEIA AVKNDVCGIG VAWKSQVSGI RILSGPITSS DEAEAMVYGL
301 DTNDIYSCSW GPTDNGKVLS EPDVIVKKAM IKGIQEGRDK KGAIYVFASG
351 NGGRFGDSCN FDGYTNSIYS ITVGAIDYKG LHPQYSEACS AVMVVTYSSG
401 SGEHIHTTDI KKKCSATHGG TSAAAPLASG IYSLILSANP NLTWRDVQYI
451 SVLSATPINE EDGNYQTTAL NRKYSHKYGY GKTDAYKMVH FAKTWVNVKP
501 QAWYYSDVIQ VNQTITTTPE QKAPSKRDSP QKIIHSSVNV SEKDLKIMNV
551 ERVEHITVKV NIDSTYRGRV GMRIISPTGV ISDLATFRVN DASTRGFQNW
601 TFMSVAHWGE TGIGEWKVEV FVDDSKGDQV EINFKDWQFR IFGESIDGDK
651 AEVYDITKDY AAIRRELLEK EKQNSKSTTT TSSTTTATTT SGGEGDQKTT
701 TSAENKESTT KVDNSASITT SQTASLTSSN EQHQPTESNS DSDSDTDDEN
751 KQEGEEDNDN DNGNKKANSD NTGFYLMSIA VVGFIAVLLV MKFHKTPGSG
801 RRRRRRDGYE FDIIPGEDYS DSDDDEDDSD TRRADEDSFD LGHRNDQRVV
851 SASQQQRQYD RQQDEARDRL FDDFNAESLP DYENDMFKIG DEEEEEEEGQ
901 QSAKAPSNSE GNSGTSTKKY KDNEADEDHK DVVGTQ
SEQ ID NO: 12
```

The reference identifiers for the genes in Table 1 are found at http://www.candidagenome.org/, where the contents of this website as of Feb. 12, 2016 and its subwebpages are incorporated by reference in their entireties.

In some embodiments, Sap proteins, specifically extracellular proteases, can serve as biofilm-specific markers useful for the discrimination between a pathogenic or non-pathogenic infection of a fungus. In the present disclosure, proteomic biomarkers for detecting *C. albicans* biofilms is described, as are reagents, kits, and methods designed to detect these biomarkers. The reagents, kits, and methods may be used in clinical application for testing for the present of *C. albicans* biofilms. In some embodiments, Sap5 is a major biofilm-specific protease. In some embodiments, Sap6 is a major biofilm-specific protease. In some embodiments, the presence of high amounts of Sap5 and/or Sap6 is a strong indication of *C. albicans* biofilm formation. In some embodiments, samples that display high levels of peptide reaction products can Sap5 and/or Sap6 are highly likely to form, or have already formed, a biofilm. In some embodiments, the presence of high amounts of Sap5 and/or Sap6 reaction products can be used to deduce or approximate the quantity of Sap5 and/or Sap6 (or functional fragments thereof) in a sample. in some embodiments, the step of quantifying the amount of Sap5, Sap6 or functional fragments thereof comprises creating a cleavage signature correlating the quantity of Sap5/Sap6 reaction products in a sample after exposure of that sample to a known library of one or a plurality of Sap5 or Sap6 substrates with known amino acid sequences.

In some embodiments, samples comprising *C. albicans*, may be screened using in vitro diagnostic methods to determine whether the samples comprise one or a plurality of planktonic and/or biofilm biomarkers. In some embodiments, samples from a subject may be screened using in vitro diagnostic methods to determine whether the samples comprise one or a plurality of planktonic and/or biofilm biomarkers from any of the species of Table 2. In some embodiments, samples from a medical device or other surface may be screened using in vitro diagnostic methods to determine whether the samples comprise one or a plurality of planktonic and/or biofilm biomarkers from any of the species of Table 2. In some embodiments, patients who are suspected of having a *C. albicans* biofilm infection may be screened using in vitro diagnostic methods to determine whether they have an infection or potential to acquire an infection of pathogenic *C. albicans*. In performing such methods, the methods comprise displaying high levels of the biofilm biomarkers as compared to levels of the same biofilm biomarkers measured from a control sample, such as a sample in which it is known that the sample does not comprise fungal cells capable of forming biofilm (such as planktonic cells or cells that are non-pathogenic strains of the same species of fungal cells).

In some embodiments, any tissue or body fluid sample may be used to detect the absence or presence of a biofilm or planktonic biomarker from *C. albicans*. Saliva, cheek swabs (buccal swabs), hair bulb, blood serum and whole blood samples are among the common forms of samples used to obtain such samples. Examples of other samples can include semen, vaginal fluid, urine, lymph fluid, cerebral spinal fluid, amniotic fluid, skin and surgically excised tissue. One skilled in the art would readily recognize other types of samples of methods of obtaining them. In some embodiments of the methods disclosed herein, any of the methods disclosed herein comprise a step of obtaining a sample from a subject such as a human patient.

*C. albicans* is one of several *Candida* species. Tables 2 and 3 below contain a listing of Sap5 and Sap6 homologues, respectively, found in several *Candida* and other closely related species. In any of the methods disclosed herein, any recitation of *C. albicans* may be replaced with the species of Table 2 or Table 3 for the detection of pathogenic fungal infections comprising one or a plurality of fungal species listed in Tables 2 or 3. In any of the methods disclosed herein, any recitation of "Sap" may be replaced with the sequences of the biomarkers of the right hand column of Table 2 or Table 3 (identified by Gene Accession Number from GenBank and incorporated by reference in its entirety) and can be used interchangeably as a biomarker for detection of pathogenic fungal infections comprising one or a plurality of fungal species listed in the left-hand column of Tables 2 or 3.

TABLE 2

Top 3 BLASTP hits for Sap5 in species tested for probe protease activity

| Species | Match Rank | Candida albicans SAP5 BLASTP Hits |
|---|---|---|
| Candida albicans | | SAP5 (C6_03030W, orf19.5585, XP_719147.1) |
| Candida dubliniensis | 1 | Cd36_63420, XP_002421072.1 |
| Candida dubliniensis | 2 | cd36_63430, XP_002421073.1 |
| Candida dubliniensis | 3 | Cd36_33460, XP_002422286.1 |
| Candida tropicalis | 1 | CTRG_02113, XP_002547806.1 |
| Candida tropicalis | 2 | CTRG_02432, XP_002548135.1 |
| Candida tropicalis | 3 | CTRG_00700, XP_002545919.1 |
| Candida parapsilosis | 1 | CPAR2_102410, SAPP1, CCE40203.1 |
| Candida parapsilosis | 2 | CPAR2_102580, SAPP2, CCE40220.1 |
| Candida parapsilosis | 3 | CPAR2_302640, CCE41276.1 |
| Spathaspora passalidarum | 1 | SPAPADRAFT_141168, EGW31352.1 |
| Spathaspora passalidarum | 2 | SPAPADRAFT_65435, EGW34280.1 |
| Spathaspora passalidarum | 3 | SPAPADRAFT_51269, EGW31240.1 |
| Meyerozyma/Candida guilliermondii | 1 | PGUG_03958, XP_001483229.1 |
| Meyerozyma/Candida guilliermondii | 2 | PGUG_03957, XP_001483228.1 |
| Meyerozyma/Candida guilliermondii | 3 | PGUG_02701, XP_001484972.1 |
| Candida glabrata | 1 | CAGL0E01793g, YPS6, XP_445767.1 |
| Candida glabrata | 2 | CAGL0E01771g, YPS5, XP_445766.1 |
| Candida glabrata | 3 | CAGL0E01815g, YPS8, XP_445768.1 |
| Saccharomyces cerevisiae | 1 | YLR120C, YPS1, NP_013221.1 |
| Saccharomyces cerevisiae | 2 | YLR121C, YPS3, NP_013222.1 |
| Saccharomyces cerevisiae | 3 | YIR039C, YPS6, NP_012305.3 |

TABLE 3

Top 3 BLASTP hits for Sap6 in species tested for probe protease activity

| Species | Match Rank | Candida albicans SAP6 BLASTP Hits |
|---|---|---|
| Candida albicans | | SAP6 (C6_02710C, orf19.5542, XP_719105.1) |
| Candida dubliniensis | 1 | Cd36_63420, XP_002421072.1 |
| Candida dubliniensis | 2 | cd36_63430, XP_002421073.1 |
| Candida dubliniensis | 3 | Cd36_33460, XP_002422286.1 |
| Candida tropicalis | 1 | CTRG_02113, XP_002547806.1 |
| Candida tropicalis | 2 | CTRG_02432, XP_002548135.1 |
| Candida tropicalis | 3 | CTRG_00700, XP_002545919.1 |
| Candida parapsilosis | 1 | CPAR2_102580, SAPP2, CCE40220.1 |
| Candida parapsilosis | 2 | CPAR2_102410, SAPP1, CCE40203.1 |
| Candida parapsilosis | 3 | CPAR2_302640, CCE41276.1 |
| Spathaspora passalidarum | 1 | SPAPADRAFT_141168, EGW31352.1 |
| Spathaspora passalidarum | 2 | SPAPADRAFT_51269, EGW31240.1 |
| Spathaspora passalidarum | 3 | SPAPADRAFT_150243, EGW32893.1 |
| Meyerozyma/Candida guilliermondii | 1 | PGUG_03958, XP_001483229.1 |
| Meyerozyma/Candida guilliermondii | 2 | PGUG_03957, XP_001483228.1 |
| Meyerozyma/Candida guilliermondii | 3 | PGUG_03959, XP_001483230.1 |
| Candida glabrata | 1 | CAGL0E01771g, YPS5, XP_445766.1 |
| Candida glabrata | 2 | CAGL0E01793g, YPS6, XP_445767.1 |
| Candida glabrata | 3 | CAGL0E01837g, YPS9, XP_445769.1 |
| Saccharomyces cerevisiae | 1 | YLR120C, YPS1, NP_013221.1 |
| Saccharomyces cerevisiae | 2 | YLR121C, YPS3, NP_013222.1 |
| Saccharomyces cerevisiae | 3 | YIR039C, YPS6, NP_012305.3 |

Any probe disclosed herein may be an antibody. The term "antibody" as used herein refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. As used herein, a "targeted binding agent" is an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. "Binding fragments" of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay). An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and di-sulphide stabilized variable region (dsFv). As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known See, for example, Bowie et al. Science 253:164 (1991), which is incorporated by reference in its entirety.

In some instances, it may be desired to modify the detection probes so that they are more readily able to bind to the analyte. In such instances, the detection probes may be modified with certain specific binding members that are adhered thereto to form conjugated probes. For instance, the detection probe may be conjugated with antibodies as are further described below that are specific to SAP proteins. The detection probe antibody may be a monoclonal or polyclonal antibody or a mixture(s) or fragment(s) thereof.

The antibodies may generally be attached to the detection probes using any of a variety of well-known techniques. For instance, covalent attachment of the antibodies to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer as the surface of the detection probe may contain a relatively high surface concentration of polar groups. In addition, although detection probes are often functionalized after synthesis, such as with poly(thiophenol), the detection probes may be capable of direct covalent linking with an antibody without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholine) ethane sulfonic acid (MES) (e.g., pH of 5.3). The resulting detection probes may then be contacted with ethanolamine, for instance, to block any remaining activated sites. Overall, this process forms a. conjugated detection probe, where the antibody is covalently attached to the probe. Besides covalent bonding, other attachment techniques, such as physical adsorption, may also be utilized in the present invention.

In one embodiment, e antibody may be detectably labeled by linking to an enzyme. The enzyme, in turn, when later exposed to a substrate or reaction product or enzyme disclosed herein, will react with a substrate or reaction product or enzyme disclosed herein in such a manner as to produce a chemical moiety which may be detected as, for example, by spectrophotometric or fluorometric means. Examples of enzymes which may be used to detectably label the antibodies as herein described include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

In some embodiments, in vivo or in vitro methods are performed to detect the presence, absence or quantity of one or a plurality of biomarkers corresponding to the likelihood of acquiring or having an infection of pathogenic fungal cells. Any of the biomarkers listed in the right-hand column of Tables 2 or 3 may be detected to correlate its expression levels (in nucleic acid or amino acid form) to the presence of a pathogenic fungal infection of the corresponding fungal species on Tables 2 or 3, including if those infections are planktonic or in the biofilm form. In some embodiments, any of the disclosed methods or series of methods comprise exposing a sample or tissue in situ with one or a plurality of antibodies, optionally tagged with a visual detection agent such as a fluorophore, which has binding affinity for one or a plurality of the biomarker disclosed herein. Antibodies suitable for practicing the methods of the invention may be monoclonal and multivalent, and may be human, humanized or chimeric antibodies, comprising single chain antibodies, Fab fragments, F(ab') fragments, fragments produced by a Fab expression library, and/or binding fragments of any of the above. In certain embodiments of the invention, the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, CH3 and CL domains. Also included in the invention are antigen-binding fragments comprising any combination of variable region(s) with a hinge region, CH1, CH2, CH3 and CL domains. Preferably, the antibodies are human, murine (e.g., mouse and rat), donkey, sheep, rabbit, goal, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulins.

The antibodies suitable for practicing the methods of the present invention may be bispecific, trispecific or of greater multispecificity. Further, the antibodies of the present invention may have low risk of toxicity against granulocyte (neutrophil), NK cells, and CD4+ cells as bystander cells.

In accordance with one embodiment of the present invention, isolated and/or purified antibodies that recognized and bind a Sap protein, a aminopeptidase, and/or a subtilisin-like protease may be generated for inclusion in a diagnostic device as disclosed herein. For instance, according to one embodiment, substantially pure recombinant polypeptide suitable for use as an immunogen may be isolated from cells in which it is produced and then polyclonal antiserum containing antibodies to heterogeneous epitopes of a Sap protein, a aminopeptidase, and/or a subtilisin-like protease may be prepared by immunizing suitable hosts with the expressed polypeptide, which may be unmodified or modified to enhance immunogenicity. As is generally known in the art, effective polyclonal antibody production may be affected by many factors related both to the antigen and the host species. For example, small molecules tend to be less immunogenic than others and may require the use of carriers and adjuvant. Also, hosts may vary in response to site of inoculations and dose, with both inadequate and excessive doses of antigen resulting in low titer antisera.

Booster injections may be given at regular intervals, and antiserum harvested when antibody titer thereof, as determined semi-quantitatively, for example, by double immunodiffusion in agar against known concentrations of the antigen, begins to fall. See, for example, Ouchterlony et al. (Handbook of Experimental Immunology, Wier, D. (ed.) chapter 19. Blackwell (1973)). In general, plateau concentration of antibody may usually be in the range of 0.1 to 0.2 mg/ml of serum. Affinity of the antisera for the antigen is determined by preparing competitive binding curves, as described, for example, by Fisher (Manual of Clinical Immunology, Ch. 42. (1980)).

Another possible approach to raising antibodies against the Sap protein, aminopeptidase, and/or subtilisin-like protease may utilize synthetic peptides synthesized on a commercially available peptide synthesizer based upon the amino acid sequence correlating to the known SAP gene sequences.

Antibodies may optionally be raised against the a Sap protein, a aminopeptidase, and/or a subtilisin-like protease or fragments thereof by subcutaneous injection of a DNA vector that expresses the polypeptide into laboratory animals, such as mice. Delivery of the recombinant vector into the animals may be achieved according to methods as are generally known in the art.

In another embodiment, monoclonal antibodies may be raised by hybridoma cells, phage display libraries, or other methodology. Monoclonal antibodies may be e.g., human, rat, or mouse derived. For the production of human monoclonal antibodies, hybridoma cells may be prepared by fusing spleen cells from an immunized host, e.g., a mouse, with a tumour cell. Appropriately secreting hybridoma cells may thereafter be selected according to, for example, the method of Kohler and Milstein (Nature 256:495(1975)), or derivative methods thereof. (Procedures for monoclonal antibody production are also described in Harlow and Lane (1988). Antibodies, A Laboratory Manual, Cold Spring Harbor Laboratory, New York; Cole, et al., "Monoclonal antibodies and Cancer Therapy, Alan R. Liss, Inc., pp. 77-96.). Rodent antibodies may be humanized using recombinant DNA technology according to techniques known in the art. Alternatively, chimeric antibodies, single chain antibodies, Fab fragments, and so forth may also be developed against the a Sap protein, a aminopeptidase, and/or a subtilisin-like protease using skills known in the art.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, EMBO J., 10:3655-3659 (1991).

According to another approach described in WO96/27011, the interface between a pair of antibody molecules can be engineered to maximize the percentage of heterodimers which are recovered from recombinant cell culture. Such interfaces may comprise at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. An alternative method links two different single chain variable regions to heat stable antigen (HSA). Using HSA as linker increases serum half-life, and has the benefit of low immunogenicity.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kos-telny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments (VH-CH1-VH-CH1) which form a pair of antigen binding regions. Linear antibodies can be bispecific or monospecific.

Within the context of the present disclosure, antibodies are understood to include monoclonal antibodies and polyclonal antibodies, antibody fragments (e.g., Fab and F(ab')2), chimeric antibodies bifunctional or bispecific antibodies and tetrameric antibody complexes. Antibodies are understood to be reactive against a selected antigen on the surface of a T cell if they bind with an appropriate affinity (association constant), e.g. greater than or equal to $10^{-7}$ M. Additionally, antibodies that may be used in the methods of the present invention may also be described or specified in terms of their binding affinities include those with a dissociation constant or Kd less than about $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, $10^{-15}$ M. In some embodiments, the antibodies may have any one of the above disassociation constants in relation to its affinity for proteins of Sap5 and/or Sap6. In some embodiments, the antibodies may have any one of the above disassociation constants in relation to its affinity for biomarkers of Tables 2 or 3. In some embodiments, the antibody may be covalently bound to Sap5 and/or Sap6 or analogs thereof. In some embodiments, the antibodies may have any one of the above disassociation constants in relation to its affinity for the amino acid sequences identified in Table 1 or analogs or functional fragments thereof. In some embodiments, the antibodies may have any one of the above disassociation constants in relation to its affinity for the amino acid sequences identified in Table 1 or analogs or functional fragments thereof. In some embodiments, the antibody may be covalently bound to any one or plurality of the amino acid sequences identified in Table 1 or analogs or functional fragments thereof. Any analogs or functional fragments of the amino acids identified in the foregoing sentences may be at least about 75%, about 80%, about 85%, about 90%, about 91%, about 92%, about 93%, about 94%, about 95%, about 96%, about 97%, about 98%, about 99% homologous to any of the sequences identifiers or sequences incorporated by reference in Tables 1, 2, or 3.

Antibodies can be fragmented using conventional techniques and the fragments screened for utility in the same manner as described above for the whole antibodies. For example, F(ab')2 fragments can be generated by treating antibody with pepsin. The resulting F(ab')2 fragment can be treated to reduce disulfide bridges to produce Fab' fragments.

The invention also contemplates using one or a plurality of chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the selected antigens on the surface of differentiated cells or tumor cells. See, for example, Morrison et al., 1985; Proc. Natl. Acad. Sci. U.S.A. 81, 6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B. In any of the disclosed methods, the methods may comprise exposing any antibody that have an affinity for any of the reaction products created by cleavage of a known substrate after exposure of the substrate to any one or plurality of enzymes set forth in Table 1.

Chemical conjugation is based on the use of homo- and heterobifunctional reagents with E-amino groups or hinge region thiol groups. Homobifunctional reagents such as 5,5'-Dithiobis(2-nitrobenzoic acid) (DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridylditio)propionate (SPDP) combine exposed amino groups of antibodies and Fab fragments, regardless of class or isotype (Van Dijk et al., 1989).

Various formats may be used to test for the presence or absence of a Sap, aminopeptidase, and/or a one subtilisin-family protease or functional fragment thereof using the assay devices of the present disclosure. For instance, a "sandwich" format typically involves mixing the test sample with probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Although various assay device configuration have been described herein, it should be understood that any known assay device may be utilized that is capable of incorporating an antibody in accordance with the present invention. For example, electrochemical affinity assay devices may also be utilized, which detect an electrochemical reaction between an SAP protein (or complex thereof) and a capture ligand on an electrode strip. For example, various electrochemical assays and assay devices are described in U.S. Pat. No. 5,508,171 to Walling, et al.; U.S. Pat. No. 5,534,132 to Vreeke, et al.; U.S. Pat. No. 6,241,863 to Monbouquette; U.S. Pat. No. 6,270,637 to Crismore, et al.; U.S. Pat. No. 6,281,006 to Heller, et al.; and U.S. Pat. No. 6,461,496 to Feldman, et al., which are incorporated herein in their entirety by reference thereto for all purposes.

The present disclosure relates to a method of treating or preventing a subject in need thereof diagnosed with or suspected as having a pathogenic fungal infection, comprising:

(a) contacting a plurality of probes specific for any enzyme disclosed herein, or a functional fragment thereof with a sample;

(b) quantifying the amount of enzyme, or a functional fragment thereof in the sample;

(c) calculating one or more scores based upon the presence, absence, or quantity of the enzymes, and/or a functional fragment thereof;

(d) correlating the one or more scores to the presence, absence, or quantity of the enzymes, or a functional fragment thereof, such that if the amount of enzyme, or functional fragment thereof is greater than the quantity of enzyme, or a functional fragment thereof in a control sample, the correlating step comprises diagnosing a subject with a pathogenic infection of a fungus; and (e) administering to the subject a therapeutically effective amount of treatment for the pathogenic fungal infection.

The present disclosure relates to methods of detecting the presence, absence, or quantity of biofilm producing species of any fungal species disclosed herein based upon measurement of the levels of Sap protein, aminopeptidase, or subtilisin protease in a sample. The present disclosure relates to methods of detecting the presence, absence, or quantity of biofilm producing species of *Candida* based upon measurement of the levels of protease in a sample. In some embodiments, one can take measurements of the presence, absence, or quantity of SAP proteins, Sap5 and/or Sap6 and/or functional fragments thereof. In some embodiments, the measurements are taken by measuring the amount of cleaved Sap5 and/or Sap6 through any one or plurality of methods: antibodies or antibody fragments binding to the cleavage products; quantum dots binding to the cleavage products; mass spectrometry of the cleavage products; quantifying or visualizing a probe associated to the cleavage products; quantifying or visualizing fluorescence of a probe associated to the cleavage products; quantifying or visualizing cleavage products through gel electrophoresis or chromatography. In some embodiments, the measurements are taken by measuring the amount of cleaved Sap5 and/or Sap6 through any one or plurality of the methods disclosed below.

The disclosure relates to a method to detect a pathogenic fungal infection in a subject, said method comprising: obtaining a sample from a subject; and detecting whether a Sap protein is present in the sample by contacting the sample with a substrate for one of the Sap proteins or a functional fragment thereof and detecting the presence of amino acid sequence that results from cleavage of one of the substrates. In some embodiments, the amino acid sequences that result from one or a plurality of cleavage reactions as between the substrate and the Sap protein is a "cleavage product."

In some embodiments, the methods further comprise detecting the presence or absence or quantity of cleavage products by contacting the sample or cleavage products to an antibodies or antibody fragments binding to the cleavage products; quantum dots binding to the cleavage products; mass spectrometry of the cleavage products; quantifying or visualizing a probe associated to the cleavage products; quantifying or visualizing fluorescence of a probe associated to the cleavage products; quantifying or visualizing cleavage products through gel electrophoresis or chromatography. In some embodiments, the methods comprise detecting the presence of Sap5 in a sample by detecting the presence or absence of Sap5 cleavage product after exposure of the sample to Sap5 substrate: VFILWRTE (SEQ ID NO: 22) or a peptide that is 99%, 98%, 97%, 96%, 95%, 94%, 93%, 92%, 91%, 90%, 89%, 88%, 87%, 86%, 85%, 84%, 83%, 82%, 81%, 80%, 70%, 65%, 62%, 60% homologous to VFILWRTE (SEQ ID NO: 22). In some embodiments, the methods comprise detecting the presence of Sap6 in a sample by detecting the presence or absence of Sap6 cleavage product after exposure of the sample to Sap6 substrate: TFSYnRWP (SEQ ID NO: 23) or a peptide that is 99%, 98%, 97%, 96%, 95%, 94%, 93%, 92%, 91%, 90%, 89%, 88%, 87%, 86%, 85%, 84%, 83%, 82%, 81%, 80%, 70%, 65%, 62%, 60% homologous to TFSYnRWP (SEQ ID NO: 23).

In some embodiments, the methods comprise diagnosing a subject as having a pathogenic planktonic or biofilm fungal infection comprising:

Optionally, (a) obtaining a sample from a subject; and (b) detecting the presence of Sap5 in the sample by detecting the presence or absence of Sap5 cleavage product after exposure of the sample to Sap5 substrate: VFILWRTE (SEQ ID NO: 22) or a peptide that is 99%, 98%, 97%, 96%, 95%, 94%, 93%, 92%, 91%, 90%, 89%, 88%, 87%, 86%, 85%, 84%, 83%, 82%, 81%, 80%, 70%, 65%, 62%, 60% homologous to VFILWRTE (SEQ ID NO: 22).

In some embodiments, the methods comprise diagnosing a subject as having a pathogenic planktonic or biofilm fungal infection comprising:

Optionally, (a) obtaining a sample from a subject; and (b) detecting the presence of Sap6 in the sample by detecting the presence or absence of Sap6 cleavage product after exposure of the sample to detecting the presence of Sap6 in a sample by detecting the presence or absence of Sap6 cleavage product after exposure of the sample to Sap6 substrate: TFSYnRWP (SEQ ID NO: 23) or a peptide that is 99%, 98%, 97%, 96%, 95%, 94%, 93%, 92%, 91%, 90%, 89%, 88%, 87%, 86%, 85%, 84%, 83%, 82%, 81%, 80%, 70%, 65%, 62%, 60% homologous to TFSYnRWP (SEQ ID NO: 23). In some embodiments, the methods comprise detecting the presence of Sap6 in a sample by detecting the presence or absence of Sap6 cleavage product after exposure of the sample to Sap6 substrate: TFSYnRWP (SEQ ID NO: 23) or a peptide that is 99%, 98%, 97%, 96%, 95%, 94%, 93%, 92%, 91%, 90%, 89%, 88%, 87%, 86%, 85%, 84%, 83%, 82%, 81%, 80%, 70%, 65%, 62%, 60% homologous to TFSYnRWP (SEQ ID NO: 23). In any of the aforementioned methods, the methods may further comprise the steps of: (i) calculating one or more scores based upon the presence, absence, or quantity of one or a plurality of: enzymes, functional fragments thereof, and/or cleavage products; and/or (ii) correlating the one or more scores to the presence, absence, or quantity of the enzymes, or a functional fragment thereof, or cleavage products disclosed herein such that if the amount of enzyme, or functional fragment thereof is greater than the quantity of enzyme, or a functional fragment thereof or cleavage product in a control sample, the correlating step comprises diagnosing a subject with a pathogenic infection of a fungus. In some embodiments, the pathogenic infection comprises one or a plurality of organisms from Tables 2 or 3.

The present disclosure relates to a method of diagnosing a subject as having a pathogenic fungal infection, comprising:

Optionally, (a) obtaining a sample from the subject;

(b) detecting the presence, absence or quantity of amino acids or functional fragments thereof chosen from any one of amino acid sequences of Table 1 in a sample by contacting the amino acids or functional fragments thereof with a substrate specific for the enzyme recognition site of the amino acid sequence or functional fragment thereof and detecting the presence, absence, quantity or pattern of cleavage products after a time period sufficient for the amino acid sequences of Table 1 to cleave the substare to form any one or more cleavage products; and/or (c) diagnosing the subject with a pathogenic fungal infection when the presence, absence, quantity or pattern of cleavage products are detected.

The present disclosure relates to a method of treating or preventing a subject in need thereof diagnosed with or suspected a having a pathogenic fungal infection, comprising:

(a) contacting a sample disclosed herein with a substrate specific for an enzyme of Table 1, or a functional fragment thereof to form a reaction mixture;

(b) quantifying an amount of the enzyme, or a functional fragment thereof, in the sample by detecting or quantifying the amount of cleavage product in the reaction mixture through any one or plurality of methods disclosed herein (for instance, fluorogenic probe visualization or quantification);

(c) calculating one or more scores based upon the presence, absence, or quantity of one or a plurality of: enzymes, functional fragments thereof, and/or cleavage products;

(d) correlating the one or more scores to the presence, absence, or quantity of the enzymes, or a functional fragment thereof, such that if the amount of enzyme, or functional fragment thereof is greater than the quantity of enzyme, or a functional fragment thereof in a control sample, the correlating step comprises diagnosing a subject with a pathogenic infection of a fungus; and (e) administering to the subject a therapeutically effective amount of treatment for the pathogenic fungal infection.

The present disclosure relates to a method of treating or preventing a subject in need thereof diagnosed with or suspected a having a pathogenic fungal infection, comprising:

(a) contacting a sample disclosed herein with a substrate specific for an enzyme of Table 1, or a functional fragment thereof to form a reaction mixture;

(b) quantifying an amount of the enzyme, or a functional fragment thereof, in the sample by detecting or quantifying the amount of cleavage product in the reaction mixture through any one or plurality of methods disclosed herein (for instance, fluorogenic probe visualization or quantification);

(c) calculating one or more scores based upon the presence, absence, or quantity of one or a plurality of: enzymes, functional fragments thereof, and/or cleavage products;

(d) correlating the one or more scores to the presence, absence, or quantity of the enzymes, or a functional fragment thereof, such that if the amount of enzyme, or functional fragment thereof is greater than the quantity of enzyme, or a functional fragment thereof in a control sample, the correlating step comprises diagnosing a subject with a biofilm infection of a fungus; and (e) administering to the subject a therapeutically effective amount of treatment for the pathogenic biofilm infection.

The present disclosure relates to a method of treating or preventing a subject in need thereof diagnosed with or suspected a having a pathogenic fungal infection, comprising:

(a) contacting a sample disclosed herein with a substrate specific for an enzyme of Table 1, or a functional fragment thereof to form a reaction mixture;

(b) quantifying an amount of the enzyme, or a functional fragment thereof, in the sample by detecting or quantifying the amount of cleavage product in the reaction mixture through any one or plurality of methods disclosed herein (for instance, fluorogenic probe visualization or quantification);

(c) calculating one or more scores based upon the presence, absence, or quantity of one or a plurality of: enzymes, functional fragments thereof, and/or cleavage products;

(d) correlating the one or more scores to the presence, absence, or quantity of the enzymes, or a functional fragment thereof, such that if the amount of enzyme, or functional fragment thereof is greater than, about equal to less than the quantity of enzyme, or a functional fragment thereof in a control sample, the correlating step comprises diagnosing a subject with a pathogenic planktonic infection of a fungus; and (e) administering to the subject a therapeutically effective amount of treatment for the pathogenic planktonic infection.

In some embodiments, the methods disclosed herein relates to methods of diagnosing, treating or preventing a subject with a planktonic or biofilm infection of an organism identified in Tables 2 and/or 3. In some embodiments, the methods disclosed herein comprise a method of identifying whether a surface of an implant or biomedical device (such as a catheter) is contaminated by any of the one or plurality of organism in Tables 2 and/or 3, said method comprising obtaining a sample from the surface of one or plurality of implants or devices and exposing the sample to a substrate specific for any one of the enzymes in Table 1 in a reaction vessel for a time period sufficient for any one of the enzymes of Table 1 to cleave the substrate thereby creating a cleavage product, and contacting the sample with a probe, antibody or antibody fragment to quantify or detect the presence or absence of the cleavage product, whereby if the quantity of cleavage product is statistically higher than the amount of cleavage product in a control sample known not to have a pathogenic fungal infection, the a surface of an implant or biomedical device is determined to have a contaminate. In some embodiments, the methods disclosed herein comprise a method of identifying whether an environmental surface (such as a laboratory benchtop) is contaminated by any of the one or plurality of organisms in Tables 2 and/or 3, said method comprising obtaining a sample from the surface of one or plurality of implants or devices and exposing the sample to a substrate specific for any one of the enzymes in Table 1 in a reaction vessel for a time period sufficient for any one of the enzymes of Table 1 to cleave the substrate thereby creating a cleavage product, and contacting the sample with a probe, antibody or antibody fragment to quantify or detect the presence or absence of the cleavage product, whereby if the quantity of cleavage product is statistically higher than the amount of cleavage product in a control sample known not to have a pathogenic fungal infection, the surface is determined to have a contaminate. In some embodiments, the methods disclosed herein comprise a method of identifying whether a sample from a subject (such as a human patient) contains pathogenic fungal cells of any of the one or plurality of organisms in Tables 2 and/or 3, said method comprising obtaining a sample from the patient and exposing the sample to a substrate specific for any one of the enzymes in Table 1 in a reaction vessel for a time period sufficient for any one of the enzymes of Table 1 to cleave the substrate thereby creating a cleavage product, and contacting the sample with a probe, antibody or antibody fragment to quantify or detect the presence or absence of the cleavage product, whereby if the quantity of cleavage product is statistically higher than the amount of cleavage product in a control sample known not to have a pathogenic fungal infection, the sample is determined to contain a pathogenic fungal cell. In some embodiments, the presence of the pathogenic fungal cell is evidence of a presence of a cell from a planktonic and/or biofilm infection.

One skilled in the art will readily appreciate the wide range of methods and techniques used for detecting the presence and/or quantity of proteins, enzymes and/or cleavage products in a complex sample. Techniques for detecting proteins or cleavage products include, but are not limited to, microscopy, immunostaining, immunoprecipitation, immunoelectrophoresis, Western blot, BCA assays, spectrophotometry, enzymatic assays, microchip assays, and mass spectrometry. In some embodiments, purification of proteins are necessary before detection of quantification techniques are employed. Techniques for purifying proteins include, but are not limited to, chromatography methods, including ion exchange, size-exclusion, and affinity chromatography, gel electrophoresis, and Bradford protein assays. In some embodiments, methods of measuring the presence, absence, or quantity of Sap5 and/or Sap6 or functional fragments thereof comprise antibodies or antibody fragments specific to Sap5 and/or Sap6 or functional fragments thereof.

As used herein, the term "score" refers to a single value that can be used as a component in a predictive model for the diagnosis, prognosis, or clinical treatment plan for a subject, wherein the single value is calculated by combining and/or normalizing raw data values with or against a control value based upon features or metrics measured in the system. In some embodiments, the score is calculated by through an interpretation function or algorithm. In some embodiments, the subject is suspected of having, is at risk of developing, or has a *Candida* infection characterized in that it is capable of or has formed a biofilm. In some embodiments, the score is calculated through an interpretation function or algorithm that normalizes the amount of an experimental value obtained through a test disclosed herein as compared to a control value obtained through a test disclosed herein or by a predetermined value conducted prior to conducting a test disclosed herein but corresponding to a control or normal (e.g. uninfected) value.

To facilitate the detection of a protease disclosed herein, such as a fungal Sap protein, within a sample, a detectable substance may be pre-applied to a surface, for example a plate, well, bead, or other solid support comprising one or a plurality of reaction vessels. In some embodiments, sample may be pre-mixed with a diluent or reagent before it is applied to a surface. The detectable substance may function as a detection probe that is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal that corresponds to the level or quantity of protease in the sample. For example, suitable fluorescent molecules may include, but are not limited to, fluorescein, europium chelates, phycobiliprotein, phycoerythrin, phycocyanin, allophycocyanin, o-phthaldehyde, fluorescamine, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine;

phenanthroline; dipyridophenazine; porphyrin; porphine; and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart. et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are not limited to, bis[(4, 4'-carbomethoxy)-2,2'-bipyridine]2-[3-(4-methyl-2,2'-bi-pyridine-4-yl)propyl]-1,3-dioxo lane ruthenium (II); bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid] ruthenium (II); tris(2, 2'bipyridine)ruthenium (II); (2,2'-bipyridine) [bis-bis(1,2-diphenylphosphino)ethylene]2-[3-(4-methyl-2,2'-bipyridine-4'-yl)propyl]-1,3-dioxolane osmium (II); bis(2, 2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butan-e]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein by reference in their entireties.

In some cases, luminescent compounds may have a relatively long emission lifetime and/or may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (I)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have narrow emission spectra, typically having bandwidths less than about 10 nanometers at about 50% emission. One suitable europium chelate is N-(p-isothiocyanatobenzyl)-diethylene triamine tetraacetic acid-Eu.sup.+3.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amin-o]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate. beta.-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein by reference in their entirety.

Detectable substances (such as those capable of associating with or reacting to the presence of the reaction products cleaved by the proteases described herein), such as described above, may be used alone or in conjunction with a particle (sometimes referred to as "beads" or "microbeads"). For instance, naturally occurring particles, such as nuclei, *mycoplasma*, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al.; U.S. Pat. No. 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 100 microns, in some embodiments, from about 1 nanometer to about 10 microns, and in some embodiments, from about 10 to about 100 nanometers.

In some instances, it may be desired to modify the detection probes so that they are more readily able to bind to the analyte. In such instances, the detection probes may be modified with certain specific binding members that are adhered thereto to form conjugated probes. For instance, the detection probe may be conjugated with antibodies as are further described below that are specific to Sap proteins. The detection probe antibody may be a monoclonal or polyclonal antibody or a mixture(s) or fragment(s) thereof.

Antibodies that are capable of binding any one or plurality of biomarkers disclosed herein may generally be attached to the detection probes using any of a variety of well-known techniques. For instance, covalent attachment of the antibodies to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer as the surface of the detection probe may contain a relatively high surface concentration of polar groups. In addition, although detection probes are often functionalized after synthesis, such as with poly(thiophenol), the detection probes may be capable of direct covalent linking with an antibody without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

In one embodiment, the antibody may be detectably labeled by linking to an enzyme. The enzyme, in turn, when later exposed to a substrate, will react with the substrate in such a manner as to produce a chemical moiety which may be detected as, for example, by spectrophotometric or fluorometric means. Examples of enzymes which may be used to detectably label the antibodies as herein described include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

Another technique that may also result in greater sensitivity when used in conjunction with the present invention consists of coupling the antibodies to low molecular weight haptens. The haptens may then be specifically detected by means of a second reaction. For example, it is common to use such haptens as biotin (reacting with avidin) or dinitrophenol, pyridoxal and fluorescamine (reacting with specific antihapten antibodies) in this manner.

The antibodies of the present invention also may be detectably labeled by coupling to a chemiluminescent compound or a fluorescent compound. The presence of the chemiluminescent-tagged antibody is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibodies as further described below. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

In some embodiments, the system disclosed herein comprises a chip, slide or other silica surface comprising one or a plurality of addressable locations or reaction vessels within which one or a plurality of peptides, protease or peptidase substrates, and/or antibodies with an affinity for the biomarkers disclosed herein are immobilized or contained. Upon contacting a sample comprising any one of the peptides or functional fragments thereof to the one or a plurality of peptides, protease or peptidase substrates, and/or antibodies with an affinity for the biomarkers disclosed herein, a reaction ensue whose reaction products are detectable by any means known in the art or disclosed herein. For instance, the reaction products may be detectable by fluorescence, optical imaging, field microscopy, mass spectrometry, or the like.

The disclosure provides for quantifying the amount or detecting the presence or absence of a planktonic or biofilm form a fungal infection by exposure of a sample taken from a subject to quantum dots (QDs). There has been substantial interest in exploiting the properties of compound semiconductor particles with dimensions on the order of about 2 to about 50 nm, often referred to as QDs or nanocrystals. These materials are of commercial interest due to their size-tunable electronic properties that can be exploited in many commercial applications.

The most studied of semiconductor materials have been the chalcogenides II-VI materials namely ZnS, ZnSe, CdS, CdSe, CdTe; especially CdSe due to its tunability over the visible region of the spectrum. Reproducible methods for the large-scale production of these materials have been developed from "bottom up" techniques, whereby particles are prepared atom-by-atom, i.e., from molecules to clusters to particles, using "wet" chemical procedures.

Two fundamental factors, both related to the size of the individual semiconductor nanoparticles, are responsible for their unique properties. The first is the large surface-to-volume ratio. As particles become smaller, the ratio of the number of surface atoms to those in the interior increases. This leads to the surface properties playing an important role in the overall properties of the material. The second factor is a change in the electronic properties of the material when the material is very small in size. At extremely small sizes quantum confinement causes the material's band gap to gradually increase as the size of the particles decrease. This effect is a consequence of the confinement of an 'electron in a box' giving rise to discrete energy levels similar to those observed in atoms and molecule rather than a continuous band as observed in the corresponding bulk semiconductor material. Thus, the "electron and hole" produced by the absorption of electromagnetic radiation are closer together than they would be in the corresponding macrocrystalline material. This leads to a narrow bandwidth emission that depends upon the particle size and composition of the nanoparticle material. QDs therefore have higher kinetic energy than the corresponding macrocrystalline material and consequently the first excitonic transition (band gap) increases in energy with decreasing particle diameter.

QD nanoparticles of a single semiconductor material tend to have relatively low quantum efficiencies due to electron-hole recombination occurring at defects and dangling bonds situated on the nanoparticle surface, which may lead to non-radiative electron-hole recombinations. One method to eliminate such defects and dangling bonds on the inorganic surface of the QD is to grow a second inorganic material, having a wider band-gap and small lattice mismatch to that of the core material, epitaxially on the surface of the core particle, producing a "core-shell" particle. Core-shell particles separate any carriers confined in the core from surface states that would otherwise act as non-radiative recombination centers. One example is QDs having a ZnS shell grown on the surface of a CdSe core.

Rudimentary QD-based light-emitting devices have been made by embedding colloidally produced QDs in an optically clear LED encapsulation medium, typically a silicone or an acrylate, which is then placed on top of a solid-state LED. The use of QDs potentially has some significant advantages over the use of the more conventional phosphors, such as the ability to tune the emission wavelength, strong absorption properties, improved color rendering, and low scattering. Any of the methods herein may comprise one or more steps comprising normalizing values obtained from exposure of a sample to a substrate specific for one or a plurality of known enzymes disclosed herein (or functional fragments thereof) comprising one or a plurality of quantum dots.

For the commercial application of QDs in next-generation light-emitting devices, the QDs are preferably incorporated into the LED encapsulating material while remaining as fully mono-dispersed as possible and without significant loss of quantum efficiency. The methods developed to date are problematic, not least because of the nature of current LED encapsulants. QDs can agglomerate when formulated into current LED encapsulants, thereby reducing the optical performance of the QDs. Moreover, once the QDs are incorporated into the LED encapsulant, oxygen can migrate through the encapsulant to the surfaces of the QDs, which can lead to photo-oxidation and, as a result, a drop in quantum yield (QY).

One way of addressing the problem of oxygen migration to the QDs has been to incorporate the QDs into a medium with low oxygen permeability to form "beads" of such a material containing QDs dispersed within the bead. The QD-containing beads can then be dispersed within an LED encapsulant. Examples of such systems are described in U.S. patent application Ser. No. 12/888,982, filed Sep. 23, 2010 (Pub. No.: 2011/0068322) and Ser. No. 12/622,012, filed Nov. 19, 2009 (Pub. No.: 2010/0123155), the entire contents of which are incorporated herein by reference.

The disclosure relates to methods of detecting a Sap protein in a patient, said method comprising: obtaining a sample from a subject; and detecting whether a Sap protein is present by quantifying a cleavage product from a Sap protein after the Sap protein is exposed to the sample for a time period sufficient to cleave a substrate specific from the Sap protein.

The disclosure relates to methods of detecting any fungal biomarker in a patient, said method comprising: obtaining a sample from a subject; and detecting whether a Sap protein is present by quantifying a cleavage product from a Sap protein after the Sap protein is exposed to the sample for a time period sufficient to cleave a substrate specific from the Sap protein.

The disclosure relates to methods of detecting any fungal biomarker in a patient, said method comprising: obtaining a sample from a subject; and detecting whether a biomarker is present by detecting the presence of a pattern of cleavage products in the sample by contacting the sample with any one or plurality of substrates specific for the enzymes disclosed in Table 1 for a time period sufficient to cleave a substrate specific to the enzymes of Table 1 and detecting the presence of cleavage products in a pattern identified in the examples section, such that if the enzymes of Table 1 are present in the sample and create one or more of the patterns of cleavage products disclosed herein, the presence of the patterns is correlated to the presence of the biomarker.

Kits

In some embodiments, kits in accordance with the present disclosure may be used to culture and/or to propagate cells or fungal cell types of interest. In some embodiments, kits in accordance with the present disclosure may be used to diagnose, prognose or calculate the likelihood that a subject has a pathogenic fungal infection or an infection capable of or existing as a biofilm or planktonic form. In some embodiments, kits for culturing cells comprises any substrate or polypeptide described herein with an affinity to one or more biomarkers; and, optionally, further comprise cell culture medium and a control cell type of interest. Any array, system, or component thereof disclosed may be arranged in a kit either individually or in combination with any other array, system, or component thereof. The invention provides a kit to perform any of the methods described herein. In some embodiments, the kit comprises at least one container comprising one or a plurality of polypeptides comprising a polypeptide sequence with an affinity for the one or plurality of enzymes or functional fragments thereof disclosed herein. In some embodiments, the kit comprises at least one container comprising any of the polypeptides or functional fragments described herein. In some embodiments, the polypeptides are in solution (such as a buffer with adequate pH and/or other necessary additive to minimize degradation of the polypeptides during prolonged storage). In some embodiments, the polypeptide are lyophilized for the purposes of resuspension after prolonged storage. In some embodiments, the kit comprises: at least one container comprising one or a plurality of polypeptides comprising a polypeptide sequence associated with fungal biofilm synthesis or maintenance (or functional fragments thereof); and a solid support upon which polypeptides with affinity for any biomarkers for such synthesis or maintenance may be affixed. In some embodiments, the kit optionally comprises instructions to perform any or all steps of any method described herein. In some embodiments, the kit comprises an array or system described herein and instructions for implementing one or a plurality of steps using a computer program product disclosed herein. It is understood that one or a plurality of the steps from any of the methods described herein can be performed by accessing a computer program product encoded on computer storage medium directly through one or more computer processors or remotely through one or more computer processors via an internet connection or other virtual connection to the one or more computer processors. In some embodiments, the kit comprises a computer-program product described herein or requisite information to access a computer processor comprising the computer program product encoded on computer storage medium remotely. In some embodiments, the computer program product, when executed by a user, calculates one or more raw values of signal intensity, normalizes the one or more values into a one or more scores based upon values from a control sample, generates one or more biofilm signatures or one or more biofilm profiles, and/or displays any of the values, biofilm signatures, biofilm profiles to a user. In some embodiments, the kit comprises a computer program product encoded on a computer-readable storage medium that comprises instructions for performing any of the steps of the methods described herein. In some embodiments, the invention relates to a kit comprising instructions for providing one or more biofilm signatures, biofilm profiles, or any combination thereof. In some embodiments, the kit comprises a computer program product encoded on a computer storage medium that when, executed on one or a plurality of computer processors, quantifies a raw value corresponding to an amount of biomarker present in a sample, determines biofilm signatures or biofilm profiles, and/or displays the signature, value, signature, and/or any combination thereof. In some embodiments, the kit comprises a computer program product encoded on a computer storage medium that, when executed by one or a plurality of computer processors, quantifies values of one or more samples and determines a biofilm signature based at least partially upon the values corresponding to the amount of biomarker present in a sample. In some embodiments, kit comprises instructions for accessing the computer storage medium, quantifying values, normalizing the values, determining a signature of a biofilm, and/or any combination of steps thereof. In some embodiments, the computer-readable storage medium comprises instructions for performing any of the methods described herein. In some embodiments, the kit comprises an array or system disclosed herein and a computer program product encoded on computer storage medium that, when executed, performs any of the method steps disclosed herein individually or in combination and provides instructions for performing any of the same steps. In some embodiments, the instructions comprise an instructions to adhere any one or plurality of polypeptides disclosed herein to a solid support.

The invention further provides for a kit comprising one or a plurality of containers that comprise one or a plurality of the polypeptides or fragments disclosed herein. In some embodiments, the kit comprises cell media that enhances the culture or proliferation of cells. In some embodiments, the kit comprises: an array disclosed herein, any cell media disclosed herein, and a computer program product disclosed herein optionally comprising instructions to perform any one or more steps of any method disclosed herein. In some embodiments, the kit comprises a device for affixing one or more polypeptides disclosed herein to a solid support.

The kit may contain two or more containers, packs, or dispensers together with instructions for preparation of an array. In some embodiments, the kit comprises at least one container comprising the array or system described herein and a second container comprising a means for maintenance, use, and/or storage of the array such as storage buffer. In some embodiments, the kit comprises a composition comprising any polypeptide disclosed herein in solution or lyophilized or dried and accompanied by a rehydration mixture. In some embodiments, the polypeptides and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The invention also provides a kit comprising: an array of polypeptides, the array comprising: a solid support and a plurality of polypeptides capable of binding to one or a plurality of biomarkers disclosed herein. In some embodiments, the kit further comprises at least one of the following: cell media, a volume of fluorescent stain or dye, a cell sample, and a set of instructions, optionally accessible remotely through an electronic medium.

In some embodiments, the disclosure provides a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof. In some embodiments, the disclosure provides a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof. In some embodiments, the disclosure provides a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof, wherein the any one or plurality of substrates comprises a fluorogenic probe, the fluorescence of which correlates to the amount of substrate converted to a reaction product upon exposure to any one or more of the enzymes disclosed herein, or functional fragments thereof. In some embodiments, the solid support is a plastic plate arranged in a single well or multiplexed format. In some embodiments, the solid support is a multi-well plate (such as a 364-well plate) in which substrates labeled with fluorogenic probes are positioned within one or a plurality of the wells.

The disclosure provides for a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof, wherein the any one or plurality of substrates comprises a fluorogenic probe, the fluorescence of which correlates to the amount of substrate converted to a reaction product upon exposure to any one or more of the enzymes disclosed herein, or functional fragments thereof. in some embodiments the substrates are capable of being cleaved upon exposure to any one or plurality of the enzymes disclosed herein. In some embodiments, the reaction products are quantifiable by fluorescence values obtained through use of a fluorimeter or spectrophotometer. In some embodiments, the reaction products are quantifiable by detecting fluorescence energy transfer of a fluorogenic probe exposed to a known wavelength of electromagnetic energy after a substrate, comprising the probe, is treated with a sample. One example of FRET measurements are provided for in US Application No. 20040191786.

The disclosure also provides for kits comprising a solid support in one container and a series of containers comprising one or a plurality of substrates comprising amino acid sequences with cleavage sites specific for any one or plurality of enzymes that are at least 70% homologous to any of the enzymes disclosed herein (for instance, those proteases listed and incorporated by reference in Tables 1, 2, or 3).

Any and all journal articles, patent applications, issued patents, or other cited references disclosed herein (including GenBank Accession numbers or other genetic information identification tags dated as of the date of the application filing) are incorporated by reference in their respective entireties. Any of the systems, methods or devices disclosed herein comprising Sap proteins may be made or performed or used with any of the aminopeptidases or subtilisin family of proteases disclosed herein. In some embodiments, the systems, methods or devices disclosed herein are selectively free of any one or combination of enzymes disclosed herein.

EXAMPLES

Example 1: Global Identification of Biofilm-Specific Proteolysis in *Candida albicans*

*Candida albicans* is a normal resident of the human microbiota, asymptomatically colonizing many areas of the body, including the gastrointestinal tract, genitourinary tract, oral cavity, and skin of healthy individuals. However, *C. albicans* is also the most prevalent fungal pathogen of humans. Alterations in host immunity, damaged barrier functions, stress, and resident microbiota can lead to fungal infections. These infections range from superficial mucosal and dermal infections, such as thrush, vaginal yeast infections, and diaper rash, to hematogenously disseminated candidiasis with mortality rates as high as 47 percent (1). *C. albicans* infections can be especially serious in immunocompromised individuals, such as patients undergoing chemotherapy, transplantation patients receiving immunosuppression therapy, and healthy individuals with implanted medical devices (2-4).

The medical impact of *C. albicans* depends on its ability to form resilient and drug resistant surface-associated communities called biofilms (5-8). Biofilms can be formed on all implanted medical devices, including catheters, pacemakers, dentures, contact lenses, and prosthetic joints, which provide efficient substrates for biofilm growth. Biofilms can also colonize biotic surfaces, such as mucosal and epithelial cells, with life-threatening colonization and invasion of parenchymal organs occurring during disseminated infections (5-8). Because *C. albicans* biofilms are resistant to existing antifungal drugs and can be a constant reservoir for systemic infections, early detection of biofilm infections is critical to improving patient outcome. In individuals with implanted medical devices, the only current treatment for device-associated biofilm infections is removal of the implanted device, oftentimes through surgical intervention (5-8).

Recent genome-wide transcriptional analysis has identified certain secreted aspartyl protease (SAP) genes as being significantly upregulated during biofilm formation (9). Members of the Sap family (there are ten total) have been previously implicated as virulence factors that appear to function in diverse roles, including host cell adhesion, invasion, nutrient acquisition, activation of inflammatory response, and immune escape (10, 11). However, increasing evidence points to distinct biological functions for each SAP gene (11), and little information exists regarding their specific roles during biofilm development.

Because certain SAP genes were transcriptionally upregulated during biofilm formation, we hypothesized that extracellular proteases could serve as biofilm-specific markers. To increase the scope of our analysis, we used a newly developed approach to identify biofilm-specific protease activity in an unbiased way. Here, a highly diverse 228-member synthetic peptide library was exposed to soluble factors produced by *C. albicans* biofilms, and peptide cleavage sites were determined using mass spectrometry. Based on these cleavages, global profiles of biofilm and suspension protease activity were deduced. This analysis, coupled with conventional proteomics analysis, identified Sap5 and Sap6 as major biofilm-specific protease activities. Profiling of recombinantly produced Sap5 and Sap6 revealed that they have non-overlapping substrate specificities. Based on these substrate specificity profiles, fluorogenic peptide substrates were synthesized that could distinguish between Sap5 and Sap6, confirming that the activities of both proteases are highly upregulated during biofilm formation. We created *C. albicans* strains deleted for SAP5 and SAP6 and found that both deletions compromised in vitro biofilm formation with the sap6Δ/Δ deletion having the larger effect. This work establishes secreted proteolytic activity as a promising enzymatic marker for detection of *C. albicans* biofilms.

Global Protease Profiling of Biofilm and Planktonic *C. albicans*.

To identify global profiles or signatures of proteolytic activity associated with biofilm formation, conditioned media from a wild-type *C. albicans* strain grown under biofilm and planktonic conditions was assayed using Multiplex Substrate Profiling by Mass Spectrometry (MSP-MS) (12). Matched 24-hour conditioned media preparations were incubated with a physicochemically diverse library of 228 synthetic peptide substrates, and time-dependent peptide cleavage products were identified through liquid chromatography-tandem mass spectrometry (LC-MS/MS). Comparison of the complex cleavage profiles revealed that biofilm conditioned media displayed an overall higher specific activity against the peptide library, based on the total number of peptide cleavages observed throughout the assay time course (n=308 for biofilm and n=185 for planktonic at 240 min) (FIGS. 1A and 6). Motif analysis subsequently was performed to quantify the global protease substrate specificities of the biofilm and planktonic conditions. iceLogo representations (13) that consider both cleaved and uncleaved positions in the peptide library were employed to represent the fold-enrichment and de-enrichment of amino acids flanking each cleavage site (cleavage occurs between P1 and P1' positions) (FIGS. 1A and 6). Among the shared specificity features identified, both the biofilm and planktonic conditions displayed an enrichment of bulky hydrophobic residues (e.g. norleucine) and arginine at the P1 position, hydrophobic residues at the P1' position, and arginine at the P2' position with the biofilm condition displaying more notable non-prime-side specificity (P4-P1).

The biofilm and planktonic conditions also yielded numerous unique cleavages against the peptide library (FIG. 1B) (n=202 for biofilm and n=79 for planktonic). To quantify differences in global substrate specificity, Z-scores (13) were used to generate a difference map derived from residue preferences at each sub-site (FIG. 1C). This analysis revealed significant physicochemical differences in substrate specificity. The biofilm condition displayed an increased preference for basic residues (lysine and arginine) at the P1 and P1' positions, whereas the planktonic condition displayed an increased preference for aspartic acid at the P1' position and certain P1 and P1' hydrophobic residues (e.g. P1'-tyrosine). In addition, the biofilm condition displayed an increased preference for non-prime-side hydrophobic residues with the strongest preference for isoleucine at the P2 position. Due to the higher specific activity evident in the *C. albicans* biofilm conditioned media, we further compared across assay time points with similar numbers of cleavages (60 min and 240 min for the biofilm and planktonic conditions, respectively) to confirm these specificity differences (FIG. 7). Together, our substrate profiling results indicate that in addition to exhibiting higher total activity against the peptide library, the biofilm condition is associated with a distinct global protease substrate specificity profile.

Proteomic Identification of Biofilm-Specific Proteases.

To identify specific proteases that have increased abundance under biofilm conditions, shotgun proteomics analysis was performed on matched conditioned media preparations from biofilm and planktonic cultures. Trypsin-derived peptides were sequenced with LC-MS/MS and searched against the *Candida* UniProt database. In the biofilm conditioned media, two members of the Sap family, Sap5 and Sap6, were the most abundant proteases identified based on spectral counting (14) with 21 and 14 spectral counts, respectively (Table 4). These proteases were found to have significantly higher relative abundance in the biofilm conditioned media compared to the planktonic conditioned media with no tryptic peptides detected for Sap6 and fewer peptides detected for Sap5 in the planktonic condition. All tryptic peptides identified were located within the mature Sap5 and Sap6 enzymes, suggesting that the proteases are predominately observed in their mature, processed forms.

TABLE 4

Protease identification in wild-type (SN425) biofilm and planktonic conditioned media with shotgun proteomics

| Protease Name | GenBank Accession | Planktonic | | | Biofilm | | |
|---|---|---|---|---|---|---|---|
| | | Unique Peptides | Percent Coverage | Protein Score | Unique Peptides | Percent Coverage | Protein Score |
| Sap5 | P43094 | 4 | 9.1 | 118.8 | 12 | 23.9 | 365.4 |
| Sap6 | Q5AC08 | | | | 10 | 28.2 | 268.3 |
| Kex2 | Q5APK9 | | | | 2 | 2.5 | 80.0 |

In addition to the Saps, tryptic peptides corresponding to the catalytic domain of the subtilisin-like serine protease Kex2 were found to have higher abundance in the biofilm conditioned media. Kex2 is a single-pass transmembrane protease with a luminal catalytic domain that is well known in *Saccharomyces cerevisiae* to fulfill a proprotein processing role in the trans-Golgi network and the late endosome/prevacuolar compartment (15). Although the release of Kex2 into conditioned media from small amounts of non-specific cell lysis cannot be ruled out, recent characterization of the *C. albicans* biofilm matrix composition identified cytosolic metabolic proteins (16), suggesting that the extracellular localization (perhaps through limited cell lysis) of typically intracellular components may represent a relevant biofilm-specific process.

Biofilm-Specific Cleavages are Attributable to Sap5 and Sap6.

To assign biofilm-specific cleavages in the peptide library to the candidate proteases, mature Sap5, Sap6, and soluble Kex2 were expressed recombinantly in *Pichia pastoris* and profiled using the MSP-MS assay. Sap5 and Sap6 were found to have broad substrate specificities against the peptide library, yielding over 140 cleavages after 240 min (FIG. 2A). Kex2 was found to have comparatively high specificity with cleavages occurring strictly after K/R-R (P2-P1) pairings (FIG. 8) in agreement with its biological processing role and as shown previously using recombinantly produced Kex2 proteases (17).

Assessment of the global substrate specificity profiles for recombinantly produced Sap5 and Sap6 revealed shared residue preferences. These preferences include lysine and bulky hydrophobic residues (phenylalanine, tyrosine, norleucine, and leucine) in the P1 position, hydrophobic residues in the P4 through P2 positions, and arginine in the P2' position (FIG. 2A), resembling the biofilm cleavage profile (FIGS. 1A and 6). Even though mature Sap5 and Sap6 share a high degree of sequence conservation (80%), they produced numerous unique cleavages against the peptide library (30% and 29% at 240 min for Sap5 and Sap6, respectively). A difference map calculated from position-specific Z-scores further revealed pronounced differences in Sap5 and Sap6 substrate specificity (FIG. 2B). Among the most prominent specificity features, this analysis demonstrated that Sap6 displays an increased preference for lysine at the P1' position, basic residues (lysine and arginine) at the P2' position as well as certain non-prime-side hydrophobic residues, such as alanine at the P3 position and isoleucine at the P2 position. In contrast, Sap5 displays an increased preference for tyrosine at the P1 position, threonine at the P1 and P1' positions, and distinct hydrophobic residues at the P2 and P3 positions.

To assess the contributions of Sap5 and Sap6 specificity to the complex conditioned media profiles, conditioned media was pretreated with the aspartyl protease inhibitor pepstatin A prior to analysis with the MSP-MS assay. Pepstatin-sensitive cleavages in the peptide library were identified (FIG. 2C) and revealed a substrate specificity motif for the biofilm condition that shared the dominant specificity features of the purified Saps (FIG. 2D). Biofilm and planktonic cleavages that both displayed pepstatin sensitivity and matched those derived from the recombinantly produced proteases were used to assign cleavages in the conditioned media profiles to Sap5 and Sap6 activity (FIG. 2E). Using this approach, a larger proportion of biofilm-specific (39%) than planktonic-specific (4%) cleavages could be attributed to the Saps, indicating significantly increased Sap5 and Sap6 activity in the biofilm condition with Sap6 accounting for a larger proportion of the biofilm-specific activity (five cleavages versus one cleavage).

To date, Sap family proteases are the only C. albicans secreted proteases that have been experimentally documented. However, our global analysis revealed numerous cleavages not attributable to Sap5 or Sap6 activity from proteases that are in lower abundance. Biofilm-specific cleavages not attributable to Sap5 or Sap6 display an overall preference for arginine and phenylalanine at the P1 position (FIG. 9). In contrast, unassigned planktonic-specific cleavages display a distinct preference for bulky hydrophobic residues at both the P1 and P1' positions. Mapping of cleavage site position along the 14-mer peptide substrates indicated comparatively higher aminopeptidase-like activity in the planktonic condition with the majority of unassigned cleavages occurring one to three positions from the peptide N-termini (FIG. 9).

Construction of Sap5 and Sap6 Fluorogenic Peptide Substrates.

To further quantify Sap5 and Sap6 proteolysis in biofilm and planktonic conditioned media, we developed fluorogenic substrates with selectivity for Sap5 and Sap6. MSP-MS peptides displaying high Sap activity were re-pooled into a smaller 25-member sub-library, and a time course was used to refine cleavage preferences for these individual peptide substrates (FIG. 3A). Among the 29 cleavages with the highest activity, 8 were found to favor Sap5 whereas 13 were found to favor Sap6 (FIG. 10). For each protease, two 8-mer peptide sequences containing P4-P4' residues from Sap5- or Sap6-favored cleavages were selected for incorporation into internally quenched fluorogenic peptides. The fluorogenic probes were synthesized bearing either a 5-carboxyfluorescein or 7-methoxycoumarin fluorophore with a corresponding quencher positioned at opposing termini such that peptide cleavage yields a fluorescence signal. Among the fluorogenic substrates evaluated, the sequences VFILWRTE (SEQ ID NO: 22) and TFSYnRWP (SEQ ID NO: 23) were found to afford both the highest specific activity and selectivity for Sap5 and Sap6, respectively (FIGS. 3B and 11).

Sap5 and Sap6 Activity are Upregulated in the Biofilm Condition.

In agreement with the prior MSP-MS cleavage site analysis, application of the fluorogenic substrates to the biofilm and planktonic conditioned media revealed a dramatic increase in substrate cleavage under the biofilm condition with the Sap6 substrate showing higher biofilm activity (FIG. 3B). Pepstatin pretreatment resulted in a significant reduction in substrate cleavage, confirming predominant aspartyl protease-derived activity (FIG. 4A). To further confirm probe selectivity for the target proteases, conditioned media preparations were also assayed from sap5Δ/Δ and sap6Δ/Δ single deletion mutant strains and a sap5/6ΔΔ/ΔΔ double deletion mutant strain (FIG. 4B). Deletion of both SAP5 and SAP6 in the double mutant significantly reduced the cleavage of both probes in the biofilm condition, indicating that Sap5 and Sap6 are the major contributing activities. To our initial surprise, the individual sap5Δ/Δ and sap6Δ/Δ mutant strains did not show reduced substrate cleavage to the levels achieved in the sap5/6ΔΔ/ΔΔ double mutant strain. In the case of the individual sap5Δ/Δ deletion strain, activity against the Sap6 substrate increased, suggesting a compensation mechanism for loss of SAP5. Indeed, shotgun proteomics analysis on matched biofilm conditioned media preparations from the wild-type reference and mutant strains confirmed an increase in Sap6 levels associated with the sap5Δ/Δ mutant strain. In contrast, there was no observable increase in Sap5 levels associated with the sap6Δ/Δ mutant strain in agreement with the activity results (Table 5). We note that substrate cleavage in the sap5/6ΔΔ/ΔΔ double deletion mutant strain indicates proteolytic activity from additional proteases that are in lower abundance, possibly reflecting compensation for loss of SAP5/SAP6.

TABLE 5

Sap identification by LC-MS/MS in biofilm conditioned media from wild-type SN250 and sap5Δ/Δ, sap6Δ/Δ, and sap5/6ΔΔ/ΔΔ deletion strains.

| Protease | | Unique Peptides | | | |
|---|---|---|---|---|---|
| Name | Accession | Wild-Type | sap5Δ/Δ | sap6Δ/Δ | sap5/6ΔΔ/ΔΔ |
| Sap5 | P43094 | 24 | 0 | 21 | 0 |
| Sap6 | Q5AC08 | 11 | 19 | 0 | 0 |

Deletion of SAP5 and SAP6 Compromises Biofilm Formation.

Next, we evaluated the effects of deletion of SAP5, SAP6, and SAP5/6 on C. albicans biofilm formation. After 24 hours of growth, the sap5Δ/Δ, sap6Δ/Δ and sap5/6ΔΔ/ΔΔ mutant strains displayed reduced biofilm growth compared to the wild-type reference strain with the sap6Δ/Δ and sap5/6ΔΔ/ΔΔ mutants having the most noticeable defects (FIG. 5A). The sap5Δ/Δ, sap6Δ/Δ, and sap5/6ΔΔ/ΔΔ mutant strains all displayed comparable growth rates in suspension cultures (Table 2), indicating that the biofilm defects were not a result of inherent growth differences. Biofilms after 24 hours of growth were quantified using a standard $OD_{600}$ biofilm assay as described previously (18) (FIG. 5B). This analysis supported a significant reduction in biofilm formation for the sap5Δ/Δ (P=4.5×10$^4$), sap6Δ/Δ (P=3.5×10$^{-3}$), and sap5/6ΔΔ/ΔΔ (P=4.8×10$^4$) deletion strains compared to the wild-type reference strain. Reintroduction of wild-type alleles of SAP5 and SAP6 into each of the sap5Δ/Δ and sap6Δ/Δ deletion mutant strains, respectively, restored normal biofilm levels, validating the functional roles of both SAP5 and SAP6 in biofilm formation.

To model physiological growth conditions, time-dependent biofilm formation for the sap5Δ/Δ, sap6Δ/Δ, and sap5/6ΔΔ/ΔΔ strains was visualized in vitro under dynamic flow conditions that mimic the blood flow rate of human catheters. Time-lapse microscopy videos of biofilm development were recorded for 720 min post-adherence using a BioFlux microfluidic device (Fluxion Biosciences) attached to a Zeiss time-lapse microscope. In agreement with the $OD_{600}$ measurements, the sap6Δ/Δ and sap5/6ΔΔ/ΔΔ mutant strains had a marked reduction in biofilm growth compared to the wild-type reference strain, with the sap5Δ/Δ strain showing a weaker defect (FIG. 5C). These results suggest that Sap6 may play a more prominent functional role in biofilm formation than Sap5.

DISCUSSION

The ability of *C. albicans* to form biofilms on biotic surfaces and implanted medical devices provides a major source of new infections and presents a treatment challenge due to the resistance of biofilms to conventional antifungal drugs (8). Identification of biofilm-specific molecular markers is predicted to improve patient outcome through early detection of biofilm-associated infections. Beginning with a global activity-based approach, we identified Sap5 and Sap6 as major secreted biofilm-specific protease activities. Global substrate specificity profiling coupled with the design of specific peptide substrates show that secreted Sap5 and Sap6 activities are highly increased during biofilm formation. Deletion of SAP5, SAP6, and SAP5/6 show directly that both proteases play important roles in in vitro models of biofilm formation and suggest that Sap5 and Sap6 may have distinct mechanisms of regulation and non-overlapping biological functions.

Global substrate specificity profiling resulted in the unanticipated finding that Sap5 and Sap6 have different cleavage site preferences. A previous effort to characterize the substrate specificities of Sap5 and Sap6 focusing on the P1 position did not report detailed differences in specificity; however this study used pooled libraries of internally quenched fluorogenic peptides (19) where the cleavage location and kinetics of individual substrates could not be readily decoupled. A comparative model (20) of Sap6 using the crystallographic structure of pepstatin-bound Sap5 (21) indicated that Sap6 has, overall, a well-conserved active site but that there are significant differences at several key amino acid positions (FIG. 13). These include a Sap5 to Sap6 G161A substitution in the S2 pocket, an R196H substitution near the base of the S1 and S3 pockets, and G207N and K270T substitutions near the pepstatin P3' position; these altered residues likely contribute to the observed specificity differences.

Differences in substrate specificities suggest that Sap5 and Sap6 may have different endogenous substrates or, at the very least, altered kinetics of substrate cleavage. Efforts to characterize the biological functions of Sap5 and Sap6 have focused on their potential invasive roles. Saps are hypothesized to degrade and distort host cell membranes to facilitate adhesion and tissue damage (11) with new evidence pointing to integrin-mediated internalization of Saps 4, 5, and 6 leading to epithelial cell apoptosis (22). In addition, SAP4-6 have been shown to be hyphae-specific genes (23, 24) with SAP6 induction only in hyphae-infiltrated tissue (25) and SAP6 induction resulting in the majority of hyphal penetration and damage to parenchymal organs in systemic models of *C. albicans* infection (26).

The results described here suggest that Sap5 and Sap6 serve additional roles during biofilm formation that are distinct from invasion of host tissues. Sap6 (and not Sap5) has recently been shown to mediate cell-cell aggregation of *C. albicans*, promoting cellular adhesion in a protease activity independent manner (27). Sap5 and Sap6 activity may serve biofilm-specific functions through adhesion, extracellular matrix formation and remodeling, or nutrient acquisition. Indeed, recent investigations into the *C. albicans* biofilm extracellular matrix composition identified a large number of metabolic proteins, including hydrolytic enzymes (16), suggesting that the biofilm matrix may be an enzymatically active reservoir. It is also possible that Sap5 and Sap6 may carry out specialized biofilm-related signaling roles. For example, secreted and surface-localized Saps have been shown to act as "sheddases" (28), with recent evidence linking extracellular Sap8-mediated shedding of the mucin Msb2 to activation of the Cek1 MAPK pathway (29). Substrate specificity preferences identified for Sap5 and Sap6 may guide the prediction and discovery of endogenous cleavage sites, further refining the mechanistic roles of Sap5 and Sap6 in biofilm development.

The work presented here clearly shows that secreted Sap5 and Sap6 proteolytic activities are up-regulated in *C. albicans* biofilms compared with planktonic culture, although further work is required to reveal their precise roles in mediating biofilm formation in distinct physiological contexts. In addition, this work shows that biofilm-secreted proteases—detectable with specific fluorogenic substrates—can be used to detect *C. albicans* biofilms. Finally, the requirement of Sap5 and Sap6 for proper biofilm formation suggests that targeting these proteases could be a therapeutic strategy for preventing biofilm formation.

Materials and Methods

Strain Construction. Construction of the sap5Δ/Δ (SAP5MS4B) and sap6Δ/Δ (SAP6MS4B) single and sap5/6ΔΔ/ΔΔ (SAP56MS4B) double mutant strains were described previously (30). SAP5 and SAP6 complementation strains, CJN2831 and CJN2833, in the sap5Δ/Δ and sap6Δ/Δ mutant backgrounds, respectively, were constructed by cloning SAP5 and SAP6 exons (containing 800 bp upstream sequence of the start codon and 500 bp downstream sequence of the stop codon) into plasmid pJCP055 (31); integration into *C. albicans* was verified by colony PCR.

Conditioned Media Preparation. *C. albicans* strains were grown overnight at 30° C. in YPD medium. These cultures were diluted to an $OD_{600}$ of 0.5 or 0.05 in RPMI medium for biofilm and planktonic conditions, respectively. For planktonic cultures, two 150 mL Erlenmeyer flasks with 25 mL of RPMI medium were seeded with overnight culture and grown at 37° C. while shaking at 300 rpm in a New Brunswick Scientific incubator for 24 hours. *C. albicans* biofilm cultures were grown in 6-well non-tissue culture polystyrene plates by first seeding 4 mL of overnight culture in RPMI medium and allowing cells to adhere for 90 min at 200 rpm in an ELMI plate shaker set to 37° C. Non-adherent cells were washed with 4 mL of PBS, 4 mL of fresh RPMI was added, and biofilms were grown for 24 hours. Conditioned media was harvested by collecting *C. albicans* from two flasks of planktonic culture or two plates of biofilm culture, spinning at 3750 rpm for 10 min to pellet cells, and collecting only the supernatant. This supernatant was then filtered using a 0.45 μm syringe filter prior to flash freezing in liquid nitrogen and storing at −80° C. Thawed conditioned media was concentrated through centrifugation with a 10 kDa molecular weight cut-off (MWCO) spin filter and buffer exchanged through >10-fold dilution into D-PBS (pH 7.4) prior to a final spin concentration step. Protein was quantified using the method of Bradford and stored at −80° C.

Recombinant Protease Expression. Recombinant proteins were produced using a *Pichia pastoris* expression system. *P. pastoris* strains expressing Sap5 and Sap6 from *C. albicans* and Kex2 from *Saccharomyces cerevisiae* have been described (32, 33). *P. pastoris* cultures (1 L) were grown to saturation in BMGY for 2 days at 30° C. Cells were harvested and resuspended in 200 mL BMMY containing 0.5% methanol. Cells were cultured 2 days for Sap5 and Sap6 expression and 1 day for Kex2 expression. Culture supernatant was passed through a 0.22 μm vacuum filter and stored at −80° C.

Recombinant Protein Purification.

Recombinant *C. albicans* Sap5 and Sap6 were purified using methods adapted from Borelli (21).

Proteomic Analysis of *C. albicans* Biofilm and Planktonic Condition Media.

Protein identification in 24-hour conditioned media was performed using peptide sequencing by mass spectrometry. Conditioned media preparations were from matched wild-type *C. albicans* (SN425 and SN250) biofilm and planktonic cultures and matched biofilm cultures from the wild-type (SN250) reference strain and sap5Δ/Δ, sap6Δ/Δ, and sap5/6ΔΔ/ΔΔ deletion strains. Secretion samples (4 μg) from three technical replicates were incubated with 6 M urea and 10 mM DTT for 20 min at 55° C. Samples underwent alkylation with 12.5 mM iodoacetamide in the dark at ambient temperature for 1 hour. Samples were quenched with 10 mM DTT and the final volume diluted 3-fold into 25 mM ammonium bicarbonate. Trypsin digestion was performed with 1:20 sequencing-grade trypsin (Promega): total protein for an overnight period at 37° C. Samples were acidified to approximately pH 2 with formic acid. Peptides were desalted using $C_{18}$ ZipTips, lyophilized, and rehydrated in 0.2% formic acid. Procedures for peptide sequencing with LC-MS/MS and data analysis are provided.

Multiplex Substrate Profiling by Mass Spectrometry (MSP-MS).

Substrate specificity profiles were determined for 24-hour conditioned media from wild-type *C. albicans* (SN425) biofilm and planktonic cultures and for recombinant Sap5, Sap6 and Kex2 using the MSP-MS assay (12). Conditioned media preparations were profiled in the absence of inhibitor and following 30 min pre-incubation on ice with 10 μM pepstatin A or 1 mM EDTA. Recombinant Saps and Kex2 were profiled in an identical manner in the absence of inhibitor and following pre-treatment with either 10 μM pepstatin A (Saps) or 1 mM EDTA (Kex2). MSP-MS assays were carried out as described previously (12). Briefly, 20 μg/mL conditioned media, 2 μg/mL Sap5, 0.2 μg/mL Sap6, 2 μg/mL Kex2, and matched no-enzyme controls were assayed against a diverse library of 228 tetradecapeptides pooled at 500 nM in D-PBS (pH 7.4) for Kex2 or matched MES at pH 5.5 (9.5 mM MES, 2.7 mM KCl, 140 mM NaCl) for recombinant Saps and conditioned media. Sap5 and Sap6 concentrations were selected to normalize for cleavage number. After 15, 60, and 240 min, 30 μL of assay mixture was removed, quenched with 7.5 μL 20% formic acid, and flash-frozen in liquid $N_2$. For sub-library profiling with the recombinant Saps, 0.2 μg/mL of Sap5 and Sap6 were assayed in the MES buffer (pH 5.5) against a sub-library of 25 tetradecapeptides pooled at 500 nM. After 1, 5, 15, 30, 120, 240, and 1440 min, 29 μL of assay mixture was removed and quenched with a mixture of 7.5 μL 20% formic acid and 1 μL 375 μM pepstatin A prior to flash-freezing in liquid $N_2$. All peptide samples were desalted using $C_{18}$ ZipTips, lyophilized, and rehydrated in 0.2% formic acid. Procedures for peptide sequencing with LC-MS/MS and data analysis are provided.

Peptide Synthesis of Fluorogenic Substrates.

Fluorogenic substrate synthesis was performed using standard solid phase peptide synthesis protocols.

Protease Activity Assays

Activity assays with internally quenched fluorogenic substrates were performed up to one hour in black 96-well round bottom plates (Costar) using a BioTek Synergy H4 Hybrid Multi-Mode Microplate Reader set to 37° C. The following excitation/emission wavelengths were used: 328 nm/393 nm (gain 96) for MCA and Ex/Em of 485 nm/538 nm (gain 94) for 5-FAM. RFU was corrected to moles of product formation as appropriate using a conversion factor calculated from the total proteolytic hydrolysis of each substrate. Activity assays with conditioned media were performed with 10 μM substrate and either 20 μg/mL protein sample for VFILWRTE (SEQ ID NO: 22) or 10 μg/mL protein sample for TFSYnRWP (SEQ ID NO: 23). For assays with recombinant Saps, 2 μg/mL Sap5 and Sap6 were used with the following substrate concentrations: VFILWRTE (10 μM; SEQ ID NO: 22), IYRnHVQL (25 μM; SEQ ID NO: 24), WPSnNKVG (25 μM; SEQ ID NO: 25), and TFSYnRWP (10 μM; SEQ ID NO: 23). Pre-incubation with 10 μM pepstatin A was performed for 30 min on ice. All activity assays were performed in the MES (pH 5.5) buffer described above, which contained 0.01% Titron X-100 for recombinant enzyme activity measurements. Initial rates are reported from a linear fit of the progress curves obtained using Gen5 software v.2.03.

Biofilm Formation Phenotype Assays.

Biofilm formation assays using $OD_{600}$ measurements were carried out as described (18). Time-dependent biofilm formation assays were performed under flow using a BioFlux EZ1000 (Fluxion Biosciences) microfluidic instrument. Briefly, overnight cultures grown at 30° C. in YPD medium were diluted to a final $OD_{600}$ of 0.5 in Spider medium. Cells for each strain were seeded in replicates on a BioFlux 48-Well Low-Shear plate (Fluxion Biosciences) and allowed to adhere at 37° C. for 20 minutes. Non-adhered cells were washed away by flowing media at 1 dyn/cm² for 5 minutes. The biofilms were grown for 12 hours at 37° C. with media passage at 0.5 dyn/cm², and time-lapse images were captured every 5 minutes using a Zeiss AX10 microscope with a 10× objective in bright-field and phase-contrast for each well. Three fields of vision were used for each replicate, and representative images from select time points are shown.

Growth Assays.

Growth assays were performed using previously described methods (34). Briefly, cells from an overnight culture grown in YPD medium at 30° C. were inoculated into 100 μL of YPD medium at a starting $OD_{600}$ of 0.01. The assay was performed in flat-bottom 96-well plates (BD Falcon) with three replicates for each strain. Growth curves were generated in a BioTek plate reader at 30° C. with 400 rpm orbital shaking. $OD_{600}$ measurements were taken every 15 min for 24 hours.

Recombinant Protein Purification.

For recombinant Sap5 and Sap6, culture supernatant was concentrated to 15 mL with a 10 kDa MWCO spin filter and dialyzed twice into 4 L of 10 mM sodium citrate buffer (pH 7.0) for four hours followed by an overnight period. Dialyzed supernatant was concentrated to 5 mL using a 10 kDa MWCO spin filter and loaded at 0.5 mL/min onto a 5 mL HiTrap SP HP column (GE Healthcare) that had been equilibrated with 10 mM sodium citrate (pH 7.0). Protein was resolved at 4 mL/min using a gradient of 10 mM sodium citrate (pH 7.0) containing 300 mM NaCl while 5 mL fractions were collected. Fractions containing the highest purity Sap5 or Sap6 as assessed by SDS-PAGE were pooled and concentrated to 1 mL using a 10 kDa MWCO spin filter.

Pooled protein was loaded at 0.25 mL/min onto a Superdex 200 10/300 GL column (GE Healthcare) that had equilibrated with 10 mM sodium citrate (pH 7.0) containing 150 mM NaCl. Protein was resolved with an isocratic flow of 1 mL/min while 1 mL fractions were collected. Fractions containing purified Sap5 or Sap6, as assessed by SDS-PAGE, were pooled and concentrated to 1 mL.

For recombinant *S. cerevisiae* Kex2, culture supernatant was prepared as described above for Sap5 and Sap6. However, dialysis was performed using 50 mM BisTris (pH 5.0). Concentrated supernatant was loaded at 0.5 mL/min onto a 5 mL HiTrap Q HP column (GE Healthcare) that had been equilibrated with 50 mM BisTris (pH 5.0). Protein was resolved at 4 mL/min using a gradient of 50 mM BisTris (pH 5.0) containing 1 M NaCl while 5 mL fractions were collected. Kex2-containing fractions were pooled and further purified using size-exclusion chromatography as described above, except employing a linear gradient of 50 mM BisTris (pH 5.0) containing 150 mM NaCl. Pooled fractions were exchanged into 50 mM BisTris (pH 7.2) containing 50% glycerol using a PD-10 desalting column (GE Healthcare) prior to concentration. All recombinant proteins were quantified using molar extinction coefficients calculated from the ExPASy ProtParam tool and stored at −80° C.

Proteomic Analysis of *C. albicans* Biofilm and Planktonic Condition Media.

Peptide sequencing by LC-MS/MS was performed on an LTQ-Orbitrap XL mass spectrometer (Thermo) equipped with a nanoACQUITY (Waters) Ultra Performance Liquid Chromatography (UPLC) system and EASY-Spray ion source (Thermo). Reversed phase chromatography was carried out with an EASY-Spray PepMap $C_{18}$ column (Thermo, ES800; 3 μm bead size, 75 μm×150 mm). The LC was operated at a 600 nL/min flow rate during sample loading for 20 min, then the flow rate was reduced to 300 nL/min, and peptides were separated over 30 min using a linear gradient from 2% to 50% (vol/vol) acetonitrile in 0.1% formic acid. For MS/MS analysis, survey scans were recorded over a mass range of 325-1500 m/z. Peptide fragmentation was performed using collision-induced dissociation (CID) on the six most intense precursor ions, with a minimum of 1,000 counts, using an isolation width of 2.0 Th, and a minimum normalized collision energy of 25. Internal recalibration to polydimethylcyclosiloxane ion (m/z=445.120025) was used for both MS and MS/MS scans.

Mass spectrometry peak lists were generated using in-house software called PAVA. Database searching was performed using Protein Prospector software (http://prospector.ucsf.edu/prospector/mshome.htm) (1) against the UniProtKB *Candida* database (downloaded 17 Jun. 2013; 26,165 entries). The database was concatenated with an equal number of fully randomized entries for estimation of false discovery rate (FDR). Database searching was carried out using tolerances of 20 ppm for parent ions and 0.8 Da for fragment ions. Peptide sequences were matched as tryptic peptides with up to 2 missed cleavages. Constant and variable modifications were set as described previously (2). Protein FDR was calculated using the formula: FDR=100× FP/(FP+TP) where FP=false positive proteins and TP=true positive proteins. The following Protein Prospector score thresholds were selected to yield a maximum protein FDR of 3.9%: a minimum protein score of 22 and minimum peptide score of 15 were used; maximum expectation values of 0.01 for protein and 0.05 or 0.005 for peptide matches were used. Proteins are reported with a minimum of 2 unique peptides for identification.

Multiplex Substrate Profiling by Mass Spectrometry (MSP-MS).

Cleavage site identification was performed using the LTQ Orbitrap-XL mass spectrometer, ion source, and UPLC system described above. The LC was operated at a 600 nL/min flow rate during sample loading for 14 min and then at a 300 nL/min flow rate for peptide separation over 65 min using a linear gradient from 2% to 50% (vol/vol) acetonitrile in 0.1% formic acid. Peptide fragmentation was performed using the CID parameters described above. Mass spectrometry peak lists were generated using MSConvert from the ProteoWizard Toolkit (3), and data were searched against the 228-member peptide library using Protein Prospector with tolerances of 20 ppm for parent ions and 0.8 Da for fragment ions. All cleavages were allowed in the search by designating no enzyme specificity. The following variable modifications were used: amino acid oxidation (proline, tryptophan, and tyrosine) and N-terminal pyroglutamate conversion from glutamine. Protein Prospector score thresholds were selected with a minimum protein score of 22 and minimum peptide score of 15. For the peptide sub-library, a minimum protein score of 15 and minimum peptide score of 10 were used. Maximum expectation values of 0.01 and 0.05 were selected for protein and peptide matches, respectively. Peptides corresponding to cleavage products in the 228-member library were imported into iceLogo software v.1.2 to generate substrate specificity profiles as described (2). Octapeptides corresponding to P4-P4' were used as the positive dataset and octapeptides corresponding to all possible cleavages in the library (N=2,964) were used as the negative data set. Kinetic calculations for the peptide sub-library were performed as described (2) except by employing precursor ion intensities for progress curve calculations. Data fitting was performed using Prism v.6.0.

Peptide Synthesis of Fluorogenic Substrates

The internally quenched fluorogenic substrate VFILWRTE (SEQ ID NO: 22) was custom synthesized bearing a 5-carboxyfluorescein (5-FAM) fluorophore and paired CPQ2 quencher as CPQ2-Val-Phe-Ile-Leu-Trp-Arg-Thr-Glu-Lys(5-FAM)-DArg-D-Arg-$NH_2$ (SEQ ID NO: 27) by CPC Scientific, Inc. The remaining substrates (IYRnHVQL (SEQ ID NO: 24), WPSnNKVG (SEQ ID NO: 25), and TFSYnRWP (SEQ ID NO: 23)) were synthesized in-house with a 7-methoxycoumarin (MCA) fluorophore and 2,4-dinitrophenyl (DNP) quencher using standard Fmoc peptide synthesis chemistry. The full peptide sequences are as follows: DArg-DArg-Lys(MCA)-Ile-Tyr-Arg-Nle-His-Val-Gln-Leu-Lys(DNP) (SEQ ID NO: 28), DArg-DArg-Lys (MCA)-Trp-Pro-Ser-Nle-Asn-Lys-Val-Gly-Lys(DNP) (SEQ ID NO: 29), and DArg-DArg-Lys(MCA)-Thr-Phe-Ser-Tyr-Nle-Arg-Trp-Pro-Lys(DNP) (SEQ ID NO: 30). The first eight Fmoc-protected amino acids for each peptide were coupled to 150 mg of preloaded Fmoc-Lys(DNP) Wang resin (AnaSpec, Inc) using a Symphony Quartet 4-channel peptide synthesizer (Protein Technologies, Inc.). Double couplings for all steps were performed in N,N-dimethylformamide (DMF) using Fmoc-amino acid (6.5 eq.), N-methylmorpholine (13 eq.), and HBTU (6.5 eq.) with the following exception. The Fmoc-Lys(MCA)-OH (AnaSpec, Inc) fluorophore (3 eq.) underwent a single overnight coupling with N-methylmorpholine (6 eq.) and HBTU (3 eq.). Fmoc deprotection for each step was afforded with 20% 4-methylpiperidine in DMF (v/v). Trifluoroacetic acid (TFA) cleavage was carried out with a solution (v/v) of TFA (95%), water (2.5%), and triisopropylsilane (2.5%). Peptides were precipitated in diethyl ether, and the crude material was dried under ambient conditions. Peptides were purified on a preparative Vydac C18 column (22 mm×250 mm, 10 μm) with reversed-phase high-performance liquid chromatography (HPLC) using a gradient of 95% acetonitrile in 0.1% aqueous TFA. Matrix Assisted Laser Desorption Ionization mass spectra (MALDI-MS) were recorded on an Applied Biosystems Voyager DE-STR MALD-TOF in positive ion mode using a 1:1 α-cyano-4-hydroxycinnamic acid: sample ratio (v/v). MS Calcd. (Found): [M+H] IYRnHVQL (SEQ ID NO: 24) 1991.0 (1993.0); [M+H] WPSnNKVG (SEQ ID NO: 25) 1849.9 (1851.6); TFSYnRWP (SEQ ID NO: 23) [M+H] 2019.0 (2020.6).

REFERENCES

All of the references, patent applications, or other documents listed in this section are herein incorporated by reference in their entireties.
1. Pappas P G, et al. (2009) Clinical practice guidelines for the management of candidiasis: 2009 update by the Infectious Diseases Society of America. *Clinical infectious diseases: an official publication of the Infectious Diseases Society of America* 48(5):503-535.
2. Calderone R A & Fonzi W A (2001) Virulence factors of *Candida albicans*. *Trends in microbiology* 9(7):327-335.
3. Kullberg B J & Oude Lashof A M (2002) Epidemiology of opportunistic invasive mycoses. *European journal of medical research* 7(5):183-191.
4. Weig M, Gross U, & Muhlschlegel F (1998) Clinical aspects and pathogenesis of *Candida* infection. *Trends in microbiology* 6(12):468-470.
5. Donlan R M (2001) Biofilm formation: a clinically relevant microbiological process. *Clinical infectious diseases: an official publication of the Infectious Diseases Society of America* 33(8):1387-1392.
6. Donlan R M & Costerton J W (2002) Biofilms: survival mechanisms of clinically relevant microorganisms. *Clinical microbiology reviews* 15(2): 167-193.
7. Kojic E M & Darouiche R O (2004) *Candida* infections of medical devices. *Clinical microbiology reviews* 17(2): 255-267.
8. Nobile C J & Johnson A D (2015) *Candida albicans* Biofilms and Human Disease. *Annual Review of Microbiology* 69.
9. Nobile C J, et al. (2012) A recently evolved transcriptional network controls biofilm development in *Candida albicans*. *Cell* 148(1-2):126-138.
10. Pericolini E, et al. (2015) Secretory Aspartyl Proteinases Cause Vaginitis and Can Mediate Vaginitis Caused by *Candida albicans* in Mice. *mBio* 6(3):e00724.
11. Naglik J R, Challacombe S J, & Hube B (2003) *Candida albicans* secreted aspartyl proteinases in virulence and pathogenesis. *Microbiology and molecular biology reviews: MMBR* 67(3):400-428, table of contents.
12. O'Donoghue A J, et al. (2012) Global identification of peptidase specificity by multiplex substrate profiling. *Nature methods* 9(11): 1095-1100.
13. Colaert N, Helsens K, Martens L, Vandekerckhove J, & Gevaert K (2009) Improved visualization of protein consensus sequences by iceLogo. *Nature methods* 6(11):786-787.
14. Liu H, Sadygov R G, & Yates J R, 3rd (2004) A model for random sampling and estimation of relative protein abundance in shotgun proteomics. *Analytical chemistry* 76(14):4193-4201.
15. Blanchette J M, Abazeed M E, & Fuller R S (2004) Cell-free reconstitution of transport from the trans-golgi network to the late endosome/prevacuolar compartment. *The Journal of biological chemistry* 279(47):48767-48773.
16. Zarnowski R, et al. (2014) Novel entries in a fungal biofilm matrix encyclopedia. *mBio* 5(4):e01333-01314.
17. Bader O, Krauke Y, & Hube B (2008) Processing of predicted substrates of fungal Kex2 proteinases from *Candida albicans*, *C. glabrata*, *Saccharomyces cerevisiae* and *Pichia pastoris*. *BMC microbiology* 8:116.
18. Fox E P, et al. (2015) An expanded regulatory network temporally controls *Candida albicans* biofilm formation. *Molecular microbiology*.
19. Aoki W, et al. (2011) Comprehensive characterization of secreted aspartic proteases encoded by a virulence gene family in *Candida albicans*. *Journal of biochemistry* 150(4):431-438.
20. Sali A & Blundell T L (1993) Comparative protein modelling by satisfaction of spatial restraints. *Journal of molecular biology* 234(3):779-815.
21. Borelli C, et al. (2008) X-ray structures of Sap1 and Sap5: structural comparison of the secreted aspartic proteinases from *Candida albicans*. *Proteins* 72(4):1308-1319.
22. Wu H, et al. (2013) *Candida albicans* secreted aspartic proteases 4-6 induce apoptosis of epithelial cells by a novel Trojan horse mechanism. *FASEB journal: official publication of the Federation of American Societies for Experimental Biology* 27(6):2132-2144.
23. Hube B, Monod M, Schofield D A, Brown A J, & Gow N A (1994) Expression of seven members of the gene family encoding secretory aspartyl proteinases in *Candida albicans*. *Molecular microbiology* 14(1):87-99.
24. White T C & Agabian N (1995) *Candida albicans* secreted aspartyl proteinases: isoenzyme pattern is determined by cell type, and levels are determined by environmental factors. *Journal of bacteriology* 177(18):5215-5221.
25. Staib P, Kretschmar M, Nichterlein T, Hof H, & Morschhauser J (2000) Differential activation of a *Candida albicans* virulence gene family during infection. *Proceedings of the National Academy of Sciences of the United States of America* 97(11):6102-6107.
26. Felk A, et al. (2002) *Candida albicans* hyphal formation and the expression of the Efg1-regulated proteinases Sap4 to Sap6 are required for the invasion of parenchymal organs. *Infection and immunity* 70(7):3689-3700.
27. Kumar R, Saraswat D, Tati S, & Edgerton M (2015) Novel aggregation properties of *Candida albicans* secreted aspartyl proteinase Sap6 mediates virulence in oral candidiasis. *Infection and immunity*.
28. Schild L, et al. (2011) Proteolytic cleavage of covalently linked cell wall proteins by *Candida albicans* Sap9 and Sap10. *Eukaryotic cell* 10(1):98-109.
29. Puri S, et al. (2012) Secreted aspartic protease cleavage of *Candida albicans* Msb2 activates Cek1 MAPK signaling affecting biofilm formation and oropharyngeal candidiasis. *PloS one* 7(11):e46020.
30. Lermann U & Morschhauser J (2008) Secreted aspartic proteases are not required for invasion of reconstituted human epithelia by *Candida albicans*. *Microbiology* 154 (Pt 11):3281-3295.
31. Perez J C, Kumamoto C A, & Johnson A D (2013) *Candida albicans* commensalism and pathogenicity are intertwined traits directed by a tightly knit transcriptional regulatory circuit. *PLoS biology* 11(3):e1001510.
32. Borg-von Zepelin M, Beggah S, Boggian K, Sanglard D, & Monod M (1998) The expression of the secreted aspartyl proteinases Sap4 to Sap6 from *Candida albicans* in murine macrophages. *Molecular microbiology* 28(3): 543-554.
33. Lesage G, Tremblay M, Guimond J, & Boileau G (2001) Mechanism of Kex2p inhibition by its proregion. *FEBS letters* 508(3):332-336.
34. Wells M L, et al. (2015) Post-transcriptional regulation of transcript abundance by a conserved member of the tristetraprolin family in *Candida albicans. Molecular microbiology* 95(6): 1036-1053.

Example 2: In Vitro Development and Evaluation of Protease-Cleavable Fluorogenic Substrates for Pathogenic and Emerging Pathogenic *Candida* Species. (Prophetic)

After the identification of biofilm-specific proteolysis in *C. albicans*, the next step is to develop optimal in vitro protease-cleavable fluorogenic substrates for other pathogenic *Candida* species. To begin, optimal assay conditions (e.g., pH) for detecting soluble proteolytic activity produced by representative pathogenic and emerging pathogenic *Candida* species need to be identified in vitro using existing fluorogenic peptide substrates developed against *C. albicans*. Assay conditions will be identified that afford the greatest biofilm selectivity for all representative *Candida* species, biofilm selectivity for individual species—(or subspecies), and broad-spectrum *Candida* detection (biofilm or planktonic). In addition, incorporation of class-specific protease inhibitors will aid in the assignment of activities to specific protease classes.

Next, soluble proteolytic activity produced by the representative *Candida* species in vitro will be profiled using our MSP-MS technology (1) to identify new candidate peptide substrates that meet the detection goals above. The MSP-MS assay provides quantitative assessment of protease cleavage specificity through mass spectrometry-based sequencing of peptide cleavage products (1). Peptide cleavage products are identified based on user-defined scoring thresholds through database searching against the MSP-MS library using ProteinProspector software (5) (N=2,964 cleavage products are possible in our 228-member library). An additional in-house algorithm is used to filter false-positive cleavage products based on user-defined activity thresholds through comparison of mass spectrometry precursor ion intensities from the experimental dataset to those from at least one negative-control dataset. Statically significant representations of cleavage motifs (or "substrate signatures") are visualized using iceLogo software by comparison of true-positive cleavages to all possible cleavages in the MSP-MS library (6). Comparison of protease activity between samples can be assessed based on the presence or absence of a peptide cleavage during experimentally matched time points and/or based on kinetic assessment of peptide cleavage rates (1). Shotgun proteomics analysis will be used to identify the corresponding proteases.

Then, new fluorogenic substrates will be constructed based on peptide cleavage products detected in the MSP-MS library from the panel of *Candida* species. These substrates will be prioritized following assay condition and inhibitor screening as described in above. Substrate prioritization also will be carried out through counter-screening against healthy (control) serum and plasma in addition to secretions produced by other common bacterial and fungal species that comprise human and rodent model host microbiota. Corresponding protease targets from the *Candida* species will be assigned based on consideration of the shotgun proteomics analysis, inhibitor reactivity, and pH optimum for activity. Protease targets will be confirmed through assaying recombinantly produced proteases and secretions from protease deletion mutant strains when possible.

Finally, protease cleavable-fluorogenic substrates identified in vitro will be tested for their ability to detect infections using biological fluids from established rodent infection models, including the disseminated, central venous catheter, dental stomatitis, gastric, oropharyngeal, and/or vaginal models of *Candida* infection (2-4). Substrate sequence selectivity will be rationally optimized as needed through identification of background protease activity in corresponding fluids from control and infected animals using the MSP-MS assay. Additional peptide sequences identified from the MSP-MS library that afford promising infection-specific detection under in vivo conditions will be used to design new fluorogenic substrates. Protease targets will be confirmed through assaying biological fluids from animal models infected with protease deletion mutant strains when possible. Lead substrates identified from screening preclinical animal models will be applied for the detection of clinical infections in the subsequent phase of development.

REFERENCES

All of the references, patent applications, or other documents listed in this section are herein incorporated by reference in their entireties.
1. O'Donoghue A J, et al. (2012) Global identification of peptidase specificity by multiplex substrate profiling. *Nature methods* 9(11): 1095-1100.
2. Andes D, et al. (2004) Development and characterization of an in vivo central venous catheter *Candida albicans* biofilm model. *Infection and immunity* 72(10):6023-6031.
3. Nett J E, Marchillo K, Spiegel C A, & Andes D R (2010) Development and validation of an in vivo *Candida albicans* biofilm denture model. *Infection and immunity* 78(9):3650-3659.
4. Conti H R, Huppler A R, Whibley N, & Gaffen S L (2014) Animal models for candidiasis. *Current protocols in immunology/edited by John E. Coligan . . .* [et al.] 105:19 16 11-19 16 17.
5. Chalkley R J, Baker P R, Medzihradszky K F, Lynn A J, & Burlingame A L (2008) In-depth analysis of tandem mass spectrometry data from disparate instrument types. *Molecular & cellular proteomics: MCP* 7(12):2386-2398.
6. Colaert N, Helsens K, Martens L, Vandekerckhove J, & Gevaert K (2009) Improved visualization of protein consensus sequences by iceLogo. *Nature methods* 6(11):786-787.

Example 3: Development of Kit for Diagnosing *Candida* Infections. (Prophetic)

A proof-of-principle microtiter plate kit for diagnosing *Candida* infections will be developed based on the fluorometric readout of protease activity. The kit will contain the following components: a black round-bottom microtiter plate, a set of substrate reagents, fluorescence activity standards, and quench solution. The substrate reagents will consist of one or a plurality of fluorogenic protease-cleavable peptides individually premixed in substrate-specific assay buffer for optimal protease activity. The activity standards will consist of fluorescent dye corresponding to each substrate premixed at a set of defined concentrations in matched assay buffer. The quench solution will consist of a defined concentration of appropriate protease inhibitor (or inhibitor cocktail) or an appropriate pH solution to quench activity. For infection testing, the activity standards and substrate reagents will be distributed in the microtiter plate at a defined volume. Biological fluids from an individual with a suspected *Candida* infection will be mixed at a defined volume with each substrate reagent. In a non-continuous assay format, the plate will be allowed to incubate for a specified time interval sufficient to cleave the fluorogenic substrate into known peptide fragments, and then the quench buffer will be added to the standard and sample wells. The absolute fluorescence produced by each well will be recorded in a microplate reader. In an alternate continuous assay format, which will allow for the more accurate kinetic measurement of protease activity, the plate will be read throughout the sample incubation time course and the quench buffer will not be required. The presence of a *Candida* infection will be assessed through comparison of the level of sample activity (i.e., fluorescence) with the activity standards. Experiments within the next 12 months will focus on establishing the sensitivity and specificity of the kit design for detecting in vivo *Candida* infections.

Example 4: In Vivo Diagnosis of a Pathogenic Biofilm-Associated and/or Disseminated Fungal Infection (Prophetic)

The purpose of this method will be to identify whether a subject is infected with a pathogenic form of a fungal biofilm.

Formation of nanoparticles: 40 nm amine-functionalized dextran-coated iron oxide nanoparticles (NP; 115,000 g/mole per iron core) will be dissolved in borate buffer (50 mM sodium borate, 5 mM EDTA, pH 8.3) at a concentration of 2 mg/mL. Vivotag-750 fluorophore will be labeled on the NPs as a fluorescent tracer such that each NP has around 2 VT-750 fluorophores. The linker maleimide-polyethylene glycol-succinimidyl carboxy methyl ester (MAL-PEG-NHS; MW=2-10 k) will be dissolved in DMSO at 20 mg/mL. The two solutions will be mixed to obtain a 1-to-7 mass ratio between iron oxide NPs and MAL-PEG-NHS for 2 hr at room temperature with shaking. Size exclusion chromatography (column diameter×height=1 cm×30 cm; media: Sephadex G-50-coarse) was used to separate out the excess MAL-PEG-NHS and to exchange NPs into 1× phosphate buffered saline (PBS; 137 mM NaCl, 10 mM Phosphate, 2.7 mM KCl, pH 7.4).

Peptide substrates (for Sap5 and/or Sap6 and/or any biomarker in Table 2 or 3) will be synthesized bearing a fluorescein group and cysteine (thiol) handle for NP attachment positioned at opposing termini such that protease cleavage results in fluorescein-NP dissociation. Fluorescein-labeled peptides will be dissolved in DMSO at 25 mg/mL. Each of the biomarker peptides of fragment thereof and activated PEG-NPs will be left to for >12 hr, making different peptide-PEG-NPs displaying different fungal biomarkers. Additional PBS will be added to the reactants to bring the DMSO to <10% of the total reaction volume.

After the linkers on the NP surface react with the fluorophore-peptides, the final-product solution will be filtered on centrifugal filter columns (Amicon, Millipore; MW=100 k) at 4,200 rcf to remove the un-conjugated peptides to <0.1% of the original conjugated quantity. 1×HEPES salt buffer (100 mM 4-(2-hydroxyethyl)-1-piperazineethane-sulfonic acid, 150 mM NaCl, pH 7.5) will be used to replace the PBS buffer and DMSO during centrifugation until <0.1% volume of PBS and <0.02% volume of the DMSO are left in the samples.

The newly made peptide-PEG-NPs (pP-NPs) will be analyzed with a spectrometer to assess the number of peptides bound to each nanoparticle. Nanoparticle spectra will be normalized to particles that had not been reacted with peptides to allow quantification of the attached fluorophore-peptide absorbance (fluorescein peak absorbance=495 nm; extinction coefficient=$72,000 \times 10^6$ cm$^{-1}$ M$^{-1}$). NP concentration will be assessed by recording its absorbance at 400 nm with an extinction coefficient of $2.07 \times 10^6$ cm$^{-1}$ M$^{-1}$. Comparison of these concentrations allow quantitation of the average fungal biomarker-to-NP ratios. All samples will be normalized to 5 µM based on peptide concentration and stored in 4° C.

Out of the selected peptide-PEG-NP (pP-NPs), a certain number of NP conjugates will be chosen for infection assessment in vivo. These pP-NPs will be re-synthesized in larger quantity (at least 100 n-moles based on peptide concentrations). Each of the pP-NPs (around 5 n-moles) will be reacted with VT-750 fluorophore (at five-fold molar excess to the peptide concentrations on the NPs) for 2 hr, and the excess un-reactive VT-750 were filtered out to <0.01% by spinning down on 100 k filter column.

After fed on a non-fluorophore diet for >1 wk, 5 nude mice will undergo IV infection with *C. albicans* ($10^6$ CFUs), and 5 nude mice will be injected with an appropriate vehicle control. After 24 hours, all mice will be each injected intravenously with the 200 µL of the 750-pP-NPs and imaged for the bio-distribution of NP chaperones in vivo (Odyssey imaging systems; Westburg, Leusden, Netherlands) by tracing VT-750 for a 2-hr period with 10-min intervals. The bio-distributions of 750-pP-NPs over time in each mouse will be quantified (ImageJ; NIH).

Urine samples of all mice will be collected after 1 hr of injections. After urine excretions for each mouse, each urine sample volume will be diluted to 500 µL by adding ddH$_2$O. 100 µL of each 500 µL urine sample will be put into a well on a black half-96-well plate, and a microplate fluorimeter (Molecular Devices Corporation; Gemini EM; excitation: 485 nm, emission: 538 nm, cutoff: 530 nm) will be used to measure the relative fluorophore units (RFU) of each sample. Furthermore, 100 µL of each 250 µL urine sample will be analyzed on HPLC-MS-MS for specific peptide sequences injected into the mice. All mice will be anesthetized with isoflurane (2-chloro-2-(difluoromethoxy)-1,1,1-trifluoro-ethane).

Statistical Analysis

Since that the sample sizes for the mice will be very small and that a normal distribution could not be assumed, a Student two-tailed t-test will be performed for all statistical tests in this study. The null hypothesis will be that the two groups (e.g. infected vs. uninfected) do not differ in the amount of peptides excreted, and p-value <0.05 would reject the null hypothesis.

Example 5: Construction of First-Generation Sap5/6 and Kex2 Cleavable Fluorogenic Peptides Fluorogenic peptide substrates cleavable by Sap5, Sap6, and Kex2 were constructed to determine whether they could be used to distinguish among the three proteases and between the biofilm and planktonic states of *C. albicans*. For Sap5 and Sap6, 8-mer peptide sequences containing P4-P4' residues (cleavage occurs between the P1 and P1' positions) developed from purified Sap5- or Sap6-favored cleavages in the MSP-MS library were selected for incorporation into internally quenched (IQ) fluorogenic substrates. The sequences VFILWRTE (SEQ ID NO: 22) and TFSYnRWP ("n" is norleucine; SEQ ID NO: 23) afforded high specific activity and selectivity for recombinant Sap5 and Sap6, respectively (FIG. 19A). Profiling of recombinant Kex2 revealed high specificity for cleavage following (P2-P1) K/R-R pairings, and, based on these results, a tetrapeptide fluorogenic substrate (P4-P1) with an ACC reporter group, HAKR-ACC, was synthesized. The ACC linkage has the advantage of fluorescing only when cleaved between the P1 position and P1' ACC group, a strategy that increases on-target selectivity (ACC substrates are not accepted efficiently by all proteases, including Sap5/6). The Sap5, Sap6, and Kex2 fluorogenic substrates were evaluated using conditioned media preparations from *C. albicans* cultures grown under both biofilm and planktonic conditions and were found to be preferentially cleaved by biofilm culture medium (B/P=10-, 4.4-, and 13-fold, respectively) (FIGS. 19B and 19C). Furthermore, cleavage of the fluorogenic substrates was severely reduced in conditioned media from a deletion strain (for SAP5/6) or upon pretreatment with the appropriate protease inhibitor (FIG. 19D).

Example 6: Additional Activities from the Global Protease Profiling of the *C. albicans* Secretome A key advantage of the global profiling strategy is the ability to uncover protease signatures in complex biological samples in an unbiased fashion. Profiling of *C. albicans* grown under different conditions identified biofilm-specific cleavages, planktonic-specific cleavages, as well as cleavages produced by both biofilms and planktonic cultures (broad-spectrum) that do not match those of Sap5, Sap6, or Kex2, indicate they arise from proteases distinct from those previously investigated (FIG. 20).

Example 7: Protease Profiling of Additional *Candida* Species with Fluorogenic Substrates The *Candida* clade includes several closely related species that have varying degrees of pathogenicity in mouse models and varying prevalence in humans. *C. albicans* displays the highest virulence during intravenous challenge in immunocompetent mice and is the most commonly found fungal species in human patient populations. *C. parapsilosis* is an emerging member of the *Candida* clade that has the largest increase in prevalence since 1990 and has become one of the most common causes of *Candida* infections in newborn babies. Although *C. glabrata* (despite its name) lies well outside the *Candida* clade, it is pathogenic, less sensitive to some classes of antifungal agents, and increasingly identified in patients in hospital settings. To provide a preliminary characterization of extracellular protease activity, the Sap5-, Sap6-, and Kex2-cleavable fluorogenic substrates were tested across these and related species (FIG. 21A). Conditioned media was harvested from 24-hour cultures grown under biofilm and planktonic conditions. Protease activity against the three substrates was highest among members of the strict *Candida* clade (i.e., excluding *C. glabrata*) under biofilm conditions. Species-specific differences were evident both in terms of total activity and biofilm versus planktonic selectivity. Pepstatin pretreatment (for the Sap5/6 probes) and EDTA pretreatment (for the Kex2 probe) revealed differential contributions of aspartyl and subtilisin-like protease activity, respectively, to substrate cleavage among the species evaluated (FIG. 21B). Although these substrates were not optimized to respond to a single species, these results suggest that differences in proteolytic activity can be exploited to distinguish between closely related members of the *Candida* clade (FIG. 21C).

Example 8: Global Identification of Infection-Specific Proteolytic Activity in the Serum of a Murine Biofilm Catheter Model of *C. albicans* Infection To provide validation of the protease activity-based diagnostic approach in a rat biofilm catheter model, blood was directly sampled from (i) the catheters of rats with introduced *C. albicans* biofilms, (ii) peripherally from the same rats, and, (iii) following IV infection, and (iv) as a control, from rats not exposed to *C. albicans*. Using the first-generation Sap6 substrate (TFSYnRWP; SEQ ID NO: 23), substrate cleavage in blood harvested from infected rats was readily detected. This cleavage activity was absent from the uninfected rats (FIG. 16 and FIG. 22) and was significantly reduced by pepstatin pretreatment, providing an additional control to rule out non-specific substrate cleavage.

The invention claimed is:

1. A method of diagnosing a subject with a pathogenic fungal infection from the genus *Candida*, comprising:
   a) exposing a sample from the subject to at least one substrate of at least one secreted aspartyl protease (Sap), wherein the at least one substrate comprises at least one enzymatic cleavage site recognizable by the at least one Sap, and wherein the at least one Sap comprises at least about 90% sequence homology to SEQ ID NO: 5 or SEQ ID NO: 6;
   b) detecting the presence, absence and/or quantity of enzymatic cleavage of the substrate by the at least one Sap in the sample; and
   c) correlating the presence, absence and/or quantity of enzymatic cleavage of the substrate by the at least one Sap to a probability or likelihood that the subject has the pathogenic fungal infection relative to a measurement of a control sample taken from a subject known to have or not to have the pathogenic fungal infection, wherein the at least one substrate of SEQ ID NO: 5 comprises a peptide with 85% sequence homology to SEQ ID NO: 31 and wherein the at least one substrate of SEQ ID NO: 6 comprises a peptide with 85% sequence homology to SEQ ID NO: 32.

2. The method of claim 1, wherein the at least one substrate of the at least one Sap is attached to a fluorogenic probe.

3. The method of claim 1, wherein the at least one Sap comprises the amino acid sequence of SEQ ID NO: 5 or SEQ ID NO: 6.

4. The method of claim 1, wherein the pathogenic infection comprises a planktonic or biofilm form of any of the species selected from the group consisting of *Candida albicans, Candida dubliniensis, Candida tropicalis, Candida parapsilosis, Meyerozyma/Candida guilhermondii*, and *Candida glabrata*.

5. The method of claim 1, wherein the presence, absence and/or quantity of enzymatic cleavage of the substrate by the at least one Sap in the sample is detected by one or a combination of: fluorescence, optical imaging, field microscopy, quantum dots, chromatography, and/or mass spectrometry.

6. The method of claim 1, wherein the sample is a human tissue sample comprising a tissue from a brushing, biopsy, or surgical resection of the subject.

7. The method of claim 1, wherein the at least one substrate of SEQ ID NO: 5 comprises the amino acid sequence of SEQ ID NO: 31 and wherein the at least one substrate of SEQ ID NO: 6 comprises the amino acid sequence of SEQ ID NO: 32.

8. The method of claim 1, wherein the presence, absence and/or quantity of enzymatic cleavage of the substrate by the at least one Sap in the sample is detected by using a bright field microscope and/or fluorescence microscopy.

9. The method of claim 1, wherein the correlating step c) further comprises diagnosing the subject with the pathogenic fungal infection from the genus *Candida*, and the method further comprises a step of administering to the subject a therapeutically effective amount of treatment for the pathogenic fungal infection.

10. The method of claim 1, further comprising calculating one or more normalized scores based upon the presence, absence and/or quantity of enzymatic cleavage of the substrate by the at least one Sap and correlating the one or more normalized scores to the probability or likelihood that the subject has the pathogenic fungal infection relative to an amount of Sap calculated from the control sample, such that if the one or more normalized scores are greater than the amount of Sap calculated from a planktonic control sample or equal to a positive biofilm control, the correlating step further comprises diagnosing the subject with the pathogenic fungal infection from the genus *Candida*.

11. A method of diagnosing a subject with a pathogenic fungal infection from the genus *Candida*, the method comprising:
   a) exposing a sample from the subject to at least one substrate of at least one secreted aspartyl protease (Sap), wherein the at least one substrate comprises at least one enzymatic cleavage site recognizable by the at least one Sap, and wherein the at least one Sap comprises at least about 90% sequence homology to SEQ ID NO: 5 or SEQ ID NO: 6;
   b) detecting the presence, absence and/or quantity of enzymatic cleavage of the substrate by the at least one Sap in the sample;
   c) calculating one or more normalized scores corresponding to the amount of enzymatic cleavage of the substrate detected in step (b);
   d) correlating the one or more normalized scores to a probability or likelihood that the subject has the pathogenic fungal infection relative to a measurement of an amount of Sap calculated from a control sample taken from a subject known to have or not to have the pathogenic fungal infection, such that if the one or more normalized scores are greater than the amount of Sap calculated from a planktonic control sample or equal to a positive biofilm control, the correlating step further comprises diagnosing the subject with the pathogenic fungal infection from the genus *Candida*; and wherein the at least one substrate comprises a peptide of about 8 amino acids in length and at least about 85% sequence homology to SEQ ID NO: 22 or SEQ ID NO: 23.

12. The method of claim 11, wherein the at least one substrate of the at least one Sap comprises the amino acid sequence of SEQ ID NO: 22 or SEQ ID NO: 23.

13. The method of claim 11, wherein the at least one substrate of the at least one Sap is attached to a fluorogenic probe.

14. The method of claim 11, wherein the at least one Sap comprises the amino acid sequence of SEQ ID NO: 5 or SEQ ID NO: 6.

15. The method of claim 11, wherein the pathogenic infection comprises a planktonic or biofilm form of any of the species selected from the group consisting of *Candida albicans, Candida dubliniensis, Candida tropicalis, Candida parapsilosis, Meyerozyma/Candida guilliermondii*, and *Candida glabrata*.

16. The method of claim 11, wherein the presence, absence and/or quantity of enzymatic cleavage of the substrate by the at least one Sap in the sample is detected by one or a combination of: fluorescence, optical imaging, field microscopy, fluorescence microscopy, quantum dots, chromatography, and/or mass spectrometry.

17. A method of diagnosing a subject with a pathogenic fungal infection from the genus *Candida*, comprising:
   a) exposing a sample from the subject to at least one substrate of at least one secreted aspartyl protease (Sap), wherein the at least one substrate comprises at least one enzymatic cleavage site recognizable by the at least one Sap, and wherein the at least one Sap comprises at least about 90% sequence homology to SEQ ID NO: 5 or SEQ ID NO: 6;
   b) detecting the presence, absence and/or quantity of enzymatic cleavage of the substrate by the at least one Sap in the sample; and
   c) correlating the presence, absence and/or quantity of enzymatic cleavage of the substrate by the at least one Sap to a probability or likelihood that the subject has the pathogenic fungal infection relative to a measurement of a control sample taken from a subject known to have or not to have the pathogenic fungal infection, wherein the at least one substrate comprises a peptide of about 8 amino acids in length and comprises the amino acid sequence comprising about 85% sequence homology to SEQ ID NO: 22, SEQ ID NO: 23, SEQ ID NO: 24, SEQ ID NO: 25, SEQ ID NO: 31, or SEQ ID NO: 32.

18. The method of claim 17, wherein the at least one substrate of the at least one Sap is attached to a fluorogenic probe.

19. The method of claim 17, wherein the at least one substrate comprises the amino acid sequence of SEQ ID NO: 22, SEQ ID NO: 23, SEQ ID NO: 24, SEQ ID NO: 25, SEQ ID NO: 31, or SEQ ID NO: 32.

20. The method of claim 17, wherein the pathogenic infection comprises a planktonic or biofilm form of any of the species selected from the group consisting of *Candida albicans, Candida* dubliniensis, *Candida tropicalis, Candida parapsilosis, Meyerozyma/Candida guilliermondii*, and *Candida glabrata*.

21. The method of claim 17, wherein the presence, absence and/or quantity of enzymatic cleavage of the substrate by the at least one Sap in the sample is detected by one or a combination of: fluorescence, optical imaging, field microscopy, fluorescence microscopy, quantum dots, chromatography, and/or mass spectrometry.

* * * * *

SEQUENCE LISTING

<160> NUMBER OF SEQ ID NOS: 32

<210> SEQ ID NO 1
<211> LENGTH: 391
<212> TYPE: PRT
<213> ORGANISM: Candida albicans

<400> SEQUENCE: 1

Met Phe Leu Lys Asn Ile Phe Ile Ala Leu Ala Ile Ala Leu Leu Val
1               5                   10                  15

Asp Ala Ser Pro Ala Lys Arg Ser Pro Gly Phe Val Thr Leu Asp Phe
            20                  25                  30

Asp Val Ile Lys Thr Pro Val Asn Ala Thr Gly Gln Glu Gly Lys Val
        35                  40                  45

Lys Arg Gln Ala Ile Pro Val Thr Leu Asn Asn Glu Leu Val Ser Tyr
    50                  55                  60

Ala Ala Asp Ile Thr Ile Gly Ser Asn Lys Gln Lys Phe Asn Val Ile
65                  70                  75                  80

```
Val Asp Thr Gly Ser Ser Asp Leu Trp Val Pro Asp Ala Ser Val Thr
                85                  90                  95

Cys Asp Lys Pro Arg Pro Gly Gln Ser Ala Asp Phe Cys Lys Gly Lys
            100                 105                 110

Gly Ile Tyr Thr Pro Lys Ser Thr Thr Ser Gln Asn Leu Gly Ser
        115                 120                 125

Pro Phe Tyr Ile Gly Tyr Gly Asp Gly Ser Ser Gln Gly Thr Leu
    130                 135                 140

Tyr Lys Asp Thr Val Gly Phe Gly Gly Ala Ser Ile Thr Lys Gln Val
145                 150                 155                 160

Phe Ala Asp Ile Thr Lys Thr Ser Ile Pro Gln Gly Ile Leu Gly Ile
                165                 170                 175

Gly Tyr Lys Thr Asn Glu Ala Ala Gly Asp Tyr Asp Asn Val Pro Val
                180                 185                 190

Thr Leu Lys Asn Gln Gly Val Ile Ala Lys Asn Ala Tyr Ser Leu Tyr
                195                 200                 205

Leu Asn Ser Pro Asn Ala Ala Thr Gly Gln Ile Ile Phe Gly Gly Val
        210                 215                 220

Asp Lys Ala Lys Tyr Ser Gly Ser Leu Ile Ala Val Pro Val Thr Ser
225                 230                 235                 240

Asp Arg Glu Leu Arg Ile Thr Leu Asn Ser Leu Lys Ala Val Gly Lys
                245                 250                 255

Asn Ile Asn Gly Asn Ile Asp Val Leu Leu Asp Ser Gly Thr Thr Ile
                260                 265                 270

Thr Tyr Leu Gln Gln Asp Val Ala Gln Asp Ile Ile Asp Ala Phe Gln
                275                 280                 285

Ala Glu Leu Lys Ser Asp Gly Gln Gly His Thr Phe Tyr Val Thr Asp
            290                 295                 300

Cys Gln Thr Ser Gly Thr Val Asp Phe Asn Phe Asp Asn Asn Ala Lys
305                 310                 315                 320

Ile Ser Val Pro Ala Ser Glu Phe Thr Ala Pro Leu Ser Tyr Ala Asn
                325                 330                 335

Gly Gln Pro Tyr Pro Lys Cys Gln Leu Leu Leu Gly Ile Ser Asp Ala
            340                 345                 350

Asn Ile Leu Gly Asp Asn Phe Leu Arg Ser Ala Tyr Leu Val Tyr Asp
            355                 360                 365

Leu Asp Asp Asp Lys Ile Ser Leu Ala Gln Val Lys Tyr Thr Ser Ala
370                 375                 380

Ser Asn Ile Ala Ala Leu Thr
385                 390

<210> SEQ ID NO 2
<211> LENGTH: 398
<212> TYPE: PRT
<213> ORGANISM: Candida albicans

<400> SEQUENCE: 2

Met Phe Leu Lys Asn Ile Phe Ile Gly Leu Ala Ile Ala Leu Leu Val
1               5                   10                  15

Asp Ala Thr Pro Thr Thr Thr Lys Arg Ser Ala Gly Phe Val Ala Leu
                20                  25                  30

Asp Phe Ser Val Val Lys Thr Pro Lys Ala Phe Pro Val Thr Asn Gly
            35                  40                  45

Gln Glu Gly Lys Thr Ser Lys Arg Gln Ala Val Pro Val Thr Leu His
```

```
                50                  55                  60
Asn Glu Gln Val Thr Tyr Ala Ala Asp Ile Thr Val Gly Ser Asn Asn
 65                  70                  75                  80

Gln Lys Leu Asn Val Ile Val Asp Thr Gly Ser Ser Asp Leu Trp Val
                 85                  90                  95

Pro Asp Val Asn Val Asp Cys Gln Val Thr Tyr Ser Asp Gln Thr Ala
                100                 105                 110

Asp Phe Cys Lys Gln Lys Gly Thr Tyr Asp Pro Ser Gly Ser Ser Ala
                115                 120                 125

Ser Gln Asp Leu Asn Thr Pro Phe Lys Ile Gly Tyr Gly Asp Gly Ser
            130                 135                 140

Ser Ser Gln Gly Thr Leu Tyr Lys Asp Thr Val Gly Phe Gly Gly Val
145                 150                 155                 160

Ser Ile Lys Asn Gln Val Leu Ala Asp Val Asp Ser Ser Ile Asp
                165                 170                 175

Gln Gly Ile Leu Gly Val Gly Tyr Lys Thr Asn Glu Ala Gly Gly Ser
                180                 185                 190

Tyr Asp Asn Val Pro Val Thr Leu Lys Lys Gln Gly Val Ile Ala Lys
            195                 200                 205

Asn Ala Tyr Ser Leu Tyr Leu Asn Ser Pro Asp Ala Ala Thr Gly Gln
210                 215                 220

Ile Ile Phe Gly Gly Val Asp Asn Ala Lys Tyr Ser Gly Ser Leu Ile
225                 230                 235                 240

Ala Leu Pro Val Thr Ser Asp Arg Glu Leu Arg Ile Ser Leu Gly Ser
                245                 250                 255

Val Glu Val Ser Gly Lys Thr Ile Asn Thr Asp Asn Val Asp Val Leu
                260                 265                 270

Leu Asp Ser Gly Thr Thr Ile Thr Tyr Leu Gln Gln Asp Leu Ala Asp
            275                 280                 285

Gln Ile Ile Lys Ala Phe Asn Gly Lys Leu Thr Gln Asp Ser Asn Gly
            290                 295                 300

Asn Ser Phe Tyr Glu Val Asp Cys Asn Leu Ser Gly Asp Val Val Phe
305                 310                 315                 320

Asn Phe Ser Lys Asn Ala Lys Ile Ser Val Pro Ala Ser Glu Phe Ala
                325                 330                 335

Ala Ser Leu Gln Gly Asp Asp Gly Gln Pro Tyr Asp Lys Cys Gln Leu
            340                 345                 350

Leu Phe Asp Val Asn Asp Ala Asn Ile Leu Gly Asp Asn Phe Leu Arg
            355                 360                 365

Ser Ala Tyr Ile Val Tyr Asp Leu Asp Asn Asn Glu Ile Ser Leu Ala
            370                 375                 380

Gln Val Lys Tyr Thr Ser Ala Ser Ser Ile Ser Ala Leu Thr
385                 390                 395

<210> SEQ ID NO 3
<211> LENGTH: 398
<212> TYPE: PRT
<213> ORGANISM: Candida albicans

<400> SEQUENCE: 3

Met Phe Leu Lys Asn Ile Phe Ile Ala Leu Ala Ile Ala Leu Leu Ala
 1               5                  10                  15

Asp Ala Thr Pro Thr Thr Phe Asn Asn Ser Pro Gly Phe Val Ala Leu
                20                  25                  30
```

Asn Phe Asp Val Ile Lys Thr His Lys Asn Val Thr Gly Pro Gln Gly
            35                  40                  45

Glu Ile Asn Thr Asn Val Asn Val Lys Arg Gln Thr Val Pro Val Lys
 50                  55                  60

Leu Ile Asn Glu Gln Val Ser Tyr Ala Ser Asp Ile Thr Val Gly Ser
 65                  70                  75                  80

Asn Lys Gln Lys Leu Thr Val Val Ile Asp Thr Gly Ser Ser Asp Leu
                 85                  90                  95

Trp Val Pro Asp Ser Gln Val Ser Cys Gln Ala Gly Gln Gly Gln Asp
                100                 105                 110

Pro Asn Phe Cys Lys Asn Glu Gly Thr Tyr Ser Pro Ser Ser Ser Ser
            115                 120                 125

Ser Ser Gln Asn Leu Asn Ser Pro Phe Ser Ile Glu Tyr Gly Asp Gly
130                 135                 140

Thr Thr Ser Gln Gly Thr Trp Tyr Lys Asp Thr Ile Gly Phe Gly Gly
145                 150                 155                 160

Ile Ser Ile Thr Lys Gln Gln Phe Ala Asp Val Thr Thr Ser Val
                165                 170                 175

Asp Gln Gly Ile Leu Gly Ile Gly Tyr Lys Thr His Glu Ala Glu Gly
            180                 185                 190

Asn Tyr Asp Asn Val Pro Val Thr Leu Lys Asn Gln Gly Ile Ile Ser
            195                 200                 205

Lys Asn Ala Tyr Ser Leu Tyr Leu Asn Ser Arg Gln Ala Thr Ser Gly
            210                 215                 220

Gln Ile Ile Phe Gly Gly Val Asp Asn Ala Lys Tyr Ser Gly Thr Leu
225                 230                 235                 240

Ile Ala Leu Pro Val Thr Ser Asp Asn Glu Leu Arg Ile His Leu Asn
                245                 250                 255

Thr Val Lys Val Ala Gly Gln Ser Ile Asn Ala Asp Val Asp Val Leu
            260                 265                 270

Leu Asp Ser Gly Thr Thr Ile Thr Tyr Leu Gln Gln Gly Val Ala Asp
            275                 280                 285

Gln Val Ile Ser Ala Phe Asn Gly Gln Glu Thr Tyr Asp Ala Asn Gly
290                 295                 300

Asn Leu Phe Tyr Leu Val Asp Cys Asn Leu Ser Gly Ser Val Asp Phe
305                 310                 315                 320

Ala Phe Asp Lys Asn Ala Lys Ile Ser Val Pro Ala Ser Glu Phe Thr
                325                 330                 335

Ala Pro Leu Tyr Thr Glu Asp Gly Gln Val Tyr Asp Gln Cys Gln Leu
            340                 345                 350

Leu Phe Gly Thr Ser Asp Tyr Asn Ile Leu Gly Asp Asn Phe Leu Arg
            355                 360                 365

Ser Ala Tyr Ile Val Tyr Asp Leu Asp Asp Asn Glu Ile Ser Leu Ala
370                 375                 380

Gln Val Lys Tyr Thr Thr Ala Ser Asn Ile Ala Ala Leu Thr
385                 390                 395

<210> SEQ ID NO 4
<211> LENGTH: 417
<212> TYPE: PRT
<213> ORGANISM: Candida albicans

<400> SEQUENCE: 4

Met Phe Leu Gln Asn Ile Leu Ser Val Leu Ala Phe Ala Leu Leu Ile
 1               5                  10                  15

```
Asp Ala Ala Pro Val Lys Arg Ser Thr Gly Phe Val Thr Leu Asp Phe
             20                  25                  30

Asn Val Lys Arg Ser Leu Val Asp Pro Lys Asp Pro Thr Val Glu Val
         35                  40                  45

Lys Arg Ser Pro Leu Phe Leu Asp Ile Glu Pro Thr Glu Ile Pro Val
 50                  55                  60

Asp Asp Thr Gly Arg Asn Asp Val Gly Lys Arg Gly Pro Val Ala Val
 65                  70                  75                  80

Lys Leu Asp Asn Glu Ile Ile Thr Tyr Ser Ala Asp Ile Thr Ile Gly
                 85                  90                  95

Ser Asn Asn Gln Lys Leu Ser Val Ile Val Asp Thr Gly Ser Ser Asp
            100                 105                 110

Leu Trp Val Pro Asp Ser Asn Ala Val Cys Ile Pro Lys Trp Pro Gly
        115                 120                 125

Asp Arg Gly Asp Phe Cys Lys Asn Asn Gly Ser Tyr Ser Pro Ala Ala
130                 135                 140

Ser Ser Thr Ser Lys Asn Leu Asn Thr Pro Phe Glu Ile Lys Tyr Ala
145                 150                 155                 160

Asp Gly Ser Val Ala Gln Gly Asn Leu Tyr Gln Asp Thr Val Gly Ile
                165                 170                 175

Gly Gly Val Ser Val Arg Asp Gln Leu Phe Ala Asn Val Arg Ser Thr
            180                 185                 190

Ser Ala His Lys Gly Ile Leu Gly Ile Gly Phe Gln Ser Asn Glu Ala
        195                 200                 205

Thr Arg Thr Pro Tyr Asp Asn Leu Pro Ile Thr Leu Lys Lys Gln Gly
210                 215                 220

Ile Ile Ser Lys Asn Ala Tyr Ser Leu Phe Leu Asn Ser Pro Glu Ala
225                 230                 235                 240

Ser Ser Gly Gln Ile Ile Phe Gly Gly Ile Asp Lys Ala Lys Tyr Ser
                245                 250                 255

Gly Ser Leu Val Asp Leu Pro Ile Thr Ser Asp Arg Thr Leu Ser Val
            260                 265                 270

Gly Leu Arg Ser Val Asn Val Met Gly Gln Asn Val Asn Val Asn Ala
        275                 280                 285

Gly Val Leu Leu Asp Ser Gly Thr Thr Ile Ser Tyr Phe Thr Pro Asn
290                 295                 300

Ile Ala Arg Ser Ile Ile Tyr Ala Leu Gly Gly Gln Val His Tyr Asp
305                 310                 315                 320

Ser Ser Gly Asn Glu Ala Tyr Val Ala Asp Cys Lys Thr Ser Gly Thr
                325                 330                 335

Val Asp Phe Gln Phe Asp Arg Asn Leu Lys Ile Ser Val Pro Ala Ser
            340                 345                 350

Glu Phe Leu Tyr Gln Leu Tyr Tyr Thr Asn Gly Glu Pro Tyr Pro Lys
        355                 360                 365

Cys Glu Ile Arg Val Arg Glu Ser Glu Asp Asn Ile Leu Gly Asp Asn
370                 375                 380

Phe Met Arg Ser Ala Tyr Ile Val Tyr Asp Leu Asp Asp Arg Lys Ile
385                 390                 395                 400

Ser Met Ala Gln Val Lys Tyr Thr Ser Gln Ser Asn Ile Val Gly Ile
                405                 410                 415

Asn
```

<210> SEQ ID NO 5
<211> LENGTH: 418
<212> TYPE: PRT
<213> ORGANISM: Candida albicans

<400> SEQUENCE: 5

Met Phe Leu Lys Asn Ile Leu Ser Val Leu Ala Phe Ala Leu Leu Ile
1               5                   10                  15

Asp Ala Ala Pro Val Lys Arg Ser Pro Gly Phe Val Thr Leu Asp Phe
            20                  25                  30

Asn Val Lys Arg Ser Leu Val Asp Pro Asp Pro Thr Val Glu Ala
        35                  40                  45

Lys Arg Ser Pro Leu Phe Leu Glu Phe Thr Pro Ser Glu Phe Pro Val
    50                  55                  60

Asp Glu Thr Gly Arg Asp Gly Asp Val Asp Lys Arg Gly Pro Val Ala
65                  70                  75                  80

Val Thr Leu His Asn Glu Ala Ile Thr Tyr Thr Ala Asp Ile Thr Val
                85                  90                  95

Gly Ser Asp Asn Gln Lys Leu Asn Val Ile Val Asp Thr Gly Ser Ser
            100                 105                 110

Asp Leu Trp Ile Pro Asp Ser Asn Val Ile Cys Ile Pro Lys Trp Arg
        115                 120                 125

Gly Asp Lys Gly Asp Phe Cys Lys Ser Ala Gly Ser Tyr Ser Pro Ala
    130                 135                 140

Ser Ser Arg Thr Ser Gln Asn Leu Asn Thr Arg Phe Asp Ile Lys Tyr
145                 150                 155                 160

Gly Asp Gly Ser Tyr Ala Lys Gly Lys Leu Tyr Lys Asp Thr Val Gly
                165                 170                 175

Ile Gly Gly Val Ser Val Arg Asp Gln Leu Phe Ala Asn Val Trp Ser
            180                 185                 190

Thr Ser Ala Arg Lys Gly Ile Leu Gly Ile Gly Phe Gln Ser Gly Glu
        195                 200                 205

Ala Thr Glu Phe Asp Tyr Asp Asn Leu Pro Ile Ser Leu Arg Asn Gln
    210                 215                 220

Gly Ile Ile Gly Lys Ala Ala Tyr Ser Leu Tyr Leu Asn Ser Ala Glu
225                 230                 235                 240

Ala Ser Thr Gly Gln Ile Ile Phe Gly Gly Ile Asp Lys Ala Lys Tyr
                245                 250                 255

Ser Gly Ser Leu Val Asp Leu Pro Ile Thr Ser Glu Lys Lys Leu Thr
            260                 265                 270

Val Gly Leu Arg Ser Val Asn Val Arg Gly Arg Asn Val Asp Ala Asn
        275                 280                 285

Thr Asn Val Leu Leu Asp Ser Gly Thr Thr Ile Ser Tyr Phe Thr Arg
    290                 295                 300

Ser Ile Val Arg Asn Ile Leu Tyr Ala Ile Gly Ala Gln Met Lys Phe
305                 310                 315                 320

Asp Ser Ala Gly Asn Lys Val Tyr Val Ala Asp Cys Lys Thr Ser Gly
                325                 330                 335

Thr Ile Asp Phe Gln Phe Gly Asn Asn Leu Lys Ile Ser Val Pro Val
            340                 345                 350

Ser Glu Phe Leu Phe Gln Thr Tyr Tyr Thr Ser Gly Lys Pro Phe Pro
        355                 360                 365

Lys Cys Glu Val Arg Ile Arg Glu Ser Glu Asp Asn Ile Leu Gly Asp
    370                 375                 380

-continued

Asn Phe Leu Arg Ser Ala Tyr Val Val Tyr Asn Leu Asp Asp Lys Lys
385                 390                 395                 400

Ile Ser Met Ala Pro Val Lys Tyr Thr Ser Glu Ser Asp Ile Val Ala
            405                 410                 415

Ile Asn

<210> SEQ ID NO 6
<211> LENGTH: 418
<212> TYPE: PRT
<213> ORGANISM: Candida albicans

<400> SEQUENCE: 6

Met Phe Leu Lys Asn Ile Leu Ser Val Leu Arg Phe Ala Leu Leu Ile
1               5                   10                  15

Asp Ala Ala Pro Val Lys Arg Ser Pro Gly Phe Val Thr Leu Asp Phe
            20                  25                  30

Asn Val Lys Arg Ser Leu Val Val Pro Asp Asp Pro Thr Ala Glu Ser
        35                  40                  45

Lys Arg Ser Pro Leu Phe Leu Asp Leu Asp Pro Thr Gln Ile Pro Val
    50                  55                  60

Asp Asp Thr Gly Arg Asn Val Gly Val Asp Lys Arg Gly Pro Val Ala
65                  70                  75                  80

Val Lys Leu Asp Asn Glu Ile Ile Thr Tyr Ser Ala Asp Ile Thr Val
                85                  90                  95

Gly Ser Asn Asn Gln Lys Leu Ser Val Ile Asp Thr Gly Ser Ser
            100                 105                 110

Asp Leu Trp Ile Pro Asp Ser Lys Ala Ile Cys Ile Pro Lys Trp Arg
        115                 120                 125

Gly Asp Cys Gly Asp Phe Cys Lys Asn Asn Gly Ser Tyr Ser Pro Ala
130                 135                 140

Ala Ser Ser Thr Ser Lys Asn Leu Asn Thr Arg Phe Glu Ile Lys Tyr
145                 150                 155                 160

Ala Asp Gly Ser Tyr Ala Lys Gly Asn Leu Tyr Gln Asp Thr Val Gly
                165                 170                 175

Ile Gly Gly Ala Ser Val Lys Asn Gln Leu Phe Ala Asn Val Trp Ser
            180                 185                 190

Thr Ser Ala His Lys Gly Ile Leu Gly Ile Gly Phe Gln Thr Asn Glu
        195                 200                 205

Ala Thr Arg Thr Pro Tyr Asp Asn Leu Pro Ile Ser Leu Lys Lys Gln
    210                 215                 220

Gly Ile Ile Ala Lys Asn Ala Tyr Ser Leu Phe Leu Asn Ser Pro Glu
225                 230                 235                 240

Ala Ser Ser Gly Gln Ile Ile Phe Gly Gly Ile Asp Lys Ala Lys Tyr
                245                 250                 255

Ser Gly Ser Leu Val Glu Leu Pro Ile Thr Ser Asp Arg Thr Leu Ser
            260                 265                 270

Val Gly Leu Arg Ser Val Asn Val Met Gly Arg Asn Val Asn Val Asn
        275                 280                 285

Ala Gly Val Leu Leu Asp Ser Gly Thr Thr Ile Ser Tyr Phe Thr Pro
    290                 295                 300

Ser Ile Ala Arg Ser Ile Ile Tyr Ala Leu Gly Gly Gln Val His Phe
305                 310                 315                 320

Asp Ser Ala Gly Asn Lys Ala Tyr Val Ala Asp Cys Lys Thr Ser Gly
                325                 330                 335

-continued

Thr Val Asp Phe Gln Phe Asp Lys Asn Leu Lys Ile Ser Val Pro Ala
            340                 345                 350

Ser Glu Phe Leu Tyr Gln Leu Tyr Tyr Thr Asn Gly Lys Pro Tyr Pro
        355                 360                 365

Lys Cys Glu Ile Arg Val Arg Glu Ser Glu Asp Asn Ile Leu Gly Asp
    370                 375                 380

Asn Phe Met Arg Ser Ala Tyr Ile Val Tyr Asp Leu Asp Asp Lys Lys
385                 390                 395                 400

Ile Ser Met Ala Gln Val Lys Tyr Thr Ser Glu Ser Asn Ile Val Ala
            405                 410                 415

Ile Asn

<210> SEQ ID NO 7
<211> LENGTH: 588
<212> TYPE: PRT
<213> ORGANISM: Candida albicans

<400> SEQUENCE: 7

Met Gln Arg Val Leu Glu Leu Leu Leu Ser Ser Thr Ala Leu Ala
1               5                   10                  15

Val Ile Gly Asp Gly Phe Ile Ala Leu Pro Val His Lys Leu Gln Ala
            20                  25                  30

Gly Glu Gly Ser Ala His Phe Pro Asn Arg Leu Pro Ile Phe Asp Val
        35                  40                  45

Val Asn Gly Val Ala Lys Ser Val Glu Asp Val Asn Gln Ile Ile
50                  55                  60

Gln Pro Ile Phe Gly Asn Gly Ile Phe Ser Gly Ser Ile Gln Gly
65                  70                  75                  80

Thr His Ser Gly Asn Gly His Ser Val Lys Tyr Glu Val Ser Leu Pro
                85                  90                  95

Ser Ser Ser Ala Gln Lys Gly Ser Asn Gly Pro Ser Ser Thr Asp Asn
            100                 105                 110

Lys Asp Thr Asp Pro Ser Lys Thr Gly Phe Ser Leu Asp Asp Leu Met
        115                 120                 125

Asn Ser Ile Ser Thr Asp Phe Trp Asn Leu Ile Gly Leu Asn Lys Ala
    130                 135                 140

Pro Thr Ser Ser Asp Asn Gly Ser Lys Asp Ala Asp Phe Thr Pro Ser
145                 150                 155                 160

Ala Val Ser Gln Val Glu Gln Pro Thr Ser Lys Ser Val Glu Ser Thr
                165                 170                 175

Ala Pro Gly Pro Ala Ser Ser Ala Ser Ser Ser Ser Ser Glu Ala
            180                 185                 190

Ala Ser Ser Ser Gln Pro Ser Glu Asp Ser Gln Pro Ser Ser Ser Ala
        195                 200                 205

Asn Lys Lys Thr Gly Ala Phe Phe Leu Ser Leu Asp Asn Thr Gln Thr
    210                 215                 220

Leu Tyr Thr Ala Thr Leu Lys Val Gly Ser Pro Ala Gln Glu Val Gln
225                 230                 235                 240

Val Met Ile Asp Thr Gly Ser Ser Asp Leu Trp Phe Ile Ser Ser Gly
                245                 250                 255

Asn Ser Gln Cys Lys Val Asn Gly Gly Ser Ile Asp Cys Asp Lys Tyr
            260                 265                 270

Gly Val Phe Asp Lys Ser Lys Ser Ser Thr Trp His Asp Asn Lys Thr
        275                 280                 285

```
Asp Tyr Ser Ile Ser Tyr Tyr Asp Gly Asp Lys Ala Ser Gly Thr Met
    290                 295                 300
Gly Gln Asp Asn Ile Thr Phe Ala Asp Gly Phe Ser Ile Glu Asn Ala
305                 310                 315                 320
Asn Phe Ala Val Ile Asp Asn Thr Thr Ser Ser Ile Gly Val Phe Gly
                325                 330                 335
Val Gly Tyr Pro Glu Leu Glu Ala Val Lys Ser Lys Tyr Thr Asn Leu
                340                 345                 350
Pro Phe Ala Met Lys Glu Gln Asn Leu Ile Ala Lys Val Ala Tyr Ser
                355                 360                 365
Leu Tyr Leu Asp Ser Arg Asp Ala Val Gln Gly Tyr Ile Leu Phe Gly
    370                 375                 380
Gly Ile Asp His Ala Lys Tyr Thr Gly Asp Leu Lys Ala Phe Asp Ile
385                 390                 395                 400
Val Gln Ser Asn Asp Lys Tyr Val Tyr Ser Gln Ile Pro Leu Thr Ser
                405                 410                 415
Val Ala Ser Ser Leu Asn Asn Tyr Thr Asn Ala Tyr Gly Leu Pro Ala
                420                 425                 430
Gly Ser Asn His Pro Lys Val Gly Ala Val Ile Tyr Asn Gly Thr Asp
    435                 440                 445
Ser Phe Asn Gly Gly Val Asp Leu Lys Asp Thr Pro Thr Leu Leu Asp
    450                 455                 460
Thr Gly Thr Thr Tyr Ser Tyr Leu Ser Lys Asp Gln Val Glu Ser Ile
465                 470                 475                 480
Val Gly Leu Tyr Gly Asn Val Thr Tyr Asn Asp Ala Gly Lys Ala Tyr
                485                 490                 495
Glu Val Pro Cys Trp Val Gly Asn Pro Gly Asn Tyr Leu Glu Phe Asn
                500                 505                 510
Phe Lys Asn Glu Gln Tyr Ile Lys Val Pro Thr Ser Glu Phe Val Ile
    515                 520                 525
Ser Val Gly Thr Tyr Ala Ser Gly Ala Glu Leu Cys Val Phe Gly Ile
    530                 535                 540
Leu Pro Gly Thr His Ser Ile Leu Gly Asp Asn Phe Met Arg Ser Val
545                 550                 555                 560
Tyr Ala Val Phe Asp Leu Glu Asp His Val Ile Ser Ile Ala Gln Ala
                565                 570                 575
Ala Tyr Asn Asp Asn His Ala Val Val Pro Ile Glu
                580                 585

<210> SEQ ID NO 8
<211> LENGTH: 405
<212> TYPE: PRT
<213> ORGANISM: Candida albicans

<400> SEQUENCE: 8

Met Val Ser Ile Ile Thr Phe Thr Lys Asn Val Leu Val Thr Leu Ala
1               5                   10                  15
Phe Ala Leu Leu Ala Gln Gly Leu Ala Ile Pro Glu Asp Ile Asp Lys
                20                  25                  30
Arg Ala Glu Lys Val Val Ser Leu Asp Phe Thr Val Thr Arg Lys Pro
            35                  40                  45
Phe Asn Ala Thr Ala His Gly Gln His His Gln Ser Gln Gln Gln Gln
    50                  55                  60
Gln Gln Gln Gln Gln Pro Ala Gln Lys Arg Gly Thr Val Gln Thr
65                  70                  75                  80
```

Ser Leu Ile Asn Glu Gly Pro Ser Tyr Ala Ala Thr Ile Thr Val Gly
            85                  90                  95

Ser Asn Lys Gln Gln Thr Val Ile Val Asp Thr Gly Ser Ser Asp
            100                 105                 110

Leu Trp Val Val Asp Ser Ala Ala Val Cys Gln Val Thr Tyr Pro Gly
            115                 120                 125

Gln Ser Pro Thr Phe Cys Lys Gln Asp Gly Thr Tyr Lys Pro Ser Ser
        130                 135                 140

Ser Thr Thr Ser Gln Asn Leu Gly Lys Ala Phe Ser Ile Arg Tyr Glu
145                 150                 155                 160

Asp Gly Ser Ser Gln Gly Thr Val Tyr Lys Asp Thr Val Gly Leu
            165                 170                 175

Gly Gly Ala Ser Ile Thr Asn Gln Gln Phe Ala Asp Val Thr Thr Thr
            180                 185                 190

Ser Val Asp Gln Gly Ile Leu Gly Ile Gly Phe Thr Gly Asp Glu Ser
            195                 200                 205

Ser Pro Thr Tyr Asp Asn Val Pro Val Thr Leu Lys Lys Gln Gly Ile
            210                 215                 220

Ile Asn Lys Asn Ala Tyr Ser Leu Tyr Leu Asn Ser Ala Ser Ala Ser
225                 230                 235                 240

Ser Gly Thr Ile Ile Phe Gly Gly Val Asp Asn Ala Lys Tyr Thr Gly
            245                 250                 255

Ser Leu Thr Ala Leu Pro Ile Thr Ser Ser Asn Glu Leu Arg Val Gln
            260                 265                 270

Leu Ser Thr Ile Asn Ile Ala Gly Thr Thr Val Ser Ala Ser Thr Thr
            275                 280                 285

Pro Val Leu Asp Ser Gly Thr Thr Leu Thr Tyr Phe Ser Gln Thr Ile
            290                 295                 300

Ala Asp Lys Leu Ala Ala Val Gly Ala Lys Trp Asn Ser Tyr Tyr
305                 310                 315                 320

Gln Leu Tyr Thr Ser Ser Cys Asn Leu Ala Gly Asn Ile Val Phe Asn
            325                 330                 335

Phe Ala Lys Gly Val Thr Ile Ser Val Pro Leu Ser Glu Phe Val Leu
            340                 345                 350

Gln Asp Gly Asn Ser Cys Tyr Phe Gly Val Ser Arg Asp Ser Ala Thr
            355                 360                 365

Ile Leu Gly Asp Asn Phe Leu Arg Arg Ala Tyr Ala Val Tyr Asp Leu
            370                 375                 380

Asp Gly Asn Thr Ile Ser Leu Ala Gln Val Lys Tyr Thr Thr Ser Ser
385                 390                 395                 400

Ser Ile Ser Thr Leu
            405

<210> SEQ ID NO 9
<211> LENGTH: 544
<212> TYPE: PRT
<213> ORGANISM: Candida albicans

<400> SEQUENCE: 9

Met Arg Leu Asn Ser Val Ala Leu Leu Ser Leu Val Ala Thr Ala Leu
1               5                   10                  15

Ala Ala Lys Ala Pro Phe Lys Ile Asp Phe Glu Val Arg Arg Gly Glu
            20                  25                  30

Ser Lys Asp Asp Leu Ser Pro Glu Asp Asp Ser Asn Pro Arg Phe Val

```
            35                  40                  45
Lys Arg Asp Gly Ser Leu Asp Met Thr Leu Thr Asn Lys Gln Thr Phe
 50                  55                  60
Tyr Met Ala Thr Leu Lys Ile Gly Ser Asn Glu Asp Glu Asn Arg Val
 65                  70                  75                  80
Leu Glu Asp Thr Gly Ser Ser Asp Leu Trp Val Met Ser His Asp Leu
                     85                  90                  95
Lys Cys Val Ser Ala Pro Ile Ser Lys Arg Asn Glu Arg Ser Phe Gly
                100                 105                 110
His Gly Thr Gly Val Lys Leu Asn Glu Arg Glu Leu Met Gln Lys Arg
            115                 120                 125
Lys Asn Leu Tyr Gln Pro Ser Arg Thr Ile Glu Thr Asp Glu Glu Lys
            130                 135                 140
Glu Ala Ser Glu Lys Ile His Asn Lys Leu Phe Gly Phe Gly Ser Ile
145                 150                 155                 160
Tyr Ser Thr Val Tyr Ile Thr Glu Gly Pro Gly Ala Tyr Ser Thr Phe
                    165                 170                 175
Ser Pro Leu Val Gly Thr Glu Gly Ser Gly Ser Gly Gly Ser
                180                 185                 190
Asn Thr Cys Arg Ser Tyr Gly Ser Phe Asn Thr Glu Asn Ser Asp Thr
                195                 200                 205
Phe Lys Lys Asn Thr Asn Asp Phe Glu Ile Gln Tyr Ala Asp Asp
            210                 215                 220
Thr Ser Ala Ile Gly Ile Trp Gly Tyr Asp Asp Val Thr Ile Ser Asn
225                 230                 235                 240
Val Thr Val Lys Asp Leu Ser Phe Ala Ile Ala Asn Glu Thr Ser Ser
                245                 250                 255
Asp Val Gly Val Leu Gly Ile Gly Leu Pro Gly Leu Glu Val Thr Thr
                260                 265                 270
Gln Leu Arg Tyr Thr Tyr Gln Asn Leu Pro Leu Lys Leu Lys Ala Asp
                275                 280                 285
Gly Ile Ile Ala Lys Ser Leu Tyr Ser Leu Tyr Leu Asn Thr Ala Asp
            290                 295                 300
Ala Lys Ala Gly Ser Ile Leu Phe Gly Ala Ile Asp His Ala Lys Tyr
305                 310                 315                 320
Gln Gly Asp Leu Val Thr Val Lys Met Met Arg Thr Tyr Ser Gln Ile
                325                 330                 335
Ser Tyr Pro Val Arg Ile Gln Val Pro Val Leu Lys Ile Asp Val Glu
                340                 345                 350
Ser Ser Ser Gly Ser Thr Thr Asn Ile Leu Ser Gly Thr Thr Gly Val
                355                 360                 365
Val Leu Asp Thr Gly Ser Thr Leu Ser Tyr Val Phe Ser Asp Thr Leu
            370                 375                 380
Gln Ser Leu Gly Lys Ala Leu Asn Gly Gln Tyr Ser Asn Ser Val Gly
385                 390                 395                 400
Ala Tyr Val Val Asn Cys Asn Leu Ala Asp Ser Ser Arg Thr Val Asp
                    405                 410                 415
Ile Glu Phe Gly Gly Asn Lys Thr Ile Lys Val Pro Ile Ser Asp Leu
                420                 425                 430
Val Leu Gln Ala Ser Lys Ser Thr Cys Ile Leu Gly Val Met Gln Gln
            435                 440                 445
Ser Ser Ser Ser Tyr Met Leu Phe Gly Asp Asn Ile Leu Arg Ser
450                 455                 460
```

```
Ala Tyr Ile Val Tyr Asp Leu Asp Asp Tyr Glu Val Ser Leu Ala Gln
465                 470                 475                 480

Val Ser Tyr Thr Asn Lys Glu Ser Ile Glu Val Ile Gly Ala Ser Gly
                485                 490                 495

Ile Thr Asn Ser Ser Gly Ser Gly Thr Thr Ser Ser Ser Gly Thr Ser
                500                 505                 510

Thr Ser Thr Ser Thr Arg His Ser Ala Gly Ser Ile Ile Ser Asn Pro
                515                 520                 525

Val Tyr Gly Leu Leu Leu Ser Leu Leu Ile Ser Tyr Tyr Val Leu Val
                530                 535                 540

<210> SEQ ID NO 10
<211> LENGTH: 453
<212> TYPE: PRT
<213> ORGANISM: Candida albicans

<400> SEQUENCE: 10

Met Asp Leu Val Ile Met Asn Phe Val Phe Leu Leu Tyr Leu Thr Ser
1               5                   10                  15

Val Val Lys Cys Ser Ile Lys Leu Asp Phe Asn Lys Val Ser Thr Pro
                20                  25                  30

Ser Lys Tyr Thr Lys Arg Asp Ala Leu Pro Met Pro Leu Ile Asn Asp
            35                  40                  45

Lys Ile Leu Tyr Thr Thr Glu Leu Glu Ile Gly Ser Asn Lys Asp Lys
50                  55                  60

Val Ser Val Ser Ile Asp Thr Gly Ser Tyr Asp Leu Trp Val Met Ser
65                  70                  75                  80

Asn Asp Ala Val Cys Tyr Lys Val Ser Glu Phe Gln Thr Glu Gly Ala
                85                  90                  95

Pro Gln Leu Pro Asp Ile Phe Asn Asp Ile Asp Gln Asp Tyr Ser Cys
            100                 105                 110

Thr Phe Asn Gly Thr Tyr Asn Ser Lys Ser Ser Lys Thr Phe Lys Asn
        115                 120                 125

Thr Ser Glu Asp Phe Ser Ile Gly Tyr Val Asp Gly Ser Ala Ala Gln
130                 135                 140

Gly Val Trp Gly Tyr Asp Ser Val Gln Phe Gly Gln Tyr Gly Val Thr
145                 150                 155                 160

Gly Leu Lys Ile Gly Ile Ala Asn Arg Ser Val Ser Asp Gly Ile
                165                 170                 175

Leu Gly Ile Gly Ile Ala Asn Gly Tyr Asp Asn Phe Pro Val Leu Leu
            180                 185                 190

Gln Lys Gln Gly Leu Ile Asn Lys Ile Ala Tyr Ser Val Tyr Leu Asn
        195                 200                 205

Ser Ser Asn Ser Thr Thr Gly Thr Ile Leu Phe Gly Ala Ile Asp His
210                 215                 220

Ala Lys Tyr Lys Gly Ala Leu Ser Thr Val Pro Val Asp Ser Lys Ser
225                 230                 235                 240

Gln Leu Ser Val Asn Val Thr Asn Leu Lys Thr Lys Asn Gly Asn Val
                245                 250                 255

Ala Ser Gly Gly His Ser Ile Leu Leu Asp Thr Gly Ser Thr Phe Ser
            260                 265                 270

Ile Phe Pro Asp Glu Trp Ile Asp Ala Leu Gly His Ser Leu Asn Ala
        275                 280                 285

Thr Tyr Asp Glu Asp Glu Ser Val Tyr Glu Ile Glu Cys Asp Gly Tyr
```

```
            290                 295                 300
Asp Glu His Phe Phe Gly Phe Ser Ile Gly Asp Ser Asp Phe Ser Val
305                 310                 315                 320

Pro Ile Gln Asp Leu Lys Thr Glu Lys Asp Gly Gln Cys Tyr Leu Ala
                325                 330                 335

Ile Met Ser Asn Ser Val Ile Gly Gly Gly Ile Leu Phe Gly Asp
                340                 345                 350

Asp Ile Leu Arg Gln Ile Tyr Leu Val Tyr Asp Leu Gln Asp Met Thr
                355                 360                 365

Ile Ser Val Ala Pro Val Val Tyr Thr Glu Asp Glu Asp Ile Glu Glu
                370                 375                 380

Ile Leu Asn Pro Asn Glu Asp Gln Asn Glu Val Pro Thr Ser Thr Ser
385                 390                 395                 400

Phe Thr Gln Ser Ala Ser Ser Ser Gly Ser Gln Pro Ser Ser Thr Ile
                405                 410                 415

Ser Gly Glu Asn Met Asp Lys Asn Thr Thr Ser Ser Ser Gly Asn
                420                 425                 430

Cys Gln Thr Arg Ser Trp Ile Ala Ile Leu Ser Ala Leu Phe Leu Val
                435                 440                 445

Tyr Ile His Ile Ile
        450

<210> SEQ ID NO 11
<211> LENGTH: 379
<212> TYPE: PRT
<213> ORGANISM: Candida albicans

<400> SEQUENCE: 11

Met Val Lys Leu Leu Ser Ile Trp Ile Ser Ile Tyr Phe Met Ala
1               5                   10                  15

Gly Ser Ser Phe Ala Ser Ser Tyr Leu Val Ser Leu His Ser Gln
                20                  25                  30

Glu Thr Ile Asp Thr Phe Met Ala Tyr Asp Ala Thr Tyr Pro Gln Asp
                35                  40                  45

Leu Gln Val Gly Glu Leu Ile Asn Ser Lys Phe Lys Ile Gly Asn Phe
        50                  55                  60

Ser Gly Phe Ser Gly Ser Phe Ser Lys Asp Ile Ile Lys Arg Leu Glu
65                  70                  75                  80

Arg Cys Pro Leu Val Asp Glu Ile Val Pro Asp Ile Thr Val Lys Ala
                85                  90                  95

Tyr Asp Ala Val Phe Gln Asp Ser Ala Pro Arg His Leu Ala Arg Ile
                100                 105                 110

Ser Arg Arg Lys Arg Met Lys Pro Ile Lys Lys Tyr Ser Tyr Ile Tyr
                115                 120                 125

Glu Ser Asp Phe Ile Gly Lys Lys Val Ser Ala Tyr Val Ile Asp Ser
                130                 135                 140

Gly Ile Ala Ile Gly His Pro Glu Phe Gln Gly Arg Ala Arg Thr Gly
145                 150                 155                 160

Lys Asp Phe Thr Asp Glu Gly Pro Gly Asp Asn Asn Gly His Gly Thr
                165                 170                 175

His Val Ala Gly Leu Ile Gly Ser His Thr Tyr Gly Val Ala Lys Gly
                180                 185                 190

Val Gln Ile Ile Asp Val Lys Ala Leu Asn Ser Lys Gly Thr Gly Ser
        195                 200                 205
```

```
Leu Ser Thr Ile Leu Val Ala Ile Glu Phe Ala Val Asn His Arg Leu
    210                 215                 220

Arg Ser Gly Arg Met Gly Val Ala Asn Leu Ser Leu Gly Ala Tyr Lys
225                 230                 235                 240

Asn Lys Leu Leu Asn Lys Ala Ile Asp Gln Ala Thr Gln Thr Gly Leu
                245                 250                 255

Val Phe Val Val Ala Ala Gly Asn Asn Asn Ile Asn Ala Cys Leu Thr
                260                 265                 270

Ser Pro Ser Ser Ser Pro Tyr Ala Ile Thr Val Gly Ala Ile Asp Asp
                275                 280                 285

Tyr Asn Asp Ser Ile Ala Ser Phe Ser Asn Trp Gly Glu Cys Val Asp
                290                 295                 300

Leu Phe Ala Ser Gly Ala Tyr Val Lys Ser Val Asn Ile Arg Ser Asp
305                 310                 315                 320

Phe Arg Pro Ser Val Leu Ser Gly Thr Ser Met Ala Ala Pro Ile Val
                325                 330                 335

Thr Gly Leu Val Ala Asn Leu Leu Asn Glu Gly Val Asp Pro Glu Leu
                340                 345                 350

Ile Lys Gly Gln Leu Ile Glu Met Ser Thr Lys His Arg Ile Ser Lys
                355                 360                 365

Ser Ser Leu Phe Leu Lys Lys Arg Thr Pro Asn
                370                 375

<210> SEQ ID NO 12
<211> LENGTH: 936
<212> TYPE: PRT
<213> ORGANISM: Candida albicans

<400> SEQUENCE: 12

Met Leu Pro Ile Lys Leu Leu Ile Phe Ile Leu Gly Tyr Leu Leu Ser
1               5                   10                  15

Pro Thr Leu Gln Gln Tyr Gln Gln Ile Pro Pro Arg Asp Tyr Glu Asn
                20                  25                  30

Lys Asn Tyr Phe Leu Val Glu Leu Asn Thr Thr Asn Ser Gln Lys Pro
                35                  40                  45

Leu Ile Asp Phe Ile Ser His Tyr Arg Gly His Tyr Asn Phe Glu His
        50                  55                  60

Gln Leu Ser Ser Leu Asp Asn His Tyr Val Phe Ser Ile Asp Lys Ser
65                  70                  75                  80

His Pro His Asn Ser Phe Leu Gly Asn His Asn Ser Asn Glu Tyr Asn
                85                  90                  95

Leu Met Lys Arg Gln Leu Gly His Glu Gln Asp Tyr Asp Glu Leu Ile
                100                 105                 110

Ser Tyr Val Glu Ser Ile His Leu Leu Pro Met Lys Lys Leu Ser Lys
                115                 120                 125

Arg Ile Pro Val Pro Ile Glu Met Glu Asp Val Val Phe Glu Asn Arg
                130                 135                 140

Asp Asp Thr Gly Ser Asp Asn His Glu Ala Thr Asp Glu Ala His Gln
145                 150                 155                 160

Lys Leu Ile Glu Ile Ala Lys Lys Leu Asp Ile His Asp Pro Glu Phe
                165                 170                 175

Thr Thr Gln Trp His Leu Ile Asn Leu Lys Tyr Pro Gly His Asp Val
                180                 185                 190

Asn Val Thr Gly Leu Trp Leu Glu Asp Ile Leu Gly Gln Gly Ile Val
                195                 200                 205
```

```
Thr Ala Leu Val Asp Asp Gly Val Asp Ala Glu Ser Asp Asp Ile Lys
            210                 215                 220

Gln Asn Phe Asn Ser Glu Gly Ser Trp Asp Phe Asn Asn Lys Gly Lys
225                 230                 235                 240

Ser Pro Leu Pro Arg Leu Phe Asp Asp Tyr His Gly Thr Arg Cys Ala
            245                 250                 255

Gly Glu Ile Ala Ala Val Lys Asn Asp Val Cys Gly Ile Gly Val Ala
            260                 265                 270

Trp Lys Ser Gln Val Ser Gly Ile Arg Ile Leu Ser Gly Pro Ile Thr
            275                 280                 285

Ser Ser Asp Glu Ala Glu Ala Met Val Tyr Gly Leu Asp Thr Asn Asp
290                 295                 300

Ile Tyr Ser Cys Ser Trp Gly Pro Thr Asp Asn Gly Lys Val Leu Ser
305                 310                 315                 320

Glu Pro Asp Val Ile Val Lys Lys Ala Met Ile Lys Gly Ile Gln Glu
            325                 330                 335

Gly Arg Asp Lys Lys Gly Ala Ile Tyr Val Phe Ala Ser Gly Asn Gly
            340                 345                 350

Gly Arg Phe Gly Asp Ser Cys Asn Phe Asp Gly Tyr Thr Asn Ser Ile
            355                 360                 365

Tyr Ser Ile Thr Val Gly Ala Ile Asp Tyr Lys Gly Leu His Pro Gln
            370                 375                 380

Tyr Ser Glu Ala Cys Ser Ala Val Met Val Val Thr Tyr Ser Ser Gly
385                 390                 395                 400

Ser Gly Glu His Ile His Thr Thr Asp Ile Lys Lys Lys Cys Ser Ala
            405                 410                 415

Thr His Gly Gly Thr Ser Ala Ala Ala Pro Leu Ala Ser Gly Ile Tyr
            420                 425                 430

Ser Leu Ile Leu Ser Ala Asn Pro Asn Leu Thr Trp Arg Asp Val Gln
            435                 440                 445

Tyr Ile Ser Val Leu Ser Ala Thr Pro Ile Asn Glu Glu Asp Gly Asn
450                 455                 460

Tyr Gln Thr Thr Ala Leu Asn Arg Lys Tyr Ser His Lys Tyr Gly Tyr
465                 470                 475                 480

Gly Lys Thr Asp Ala Tyr Lys Met Val His Phe Ala Lys Thr Trp Val
            485                 490                 495

Asn Val Lys Pro Gln Ala Trp Tyr Tyr Ser Asp Val Ile Gln Val Asn
            500                 505                 510

Gln Thr Ile Thr Thr Pro Glu Gln Lys Ala Pro Ser Lys Arg Asp
            515                 520                 525

Ser Pro Gln Lys Ile Ile His Ser Ser Val Asn Val Ser Glu Lys Asp
            530                 535                 540

Leu Lys Ile Met Asn Val Glu Arg Val Glu His Ile Thr Val Lys Val
545                 550                 555                 560

Asn Ile Asp Ser Thr Tyr Arg Gly Arg Val Gly Met Arg Ile Ile Ser
            565                 570                 575

Pro Thr Gly Val Ile Ser Asp Leu Ala Thr Phe Arg Val Asn Asp Ala
            580                 585                 590

Ser Thr Arg Gly Phe Gln Asn Trp Thr Phe Met Ser Val Ala His Trp
            595                 600                 605

Gly Glu Thr Gly Ile Gly Glu Trp Lys Val Glu Val Phe Val Asp Asp
610                 615                 620
```

```
Ser Lys Gly Asp Gln Val Glu Ile Asn Phe Lys Asp Trp Gln Phe Arg
625                 630                 635                 640

Ile Phe Gly Glu Ser Ile Asp Gly Asp Lys Ala Glu Val Tyr Asp Ile
            645                 650                 655

Thr Lys Asp Tyr Ala Ala Ile Arg Arg Glu Leu Leu Glu Lys Glu Lys
        660                 665                 670

Gln Asn Ser Lys Ser Thr Thr Thr Ser Ser Thr Thr Thr Ala Thr
    675                 680                 685

Thr Thr Ser Gly Gly Glu Gly Asp Gln Lys Thr Thr Thr Ser Ala Glu
690                 695                 700

Asn Lys Glu Ser Thr Thr Lys Val Asp Asn Ser Ala Ser Ile Thr Thr
705                 710                 715                 720

Ser Gln Thr Ala Ser Leu Thr Ser Ser Asn Glu Gln His Gln Pro Thr
            725                 730                 735

Glu Ser Asn Ser Asp Ser Asp Ser Asp Thr Asp Asp Glu Asn Lys Gln
        740                 745                 750

Glu Gly Glu Glu Asp Asn Asp Asn Asp Asn Gly Asn Lys Lys Ala Asn
    755                 760                 765

Ser Asp Asn Thr Gly Phe Tyr Leu Met Ser Ile Ala Val Val Gly Phe
770                 775                 780

Ile Ala Val Leu Leu Val Met Lys Phe His Lys Thr Pro Gly Ser Gly
785                 790                 795                 800

Arg Arg Arg Arg Arg Asp Gly Tyr Glu Phe Asp Ile Ile Pro Gly
            805                 810                 815

Glu Asp Tyr Ser Asp Ser Asp Asp Glu Asp Ser Asp Thr Arg
        820                 825                 830

Arg Ala Asp Glu Asp Ser Phe Asp Leu Gly His Arg Asn Asp Gln Arg
    835                 840                 845

Val Val Ser Ala Ser Gln Gln Gln Arg Gln Tyr Asp Arg Gln Gln Asp
850                 855                 860

Glu Ala Arg Asp Arg Leu Phe Asp Phe Asn Ala Glu Ser Leu Pro
865                 870                 875                 880

Asp Tyr Glu Asn Asp Met Phe Lys Ile Gly Asp Glu Glu Glu Glu
            885                 890                 895

Glu Glu Gly Gln Gln Ser Ala Lys Ala Pro Ser Asn Ser Glu Gly Asn
        900                 905                 910

Ser Gly Thr Ser Thr Lys Lys Tyr Lys Asp Asn Glu Ala Asp Glu Asp
    915                 920                 925

His Lys Asp Val Val Gly Thr Gln
930                 935

<210> SEQ ID NO 13
<211> LENGTH: 490
<212> TYPE: PRT
<213> ORGANISM: Candida albicans

<400> SEQUENCE: 13

Met Lys Ser Arg Ile Ala Leu Thr Leu Arg Arg Phe Ile Ser Thr Arg
1               5                   10                  15

Pro Arg Leu Phe Thr Thr Tyr Thr Thr Gly Gln Pro Tyr Glu Thr
            20                  25                  30

Arg Pro His Ile Ile Thr Gln Pro Gly Asp Leu Thr Pro Gly Ile Ser
        35                  40                  45

Ala Met Glu Tyr Tyr Gln Arg Arg Leu Lys Leu Ser Thr His Leu Pro
    50                  55                  60
```

```
Ser Lys Ser Leu Ala Ile Ile Ile Gly Asn Thr Thr Gln Phe Ser Ser
 65                  70                  75                  80

Gly Ser Val Phe Tyr Asp Phe Gln Gln Asp Asn Asp Leu Tyr Tyr Leu
                 85                  90                  95

Thr Gly Trp Leu Glu Pro Asp Ser Ile Val Ala Ile Glu Lys Lys Gly
            100                 105                 110

Asp Asn Gly Glu Asp Asp Val Val Leu His Met Leu Val Pro Pro Lys
        115                 120                 125

Asp Pro Lys Lys Glu Leu Trp Glu Gly Pro Lys Ser Gly Leu Glu Gly
    130                 135                 140

Ala Tyr Asn Ile Phe Asn Ala Asp Leu Val Glu Asp Ile Ser Gln Ala
145                 150                 155                 160

Pro Ser Tyr Leu Lys Gln Leu Ile Lys Gln Asn Asp Tyr Ile Tyr Trp
                165                 170                 175

Asp Lys Lys Phe Asn Ser Lys Gln Asn Glu Gly Leu Arg Gln Phe Phe
            180                 185                 190

Asn Phe Ser Thr Asn His Arg His Gln Gly Ile Asn Glu Ile Ile
        195                 200                 205

Glu Asn Ser Lys Lys Ser Val Gln Lys Leu Ser Pro Ile Val Ala Lys
    210                 215                 220

Leu Arg Val Ile Lys Ser Asp Ala Glu Val Ser Val Met Lys Arg Ala
225                 230                 235                 240

Cys Glu Ile Ser Ser Val Ala Ile Asn Arg Ala Met Ala Thr Val Gly
                245                 250                 255

Ser Asp Asp Pro Ile Asn Ser Glu Asn Thr Leu Ala Arg Tyr Leu Glu
            260                 265                 270

Tyr Gln Phe Val Lys Gly Gly Cys Glu Lys Asn Ala Tyr Ile Pro Val
        275                 280                 285

Val Ala Ser Gly Ser Asn Ala Leu Cys Leu His Tyr Thr Arg Asn Asp
    290                 295                 300

Asp Leu Ile Lys Lys Asn Glu Leu Ile Phe Ile Asp Ala Gly Gly Lys
305                 310                 315                 320

Leu Gly Gly Tyr Cys Ala Asp Ile Ser Arg Ala Trp Pro Asn Ser Thr
                325                 330                 335

Asp Gly Phe Thr Asp Ala Gln Arg Asp Ile Tyr Glu Val Val Leu Ala
            340                 345                 350

Thr Asn Lys Lys Cys Ile Thr Leu Cys Ser Glu Ser Leu Gly Tyr Ser
        355                 360                 365

Phe His Asp Ile His Glu Val Ser Val Asn Thr Leu Lys His Glu Leu
    370                 375                 380

Lys Asn Leu Pro Gly Phe Gly Asp Val Thr Phe Ser Asp Ile Ser Arg
385                 390                 395                 400

Ile Tyr Tyr Pro His Tyr Val Gly His Asn Val Gly Leu Asp Leu His
                405                 410                 415

Asp Ile Pro Ser Val Ser Asn Arg Leu Pro Leu Lys Gln Asn Gln Val
            420                 425                 430

Ile Thr Ile Glu Pro Gly Leu Tyr Ile Pro His Asp Gly Pro Lys His
        435                 440                 445

Tyr Arg Gly Ile Gly Leu Arg Ile Glu Asp Asn Val Val Val Gly Lys
    450                 455                 460

Thr His Arg Asp Ile Ile Asn Leu Thr Ser Gly Cys Lys Lys Glu Val
465                 470                 475                 480
```

```
Ser Asp Ile Glu Ala Leu Val Arg Gly Gly
                485                 490
```

<210> SEQ ID NO 14
<211> LENGTH: 578
<212> TYPE: PRT
<213> ORGANISM: Candida albicans

<400> SEQUENCE: 14

```
Met Asn Pro Ala Tyr Asn Pro Asn Pro Lys Glu Thr Phe Val Ser Ile
1               5                   10                  15

Thr Arg Asp Ser Asp Asp Ser Leu Ile Ser Thr Thr Pro Asp Ile Ser
            20                  25                  30

Glu Thr Glu Phe Glu Asp Gly Glu Asn Leu Ser Thr Pro Asp Ile Ser
        35                  40                  45

Ile Ile Asp Asp Glu Tyr Thr Asp Asn Glu Pro Ile Asp Glu Phe Glu
    50                  55                  60

Asn Glu Asn Gln Ile Pro Ala Asp Ser Met Phe Gln Phe Gln Leu Pro
65                  70                  75                  80

Asp Met Ser Thr Thr Ile Pro Arg Leu Pro Ser Asn Gln Asp Val Pro
                85                  90                  95

Ser Ala Lys Asp Asp Thr Phe Asp Asn Tyr Tyr Glu Ser Tyr Ser Glu
            100                 105                 110

Lys Tyr Ile Glu Phe Met Asn Asn Asn Pro Thr Thr Tyr His Thr Ile
        115                 120                 125

Ser His Phe Lys Ser Leu Leu Glu Asn Asn Gly Phe Ile Phe Leu Pro
    130                 135                 140

Asp Asn Lys Pro Ile Ser Asp Leu Ser Pro Gly Phe Tyr Phe Thr Ser
145                 150                 155                 160

Lys Asp Asp Gln Cys Leu Val Ala Phe Ile Ile Gly Gly Asn Trp Lys
                165                 170                 175

Pro Glu Lys Gly Ser Cys Phe Val Gly Ser His Cys Asp Ala Leu Ser
            180                 185                 190

Val Lys Ile Asn Pro Arg Gly Ser Leu Arg Asp Asn Val Asn Gly Tyr
        195                 200                 205

Glu Leu Leu Gly Val Ala Pro Tyr Ser Gly Ser Leu Asn Lys Leu Trp
    210                 215                 220

Leu Ser Arg Asp Leu Gly Leu Ala Gly Ser Val Leu Val Lys Asp Asn
225                 230                 235                 240

Asp Thr Gly Lys Ile Ser Arg Lys Leu Ile Lys Ser His Pro Asp Pro
                245                 250                 255

Ile Ala Phe Ile Pro Gln Leu Pro Glu Val Phe Pro Glu Ser Pro Lys
            260                 265                 270

Glu Tyr Asn Thr Gln Thr Gln Met Val Pro Ile Cys Gly Tyr Thr Thr
        275                 280                 285

Glu Thr Leu Val Pro Thr Asp Glu Glu Lys Arg Ser Lys Phe Tyr Lys
    290                 295                 300

Arg His Ser Leu Ser Leu Arg Tyr Val Ser Lys Leu Ala Glu Val
305                 310                 315                 320

Pro Leu Ala Ser Ile Val Asp Leu Asp Leu Val Asp Ile Gln
                325                 330                 335

Thr Ser Cys Arg Gly Gly Leu Asp Asn Glu Phe Ile Tyr Ser Gly Ser
            340                 345                 350

Leu Asp Asp Arg Leu Cys Ala Phe Asp Ser Val Tyr Gly Leu Ile Glu
        355                 360                 365
```

```
Tyr Ser Gln Arg Phe Tyr Leu Asp Lys Asp Ile Lys Thr Phe Asp Gly
        370                 375                 380

Leu Asn Gly Ile Tyr Leu Ala Asn His Glu Glu Ile Gly Ser Gly Ser
385                 390                 395                 400

Arg Thr Gly Ala Lys Gly Gly Phe Leu Ile Asp Val Leu Lys Ser Ile
                405                 410                 415

Val Ser Asp Lys Tyr Lys Thr His Thr Pro Glu Ala Val Ala Asn Leu
                420                 425                 430

Thr Thr Asn Thr Ile Phe Leu Ser Ser Asp Val Thr His Ala Leu Asn
                435                 440                 445

Pro Asn Phe Lys Asn Val Tyr Leu Glu Asn Asn Phe Pro Val Pro Asn
450                 455                 460

Thr Gly Pro Ser Ile Lys Phe Asp Ser Asn Phe His Val Leu Ser Asp
465                 470                 475                 480

Ser Lys Gly Asn Glu Phe Leu Thr Arg Ile Ile Asp Asp Leu Pro Gly
                485                 490                 495

Ile Lys Leu Gln His Phe His Ile Arg Asn Asp Ser Arg Ser Gly Gly
                500                 505                 510

Thr Ile Gly Pro Ile Met Ser Asp Ser Arg Arg Gly Ile Asn Gly Ala
                515                 520                 525

Lys Leu Ile Ile Asp Val Gly Leu Pro Ile Leu Ser Met His Ser Ile
530                 535                 540

Arg Ser Ile Ala Gly Tyr Lys Asp Val Gly Ile Gly Ile Arg Phe Phe
545                 550                 555                 560

Lys Glu Val Phe Ser Lys Trp Gln Ser Thr Ile Asn Thr Ile Glu Asn
                565                 570                 575

Gly Lys

<210> SEQ ID NO 15
<211> LENGTH: 450
<212> TYPE: PRT
<213> ORGANISM: Candida albicans

<400> SEQUENCE: 15

Met Thr Thr Pro Ser Lys Tyr Pro Ala Arg Ser His Ala Arg Lys Val
1               5                   10                  15

Tyr Ser His Ile Lys Ala Pro Phe Phe Ile Ser Gly Glu Asp Leu Val
                20                  25                  30

Leu Tyr Lys Tyr Cys Asp Gln Thr Lys Pro Phe Arg Gln Asn Arg Tyr
                35                  40                  45

Phe Phe Tyr Leu Thr Gly Cys Asn Ile Pro Gly Ser His Val Leu Tyr
50                  55                  60

Thr His Asp Lys Leu Val Leu Tyr Leu Pro Asp Val Asp His Glu Asp
65                  70                  75                  80

Ile Met Trp Ser Gly Leu Pro Leu Ser Pro Glu Gln Ala Leu Ala Lys
                85                  90                  95

Tyr Asp Val Asp Glu Val Lys Phe Ala Ala Asp Ile Glu Ser Asp Leu
                100                 105                 110

Lys Asn Leu Gly Thr Val Tyr Thr Thr Asp Thr Ser His Pro His Leu
                115                 120                 125

Lys Pro Tyr Leu Thr Glu Ser Asp Pro Ala Phe Phe Ala Leu Asp
                130                 135                 140

Glu Ser Arg Leu Ile Lys Asp Asp Tyr Glu Ile Glu Leu Met Arg His
145                 150                 155                 160
```

Ala Ala Lys Ile Thr Asp Asn Cys His Leu Ala Val Met Ser Ala Leu
            165                 170                 175

Pro Ile Glu Thr Lys Glu Thr His Ile His Ala Glu Phe Met Tyr His
            180                 185                 190

Ala Leu Arg Gln Gly Ala Lys Asn Gln Ser Tyr Asp Pro Ile Cys Cys
            195                 200                 205

Ser Gly Glu Thr Cys Ser Thr Leu His Trp Val Lys Asn Asp Gly Asp
        210                 215                 220

Ile Thr Pro Glu Lys Arg Ser Val Leu Ile Asp Ala Gly Ala Glu Trp
225                 230                 235                 240

Glu Cys Tyr Ala Ser Asp Val Thr Arg Cys Phe Pro Val Asn Gly Asp
                245                 250                 255

Trp Ala Lys Glu His Leu Glu Ile Tyr Asn Leu Val Leu Lys Met Gln
            260                 265                 270

Ser Ala Ala Tyr Glu Met Met Lys Pro Gly Val Glu Trp Glu Asp Ile
            275                 280                 285

His Leu Gln Ala His Lys Val Leu Ile Gln Gly Phe Leu Glu Leu Gly
            290                 295                 300

Ile Phe Asn Ser Lys Tyr Ser Ala Glu Glu Leu Phe Ala Ala Lys Ala
305                 310                 315                 320

Ser Ala Arg Phe Phe Pro His Gly Leu Gly His Val Leu Gly Met Asp
                325                 330                 335

Thr His Asp Val Gly Gly Arg Ala Asn Tyr Ser Asp Pro Asp Pro Leu
            340                 345                 350

Leu Cys Tyr Leu Arg Ile Arg Arg Lys Leu Glu Pro Asn Met Val Val
            355                 360                 365

Thr Asn Glu Pro Gly Cys Tyr Phe Ser Pro Phe Leu Leu Glu Glu Val
            370                 375                 380

Leu Asn Asn Pro Asp Gln Ala Lys Phe Ile Asn Arg Asp Val Leu Asp
385                 390                 395                 400

Lys Tyr Trp Tyr Val Gly Gly Val Arg Ile Glu Asp Asp Val Leu Ile
                405                 410                 415

Thr Pro Thr Gly Tyr Glu Ile Phe Thr Lys Ile Thr Lys Asp Pro Ala
            420                 425                 430

Glu Ile Ser Lys Ile Val Lys Ala Gly Leu Ala Lys Lys Phe His Asn
            435                 440                 445

Ile Val
    450

<210> SEQ ID NO 16
<211> LENGTH: 517
<212> TYPE: PRT
<213> ORGANISM: Candida albicans

<400> SEQUENCE: 16

Met Ser Asn Ile Asp Asp Ile Leu Leu Ser Ile Ser Glu Ser Leu Lys
1               5                   10                  15

Gln Leu Gln Lys Ala Ser Gln Glu Lys Pro Ile Glu Gln Thr Gln Pro
            20                  25                  30

Val Gln Ile Gln Asn Leu Glu Val Asn Ser Thr Lys Lys Phe Thr Asp
            35                  40                  45

Asp Tyr Tyr Ser Lys Ile Ala Asp Asp Tyr Ile Glu Phe Thr Tyr Lys
        50                  55                  60

Asn Pro Thr Ile Tyr His Val Val Asn Phe Phe Lys Ser Gln Leu Glu

-continued

```
          65                  70                  75                  80
Ser Lys Gly Phe Thr Tyr Leu Pro Glu Ser Lys Ser Trp Ala Asp Leu
                    85                  90                  95
Lys Ala Gly Lys Tyr Phe Thr Thr Arg Asn Gly Ser Ser Leu Ala Ala
            100                 105                 110
Phe Val Val Gly Lys Asp Trp Gln Ala Ser Lys Gly Val Gly Ala Ile
        115                 120                 125
Gly Ser His Ile Asp Ser Leu Thr Thr Val Leu Lys Pro Asn Ser Thr
    130                 135                 140
Lys Ala Lys Val Asp Gly Tyr Glu Leu Leu Gly Val Ala Pro Tyr Ala
145                 150                 155                 160
Gly Thr Leu Gly Ser Val Trp Trp Asp Arg Asp Leu Gly Ile Gly Gly
                    165                 170                 175
Arg Leu Leu Val Lys Asp Gly Lys Gly Lys Val Ser Gln His Leu Val
                180                 185                 190
Asp Ser Thr Pro His Pro Ile Ala His Ile Pro Thr Leu Ala Pro His
            195                 200                 205
Phe Gly Ala Pro Ala Asn Gly Pro Phe Asn Thr Glu Thr Gln Ala Val
        210                 215                 220
Pro Val Val Gly Phe Ser Gly Glu Asn Asp Lys Glu Glu Glu Gln Pro
225                 230                 235                 240
Thr Glu Glu Glu Lys Asn Ala Pro Leu Tyr Gly Lys His Pro Leu Lys
                    245                 250                 255
Leu Leu Arg Tyr Ile Ala Lys Leu Ala Asn Val Ser Val Gly Asp Ile
                260                 265                 270
Leu Gln Trp Asp Leu Gln Leu Tyr Asp Val Gln Lys Gly Thr Lys Gly
            275                 280                 285
Gly Leu Asn Lys Glu Phe Val Phe Ala Pro Arg Val Asp Asp Arg Val
        290                 295                 300
Cys Ser Phe Ala Ala Leu Asn Ala Leu Ile Asp Ser Thr Val Asp Asn
305                 310                 315                 320
Asn Leu Ala Glu Asp Ser Phe Ser Ile Val Gly Leu Phe Asp Asn Glu
                    325                 330                 335
Glu Ile Gly Ser Leu Thr Arg Gln Gly Ala Arg Gly Gly Leu Ile Glu
                340                 345                 350
Leu Val Val Asp Arg Val Leu Ser Ser Asn Phe Tyr Asn Pro Glu Val
            355                 360                 365
Leu Asp Ile Gln Glu Ser Leu Arg Leu Thr Tyr Ala Asn Ser Ile Val
        370                 375                 380
Leu Ser Ala Asp Val Asn His Leu Phe Asn Pro Asn Phe Pro Gly Val
385                 390                 395                 400
Tyr Leu Glu His His Lys Pro Leu Pro Asn Ile Gly Val Thr Leu Ser
                    405                 410                 415
Leu Asp Pro Asn Gly His Met Ala Thr Asp Ser Ile Gly Leu Ala Leu
                420                 425                 430
Ala Glu Glu Leu Ala Lys Lys Asn Gly Asp Lys Val Gln Tyr Phe Gln
            435                 440                 445
Ile Arg Asn Asp Ser Arg Ser Gly Gly Thr Ile Gly Pro Ala Ile Ser
        450                 455                 460
Thr Ser Thr Gly Ala Arg Thr Ile Asp Leu Gly Ile Pro Gln Leu Ser
465                 470                 475                 480
Met His Ser Ile Arg Ala Thr Leu Gly Ser Lys Asp Ile Gly Leu Gly
                    485                 490                 495
```

Ile Lys Phe Phe Tyr Gly Phe Lys Asn Trp Arg Asp Val Tyr Asp
            500                 505                 510

Asn Phe Val Asp Leu
        515

<210> SEQ ID NO 17
<211> LENGTH: 509
<212> TYPE: PRT
<213> ORGANISM: Candida albicans

<400> SEQUENCE: 17

Met Gly Ser Asn Thr Ser Lys Thr Ile Met Pro Ala Ser Thr Lys Ser
1               5                   10                  15

Pro Leu Pro Glu Thr Glu Glu Ile Phe Asn Glu Lys Pro Tyr Ser
            20                  25                  30

Ser Thr Ser Thr Phe Asp Asn Phe Arg Glu Gln Phe Glu Gly Leu Glu
            35                  40                  45

Leu Glu Asn Ala Glu Asn Glu Ile Asn Pro Ile Ser Glu Asn Ile Leu
        50                  55                  60

Ser Lys Trp Glu Asp Asp Phe Lys Ser Gln Thr Lys Asn Leu Leu Ala
65                  70                  75                  80

Gln Asn Ala Leu Ala Lys Asn Ala Ile Val Asp Val Ile Ala Lys Asn
                85                  90                  95

Ser Val Gly Lys Gln Ser Leu Lys Asp Arg Tyr Leu Phe Asn Ile Thr
            100                 105                 110

Val Asp Thr Ile Gly Ser Pro Ala His Leu Asn Asn Gln Lys Ser Ser
        115                 120                 125

Gly Arg Cys Trp Ile Phe Ala Ser Ser Asn Val Leu Arg Thr His Val
130                 135                 140

Ile Lys Asn Tyr Asn Leu Lys Glu Asp Asp Phe Gln Leu Ser Gln Ser
145                 150                 155                 160

Tyr Leu Tyr Phe Tyr Asp Lys Leu Glu Lys Ala Asn Phe Phe Leu Glu
                165                 170                 175

Asn Ile Glu Asp Thr Ser Ser Glu Asp Leu Asp Ser Arg Leu Ile Ser
            180                 185                 190

Tyr Leu Phe Ser Asn Pro Val Asn Asp Gly Gly Gln Trp Asp Met Ile
        195                 200                 205

Val Asn Leu Val Asn Lys Tyr Gly Val Val Pro Asn Glu Val Phe Pro
210                 215                 220

Asp Asn Ala Gln Ser Thr Asn Ser Ser Lys Leu Asn Tyr Val Val Thr
225                 230                 235                 240

Glu Lys Leu Arg Glu Tyr Gly Leu Lys Leu Arg Ser Leu Ile Ala Lys
                245                 250                 255

Asp Ala Pro Lys Asn Val Ile Ser Ser Phe Lys Ala Ser Ala Ile Lys
            260                 265                 270

Ser Ile Tyr Lys Thr Ile Ala Leu Ala Leu Gly Thr Pro Pro Lys Pro
        275                 280                 285

Thr Asp Glu Phe Leu Trp Glu Phe Ile Asp Lys Asp Gly Lys Tyr Lys
    290                 295                 300

Ser Phe Lys Thr Asn Pro Leu Asp Phe Tyr Lys Thr His Val Arg Phe
305                 310                 315                 320

Asp Ala Ser Glu His Phe Ser Leu Ile His Asp Pro Arg Asn Glu Tyr
                325                 330                 335

Asn Lys Leu Tyr Thr Val Glu Arg Leu Asn Asn Ile Phe Gly Gly Lys

```
                  340                 345                 350
Pro Ile Glu Tyr Ile Asn Leu Glu Ile Asp Glu Ile Lys Gln Val Ala
            355                 360                 365
Ile Lys Met Leu Lys Asp Asn Glu Pro Val Phe Phe Gly Ser Asp Val
            370                 375                 380
Gly Lys Phe Ser Asp Ser Lys Ser Gly Ile Leu Asp Thr Thr Ala Tyr
385                 390                 395                 400
Asp Tyr Ser Thr Ala Phe Asp Phe Ser Leu Asp Ile Thr Lys Ser Gln
                405                 410                 415
Arg Leu Lys Val Gly Ser Ser Gln Met Thr His Ala Met Val Ile Thr
            420                 425                 430
Gly Val His Ile Asp Pro Gln Thr Asn Lys Pro Val Arg Trp Lys Ile
            435                 440                 445
Glu Asn Ser Trp Gly Glu Asp Ser Gly Gln Lys Gly Trp Phe Met Met
            450                 455                 460
Thr Asp Glu Trp Phe Asp Glu Tyr Val Phe Gln Ile Val Thr Asn Lys
465                 470                 475                 480
Lys Tyr Ser Gly Lys Lys Ala Tyr Asp Ile Trp Lys Ser Lys Glu Phe
                485                 490                 495
Asn Thr Leu Pro Tyr Tyr Asp Pro Met Gly Ala Leu Ala
            500                 505
```

```
<210> SEQ ID NO 18
<211> LENGTH: 496
<212> TYPE: PRT
<213> ORGANISM: Candida albicans

<400> SEQUENCE: 18

Met Ala Ser Ala Ser Thr Ser Lys Glu Leu Lys Tyr Ala Gln Glu Phe
1               5                   10                  15
Val Asp Phe Val Asn Ala Ser Pro Thr Pro Tyr His Ala Val Asn Ser
            20                  25                  30
Val Lys Ser Leu Leu Ser Glu Ala Gly Phe Glu Glu Ile His Glu Arg
        35                  40                  45
Thr Asn Trp Phe Lys Ser His Thr Leu Gln Lys Gly Gly Lys Tyr Phe
    50                  55                  60
Val Thr Arg Asn Gly Ser Ser Ile Ile Ala Phe Thr Ile Gly Glu Gln
65                  70                  75                  80
Phe Lys Asn Gly Asn Gly Ile Ala Ile Val Gly Ala His Thr Asp Ser
                85                  90                  95
Pro Cys Leu Arg Ile Lys Pro Ile Ser Lys Lys Thr Ser Glu Gly Phe
            100                 105                 110
Ile Gln Ile Gly Val Glu Gln Tyr Gly Gly Leu Ile Ala His Ser Trp
        115                 120                 125
Phe Asp Arg Asp Leu Ser Ile Ala Gly Arg Val Tyr Val Asn Glu Asn
    130                 135                 140
Gly Gln Phe Val Pro Lys Leu Leu Lys Ile Asp Lys Pro Leu Leu Arg
145                 150                 155                 160
Ile Pro Thr Leu Ala Ile His Leu Asp Arg Glu Val Asn Thr Lys Phe
                165                 170                 175
Glu Phe Asn Lys Glu Thr Lys Leu Val Pro Ile Ala Gly Gln Thr Ser
            180                 185                 190
Ile Asp Lys Asn Glu Lys Glu Ser Ser Ala Ser Ala Ser Lys Ser Cys
        195                 200                 205
```

```
Ala Asp Asp Pro Asn Leu Gln Leu Thr Pro Asp Gln Phe Glu Ser Val
    210                 215                 220

Gln Asn Val Ile Ser Arg His Asn Lys Ser Leu Val Glu Leu Ile Ala
225                 230                 235                 240

Lys Glu Leu Asn Val Glu Pro Thr Gln Ile Glu Asp Phe Glu Leu Ile
                245                 250                 255

Leu Phe Asp His Gln Lys Ser Thr Ile Gly Gly Leu Asn Asp Glu Phe
            260                 265                 270

Ile Phe Ser Pro Arg Leu Asp Asn Leu Thr Ser Cys Phe Thr Ala Ala
        275                 280                 285

Lys Gly Leu Val Glu Ser Ile Lys Asn Leu Pro Lys Glu Gly Ile
    290                 295                 300

Ser Leu Ile Ser Leu Phe Asp His Glu Glu Ile Gly Ser Val Ser Ala
305                 310                 315                 320

Gln Gly Ala Asp Ser Thr Phe Leu Pro Asp Ile Ile Gln Arg Leu Thr
                325                 330                 335

Lys Phe Asp Phe Asp Asn Thr Asn Ser Ser Asp Asn Val Asp Tyr Phe
            340                 345                 350

His Glu Thr Met Ser Lys Ser Phe Leu Leu Ser Ser Asp Met Ala His
        355                 360                 365

Gly Val His Pro Asn Tyr Ala Asp Lys Tyr Glu Gly Gln Asn Arg Pro
    370                 375                 380

Gln Leu Asn Leu Gly Pro Val Ile Lys Ile Asn Ala Asn Gln Arg Tyr
385                 390                 395                 400

Ala Thr Asn Ser Pro Gly Ile Val Leu Leu Lys Lys Val Ala Asp Lys
                405                 410                 415

Val Gln Val Pro Leu Gln Leu Phe Val Val Arg Asn Asp Ser Pro Cys
            420                 425                 430

Gly Ser Thr Ile Gly Pro Ile Leu Ala Ala Lys Leu Gly Ile Arg Thr
        435                 440                 445

Leu Asp Leu Gly Asn Pro Gln Leu Ser Met His Ser Ile Arg Glu Thr
    450                 455                 460

Gly Gly Thr Phe Asp Ile Leu Lys Leu Thr Asp Leu Phe Lys Ser Phe
465                 470                 475                 480

Phe Glu Asn Tyr Ile Glu Leu Asp Arg Lys Ile Leu Val Asp His Leu
                485                 490                 495

<210> SEQ ID NO 19
<211> LENGTH: 838
<212> TYPE: PRT
<213> ORGANISM: Candida albicans

<400> SEQUENCE: 19

Met Thr Ser Ile Arg Tyr Asp Tyr Phe Lys Glu Ser Gly Gly Ser Asp
1               5                   10                  15

Gly Gly Ser Pro Thr Arg Thr Ile Ile Ser Tyr Lys Arg Phe Ile Tyr
                20                  25                  30

Val Gly Thr Leu Leu Ala Ile Leu Ile Tyr Gly Ser Ser Phe Leu Ile
            35                  40                  45

Thr Thr Ile Glu Asn Phe Thr Leu Lys Phe Glu Ser Gln Ser Ile Ser
        50                  55                  60

Ser Ile Asp Ser Phe Lys Gly Glu Arg Pro Asp Tyr Ala Ser Pro Ser
65                  70                  75                  80

Ser Lys Ser Thr Asp Phe Lys Gly Lys Ile Pro Phe Ser Lys Glu Val
                85                  90                  95
```

-continued

```
Tyr Asp Lys His Ile Leu Ser Pro Lys Leu His Ser Ile Gln Trp Ile
            100                 105                 110
Arg Ala Pro Glu Ser Ile His Asp Asp Arg Gly Thr Tyr Val Ile Lys
            115                 120                 125
Glu Asp Lys Asp Lys Gly Phe Arg Val Val Lys Ser Ile Ala
130                 135                 140
Asp Glu Glu Tyr Glu Lys Glu Leu Ile Gly Asn Ser Ile Phe Lys Tyr
145                 150                 155                 160
Lys Gly Glu Glu His Glu Ile Val Asp Tyr Phe Ala Ser Pro Asp Leu
                165                 170                 175
Gln Lys Val Ile Leu Lys Thr Asp Val Thr Ser Leu Trp Arg Tyr Ser
            180                 185                 190
Ser Ile Ala Tyr Tyr Trp Val Leu Asp Ile Asn Asn Gly Asp Ile Lys
            195                 200                 205
Pro Val Phe Asn Asp Val Asp Lys Ile Ser Thr Ala Ser Trp Ser Pro
            210                 215                 220
Asp Ser Ser Lys Ile Ala Phe Ile Tyr Glu Asn Asn Leu Tyr Tyr Lys
225                 230                 235                 240
Ser Leu Gln His Asp Glu Ile Val Gln Ile Thr Phe Asp Gly Ser Thr
                245                 250                 255
Glu Ile Phe Asn Gly Lys Pro Asp Trp Val Tyr Glu Glu Val Tyr
            260                 265                 270
Gly Ser Asp His Val Phe Trp Trp Ser Pro Glu Ser Asp Lys Val Ala
            275                 280                 285
Phe Leu Arg Ser Asn Asn Thr Gln Val Pro Glu Phe Ile Ile Pro Phe
            290                 295                 300
Tyr Ala Gln Ser Asp His Gln Asp Tyr Pro Glu Ile Val Lys Ile Lys
305                 310                 315                 320
Tyr Pro Lys Ala Gly Tyr Pro Asn Pro Ile Val Asp Val Leu Thr Tyr
                325                 330                 335
Asp Leu Asn Thr Lys Asn Leu His Asn His Leu Lys Ser Glu Lys
            340                 345                 350
Ile Asn Leu Glu Asn Arg Leu Ile Thr Glu Val Val Trp Ile Gly Asp
            355                 360                 365
Ser Leu Lys Val Lys Thr Ser Asn Arg His Ser Asp Leu Leu Glu Ile
            370                 375                 380
Phe Leu Val Asp Lys His Glu Lys Val Asn Leu Ile Arg Thr Leu Thr
385                 390                 395                 400
Ala Ser Asp Ser Trp Phe Glu Ala Thr Ser Ser Thr Leu Tyr Ile Pro
                405                 410                 415
Ala Asn Lys Thr Leu Gly Arg Lys Tyr Asp Gly Tyr Leu Asp Ile Val
            420                 425                 430
Val Glu Asn Gly Tyr Asn His Leu Ala Tyr Phe Ser Pro Pro Asp Asn
            435                 440                 445
Ser Glu Tyr Glu Leu Leu Thr Lys Gly Asn Trp Glu Val Thr Gly Gly
            450                 455                 460
Val Thr Phe Asp Phe Thr Ser Asn Thr Val Tyr Phe Thr Ser Thr Ala
465                 470                 475                 480
Lys Ser Pro Ile Glu Arg His Ile His Ser Ile Asn Leu Leu Asp Arg
                485                 490                 495
Ser Asp Asn Gly Leu Pro Tyr Ile Lys Asp Ile Thr Thr Lys Glu Gly
            500                 505                 510
```

-continued

```
Trp Tyr Gln Ser Ser Phe Ser Ser Gly Ala Arg Phe Leu Phe Leu Ser
            515                 520                 525

Glu Leu Gly Pro Gly Val Pro Thr Gln Arg Val Asn Asp Leu Lys Met
530                 535                 540

His Lys Asn Val Lys Thr Ile Glu Asp Asn Ser Glu Leu Val Glu Thr
545                 550                 555                 560

Leu Arg Asn Tyr Val Val Pro Glu Val Lys Tyr Ser Gln Val Glu Leu
                565                 570                 575

Asp Asp Lys Glu Thr Gly Gln Pro Phe Leu Val Thr Ala Met Glu Thr
            580                 585                 590

Leu Pro Leu Asn Phe Asp Lys Thr Lys Lys Tyr Pro Val Leu Phe Tyr
        595                 600                 605

Ile Tyr Gly Gly Pro Gly Ser Gln Thr Val Thr Lys Lys Trp Ala Leu
    610                 615                 620

Ser Phe Ser Ser Leu Ile Ala Ala Glu Leu Asp Ala Val Val Val Thr
625                 630                 635                 640

Ile Asp Gly Arg Gly Thr Gly Phe Asn Asn Leu Asn Tyr Lys Leu Gly
                645                 650                 655

Ser Lys Phe Lys Phe Ile Val Arg Asp Arg Leu Gly Gln Tyr Glu Pro
            660                 665                 670

Ile Asp Val Ile Ser Ala Ala Asn Lys Trp Ala Glu Lys Ser Tyr Val
        675                 680                 685

Asp Pro Glu Arg Ile Ala Val Trp Gly Trp Ser Tyr Gly Gly Phe Leu
    690                 695                 700

Thr Leu Lys Thr Leu Glu Thr Asp Ile Asp Asn Pro Ile Phe Asn Tyr
705                 710                 715                 720

Ala Val Ala Ile Ala Pro Val Thr Arg Trp Arg Leu Tyr Asp Ser Ile
                725                 730                 735

Tyr Thr Glu Arg Tyr Leu Asn Thr Pro Gln Glu Asn Pro Lys Gly Tyr
            740                 745                 750

Glu Thr Gly Ser Ile His Asn Val Thr Asn Phe Lys His Val Lys Lys
        755                 760                 765

Phe Phe Ile Gly His Gly Ser Gly Asp Asp Asn Val His Val Gln Asn
    770                 775                 780

Ser Leu Gln Leu Leu Asp Glu Phe Asn Leu Ala Glu Val Glu Asn Phe
785                 790                 795                 800

Glu Phe Met Ile Phe Pro Asp Ser Asn His Gly Met Asn Tyr His Asn
                805                 810                 815

Gly Phe Asn Val Val Tyr Asp Arg Ile Leu Asp Phe Phe Lys Arg Ala
            820                 825                 830

Phe Asp Trp Glu Phe Val
        835

<210> SEQ ID NO 20
<211> LENGTH: 930
<212> TYPE: PRT
<213> ORGANISM: Candida albicans

<400> SEQUENCE: 20

Met Phe Thr His Lys Arg Val Pro Gln His Glu Glu Tyr Glu Leu Val
1               5                   10                  15

Asn Gln Val Pro Pro Thr Gln Ser Pro Thr Asp Ser Pro Thr Arg Ser
            20                  25                  30

Glu Ser Asp Phe Arg Asn Ser Thr Asp Ser Gln Leu Ser Asp Ile Phe
        35                  40                  45
```

```
Glu Asp Leu Glu Asn Tyr Ser Gly Ser Ser Gly Gln Lys Ile Glu Asp
 50                  55                  60
Phe Asn Asp Ser Pro Leu Phe Gln Ser Val Leu Met Arg Tyr Lys Asn
 65                  70                  75                  80
Glu Gly Ile Ser Gly Arg Thr Cys Gly Ile Phe Ser Leu Val Ala Ile
                 85                  90                  95
Phe Leu Trp Ile Gly Ser Val Ile Ile Tyr Ser Arg Val Asn His Ser
            100                 105                 110
Thr Ile Gly Asn Asp Leu Thr Trp Lys Thr Asn Ile Ile Gln Leu Asn
        115                 120                 125
Gly Glu Asn Ile Thr Leu Asn Glu Tyr Asn Pro Asn Phe Lys Asn Ile
    130                 135                 140
Thr Met Asn Asp Trp Arg Lys Gly Lys Tyr His Thr Phe Glu Lys Gln
145                 150                 155                 160
Ile Arg Trp Leu Thr Ser Lys Gln Ser Pro Lys Ser Lys His Gly Gly
                165                 170                 175
Gly Phe Tyr Val Leu Asp Glu His Asp Lys Ile Val Val Asn Gln Ile
            180                 185                 190
Gly Gln Val Asp Lys Ser Asp Thr Phe Leu Ser Asn Lys Gln Phe Glu
        195                 200                 205
Tyr Gly Asn Asn Phe Phe Lys Ile Gln Asp Phe Ile Leu Asn Pro Ser
    210                 215                 220
Gln Ser Ile Glu Asp Ser Glu Val Val His Ile Ile Thr Asp Thr
225                 230                 235                 240
Val His Gln Trp Arg His Ser Ser Phe Ala Leu Tyr Trp Leu Phe Lys
                245                 250                 255
Pro Leu Val Gly Thr Tyr Thr Pro Ile Gln Pro Pro Arg Asn Asn Asn
            260                 265                 270
Lys Gly Asn Gly Leu Glu Val Asp Ala Leu Asp Lys Leu His Tyr Ala
        275                 280                 285
Asp Phe Ser Ser Asp Gly Lys Tyr Ile Val Phe Gly Phe Glu His Asn
    290                 295                 300
Leu Phe Ile Gln Asp Leu Ala Thr Gly Glu Ile Gln Gln Ile Thr Asp
305                 310                 315                 320
Asp Gly Ser Pro Asn Ile Ile Asn Gly Lys Ser Asp Trp Ile Tyr Glu
                325                 330                 335
Glu Glu Val Ile Ala Ser Asn Lys Met Ile Trp Trp Ser Pro Ser Gly
            340                 345                 350
Asn His Phe Ile Phe Ala Lys Ile Asn Glu Thr Lys Val Gln Glu Val
        355                 360                 365
Asp Met Asp Tyr Tyr Thr Lys Gln Asn Thr Asn Ile Gly Met Gln Tyr
370                 375                 380
Gln Gln Val Gly Glu Ser Lys Tyr Glu Gly Val Asn Gln Tyr Pro Ile
385                 390                 395                 400
Asn Thr Gln Leu Lys Tyr Pro Lys Pro Gly Thr Ser Asn Pro Ile Leu
                405                 410                 415
Ser Leu Tyr Ile Tyr Asp Ile Ala Asn Lys Lys Thr Glu Glu Ile Ile
            420                 425                 430
Asp Gly Asp Asp Asn Leu Gly Thr Glu Tyr Ile Leu Tyr Tyr Ala Lys
        435                 440                 445
Trp Ile Asp Ala Asn Ser Phe Leu Met Lys Gln Ser Asp Arg Thr Ser
    450                 455                 460
```

```
Ser Val Leu Thr Lys Lys Leu Tyr Asp Leu Asp Lys Asn His Val Ser
465                 470                 475                 480

Ile Val Ser Ser Ser Asn Val Thr Lys Glu Tyr Lys Gly Trp Val Glu
                485                 490                 495

Arg Met Asn Pro Ile Thr Leu Leu Asp Asp Gly Lys Tyr Ile Asp Asn
            500                 505                 510

Val Val Ile Asp Asn Arg Asn Thr Leu Ala Leu Phe Asp Ser Pro His
        515                 520                 525

Ser Val Ser Pro Ser Lys Val Leu Val Asp Asn Lys Asp Trp Asp Ile
    530                 535                 540

Thr Gly Glu Ala Ile Tyr Asp Ala Gln Glu Lys Phe Val Tyr Phe Leu
545                 550                 555                 560

Ser Thr Val Arg Ser Ser Met Asp Ala His Leu Val Gly Ile Asp Leu
                565                 570                 575

Ala Asp Asn Tyr Lys Leu Tyr Asn Ile Thr Asp Thr Lys Lys Asp Gly
            580                 585                 590

Ile Phe Glu Thr Lys Phe Ser Glu Asn Gly Gln Tyr Leu Ser Leu Val
        595                 600                 605

Tyr Gln Gly Pro Asn Gln Pro Trp Gln Arg Leu Ile Asn Met Ala Asn
    610                 615                 620

Val His Asp Phe Ile Lys Ser Glu Glu Tyr Gly Lys Ser Thr Ile Glu
625                 630                 635                 640

Glu Ala Val Ile Leu Asn Gln Pro Ile Val Asn Ser Leu Ala Asn Leu
                645                 650                 655

Lys Glu Ile Asn Leu Pro Thr Val Arg Tyr Lys Glu Val Thr Ile Gly
            660                 665                 670

Lys Lys Glu Asp Gln Val Thr Leu Asn Ile Met Glu Ile Leu Pro Pro
        675                 680                 685

Asn Phe Lys Ala Lys Asn Gln Lys Tyr Pro Leu Phe Val Tyr Thr Tyr
    690                 695                 700

Gly Gly Pro Gly Ser Gln Thr Val Met Lys Lys Phe Asp Ile Gly Phe
705                 710                 715                 720

Leu Gln Ile Val Ser Ala Arg Leu Asn Ser Ile Ile Leu Val Ile Asp
                725                 730                 735

Pro Arg Gly Thr Gly Gly Lys Gly Trp Lys Phe Glu Ser Phe Ala Lys
            740                 745                 750

Asn Asn Ile Gly Tyr Trp Glu Ser Arg Asp Leu Lys Thr Ile Thr Ser
    755                 760                 765

Glu Tyr Ile Lys Lys Asn Lys Lys Leu Ile Asp Lys Glu Arg Val Ala
770                 775                 780

Leu Trp Gly Trp Ser Tyr Gly Gly Phe Val Thr Leu Lys Thr Leu Glu
785                 790                 795                 800

Tyr Asp Lys Gly Glu Val Phe Lys Tyr Gly Met Ala Val Ala Pro Val
            805                 810                 815

Thr Asn Trp Leu Phe Tyr Asp Ser Ile Tyr Thr Glu Arg Tyr Met Gly
        820                 825                 830

Leu Pro Asp Thr Asp Pro Asn Tyr Glu Thr Ser Ala Arg Ile Asn Asp
    835                 840                 845

Phe Asp Asn Phe Lys Ser Val Lys Arg Phe Leu Leu Val His Gly Thr
                855                 860
            850

Gly Asp Asp Asn Val His Val Gln Asn Leu Met Trp Leu Leu Asp Gln
865                 870                 875                 880

Leu Asn Ile His Asn Val Glu Asn Tyr Asp Met His Leu Phe Pro Asp
```

```
                        885                 890                 895
Ser Asp His Ser Ile Ser Tyr Asp Asn Ala Gly Val Ile Val Tyr Asp
                    900                 905                 910

Lys Leu Tyr Tyr Trp Leu Gln Asn Ala Phe Arg Gly Asn Phe Asp Glu
                915                 920                 925

Leu Asn
    930

<210> SEQ ID NO 21
<211> LENGTH: 550
<212> TYPE: PRT
<213> ORGANISM: Candida albicans

<400> SEQUENCE: 21

Met Lys Phe Leu Thr Leu Thr Thr Ser Leu Ser Ile Ile Val Ser Ile
1               5                   10                  15

Asn Ala Leu Pro Thr Ser Phe Gly Phe Trp Lys Asn Trp Phe Asn Leu
            20                  25                  30

Gly Glu Lys Leu Thr Gln Glu Ile Met Asp Asp Ile Ser Asp Gln
        35                  40                  45

Phe Ile Asn Asn Asp Glu Asn Glu Asn Asn Asn Asp Asn Asn Leu
50                  55                  60

Ile Ile Asp Gly Val Ile Asp Glu Thr Val Tyr Asn Ser Leu Pro Glu
65                  70                  75                  80

Ile Asp Thr Glu Ser Leu Gln Ser Leu Ile Asn Glu Lys Gly Leu Arg
                85                  90                  95

Ser Arg Ala Glu Asp Leu Phe Glu Ile Ala Gln Arg Ser Ile Gly Lys
            100                 105                 110

Tyr Asp His Pro Thr Arg Val Ile Gly Ser Pro Gly His Trp Gly Thr
        115                 120                 125

Ile Gly Tyr Ile Ile Ser Glu Ile Lys Lys Leu Lys Gly Tyr Tyr Asn
    130                 135                 140

Val Lys Thr Gln Ser Phe Lys Ala Leu Asp Gly Lys Val Lys Ser Phe
145                 150                 155                 160

Ser Leu Leu Ile Asp Gly Val Glu Pro Lys Ser Leu Ser Pro Phe Ser
                165                 170                 175

Leu Thr Pro Pro Thr Val Asp Gly Lys Pro Ala His Gly Asn Leu Val
            180                 185                 190

Leu Val Asp Asp Phe Gly Cys Lys Pro Asp Asn Phe Pro Glu Phe Thr
        195                 200                 205

Lys Gly Asn Ile Val Leu Ile Lys Arg Gly Glu Cys Ala Phe Gly Asp
    210                 215                 220

Lys Ser Arg Asn Ala Gly Ile Ala Gly Ala Leu Gly Ala Ile Ile Tyr
225                 230                 235                 240

Asp Asp Glu Pro Val Arg Gly Thr Leu Gly Asn Pro Thr Gly Lys Glu
                245                 250                 255

Val Ala Thr Val Ser Val Ala Lys Lys Asp Val Glu Lys Tyr Ile Glu
            260                 265                 270

Lys Leu Ser Lys Asp Pro Lys Tyr Ala Phe Glu Thr Thr Leu Tyr Val
        275                 280                 285

Asp Ser Tyr Val Lys Tyr Ile Lys Thr Leu Asn Val Ile Ala Asp Ser
    290                 295                 300

Val Phe Gly Asp His Asp Asn Ile Val Ser Leu Gly Ala His Ser Asp
305                 310                 315                 320
```

-continued

```
Ser Val Ala Glu Gly Pro Gly Ile Asn Asp Asp Gly Ser Gly Thr Ile
            325                 330                 335
Ser Leu Leu Glu Val Ala Lys His Leu Thr Gln Phe Lys Leu Asn Asn
        340                 345                 350
Ala Val Arg Phe Ala Trp Trp Ala Ala Glu Glu Gly Leu Leu Gly
    355                 360                 365
Ser Thr Tyr Tyr Ala Glu His Leu Thr Ala Glu Glu Asn Ser Lys Leu
370                 375                 380
Arg Leu Phe Met Asp Tyr Asp Met Met Ala Ser Pro Asn Tyr Glu Tyr
385                 390                 395                 400
Gln Val Tyr Asp Ala Asn Asn Lys Asp His Pro Asn Gly Ser Gly Asn
            405                 410                 415
Leu Lys Asp Leu Tyr Ile Asp Trp Tyr Thr Ser His Gly Leu Asn Tyr
        420                 425                 430
Thr Leu Thr Pro Phe Asp Gly Arg Ser Asp Tyr Val Gly Phe Ile Glu
    435                 440                 445
Asn Gly Ile Pro Gly Gly Ile Ala Thr Gly Ala Glu Gly Val Lys
            450                 455                 460
Asp Ala Lys Gly Gln Glu Lys Phe Gly Gly Lys Val Gly Glu Trp Phe
465                 470                 475                 480
Asp Pro Cys Tyr His Gln Leu Cys Asp Asn Leu Asp Asn Pro Asp Tyr
                485                 490                 495
Glu Ala Trp Val Ile Asn Thr Lys Leu Ile Ala His Ser Val Ala Val
            500                 505                 510
Tyr Ala Lys Ser Phe Glu Gly Phe Pro Lys Arg Glu Pro Lys Lys Glu
        515                 520                 525
Val Ala Ser Ala Ser Asn Ser Glu Lys Pro Asn Glu Phe Ile Tyr Arg
    530                 535                 540
Gly Ser Lys Leu Ile Met
545                 550

<210> SEQ ID NO 22
<211> LENGTH: 8
<212> TYPE: PRT
<213> ORGANISM: Artificial Sequence
<220> FEATURE:
<223> OTHER INFORMATION: Substrate peptide

<400> SEQUENCE: 22

Val Phe Ile Leu Trp Arg Thr Glu
1               5

<210> SEQ ID NO 23
<211> LENGTH: 8
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (5)..(5)
<223> OTHER INFORMATION: Xaa is Nle

<400> SEQUENCE: 23

Thr Phe Ser Tyr Xaa Arg Trp Pro
1               5

<210> SEQ ID NO 24
<211> LENGTH: 8
<212> TYPE: PRT
```

```
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (4)..(4)
<223> OTHER INFORMATION: Xaa is Nle

<400> SEQUENCE: 24

Ile Tyr Arg Xaa His Val Gln Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (4)..(4)
<223> OTHER INFORMATION: Xaa is Nle

<400> SEQUENCE: 25

Trp Pro Ser Xaa Asn Lys Val Gly
1               5

<210> SEQ ID NO 26
<211> LENGTH: 14
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (11)..(11)
<223> OTHER INFORMATION: Xaa is Nle

<400> SEQUENCE: 26

Lys Trp Leu Ile His Pro Thr Phe Ser Tyr Xaa Arg Trp Pro
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Substrate peptide

<400> SEQUENCE: 27

Val Phe Ile Leu Trp Arg Thr Glu Lys Arg Arg
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (7)..(7)
<223> OTHER INFORMATION: Xaa is Nle

<400> SEQUENCE: 28

Arg Arg Lys Ile Tyr Arg Xaa His Val Gln Leu Lys
1               5                   10

<210> SEQ ID NO 29
```

```
<211> LENGTH: 12
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (7)..(7)
<223> OTHER INFORMATION: Xaa is Nle

<400> SEQUENCE: 29

Arg Arg Lys Trp Pro Ser Xaa Asn Lys Val Gly Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (8)..(8)
<223> OTHER INFORMATION: Xaa is Nle

<400> SEQUENCE: 30

Arg Arg Lys Thr Phe Ser Tyr Xaa Arg Trp Pro Lys
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (1)..(1)
<223> OTHER INFORMATION: Xaa is Leu, Gly, Nle, Thr, Glu, Trp, Asp, or
      Phe
<220> FEATURE:
<221> NAME/KEY: MISC_FEATURE
<222> LOCATION: (2)..(2)
<223> OTHER INFORMATION: Xaa is Val, Leu, Ile, Nle, Phe, or Tyr
<220> FEATURE:
<221> NAME/KEY: MISC_FEATURE
<222> LOCATION: (3)..(3)
<223> OTHER INFORMATION: Xaa is Ile, Lys, Nle, Arg, or Val
<220> FEATURE:
<221> NAME/KEY: MISC_FEATURE
<222> LOCATION: (4)..(4)
<223> OTHER INFORMATION: Xaa is Lys, Tyr, Nle, Leu, or Phe
<220> FEATURE:
<221> NAME/KEY: MISC_FEATURE
<222> LOCATION: (5)..(5)
<223> OTHER INFORMATION: Xaa is Trp, Nle, Thr, Phe, or Asn
<220> FEATURE:
<221> NAME/KEY: MISC_FEATURE
<222> LOCATION: (6)..(6)
<223> OTHER INFORMATION: Xaa is Arg, Phe, or Nle
<220> FEATURE:
<221> NAME/KEY: MISC_FEATURE
<222> LOCATION: (7)..(7)
<223> OTHER INFORMATION: Xaa is Nle, Thr, Ala, Gln, or Trp
<220> FEATURE:
<221> NAME/KEY: MISC_FEATURE
<222> LOCATION: (8)..(8)
<223> OTHER INFORMATION: Xaa is Glu, Ala, or Pro

<400> SEQUENCE: 31

Xaa Xaa Xaa Xaa Xaa Xaa Xaa Xaa
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (1)..(1)
<223> OTHER INFORMATION: Xaa is Leu, Gly, Nle, or Trp
<220> FEATURE:
<221> NAME/KEY: MISC_FEATURE
<222> LOCATION: (2)..(2)
<223> OTHER INFORMATION: Xaa is Leu, Phe, Tyr, Nle, Ala, Val, or Ile
<220> FEATURE:
<221> NAME/KEY: MISC_FEATURE
<222> LOCATION: (3)..(3)
<223> OTHER INFORMATION: Xaa is Ile, Nle, Ser, Lys, or Arg
<220> FEATURE:
<221> NAME/KEY: MISC_FEATURE
<222> LOCATION: (4)..(4)
<223> OTHER INFORMATION: Xaa is Lys, Leu, Phe, Nle, or Tyr
<220> FEATURE:
<221> NAME/KEY: MISC_FEATURE
<222> LOCATION: (5)..(5)
<223> OTHER INFORMATION: Xaa is Nle, Ser, Lys, or Trp
<220> FEATURE:
<221> NAME/KEY: MISC_FEATURE
<222> LOCATION: (6)..(6)
<223> OTHER INFORMATION: Xaa is Arg, Lys, or Phe
<220> FEATURE:
<221> NAME/KEY: MISC_FEATURE
<222> LOCATION: (7)..(7)
<223> OTHER INFORMATION: Xaa is Trp or Arg

<400> SEQUENCE: 32

Xaa Xaa Xaa Xaa Xaa Xaa Xaa Pro
1               5
```